US010526404B2

(12) United States Patent
Corti et al.

(10) Patent No.: US 10,526,404 B2
(45) Date of Patent: Jan. 7, 2020

(54) MULTISPECIFIC ANTI GM-CSF ANTIBODIES

(71) Applicant: INSTITUTE FOR RESEARCH IN BIOMEDICINE, Bellinzona (CH)

(72) Inventors: Davide Corti, Bellinzona (CH); Antonio Lanzavecchia, Porza (CH); Luca Piccoli, Bellinzona (CH)

(73) Assignee: INSTITUTE FOR RESEARCH IN BIOMEDICINE, Bellinzona (CH)

( * ) Notice: Subject to any disclaimer, the term of this patent is extended or adjusted under 35 U.S.C. 154(b) by 0 days.

(21) Appl. No.: 15/568,325

(22) PCT Filed: Apr. 29, 2015

(86) PCT No.: PCT/EP2015/000879

§ 371 (c)(1),
(2) Date: Oct. 20, 2017

(87) PCT Pub. No.: WO2016/173605

PCT Pub. Date: Nov. 3, 2016

(65) Prior Publication Data

US 2018/0142014 A1 May 24, 2018

(51) Int. Cl.
*C07K 16/24* (2006.01)
*C07K 16/46* (2006.01)
*A61K 39/00* (2006.01)

(52) U.S. Cl.
CPC ...... *C07K 16/243* (2013.01); *A61K 2039/505* (2013.01); *C07K 2317/31* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| | | | |
|---|---|---|---|
| WO | 2009/038760 | A2 | 3/2009 |
| WO | 2009/149189 | A2 | 12/2009 |
| WO | 2012/006490 | A2 | 1/2012 |

OTHER PUBLICATIONS

Behrens et al., "MOR103, a human monoclonal antibody to granulocyte-macrophage colony-stimulating factor, in the treatment of patients with moderate rheumatoid arthritis: results of a phase lb/lla randomised, double-blind, placebo-controlled, dose-escalation trial," *Ann Rheum Dis 74*:1058-1064 (2015).
Laventie et al., "Heavy chain-only antibodies and tetravalent bispecific antibody neutralizing *Staphylococcus aureus* leukotoxins," *PNAS 108*(39):16404-16409 (Sep. 27, 2011).
Lewis, "GM-CSF: A Target for Brain Inflammation Intervention in MS?" *New Findings* (3 pages) (Jun. 23, 2014).
Rasouli et al., "Expression of GM-CSF in T Cells is Increased in Multiple Sclerosis and Suppressed by IFN-β Therapy," *J Immunol* published online Apr. 27, 2015, http://www.jimmunol.org/content/early/2015/04/25/jimmuno1.1403243.
Wu et al., "Molecular construction and optimization of anti-human IL-1α/β dual variable domain immunoglobulin (DVD-Ig™) molecules," *Landes Bioscience mAbs 1*(4):339-347 (Jul./Aug. 2009).

*Primary Examiner* — Elly-Gerald Stoica
(74) *Attorney, Agent, or Firm* — Seed IP Law Group LLP

(57) ABSTRACT

The present invention provides multispecific antibodies, and antigen binding fragments thereof, that potently neutralize a cytokine and that may thus be useful in the prevention and/or treatment of inflammatory and/or autoimmune diseases. In particular, the present invention provides a multispecific antibody, or an antigen binding fragment thereof, comprising at least two different domains specifically binding to at least two different, non-overlapping sites in a cytokine and an Fc moiety. The invention also relates to nucleic acids that encode such antibodies and antibody fragments and immortalized B cells and cultured plasma cells that produce such antibodies and antibody fragments. In addition, the invention relates to the use of the antibodies and antibody fragments of the invention in screening methods as well as in the diagnosis, prophylaxis and treatment of inflammatory and/or autoimmune diseases.

26 Claims, 7 Drawing Sheets

Specification includes a Sequence Listing.

MULTISPECIFIC ANTI GM-CSF ANTIBODIES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 480369C_403USPC_SEQUENCE_LISTING.txt. The text file is 209 KB, was created on Jun. 2, 2019 and is being submitted electronically via EFS-Web.

The present invention relates to multispecific anti-cytokine, preferably anti-GM-CSF, antibodies, and antigen binding fragments thereof, that potently neutralize cytokines, in particular GM-CSF. The multispecific anti-cytokine, preferably anti-GM-CSF, antibodies of the present invention comprise at least two different domains specifically binding to at least two different, non-overlapping sites on a single cytokine molecule. The invention also relates to nucleic acids that encode and immortalized B cells and cultured plasma cells that produce such antibodies and antibody fragments. In addition, the invention relates to the use of the antibodies and antibody fragments of the invention in screening methods as well as in the diagnosis, prophylaxis and treatment of diseases, in particular inflammatory and autoimmune diseases.

Cytokines are a family of immune-modulatory molecules that are secreted by a variety of cells and act locally or systemically on other cells. Most cytokines have immune-modulatory activity, being involved in the control of different types of inflammatory processes and mechanisms of host defense. Cytokines include chemokines, interferons, interleukins, lymphokines, tumour necrosis factor, monokines and colony stimulating factors. Cytokines are produced by a broad range of cells, including immune cells like macrophages, B lymphocytes, T lymphocytes and mast cells, as well as endothelial cells, fibroblasts, and various stromal cells; a given cytokine may be produced by more than one type of cell.

The cytokine granulocyte macrophage-colony stimulating factor (GM-CSF) is a monomeric protein of 127 amino acids with a molecular weight ranging between 14 kDa and 35 kDa depending on the variable degree of glycosylation. Non-glycosylated and glycosylated GM-CSF show similar activity in vitro (Cebon, J., Nicola, N., Ward, M., Gardner, I., Dempsey, P., Layton, J., Dührsen, U., Burgess, A. W., Nice, E., and Morstyn, G. (1990). Granulocyte-macrophage colony stimulating factor from human lymphocytes. The effect of glycosylation on receptor binding and biological activity. J. Biol. Chem. 265, 4483-4491). GM-CSF exerts its biological activity by binding to its receptor (Hansen, G., Hercus, T. R., McClure, B. J., Stomski, F. C., Dottore, M., Powell, J., Ramshaw, H., Woodcock, J. M., Xu, Y., Guthridge, M., et al. (2008). The structure of the GM-CSF receptor complex reveals a distinct mode of cytokine receptor activation. Cell 734, 496-507), which is expressed on the cell surface of myeloid cells and endothelial cells but absent on lymphocytes. The receptor is heterodimeric and is composed of alpha and beta subunits. The alpha subunit binds GM-CSF with nanomolar affinity. The beta subunit is also part of the interleukin-3 and interleukin-5 receptor complexes and, in association with the GM-CSF receptor alpha subunit and GM-CSF, leads to the formation of a multimeric complex where GM-CSF is bound with picomolar binding affinity.

GM-CSF can be expressed by a variety of cell types including T lymphocytes, macrophages, NK cell, mast cells, endothelial cells, fibroblasts and some malignant cells (Gasson, J. C. (1991). Molecular physiology of granulocyte-macrophage colony-stimulating factor. Blood 77, 1131-1145; Hamilton, J. A., and Anderson, G. P. (2004). GM-CSF Biology. Growth Factors 22, 225-231; Sergeeva, A., Ono, Y., Rios, R., and Molldrem, J. J. (2008). High titer autoantibodies to GM-CSF in patients with AML, CML and MDS are associated with active disease. Leukemia 22, 783-790). GM-CSF acts as a growth factor on hemopoietic precursor cells to produce granulocytes and monocytes. It is also essential for the development of microglia and for the function of alveolar macrophages. In addition, GM-CSF has also a variety of pro-inflammatory effects on cells of the immune system expressing the GM-CSF receptor. The most important of these functions is the activation of monocytes, macrophages and granulocytes in several inflammatory and autoimmune diseases (Hamilton, J. A. (2002). GM-CSF in inflammation and autoimmunity. Trends Immunol 23, 403-408), which in turn result in the production of other cytokines and chemokines, matrix degrading proteases, increased HLA expression and increased expression of adhesion molecules or CC-chemokines receptors. GM-CSF can also synergize with other inflammatory factors like other cytokines or LPS (Parajuli, B., Sonobe, Y., Kawanokuchi, J., Doi, Y., Noda, M., Takeuchi, H., Mizuno, T., and Suzumura, A. (2012). GM-CSF increases LPS-induced production of proinflammatory mediators via upregulation of TLR4 and CD14 in murine microglia. J Neuroinflammation 9, 268). Taken together, GM-CSF is thus part of the immune/inflammatory cascade.

GM-CSF can therefore be considered as a target for anti-inflammatory and autoimmune therapies. Chronic and acute inflammatory and/or autoimmune diseases such as for example rheumatoid arthritis (RA), multiple sclerosis (MS), Crohn's disease, psoriasis, asthma, atopic dermatitis or shock may benefit from GM-CSF neutralization and the consequent pro-inflammatory cascade. For example in MS elevated levels of GM-CSF correlate with the active phase of MS (McQualter, J. L., Darwiche, R., Ewing, C., Onuki, M., Kay, T. W., Hamilton, J. A., Reid, H. H., and Bernard, C. C. (2001). Granulocyte macrophage colony-stimulating factor: a new putative therapeutic target in multiple sclerosis. J Exp Med 194, 873-882; Noster, R., Riedel, R., Mashreghi, M.-F., Radbruch, H., Harms, L., Haftmann, C., Chang, H.-D., Radbruch, A., and Zielinski, C. E. (2014). IL-17 and GM-CSF expression are antagonistically regulated by human T helper cells. Sci Transl Med 6, 241ra80-241ra80) and GM-CSF deficient mice fail to develop disease in the experimental autoimmune encephalomyelitis (EAE) murine model for multiple sclerosis (McQualter, J. L., Darwiche, R., Ewing, C., Onuki, M., Kay, T. W., Hamilton, J. A., Reid, H. H., and Bernard, C. C. (2001). Granulocyte macrophage colony-stimulating factor: a new putative therapeutic target in multiple sclerosis. J Exp Med 194, 873-882).

In asthma, increased levels of GM-CSF are found in the airways of asthmatic patients (Broide, D. H., and Firestein, G. S. (1991). Endobronchial allergen challenge in asthma. Demonstration of cellular source of granulocyte macrophage colony-stimulating factor by in situ hybridization. J Clin Invest 88, 1048-1053; Sousa, A. R., Poston, R. N., Lane, S. J., Nakhosteen, J. A., and Lee, T. H. (1993). Detection of GM-CSF in asthmatic bronchial epithelium and decrease by inhaled corticosteroids. Am. Rev. Respir. Dis. 147, 1557-1561). Indeed, GM-CSF in synergy with IL-5 promotes the differentiation, activation and survival of eosinophils (Yamashita, N., Tashimo, H., Ishida, H., Kaneko, F., Nakano, J., Kato, H., Hirai, K., Horiuchi, T., and Ohta, K. (2002). Attenuation of airway hyperresponsiveness in a murine asthma model by neutralization of granulocyte-macrophage colony-stimulating factor (GM-CSF). Cellular Immunology 219, 92-97). The usefulness of GM-CSF neutralizing antibodies was demonstrated in a mouse model of asthma where their administration led to significant reduction of airway hyperresponsiveness and inflammation (Yamashita, N., Tashimo, H., Ishida, H., Kaneko, F., Nakano, J., Kato, H., Hirai, K., Horiuchi, T., and Ohta, K. (2002). Attenuation of airway hyperresponsiveness in a murine asthma model by neutralization of granulocyte-macrophage colony-stimulating factor (GM-CSF). Cellular Immunology 219, 92-97)).

In lung diseases, GM-CSF has also a role where high neutrophil numbers, protease induction, and TNF-alpha overproduction are believed to be central agents in disease pathogenesis, like occupational lung diseases caused by LPS-containing bioaerosols. Indeed, in a mouse model LPS-dependent inflammation of the lung was reduced by using a GM-CSF neutralizing antibody (Bozinovski, S., Jones, J., Beavitt, S.-J., Cook, A. D., Hamilton, J. A., and Anderson, G. P. (2004). Innate immune responses to LPS in mouse lung are suppressed and reversed by neutralization of GM-CSF via repression of TLR-4. Am. J. Physiol. Lung Cell Mol. Physiol. 286, L877-L885).

In RA, multiple groups have measured high levels of GM-CSF in the synovial joint fluids (Alvaro-Gracia, J. M., Zvaifler, N. J., Brown, C. B., Kaushansky, K., and Firestein, G. S. (1991). Cytokines in chronic inflammatory arthritis. VI. Analysis of the synovial cells involved in granulocyte-macrophage colony-stimulating factor production and gene expression in rheumatoid arthritis and its regulation by IL-1 and tumor necrosis factor-alpha. J Immunol 146, 3365-3371; Haworth, C., Brennan, F. M., Chantry, D., Turner, M., Maini, R. N., and Feldmann, M. (1991). Expression of granulocyte-macrophage colony-stimulating factor in rheumatoid arthritis: regulation by tumor necrosis factor-alpha. Eur J Immunol 21, 2575-2579; Fiehn, C., Wermann, M., Pezzutto, A., Huffier, M., and Heilig, B. (1992). [Plasma GM-CSF concentrations in rheumatoid arthritis, systemic lupus erythematosus and spondyloarthropathy]. Z Rheumatol 51, 121-126) and treatment with recombinant GM-CSF after chemotherapy was shown to cause flares of RA (de Vries, E. G., Willemse, P. H., Biesma, B., Stern, A. C., Limburg, P. C., and Vellenga, E. (1991). Flare-up of rheumatoid arthritis during GM-CSF treatment after chemotherapy. The Lancet 338, 517-518). The therapeutic potential of GM-CSF neutralizing antibodies in RA was suggested from their efficacy in a collagen-induced arthritis model in mice (Cook, A. D., Braine, E. L., Campbell, I. K., Rich, M. J., and Hamilton, J. A. (2001). Blockade of collagen-induced arthritis post-onset by antibody to granulocyte-macrophage colony-stimulating factor (GM-CSF): requirement for GM-CSF in the effector phase of disease. Arthritis Res. 3, 293-298; Cornish, A. L., Campbell, I. K., McKenzie, B. S., Chatfield, S., and Wicks, I. P. (2009). G-CSF and GM-CSF as therapeutic targets in rheumatoid arthritis. Nat Rev Rheumatol 5, 554-559).

Antibodies able to neutralize GM-CSF may thus represent new effective preventions and/or therapies for inflammatory and/or autoimmune diseases such as MS, RA and other autoimmune and inflammatory diseases. In principle, cytokine neutralization can be achieved by an antibody that binds to its target soluble cytokine or to the cytokine receptor displayed on the cell's membrane. MOR103 and Namilumab are two phage-derived human monoclonal antibodies that neutralizes GM-CSF and that are being developed as therapeutics in RA and MS (Steidl, S., Ratsch, O., Brocks, B., Dürr, M., and Thomassen-Wolf, E. (2008). In vitro affinity maturation of human GM-CSF antibodies by targeted CDR-diversification. Mol Immunol 46, 135-144; Krinner, E.-M., Raum, T., Petsch, S., Bruckmaier, S., Schuster, I., Petersen, L., Cierpka, R., Abebe, D., Molhoj, M., Wolf, A., et al. (2007). A human monoclonal IgG1 potently neutralizing the pro-inflammatory cytokine GM-CSF. Mol Immunol 44, 916-925; Behrens, F., Tak, P. P., Ostergaard, M., Stoilov, R., Wiland, P., Huizinga, T. W., Berenfus, V. Y., Vladeva, S., Rech, J., Rubbert-Roth, A., et al. (2014). MOR103, a human monoclonal antibody to granulocyte-macrophage colony-stimulating factor, in the treatment of patients with moderate rheumatoid arthritis: results of a phase Ib/IIa randomised, double-blind, placebo-controlled, dose-escalation trial. Ann Rheum Dis) and mavrilimumab is a human monoclonal antibody targeting GM-CSF receptor-alpha under development in RA patients (Burmester, G. R., Feist, E., Sleeman, M. A., Wang, B., White, B., and Magrini, F. (2011). Mavrilimumab, a human monoclonal antibody targeting GM-CSF receptor-α, in subjects with rheumatoid arthritis: a randomised, double-blind, placebo-controlled, phase I, first-in-human study. Ann Rheum Dis 70, 1542-1549).

However, single GM-CSF neutralizing antibodies lead in vivo to the accumulation of a large pool of long-lived GM-CSF that is still able to dissociate and trigger the receptor and that could be the basis of the enhancing activity of monoclonal antibodies to common gamma-chain cytokines in vivo (Boyman, O., Kovar, M., Rubinstein, M. P., Surh, C. D., and Sprent, J. (2006). Selective stimulation of T cell subsets with antibody-cytokine immune complexes. Science 311, 1924-1927).

In view of the above, it is an object of the present invention to provide an antibody, which neutralizes cytokines, in particular GM-CSF, more potently and efficiently than the antibodies presently available. Such an antibody can be used at lower doses, thereby reducing the risks of side effects and saving costs. Moreover, it is an object of the present invention to provide an antibody, which neutralizes cytokines, in particular GM-CSF, but which does not result in accumulation of a large pool of long-lived cytokines, in particular GM-CSF, which is still able to dissociate and to trigger their receptor. Taken together, it is thus the object of the present invention to provide improved antibodies, or antigen binding fragments thereof, as well as related nucleic acid molecules, vectors and cells and pharmaceutical compositions, which overcome the disadvantages of the prior art by a cost-effective and straight-forward approach.

The object underlying the present invention is solved by the claimed subject matter.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value×means× ±10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a subject or patient is intended to include prevention, prophylaxis, attenuation, amelioration and therapy. The terms "subject" or "patient" are used interchangeably herein to mean all mammals including humans. Examples of subjects include humans, cows, dogs, cats, horses, goats, sheep, pigs, and rabbits. In one embodiment, the patient is a human.

As used herein, the term "antibody" encompasses various forms of antibodies, preferably monoclonal antibodies including but not being limited to whole antibodies, antibody fragments, human antibodies, chimeric antibodies, humanized antibodies and genetically engineered antibodies (variant or mutant antibodies) as long as the characteristic properties according to the invention are retained. Especially preferred are human or humanized monoclonal antibodies, especially as recombinant human antibodies.

The term "human antibody", as used herein, is intended to include antibodies having variable and constant regions derived from human germ line immunoglobulin sequences. Human antibodies are well-known in the state of the art (van Dijk, M. A., and van de Winkel, J. G., *Curr. Opin. Chem. Biol.* 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., *Proc. Natl. Acad. Sci. USA* 90 (1993) 2551-2555; Jakobovits, A., et al., *Nature* 362 (1993) 255-258; Bruggemann, M., et al., *Year Immunol.* 7 (1993) 3340). Human antibodies can also be produced in phage display libraries (Hoogenboom, H. R., and Winter, G., *J. Mol. Biol.* 227 (1992) 381-388; Marks, J. D., et al., *J. Mol. Biol.* 222 (1991) 581-597). The techniques of Cole et al. and Boerner et al. are also available for the preparation of human monoclonal antibodies (Cole et al., *Monoclonal Antibodies and Cancer Therapy*, Alan R. Liss, p. 77 (1985); and Boerner, P., et al., *J. Immunol.* 147 (1991) 86-95). The term "human antibody" as used herein also comprises such antibodies which are modified, e.g. in the variable region to generate the properties according to the invention.

As used herein, the term "recombinant human antibody" is intended to include all human antibodies that are prepared, expressed, created or isolated by recombinant means, such as antibodies isolated from a host cell such as for example a CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the $V_H$ and $V_L$ regions of the recombinant antibodies are sequences that, while derived from and related to human germ line $V_H$ and $V_L$ sequences, may not naturally exist within the human antibody germ line repertoire in vivo.

As used herein, the terms "antigen binding fragment," "fragment," and "antibody fragment" are used interchangeably to refer to any fragment of an antibody of the invention that retains the specific binding activity of the antibody according to the invention and the Fc moiety. Examples of antibody fragments include, but are not limited to, a single chain antibody, Fab, Fab', $F(ab')_2$, Fv or scFv. Fragments of the antibodies of the invention can be obtained from the antibodies by methods that include digestion with enzymes, such as pepsin or papain, and/or by cleavage of disulfide bonds by chemical reduction. Alternatively, fragments of antibodies can be obtained by cloning and expression of part of the sequences of the heavy and/or light chains. "Fragments" include, but are not limited to, Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker. Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136). Although the specification, including the claims, may, in some places, refer explicitly to antigen binding fragment(s), antibody fragment(s), variant(s) and/or derivative(s) of antibodies, it is understood that the term "antibody" or "antibody of the invention" includes all categories of antibodies, namely, antigen binding fragment(s), antibody fragment(s), variant(s) and derivative(s) of antibodies. Further, the term "antibody" as used herein includes both antibodies and antigen binding fragments thereof.

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used alone, or in combination, as prophylactic or therapeutic agents upon appropriate formulation, in association with active vaccination, as a diagnostic tool, or as a production tool as described herein.

As used herein, the term "variable region" (variable region of a light chain (VL), variable region of a heavy chain (W)) denotes each of the pair of light and heavy chains which is involved directly in binding the antibody to the antigen. In a native antibody, the domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

As used herein, the term "hypervariable region" refers to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of a native antibody comprise from N- to C-terminus the domains FR1, CDR1, FR2, CDR2, FR3, CDR3, and FR4.

CDRs on each chain are separated by such framework amino acids. Especially, CDR3 of the heavy chain is the region which contributes most to antigen binding. CDR and FR regions are determined according to the standard definition of Kabat et al., Sequences of Proteins of Immunological Interest, 5th ed., Public Health Service, National Institutes of Health, Bethesda, Md. (1991).

As used herein, the term "constant domains" refers to domains of an antibody which are not involved directly in binding an antibody to an antigen, but exhibit various effector functions.

Depending on the amino acid sequence of the constant region of their heavy chains, antibodies or immunoglobulins are divided in the classes: IgA, IgD, IgE, IgG and IgM, and several of these may be further divided into subclasses, e.g. IgG1, IgG2, IgG3, and IgG4, IgA1 and IgA2. The heavy chain constant regions that correspond to the different classes of immunoglobulins are called α, ε, γ, and μ, respectively. The antibodies according to the invention are preferably of IgG type.

As used herein, the term "nucleic acid or nucleic acid molecule" is intended to include DNA molecules and RNA molecules. A nucleic acid molecule may be single-stranded or double-stranded, but preferably is double-stranded DNA.

As used herein, the terms "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

Doses are often expressed in relation to the bodyweight. Thus, a dose which is expressed as [g, mg, or other unit]/kg (or g, mg etc.) usually refers to [g, mg, or other unit] "per kg (or g, mg etc.) bodyweight", even if the term "bodyweight" is not explicitly mentioned.

The term "specifically binding" and similar reference does not encompass non-specific sticking.

The term "vaccine" as used herein is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response. In particular, an "antigen" or an "immunogen" refers typically to a substance which may be recognized by the immune system, preferably by the adaptive immune system, and which is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells.

As used herein, "sequence variant" refers to any alteration in a reference sequence, whereby a reference sequence is any of the sequences listed in the "Table of Sequences and SEQ ID Numbers" (sequence listing), i.e. SEQ ID NO: 1 to SEQ ID NO: 190. Thus, the term "sequence variant" includes nucleotide sequence variants and amino acid sequence variants. In particular, in a "sequence variant" the functionality (of the reference sequence) is preserved, i.e. the sequence variant is functional. A "sequence variant" as used herein typically has a sequence which is at least 70% identical to the reference sequence, preferably at least 80% identical to the reference sequence, more preferably at least 90% identical, even more preferably at least 95% identical, and particularly preferably at least 99% identical to the reference sequence.

Sequence identity is usually calculated with regard to the full length of the reference sequence (i.e. the sequence recited in the application). Percentage identity, as referred to herein, can be determined, for example, using BLAST using the default parameters specified by the NCBI (the National Center for Biotechnology Information; http://www.ncbi.nlm.nih.gov/) [Blosum 62 matrix; gap open penalty=11 and gap extension penalty=1].

As used herein, a "nucleotide sequence variant" has an altered sequence in which one or more of the nucleotides in the reference sequence is deleted, or substituted, or one or more nucleotides are inserted into the sequence of the reference nucleotide sequence. Nucleotides are referred to herein by the standard one-letter designation (A, C, G, or T). Due to the degeneracy of the genetic code, a "nucleotide sequence variant" can either result in a change in the respective reference amino acid sequence, i.e. in an "amino acid sequence variant" or not. Preferred sequence variants are such nucleotide sequence variants, which do not result in amino acid sequence variants (silent mutations), but other non-silent mutations are within the scope as well, in particular mutant nucleotide sequences, which result in an amino acid sequence, which is at least 70% identical to the reference sequence, preferably at least 80% identical to the reference sequence, more preferably at least 90% identical, even more preferably at least 95% identical, and particularly preferably at least 99% identical to the reference sequence.

As used herein, term "mutation" or "mutating" shall be understood to include physically making a mutation, e.g. in an nucleic acid sequence (e.g., by altering, e.g., by site-directed mutagenesis, a codon of a nucleic acid molecule encoding one amino acid to result in a codon encoding a different amino acid) or synthesizing a sequence variant (e.g., by knowing the nucleotide sequence of a nucleic acid molecule encoding a polypeptide and by designing the synthesis of a nucleic acid molecule comprising a nucleotide sequence encoding a variant of the polypeptide without the need for mutating one or more nucleotides of a nucleic acid molecule).

An "amino acid sequence variant" has an altered sequence in which one or more of the amino acids in the reference sequence is deleted or substituted, or one or more amino acids are inserted into the sequence of the reference amino acid sequence. As a result of the alterations, the amino acid sequence variant has an amino acid sequence which is at least 70% identical to the reference sequence, preferably at least 80% identical to the reference sequence, more preferably at least 90% identical, even more preferably at least 95% identical, and particularly preferably at least 99% identical to the reference sequence. Variant sequences which are at least 90% identical have no more than 10 alterations, i.e. any combination of deletions, insertions or substitutions, per 100 amino acids of the reference sequence.

In the context of peptides/proteins, a "linear sequence" or a "sequence" is the order of amino acids in a peptide/protein in an amino to carboxyl terminal direction in which residues that neighbor each other in the sequence are contiguous in the primary structure of the peptide/protein.

While it is possible to have non-conservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydoxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include the fusion to the N- or C-terminus of an amino acid sequence to a reporter molecule or an enzyme.

Importantly, the sequence variants are functional sequence variants, i.e. the alterations in the sequence variants do not abolish the functionality of the respective reference sequence, in the present case, e.g., the functionality of a sequence of an antibody, or antigen binding fragment thereof, to bind to the same non-overlapping epitopes/sites of a cytokine, in particular GM-CSF, and/or to sufficiently neutralize the cytokine, in particular GM-CSF.

Guidance in determining which nucleotides and amino acid residues, respectively, may be substituted, inserted or deleted without abolishing such functionality are found by using computer programs well known in the art.

As used herein, a nucleic acid sequence or an amino acid sequence "derived from" a designated nucleic acid, peptide, polypeptide or protein refers to the origin of the polypeptide. Preferably, the nucleic acid sequence or amino acid sequence which is derived from a particular sequence has an amino acid sequence that is essentially identical to that sequence or a portion thereof, from which it is derived, whereby "essentially identical" includes sequence variants as defined above. Preferably, the nucleic acid sequence or amino acid sequence which is derived from a particular peptide or protein, is derived from the corresponding domain in the particular peptide or protein. Thereby, "corresponding" refers in particular to the same functionality. For example, a CDR (or CDRH1) amino acid sequence or nucleic acid sequence in a multispecific antibody, which is "derived from a (particular) monospecific antibody" is usually derived from the (corresponding) CDR (or CDRH1) amino acid sequence or nucleic acid sequence of this monospecific antibody (and not from another (non-corresponding) part of the monospecific antibody). "Corresponding" parts of peptides, proteins and nucleic acids are thus easily identifiable to one of ordinary skill in the art (e.g. CDR1 corresponds to CDR1, CDR2 corresponds to CDR2, etc.). Likewise, sequences "derived from" another sequence are usually easily identifiable to one of ordinary skill in the art as having its origin in the sequence.

Preferably, a nucleic acid sequence or an amino acid sequence derived from another nucleic acid, peptide, polypeptide or protein may be identical to the starting nucleic acid, peptide, polypeptide or protein (from which it is derived). However, a nucleic acid sequence or an amino acid sequence derived from another nucleic acid, peptide, polypeptide or protein may also have one or more mutations relative to the starting nucleic acid, peptide, polypeptide or protein (from which it is derived), in particular a nucleic acid sequence or an amino acid sequence derived from another nucleic acid, peptide, polypeptide or protein may be a functional sequence variant as described above of the starting nucleic acid, peptide, polypeptide or protein (from which it is derived). For example, in a peptide/protein one or more amino acid residues may be substituted with other amino acid residues or one or more amino acid residue insertions or deletions may occur.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

The invention is based, amongst other findings, on the discovery that a cocktail of three antibodies binding to different non-overlapping sites in the same cytokine, in particular GM-CSF, is, on a weight basis, more potent than presently available antibodies MOR103 or Namilumab. In particular, when a cocktail of three antibodies is used, no accumulation of a large pool of long-lived GM-CSF occurs, but the antibodies form immune complexes that are rapidly degraded in vivo in an Fc-dependent fashion. This prompted the present inventors to design multispecific antibodies originated by the combination of the above described antibodies. Surprisingly, such multispecific antibodies have a greatly enhanced neutralizing activity not only compared to the presently available GM-CSF antibodies, but also compared to cocktail of antibodies, wherein each antibody is specific only for a single site of the cytokine. It is suggested that in the multispecific antibody constructs according to the present invention the cytokine, in particular GM-CSF, becomes irreversibly sequestered and no longer available for interaction with the receptor. These multispecific antibodies can be used at extremely low dosage to treat several cytokine-dependent, in particular GM-CSF-dependent, diseases such as autoimmune and inflammatory diseases.

Multispecific Antibodies, or Antigen Binding Fragments Thereof

In a first aspect, the present invention provides an isolated multispecific anti-cytokine, preferably anti-GM-CSF, antibody, or an antigen binding fragment thereof, comprising:

(a) at least two different epitope binding sites, each of them specifically binding to an individual epitope of a cytokine, whereby the individual epitopes of a cytokine to which the at least two different epitope binding sites bind, are non-overlapping epitopes; and (b) an Fc moiety.

Such a multispecific anti-cytokine, preferably anti-GM-CSF, antibody, or antigen binding fragment thereof, according to the present invention typically potently neutralizes a cytokine, in particular a target effect of said cytokine, for example the multispecific antibody, or antigen binding fragment thereof, according to the present invention typically potently neutralizes a GM-CSF, in particular a target effect of said GM-CSF. Such neutralization may be assessed in a neutralization assay as known to the skilled person and described below.

Preferably, the multispecific anti-cytokine, preferably anti-GM-CSF, antibody, or antigen binding fragment thereof, according to the present invention comprises an amino acid sequence which is not naturally occurring.

As used herein, a "multispecific" antibody refers to an antibody, wherein a single antibody molecule can bind to at least two different epitopes, e.g. to at least two different, non-overlapping sites in a cytokine, in particular GM-CSF. In contrast to most known multispecific antibodies, which usually bind to at least two different epitopes on distinct molecules, a single molecule of the multispecific anti-cytokine, preferably anti-GM-CSF, antibody, or of the antigen binding fragment thereof, according to the present invention can bind to at least two different, non-overlapping sites on a single cytokine molecule, in particular on a single GM-CSF molecule. Thus, the multispecific antibody, or antigen binding fragment thereof, according to the present invention is "multispecific" in respect to a single cytokine (molecule).

Preferably, the multispecific anti-cytokine, preferably anti-GM-CSF, antibody, or antigen binding fragment thereof, according to the present invention is bispecific, trispecific, tetraspecific or pentaspecific, more preferably the antibody, or the antigen binding fragment thereof, is bispecific, trispecific or tetraspecific, even more preferably the antibody, or the antigen binding fragment thereof, is bispecific or trispecific, and particularly preferably the antibody, or the antigen binding fragment thereof, is trispecific. Thereby it is meant that the multispecific anti-cytokine, preferably anti-GM-CSF, antibody, or antigen binding fragment thereof, according to the present invention is bispecific, trispecific, tetraspecific or pentaspecific in respect to a single cytokine (molecule), in particular in respect to a single GM-CSF (molecule).

The epitopes, i.e. the sites in a cytokine, in particular in a single cytokine molecule, for example in GM-CSF, in particular in a single GM-CSF molecule, to which the antibodies of the invention bind, may be linear (continuous) or conformational (discontinuous). Preferably, the antibodies and antibody fragments of the invention bind a conformational epitope, more preferably the conformational epitope is present only under non-reducing conditions. However, antibodies and antibody fragments of the invention may also bind to a linear epitope, more preferably the linear epitope is present under both, non-reducing conditions and reducing conditions.

The antibody according to the present invention comprises at least two different epitope binding sites, each of them specifically binding to an individual epitope of a cytokine, whereby the individual epitopes of a cytokine to which the at least two different epitope binding sites bind, are non-overlapping epitopes, in particular non-overlapping epitopes of the primary sequence of the cytokine, e.g. GM-CSF. Importantly, the epitopes, i.e. the sites in a cytokine, in particular in a single cytokine molecule, for example in GM-CSF, in particular in a single GM-CSF molecule, to which the antibody of the invention binds, are different (i.e. not the same) and non-overlapping. In a single cytokine (e.g. GM-CSF) molecule the epitopes (also referred to as "sites"), to which the multispecific anti-cytokine, preferably anti-GM-CSF, antibody according to the present invention binds, may be arranged directly adjacently or may be separated, e.g. by a linker, by another antibody domain, etc., but according to the present invention the epitopes must not overlap. Thereby, non-overlapping means that no amino acid in the amino acid sequence of the cytokine (e.g. GM-CSF) is used in more than one epitope/site to which the antibody according to the invention binds. In other words, each amino acid in the amino acid sequence of the cytokine (e.g. GM-CSF) is either part of one single epitope to which the antibody according to the invention binds or is no part of any epitope to which the antibody according to the invention binds.

Accordingly, the antibody, or antigen binding fragment thereof, according to the present invention can also be used to map the epitopes of the cytokine (e.g. GM-CSF) to which they bind.

The antibody, or antigen binding fragment thereof, according to the present invention comprises at least two different domains for specifically binding to the at least two different, non-overlapping sites in a cytokine (e.g. GM-CSF). In other words, the antibody, or antigen binding fragment thereof, according to the present invention comprises at least one first domain specifically binding to a first site in a cytokine (e.g. GM-CSF) and at least one second domain, which is different from the at least one first domain and which specifically binds to a second site in a cytokine (e.g. GM-CSF), whereby the second site in the cytokine (e.g. GM-CSF) is different from and non-overlapping with the first site in the cytokine (e.g. GM-CSF).

Herein the domains of the antibody, which specifically bind to the cytokine (e.g. GM-CSF), may be also termed "binding domains", "epitope binding domains" or "epitope binding sites". Preferably, such an epitope binding site of the antibody comprises at least one, preferably three and more preferably six CDRs, which fulfill at least the minimal requirements for specifically binding to a distinct epitope (thus constituting an "epitope binding site") and which may be for example derived from a monospecific antibody. Accordingly, it is more preferred if such an epitope binding site of the antibody comprises six CDRs forming together the epitope binding site, e.g. CDR1, CDR2, and CDR3 derived from a heavy chain of a monospecific antibody and CDR1, CDR2, and CDR3 derived from the corresponding light chain of the same monospecific antibody. Even more preferably, such an epitope binding site of the multispecific anti-cytokine, preferably anti-GM-CSF, antibody according to the present invention may comprise a heavy chain variable region and/or a (corresponding) light chain variable region, which may be for example derived from (the same) monospecific antibody.

In principle, each different epitope binding site of the multispecific anti-cytokine, preferably anti-GM-CSF, antibody, or of the antigen binding fragment thereof, according to the present invention may be present in the antibody one or more, e.g. two, three, four, five, six, or more times. For example, native IgG is bivalent and monospecific, because it contains two identical Fabs, both recognizing the same epitope. Thus, the multispecific antibody, or the antigen binding fragment thereof, according to the present invention is at least bivalent, i.e. in the case of two different epitope binding sites each occurring once in the antibody. Moreover, the multispecific antibody, or the antigen binding fragment thereof, according to the present invention may also be trivalent, e.g. in the case of three different epitope binding sites each occurring once or in the case of two different epitope binding sites, one occurring once and the other twice; tetravalent, e.g. in the case of four different epitope binding sites each occurring once or in the case of three different epitope binding sites, two occurring once each and the third one occurring twice or in the case of two different epitope binding sites each occurring twice or one occurring once and the other three times; pentavalent; hexavalent; heptavalent; octavalent; nonavalent; decavalent; undecavalent; dodecavalent; tridecavalent; tetradecavalent etc.

Preferably, each of the different epitope binding sites occurs twice in the antibody molecule according to the present invention. In other words, the antibody molecule according to the present invention comprises exactly two copies of each of the different domains specifically binding to at least two different, non-overlapping sites in a cytokine comprised by the antibody, or the antigen binding fragment thereof. Accordingly, the multispecific antibody, or the antigen binding fragment thereof, according to the present invention is preferably tetravalent, hexavalent, octavalent, decavalent, dodecavalent, tetradecavalent, etc., whereby the antibody molecule comprises exactly two copies of each of the different epitope binding sites. More preferably, the multispecific anti-cytokine, preferably anti-GM-CSF, antibody, or the antigen binding fragment thereof, according to the present invention is a bispecific tetravalent antibody, a trispecific hexavalent antibody, or a tetraspecific octavalent antibody; even more preferably, the multispecific antibody, or the antigen binding fragment thereof, according to the present invention is a bispecific tetravalent antibody or a trispecific hexavalent antibody.

In general, it is preferred that the antibody, or the antigen binding fragment thereof, according to the present invention is a monoclonal antibody or antigen binding fragment thereof. Monoclonal antibodies are usually produced by a single clone of B lymphocytes, for example by making hybrid antibody-forming cells, e.g. from a fusion of nonsecreting myeloma cells with immune spleen cells. In contrast to polyclonal antibodies, multispecific monoclonal antibodies bind to (pre)defined epitopes. Therefore, unexpected binding, in particular to undefined epitopes, is largely avoided and monoclonal antibodies are considered as safer compared to polyclonal antibodies.

Preferably, the antibody according to the present invention, or the antigen binding fragment thereof, is a human antibody, a monoclonal antibody, a human monoclonal antibody, or a purified antibody. The antibody according to the present invention, or the antigen binding fragment thereof, may also be a single chain antibody.

Fc Moiety

The multispecific antibody, or antigen binding fragment thereof, according to the present invention comprises an Fc moiety. Preferably, the Fc moiety is derived from human origin, e.g. from human IgG1, IgG2, IgG3, and/or IgG4, whereby human IgG1 is particularly preferred.

As used herein, the term "Fc moiety" refers to a sequence derived from the portion of an immunoglobulin heavy chain beginning in the hinge region just upstream of the papain cleavage site (e.g., residue 216 in native IgG, taking the first residue of heavy chain constant region to be 114) and ending at the C-terminus of the immunoglobulin heavy chain. Accordingly, an Fc moiety may be a complete Fc moiety or a portion (e.g., a domain) thereof. A complete Fc moiety comprises at least a hinge domain, a CH2 domain, and a CH3 domain (e.g., EU amino acid positions 216-446). An additional lysine residue (K) is sometimes present at the extreme C-terminus of the Fc moiety, but is often cleaved from a mature antibody. Each of the amino acid positions within an Fc region have been numbered according to the art-recognized EU numbering system of Kabat, see e.g., by Kabat et al., in "Sequences of Proteins of Immunological Interest", U.S. Dept. Health and Human Services, 1983 and 1987.

Preferably, in the context of the present invention an Fc moiety comprises at least one of: a hinge (e.g., upper, middle, and/or lower hinge region) domain, a CH2 domain, a CH3 domain, or a variant, portion, or fragment thereof. In preferred embodiments, an Fc moiety comprises at least a hinge domain, a CH2 domain or a CH3 domain. More preferably, the Fc moiety is a complete Fc moiety. The Fc moiety may also comprises one or more amino acid insertions, deletions, or substitutions relative to a naturally-occurring Fc moiety. For example, at least one of a hinge domain, CH2 domain or CH3 domain (or portion thereof) may be deleted. For example, an Fc moiety may comprise or consist of: (i) hinge domain (or portion thereof) fused to a CH2 domain (or portion thereof), (ii) a hinge domain (or portion thereof) fused to a CH3 domain (or portion thereof), (iii) a CH2 domain (or portion thereof) fused to a CH3 domain (or portion thereof), (iv) a hinge domain (or portion thereof), (v) a CH2 domain (or portion thereof), or (vi) a CH3 domain or portion thereof.

It will be understood by one of ordinary skill in the art that the Fc moiety may be modified such that it varies in amino acid sequence from the complete Fc moiety of a naturally occurring immunoglobulin molecule, while retaining at least one desirable function conferred by the naturally-occurring Fc moiety. Such functions include Fc receptor (FcR) binding, antibody half-life modulation, ADCC function, protein A binding, protein G binding, and complement binding. The portions of naturally-occuring Fc moieties, which are responsible and/or essential for such functions are well known by those skilled in the art.

For example, to activate the complement cascade C1q binds to at least two molecules of IgG1 or one molecule of IgM, attached to the antigenic target (Ward, E. S., and Ghetie, V., *Ther. Immunol.* 2 (1995) 77-94). Burton, D. R., described (*Mol. Immunol.* 22 (1985) 161-206) that the heavy chain region comprising amino acid residues 318 to 337 is involved in complement fixation. Duncan, A. R., and Winter, G. (*Nature* 332 (1988) 738-740), using site directed mutagenesis, reported that Glu318, Lys320 and Lys322 form the binding site to C1q. The role of Glu318, Lys320 and Lys 322 residues in the binding of C1q was confirmed by the ability of a short synthetic peptide containing these residues to inhibit complement mediated lysis.

For example, FcR binding can be mediated by the interaction of the Fc moiety (of an antibody) with Fc receptors (FcRs), which are specialized cell surface receptors on hematopoietic cells. Fc receptors belong to the immunoglobulin superfamily, and were shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC; Van de Winkel, J. G., and Anderson, C. L., *J. Leukoc. Biol.* 49 (1991) 511-524). FcRs are defined by their specificity for immunoglobulin classes; Fc receptors for IgG antibodies are referred to as FcγR, for IgE as FcεR, for IgA as FcαR and so on and neonatal Fc receptors are referred to as FcRn. Fc receptor binding is described for example in Ravetch, J. V., and Kinet, J. P., *Annu. Rev. Immunol.* 9 (1991) 457-492; Capel, P. J., et al., *Immunomethods* 4 (1994) 25-34; de Haas, M., et al., *J Lab. Clin. Med.* 126 (1995) 330-341; and Gessner, J. E., et al., *Ann. Hematol.* 76 (1998) 231-248.

Cross-linking of receptors by the Fc domain of native IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are: (i) FcγRI (CD64), which binds monomeric IgG with high affinity and is expressed on macrophages, monocytes, neutrophils and eosinophils; (ii) FcγRII (CD32), which binds complexed IgG with medium to low affinity, is widely expressed, in particular on leukocytes, is known to be a central player in antibody-mediated immunity, and which can be divided into FcγRIIA, FcγRIIB and FcγRIIC, which perform different functions in the immune system, but bind with similar low affinity to the IgG-Fc, and the ectodomains of these receptors are highly homologuous; and (iii) FcγRIII (CD16), which binds IgG with medium to low affinity and exists as two types: FcγRIIIA found on NK cells, macrophages, eosinophils and some monocytes and T cells and mediating ADCC and FcγRIIIB, which is highly expressed on neutrophils. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. On B-cells it seems to function to suppress further immunoglobulin production and isotype switching to say for example the IgE class. On macrophages, FcγRIIB acts to inhibit phagocytosis as mediated through FcγRIIA. On eosinophils and mast cells the b form may help to suppress activation of these cells through IgE binding to its separate receptor.

Regarding FcγRI binding, modification in native IgG of at least one of E233-G236, P238, D265, N297, A327 and P329 reduces binding to FcγRI. IgG2 residues at positions 233-236, substituted into IgG1 and IgG4, reduces binding to FcγRI by $10^3$-fold and eliminated the human monocyte response to antibody-sensitized red blood cells (Armour, K. L., et al. *Eur. J. Immunol.* 29 (1999) 2613-2624). Regarding FcγRII binding, reduced binding for FcγRIIA is found e.g. for IgG mutation of at least one of E233-G236, P238, D265, N297, A327, P329, D270, Q295, A327, R292 and K414. Regarding FcγRIII binding, reduced binding to FcγRIIIA is found e.g. for mutation of at least one of E233-G236, P238, D265, N297, A327, P329, D270, Q295, A327, S239, E269, E293, Y296, V303, A327, K338 and D376. Mapping of the binding sites on human IgG1 for Fc receptors, the above mentioned mutation sites and methods for measuring binding to FcγRI and FcγRIIA are described in Shields, R. L., et al., *J. Biol. Chem.* 276 (2001) 6591-6604.

Regarding binding to the crucial FcγRII, two regions of native IgG Fc appear to be critical for interactions of FcγRIIs and IgGs, namely (i) the lower hinge site of IgG Fc, in particular amino acid residues L, L, G, G (234-237, EU numbering), and (ii) the adjacent region of the CH2 domain of IgG Fc, in particular a loop and strands in the upper CH2 domain adjacent to the lower hinge region, e.g. in a region of P331 (Wines, B. D., et al., J. Immunol. 2000; 164: 5313-5318). Moreover, FcγRI appears to bind to the same site on IgG Fc, whereas FcRn and Protein A bind to a different site on IgG Fc, which appears to be at the CH2-CH3 interface (Wines, B. D., et al., J. Immunol. 2000; 164: 5313-5318).

For example, the Fc moiety may comprise or consist of at least the portion of an Fc moiety that is known in the art to be required for FcRn binding or extended half-life. Alternatively or additionally, the Fc moiety of the antibody of the invention comprises at least the portion of known in the art to be required for Protein A binding and/or the Fc moiety of the antibody of the invention comprises at least the portion of an Fc molecule known in the art to be required for protein G binding. Preferably, the retained function is the clearance of cytokine-immune complexes, e.g. GM-CSF-immune complexes, which is assumed to be mediated by FcγR binding. Accordingly, a preferred Fc moiety comprises at least the portion known in the art to be required for FcγR binding. As outlined above, a preferred Fc moiety may thus at least comprise (i) the lower hinge site of native IgG Fc, in particular amino acid residues L, L, G, G (234-237, EU numbering), and (ii) the adjacent region of the CH2 domain of native IgG Fc, in particular a loop and strands in the upper CH2 domain adjacent to the lower hinge region, e.g. in a region of P331, for example a region of at least 3, 4, 5, 6, 7, 8, 9, or 10 consecutive amino acids in the upper CH2 domain of native IgG Fc around P331, e.g. between amino acids 320 and 340 (EU numbering) of native IgG Fc.

Preferably, the multispecific anti-cytokine, preferably anti-GM-CSF, antibody, or antigen binding fragment thereof, according to the present invention comprises an Fc region. As used herein, the term "Fc region" refers to the portion of an immunoglobulin formed by two or more Fc moieties of antibody heavy chains. For example, the Fc region may be monomeric or "single-chain" Fc region (i.e., a scFc region). Single chain Fc regions are comprised of Fc moieties linked within a single polypeptide chain (e.g., encoded in a single contiguous nucleic acid sequence). Exemplary scFc regions are disclosed in WO 2008/143954 A2.

Preferably, the Fc region is a dimeric Fc region. A "dimeric Fc region" or "dcFc" refers to the dimer formed by the Fc moieties of two separate immunoglobulin heavy chains. The dimeric Fc region may be a homodimer of two identical Fc moieties (e.g., an Fc region of a naturally occurring immunoglobulin) or a heterodimer of two non-identical Fc moieties.

The Fc moieties of the Fc region may be of the same or different class and/or subclass. For example, the Fc moieties may be derived from an immunoglobulin (e.g., a human immunoglobulin) of an IgG1, IgG2, IgG3 or IgG4 subclass. Preferably, the Fc moieties of Fc region are of the same class and subclass. However, the Fc region (or one or more Fc moieties of an Fc region) may also be chimeric, whereby a chimeric Fc region may comprise Fc moieties derived from different immunoglobulin classes and/or subclasses. For example, at least two of the Fc moieties of a dimeric or single-chain Fc region may be from different immunoglobulin classes and/or subclasses. Additionally or alternatively, the chimeric Fc regions may comprise one or more chimeric Fc moieties. For example, the chimeric Fc region or moiety may comprise one or more portions derived from an immunoglobulin of a first subclass (e.g., an IgG1, IgG2, or IgG3 subclass) while the remainder of the Fc region or moiety is of a different subclass. For example, an Fc region or moiety of an Fc polypeptide may comprise a CH2 and/or CH3 domain derived from an immunoglobulin of a first subclass (e.g., an IgG1, IgG2 or IgG4 subclass) and a hinge region from an immunoglobulin of a second subclass (e.g., an IgG3 subclass). For example, the Fc region or moiety may comprise a hinge and/or CH2 domain derived from an immunoglobulin of a first subclass (e.g., an IgG4 subclass) and a CH3 domain from an immunoglobulin of a second subclass (e.g., an IgG1, IgG2, or IgG3 subclass). For example, the chimeric Fc region may comprise an Fc moiety (e.g., a complete Fc moiety) from an immunoglobulin for a first subclass (e.g., an IgG4 subclass) and an Fc moiety from an immunoglobulin of a second subclass (e.g., an IgG1, IgG2 or IgG3 subclass). For example, the Fc region or moiety may comprise a CH2 domain from an IgG4 immunoglobulin and a CH3 domain from an IgG1 immunoglobulin. For example, the Fc region or moiety may comprise a CH1 domain and a CH2 domain from an IgG4 molecule and a CH3 domain from an IgG1 molecule. For example, the Fc region or moiety may comprise a portion of a CH2 domain from a particular subclass of antibody, e.g., EU positions 292-340 of a CH2 domain. For example, an Fc region or moiety may comprise amino acids a positions 292-340 of CH2 derived from an IgG4 moiety and the remainder of CH2 derived from an IgG1 moiety (alternatively, 292-340 of CH2 may be derived from an IgG1 moiety and the remainder of CH2 derived from an IgG4 moiety).

Moreover, an Fc region or moiety may (additionally or alternatively) for example comprise a chimeric hinge region. For example, the chimeric hinge may be derived, e.g. in part, from an IgG1, IgG2, or IgG4 molecule (e.g., an upper and lower middle hinge sequence) and, in part, from an IgG3 molecule (e.g., an middle hinge sequence). In another example, an Fc region or moiety may comprise a chimeric hinge derived, in part, from an IgG1 molecule and, in part, from an IgG4 molecule. In another example, the chimeric hinge may comprise upper and lower hinge domains from an IgG4 molecule and a middle hinge domain from an IgG1 molecule. Such a chimeric hinge may be made, for example, by introducing a proline substitution (Ser228Pro) at EU position 228 in the middle hinge domain of an IgG4 hinge region. In another embodiment, the chimeric hinge can comprise amino acids at EU positions 233-236 are from an IgG2 antibody and/or the Ser228Pro mutation, wherein the remaining amino acids of the hinge are from an IgG4 antibody (e.g., a chimeric hinge of the sequence ESKYG-PPCPPCPAPPVAGP; SEQ. ID NO. 191). Further chimeric hinges, which may be used in the Fc moiety of the antibody according to the present invention are described in US 2005/0163783 A1.

Specifically included within the definition of "Fc region" is an "aglycosylated Fc region". The term "aglycosylated Fc region" refers to an Fc region that lacks a covalently linked oligosaccharide or glycan, e.g., at the N-glycosylation site at EU position 297, in one or more of the Fc moieties thereof. For example, the aglycosylated Fc region may be fully aglycosylated, i.e., all of its Fc moieties lack carbohydrate. Alternatively, the aglycosylated Fc region may be partially aglycosylated (i.e., hemi-glycosylated). The aglycosylated Fc region may be a deglycosylated Fc region, that is an Fc region for which the Fc carbohydrate has been removed, for example chemically or enzymatically. Alternatively or additionally, the aglycosylated Fc region may be a nonglycosylated or unglycosylated, that is an antibody that was expressed without Fc carbohydrate, for example by mutation of one or residues that encode the glycosylation pattern, e.g., at the N-glycosylation site at EU position 297 or 299, by expression in an organism that does not naturally attach carbohydrates to proteins, (e.g., bacteria), or by expression in a host cell or organism whose glycosylation machinery has been rendered deficient by genetic manipulation or by the addition of glycosylation inhibitors (e.g., glycosyltransferase inhibitors). Alternatively, the Fc region is a "glycosylated Fc region", i.e., it is fully glycosylated at all available glycosylation sites.

In the present invention it is preferred that the Fc moiety, or the Fc region, comprises or consists of an amino acid sequence derived from a human immunoglobulin sequence (e.g., from an Fc region or Fc moiety from a human IgG molecule). However, polypeptides may comprise one or more amino acids from another mammalian species. For example, a primate Fc moiety or a primate binding site may be included in the subject polypeptides. Alternatively, one or more murine amino acids may be present in the Fc moiety or in the Fc region.

Preferably, the multispecific anti-cytokine, preferably anti-GM-CSF, antibody according to the present invention comprises, in particular in addition to an Fc moiety as described above, other parts derived from a constant region, in particular from a constant region of IgG, preferably from a constant region of IgG1, more preferably from a constant region of human IgG1. More preferably, the multispecific antibody according to the present invention comprises, in particular in addition to an Fc moiety as described above, all other parts of the constant regions, in particular all other parts of the constant regions of IgG, preferably all other parts of the constant regions of IgG1, more preferably all other parts of the constant regions of human IgG1.

As outlined above, a particularly preferred multispecific antibody according to the present invention comprises a (complete) Fc region derived from human IgG1. More preferably, the multispecific antibody according to the present invention comprises, in particular in addition to a (complete) Fc region derived from human IgG1 also all other parts of the constant regions of IgG, preferably all other parts of the constant regions of IgG1, more preferably all other parts of the constant regions of human IgG1.

Cytokines

The multispecific anti-cytokine, preferably anti-GM-CSF, antibody, or antigen binding fragment thereof, according to the present invention binds to a cytokine, preferably to GM-CSF. Cytokines are usually small proteins (~5-20 kDa) that are important in cell signaling.

They are released by cells and affect the behavior of other cells, and sometimes affect the behavior of the releasing cell itself. Cytokines include chemokines, interferons, interleukins, lymphokines, tumor necrosis factor, monokines and colony stimulating factors, but generally not hormones. Cytokines are produced by a broad range of cells, including immune cells like macrophages, B lymphocytes, T lymphocytes and mast cells, as well as endothelial cells, fibroblasts, and various stromal cells, whereby a given cytokine may be produced by more than one type of cell.

Chemokines mediate chemoattraction (chemotaxis) between cells. Cytokine proteins are classified as chemokines according to behavior and structural characteristics. In addition to being known for mediating chemotaxis, chemokines are all approximately 8-10 kDa in size have four cysteine residues in conserved locations that are key to forming their 3-dimensional shape. These proteins have historically been known under several other names including the SIS family of cytokines, SIG family of cytokines, SCY family of cytokines, Platelet factor-4 superfamily or intercrines. Chemokines can classified into four main subfamilies: CXC, CC, CX3C and XC.

CC chemokine (or (3-chemokine) proteins have two adjacent cysteines (amino acids), near their amino terminus. There have been at least 27 distinct members of this subgroup reported for mammals, called CC chemokine ligands (CCL)-1 to -28; CCL10 is the same as CCL9. Chemokines of this subfamily usually contain four cysteines (C4-CC chemokines), but a small number of CC chemokines possess six cysteines (C6-CC chemokines). C6-CC chemokines include CCL1, CCL15, CCL21, CCL23 and CCL28. CC chemokines induce the migration of monocytes and other cell types such as NK cells and dendritic cells. Examples of CC chemokine include monocyte chemoattractant protein-1 (MCP-1 or CCL2) which induces monocytes to leave the bloodstream and enter the surrounding tissue to become tissue macrophages. CCL5 (or RANTES) attracts cells such as T cells, eosinophils and basophils that express the receptor CCR5. Increased CCL11 levels in blood plasma are associated with aging (and reduced neurogenesis) in mice and humans. CC chemokine include for example CCL1-CCL28.

The two N-terminal cysteines of CXC chemokines (or α-chemokines) are separated by one amino acid, represented in this name with an "X". There have been 17 different CXC chemokines described in mammals, that are subdivided into two categories, those with a specific amino acid sequence (or motif) of glutamic acid-leucine-arginine (or ELR for short) immediately before the first cysteine of the CXC motif (ELR-positive), and those without an ELR motif (ELR-negative). ELR-positive CXC chemokines specifically induce the migration of neutrophils, and interact with chemokine receptors CXCR1 and CXCR2. An example of an ELR-positive CXC chemokine is interleukin-8 (IL-8), which induces neutrophils to leave the bloodstream and enter into the surrounding tissue. Other CXC chemokines that lack the ELR motif, such as CXCL13, tend to be chemoattractant for lymphocytes. CXC chemokines bind to CXC chemokine receptors, of which seven have been discovered to date, designated CXCR1-7. CXC chemokine include for example CXCL1-CXCL17.

The third group of chemokines is known as the C chemokines (or γ chemokines), and is unlike all other chemokines in that it has only two cysteines; one N-terminal cysteine and one cysteine downstream. Two chemokines have been described for this subgroup and are called XCL1 (lymphotactin-α) and XCL2 (Iymphotactin-(β).

A fourth group has also been discovered and members have three amino acids between the two cysteines and is termed $CX_3C$ chemokine (or d-chemokines). The only $CX_3C$ chemokine discovered to date is called fractalkine (or $CX_3CL1$). It is both secreted and tethered to the surface of the cell that expresses it, thereby serving as both a chemoattractant and as an adhesion molecule.

Interferons (IFNs) are a group of cytokines made and released for example in response to the presence of pathogens, such as viruses, bacteria, parasites, or tumor cells. In a typical scenario, a virus-infected cell will release interferons causing nearby cells to heighten their anti-viral defenses. More than twenty distinct IFN genes and proteins have been identified in animals, including humans. Human interferons have been classified into three major types: Type I IFN, Type II IFN, and Type III IFN based on the type of receptor through which they signal. IFNs belonging to all three classes are important for fighting viral infections and for the regulation of the immune system.

All type I IFNs bind to a specific cell surface receptor complex known as the IFN-α/β receptor (IFNAR) that consists of IFNAR1 and IFNAR2 chains. The type I interferons present in humans are IFN-α, IFN-β, IFN-ε, IFN-κ and IFN-ω. In general, type I interferons are produced when the body recognizes a virus has invaded it. They are produced by fibroblasts and monocytes. However, the production of type I IFN-α can be prohibited by another cytokine known as Interleukin-10. Once activated, type I interferons are able to create molecules which prevent the virus from producing and replicating it's RNA and DNA. Overall, IFN-α is suggested to be used to treat hepatitis B and C infections, while IFN-β is suggested to be used to treat multiple sclerosis.

Interferon type II is also known as immune interferon and is activated in particular by Interleukin-12. Furthermore, type II interferons are released by T helper cells, type 1 specifically. However, they are able to block the proliferation of T helper cells type two. The previous results in an inhibition of Th2 immune response and a further induction of Th1 immune response, which leads to the development of debilitating diseases such as multiple sclerosis. IFN type II binds to IFNGR, which consists of IFNGR1 and IFNGR2 chains. In humans an exemplary IFN type II is IFN-γ.

Interferons type III signal through a receptor complex consisting of IL10R2 (also called CRF2-4) and IFNLR1 (also called CRF2-12). Although discovered more recently than type I and type II IFNs, recent information demonstrates the importance of Type III IFNs in some types of virus infections.

Interleukins are a group of cytokines that were first seen to be expressed by white blood cells (leukocytes). The function of the immune system depends in a large part on interleukins, and rare deficiencies of a number of them have been described, all featuring autoimmune diseases or immune deficiency. The majority of interleukins are synthesized by helper CD4 T lymphocytes, as well as through monocytes, macrophages, and endothelial cells. They promote the development and differentiation of T and B lymphocytes, and hematopoietic cells. Examples of interleukins includes IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and IL-36.

Lymphokines are a subset of cytokines that are produced by a lymphocytes. They are protein mediators typically produced by T cells to direct the immune system response by signalling between its cells. Lymphokines have many roles, including the attraction of other immune cells, including macrophages and other lymphocytes, to an infected site and their subsequent activation to prepare them to mount an immune response. Circulating lymphocytes can detect a very small concentration of lymphokine and then move up the concentration gradient towards where the immune response is required. Lymphokines aid B cells to produce antibodies. Important lymphokines secreted by T helper cells include: IL-2, IL-3, IL-4, IL-5, IL-6, GM-CSF, and Interferon-gamma.

Tumor necrosis factors (or the TNF family) refer to a group of cytokines that can cause cell death (apoptosis). Nineteen proteins were identified as part of the TNF family on the basis of sequence, functional, and structural similarities, including Tumor Necrosis Factor (TNF) (also known as cachectin or TNF alpha), which is a cytokine that has a wide variety of functions, e.g. it can cause cytolysis of certain tumor cell lines, it is involved in the induction of cachexia, it is a potent pyrogen causing fever by direct action or by stimulation of interleukin-1 secretion, and it can stimulate cell proliferation and induce cell differentiation under certain conditions; Lymphotoxin-alpha (LT-alpha) and lymphotoxin-beta (LT-beta), two related cytokines produced by lymphocytes that are cytotoxic for a wide range of tumor cells in vitro and in vivo; T cell antigen gp39 (CD40L), a cytokine that seems to be important in B-cell development and activation; CD27L, a cytokine that plays a role in T-cell activation and which induces the proliferation of co-stimulated T cells and enhances the generation of cytolytic T cells; CD30L, a cytokine that induces proliferation of T cells; FASL, a cell surface protein involved in cell death; 4-1 BBL, an inducible T cell surface molecule that contributes to T-cell stimulation; OX40L, a cell surface protein that co-stimulates T cell proliferation and cytokine production; and TNF-related apoptosis inducing ligand (TRAIL), a cytokine that induces apoptosis.

All these TNF family members seem to form homotrimeric (or heterotrimeric in the case of LT-alpha/beta) complexes that are recognized by their specific receptors. Strong hydrogen bonds between the monomers stabilize the tertiary structure. One such example is the Asn34-Arg82 hydrogen bond in the *M. musculus* TNF alpha. The PROSITE pattern for this family is located in a beta-strand in the central section of the protein that is conserved across all members. All members of the TNF family, with the exception of the secreted lymphotoxin and a proliferation-inducing ligand (APRIL), are type II transmembrane proteins that protrude from immune cells. Such membrane-bound TNF ligands frequently signal back to the immune cells when they contact and bind their cognate receptors on other cells. Examples of members of the TNF family include CD40LG (TNFSF5); CD70 (TNFSF7); EDA; FASLG (TNFSF6); LTA (TNFSF1); LTB (TNFSF3); TNF, TNFSF4 (OX40L); TNFSF8 (CD153); TNFSF9; TNFSF10 (TRAIL); TNFSF11 (RANKL); TNFSF12 (TWEAK); TNFSF13; TNFSF13B; TNFSF14; TNFSF15; TNFSF18.

Monokines are cytokines, which are produced primarily by monocytes and macrophages. Examples of monokines include IL-1, TNF alpha, interferon alpha and beta, and colony stimulating factors.

Colony stimulating factors (CSFs) are secreted glycoproteins that bind to receptor proteins on the surfaces of hemopoietic stem cells, thereby activating intracellular signaling pathways that can cause the cells to proliferate and differentiate into a specific kind of blood cell. Colony-stimulating factors are usually soluble, in contrast to other, membrane-bound substances of the hematopoietic microenvironment. This is sometimes used as the definition of CSFs. They transduce by paracrine, endocrine, or autocrine signaling. Examples of colony stimulating factors include CSF1 (also known as "macrophage colony-stimulating factor"), CSF2 (also known as "granulocyte macrophage colony-stimulating factor"; GM-CSF and sargramostim), CSF3 (also known as "granulocyte colony-stimulating factor"; G-CSF and filgrastim), as well as synthetic CSFs, such as Promegapoietin.

In the context of the present invention it is preferred that the cytokine, to which the multispecific anti-cytokine, preferably anti-GM-CSF, antibody binds, in particular with two different domains binding to two different non-overlapping sites in the cytokine, is a colony stimulating factor or an interferon. Among the colony stimulating factors, naturally occurring CSFs are preferred (in particular CSF1, CSF2 (GM-CSF) and CSF3 (G-CSF), and GM-CSF is more preferred. Among interferons, type I and type II interferons are preferred, type I interferons are more preferred, and interferon beta is even more preferred. Thus, the cytokine is preferably GM-CSF or interferon beta, more preferably the cytokine is GM-CSF.

Linkers

Preferably, the antibody, or the antigen binding fragment thereof, according to the present invention further comprises:

(c) at least one linker.

In general, the linkage between two components of the multispecific anti-cytokine, preferably anti-GM-CSF, antibody according to the present invention may be directly or indirectly, i.e. two components directly adjoin or they may be linked by an additional component of the complex, e.g. by a linker. In particular, some of the components of the multispecific antibody according to the present invention may be directly linked, whereas others are linked by a linker. Preferably, the multispecific antibody according to the present invention comprises a linker in the heavy chain for example between two VH sequences, two VL sequences, and/or a VH sequence and a VL sequence (a "VH sequence" is derived from a heavy chain of a monospecific antibody and thus referred to as "VH", even though it may be present in the heavy chain or the light chain of the multispecific antibody according to the present invention and a "VL sequence" is derived from a light chain of a monospecific antibody and thus referred to as "VL", even though it may be present in the heavy chain or the light chain of the multispecific antibody according to the present invention). Accordingly, in the light chain a linker may be preferably present between two VH sequences, two VL sequences, and/or a VH sequence and a VL sequence. Additionally, it is also preferred if a linker is present in the heavy chain of the multispecific antibody according to the present invention between a constant domain, for example CH3 (e.g. in IgG CH1-CH2-CH3), and a VH/VL sequence.

As used herein, the terms "linked", "fused", or "fusion", are used interchangeably. These terms refer to the joining together of two more elements or components, by whatever means including chemical conjugation or recombinant means. Methods of chemical conjugation (e.g., using heterobifunctional crosslinking agents) are known in the art. Preferably, the components of the antibody according to the present invention are linked by covalent linkage or attachment of two or more proteins, polypeptides, or fragments thereof, e.g. via their individual peptide backbones, for example through expression of a single protein molecule encoding those components or peptide fragments. Preferred fusions are in frame, i.e., on the level of the encoding nucleic acid molecule two or more open reading frames (ORFs) are fused to form a continuous longer ORF, in a manner that maintains the correct reading frame of the original ORFs. Thus, the resulting recombinant fusion protein is a single polypeptide containing two or more protein segments that correspond to polypeptides encoded by the original ORFs (which segments are not normally so joined in nature). Although the reading frame is thus made continuous throughout the fused genetic segments, the protein segments may be physically or spatially separated by, for example, an (in-frame) peptide linker.

Accordingly, the linker, which links two components of the multispecific antibody may be a peptide linker. Alternatively, the linker may also be non-peptidic, e.g. a cross-linking agent, however, a peptide linker is preferred.

A non-peptidic spacer can include or may be an ester, a thioester, and a di-sulfide. Cross-linking agents for peptide or protein crosslinking include for example (i) amine-to-amine crosslinkers, e.g. homobifunctional amine-specific protein crosslinking reagents based on NHS-ester and imidoester reactive groups for selective conjugation of primary amines; available in short, long, cleavable, irreversible, membrane permeable, and cell surface varieties; (ii) sulfhydryl-to-carbohydrate crosslinkers, e.g. crosslinking reagents based on maleimide and hydrazide reactive groups for conjugation and formation of covalent crosslinks; (iii) sulfhydryl-to-sulfhydryl crosslinkers, e.g. homobifunctional sulfhydryl-specific crosslinking reagents based on maleimide or pyridyldithiol reactive groups for selective covalent conjugation of protein and peptide thiols (reduced cysteines) to form stable thioether bonds; (iv) photoreactive crosslinkers, e.g. aryl azide, diazirine, and other photo-reactive (light-activated) chemical heterobifunctional crosslinking reagents to conjugate proteins, nucleic acids and other molecular structures involved in receptor-ligand interaction complexes via two-step activation; (v) amine-to-sulfhydryl crosslinkers, e.g. heterobifunctional protein crosslinking reagents for conjugation between primary amine (lysine) and sulfhydryl (cysteine) groups of proteins and other molecules; available with different lengths and types of spacer arms; and (vi) amine-to-amine crosslinkers, e.g. carboxyl-to-amine crosslinkers, e.g. Carbodiimide crosslinking reagents, DCC and EDC (EDAC), for conjugating carboxyl groups (glutamate, aspartate, C-termini) to primary amines (lysine, N-termini) and also N-hydroxysuccinimide (NHS) for stable activation of carboxylates for amine-conjugation.

A peptidic linker preferably consists of about 1-30 amino acids, whereby a "short linker" consists preferably of about 1, 2, 3, 4, 5, 6, 7, 8, 9, or 10 amino acids, more preferably of about 1, 2, 3, 4, 5 or 6 amino acids, even more preferably 4-6 amino acids, particularly preferably 5 amino acids, which may be preferably according to SEQ ID NO:143 or a functional sequence variant thereof. A "long linker", in contrast, consists preferably of about 10-30 amino acids, more preferably of about 12-25 amino acids, and even more preferably of about 14-20 amino acids. A particularly preferred long linker has 15-17 amino acids, preferably 16 amino acids, more preferably according to SEQ ID NO: 144 or a functional sequence variant thereof. In the multispecific antibody according to the present invention a long linker preferably links a VH sequence and a corresponding VL sequence ("corresponding" refers herein to a VH and VL sequence forming together an epitope binding site), e.g. a VH sequence and a VL sequence derived from the same monospecific antibody. A short linker may preferably link VH/VL sequences with "non-corresponding" VH/VL sequences, e.g. from different monospecific antibodies and/or may preferably link a constant domain, for example CH3 (e.g. in IgG CH1-CH2-CH3), with a VH/VL sequence.

Preferred linkers comprise or consist of an amino acid sequence according to SEQ ID NO: 143 or SEQ ID NO: 144 or a functional sequence variant thereof.

Alternatively, the amino acid sequence of the peptidic linker may be identical to that of the N-terminal or C-terminal flanking region. Alternatively a peptidic linker can consist of non-natural amino acid sequences such as an amino acid sequence resulting from conservative amino acid substitutions of said natural flanking regions In a particular embodiment, the peptidic spacer does not contain any Cys (C) residues. In a preferred embodiment the linker sequence contains at least 20%, more preferably at least 40%, even more preferably at least 50%, and particularly preferably at least 70% Gly (G) or β-alanine residues (A). More preferably, the linker sequence contains at least 20%, more preferably at least 40%, even more preferably at least 50%, and particularly preferably at least 70% Gly (G) residues. Appropriate linker sequences can be easily selected and prepared by a person skilled in the art. They may be composed of D and/or L amino acids.

Antibody Formats and Construct Types

In principle, the multispecific antibody according to the present invention, may be of any antibody format as long as the antibody comprises at least two different domains specifically binding to at least two different, non-overlapping sites in a cytokine (e.g. GM-CSF) and an Fc moiety.

For example, the antibody may be a multispecific antibody fragment with an Fc moiety. Examples, in particular for a bispecific antibody fragment with an Fc moiety, are Tandem scFv-Fc, scFv-Fc, scFv-Fc knobs-into-holes, scFv-Fc-scFv, and scDiabody-Fc, which are shown for example in FIG. 3*b* of Chan, A.C. and Carter, P.J. (2010) Nat Rev Immu 10: 301-316 and described in said article.

The antibody according to the present invention may be based on any immunoglobulin class (e.g., IgA, IgG, IgM etc.) and subclass (e.g. IgA1, IgA2, IgG1, IgG2, IgG3, IgG4 etc.).

Preferably, the multispecific antibody according to the present invention is based on IgG (also referred to as "IgG type"). Within the IgG class, antibodies may be based on the IgG1, IgG2, IgG3 or IgG4 subclass, whereby an antibody based on IgG1 (also referred to as "IgG1 type") is preferred. Preferably, antibodies of the invention may have a κ or a λ light chain.

IgG-based multispecific antibody formats are well-known to the skilled person and preferred IgG-based antibody formats include for example hybrid hybridoma, knobs-into-holes with a common light chain, various IgG-scFv formats, various scFv-IgG formats, two-in-one IgG, dual (or multiple, respectively, e.g. 3 times, 4 times etc.) V domain IgG, IgG-V, and V-IgG, which are shown in FIG. 3*c* of Chan, A. C. and Carter, P. J. (2010) Nat Rev Immu 10: 301-316 and described in said article, for bispecific IgG-based antibodies, or any combination thereof resulting in a multispecific antibody of the IgG-type. Other preferred IgG-based antibody formats include for example DAF, CrossMab, IgG-dsscFv, DVD, IgG-dsFV, IgG-scFab, scFab-dsscFv and Fv2-Fc, which are shown in FIG. 1A of Weidle U. H. et al. (2013) Cancer Genomics and Proteomics 10: 1-18 and described in said article.

Preferably, the multispecific antibody, or the antigen binding fragment thereof, according to the present invention, is of the IgG type, preferably of the IgG1 type, more preferably comprising a heavy chain constant region of the IgG1 CH1-CH2-CH3 type and a light chain constant region of the IgG CK type, even more preferably comprising a heavy chain constant region of the IgG1 CH1-CH2-CH3 type comprising or consisting of an amino acid sequence according to SEQ ID NO: 140 or functional sequence variants thereof, and a light chain constant region of the IgG CK type comprising or consisting of an amino acid sequence according to SEQ ID NO: 141 or functional sequence variants thereof.

Since IgG has two native epitope binding sites, further epitope binding sites, i.e. "non-native" epitope binding sites, are preferably conjugated to the CH3-domain, preferably to the C-terminus of the CH3-domain, of one or both heavy chains constituting the IgG antibody format. Alternatively, further epitope binding sites, i.e. "non-native" epitope binding sites, are preferably conjugated to one or both of the light chain variable regions, preferably to the N-terminus of one or both of the light chain variable regions, of the native epitope binding sites of the IgG antibody format and/or to one or both of the heavy chain variable regions, preferably to the N-terminus of one or both of the heavy chain variable regions, of the native epitope binding sites of the IgG antibody format. Alternatively, further epitope binding sites, i.e. "non-native" epitope binding sites, are preferably conjugated to the CH3-domain, preferably to the C-terminus of the CH3-domain, of one or both heavy chains constituting the IgG antibody format and to one or both of the light chain variable regions, preferably to the N-terminus of one or both of the light chain variable regions, of the native epitope binding sites of the IgG antibody format. Alternatively, further epitope binding sites, i.e. "non-native" epitope binding sites, are preferably conjugated to the CH3-domain, preferably to the C-terminus of the CH3-domain, of one or both heavy chains constituting the IgG antibody format and to one or both of the heavy chain variable regions, preferably to the N-terminus of one or both of the heavy chain variable regions, of the native epitope binding sites of the IgG antibody format.

At any such attachment site of the IgG antibody format, preferably at the light and/or the heavy chain variable regions of the native epitope binding sites and/or the CH3-domain of the heavy chain, one or more than one, e.g. two, three, four or more, non-native epitope binding site(s) may be attached, whereby the attachment of one or two non-native epitope binding site(s) is preferred and the attachment of one non-native epitope binding site is more preferred.

For example, if the antibody according to the present invention, is a bispecific antibody of the IgG format, one "specificity" is preferably provided by a native epitope binding site and the other "specificity" is preferably provided by a non-native epitope binding site. In particular, the non-native epitope binding site may then be attached to any of the above mentioned attachment sites, preferably the light chain variable region of the native epitope binding site, the heavy chain variable region of the native epitope binding site, or the CH3-domain of the heavy chain of the IgG antibody format.

For example, if the antibody according to the present invention, is a trispecific antibody of the IgG format, one "specificity" ("specificity 1") is preferably provided by a native epitope binding site and the other two "specificities" ("specificity 2" and "specificity 3") are preferably provided by a non-native epitope binding site. Thereby, the non-native epitope binding site for "specificity 2" may be preferably attached to any of the above mentioned attachment sites, preferably the light chain variable region of the native epitope binding site, the heavy chain variable region of the native epitope binding site, or the CH3-domain of the heavy chain of the IgG antibody format, while the non-native epitope binding site for "specificity 3" may be preferably attached to any other of the above mentioned attachment sites, i.e. to any attachment site, where no non-native epitope binding site for "specificity 2" is attached. Alternatively, the non-native epitope binding sites for the other two "specificities" ("specificity 2" and "specificity 3") may be preferably attached to the same attachment site, e.g. the non-native epitope binding sites for the other two "specificities" ("specificity 2" and "specificity 3") are both attached to the light chain variable region of the native epitope binding site, or the non-native epitope binding sites for the other two "specificities" ("specificity 2" and "specificity 3") are both attached to the heavy chain variable region of the native epitope binding site, or the non-native epitope binding sites for the other two "specificities" ("specificity 2" and "specificity 3") are both attached to the CH3-domain of the heavy chain of the IgG antibody format. In this case, i.e. the non-native epitope binding sites for the other two "specificities" ("specificity 2" and "specificity 3") are both attached to the same attachment site, the non-native epitope binding sites for "specificity 2" and the non-native epitope binding sites for "specificity 3" are preferably arranged consecutively, i.e. only one of the non-native epitope binding sites is directly (or via a linker as described herein) attached to the attachment site, whereas the other of the non-native epitope binding sites is preferably linked to the first of the non-native epitope binding sites.

In particular, the antibody according to the present invention preferably comprises two copies of each of the epitope binding sites, whereby it is preferred that the two copies are attached at corresponding positions of the first and the second heavy chain of the IgG-based antibody, e.g. (i) one copy is conjugated to the heavy chain variable region of the native epitope binding sites of the first heavy chain of the IgG antibody format and the other copy is conjugated to the heavy chain variable region of the native epitope binding sites of the second heavy chain of the IgG antibody format; or (ii) one copy is conjugated to the light chain variable region of the native epitope binding sites of the first light chain of the IgG antibody format and the other copy is conjugated to the light chain variable region of the native epitope binding sites of the second light chain of the IgG antibody format; or (iii) one copy is conjugated to the CH3-domain of the first heavy chain of the IgG antibody format and the other copy is conjugated to the CH3-domain of the first light chain of the IgG antibody format.

Preferred antibody formats for the multispecific antibodies according to the present invention, as well as their construction, are described in US 2009/0155275 A1, which relates specifically to multispecific epitope binding proteins comprising an Fc region of an antibody constant domain. Thus, the antibody formats disclosed in US 2009/0155275 A1 are preferably used for the multispecific antibodies according to the present invention.

Exemplary construct types of the antibody according to the present invention include the construct types "Bs1", "Bs2", "Bs3", "Ts1", "Ts2" and "Ts3", which are shown in FIG. 4. Accordingly, the multispecific antibody, or the antigen binding fragment thereof, according to the present invention, is preferably according to a construct type selected from the group comprising Bs1, Bs2, Bs3, Ts1, Ts2 and Ts3. More preferably, the multispecific antibody, or the antigen binding fragment thereof, according to the present invention, is according to the construct type Ts3, preferably the antibody, or the antigen binding fragment thereof, is a trispecific antibody according to the construct type Ts3.

Construct type "Bs1" is a bispecific, tetravalent antibody format based on IgG, preferably based on IgG1. A heavy chain of Bs1 comprises (in this order from N to C terminus):
(a) a first variable region, e.g. derived from a heavy or light chain of a first monospecific antibody; preferably a VH sequence, i.e. a heavy chain variable region, derived from a first monospecific antibody;
(b) a corresponding second variable region forming a first epitope binding site with the first variable region (a), e.g. the corresponding heavy or light chain variable region derived from a first monospecific antibody; preferably a VL sequence, i.e. a light chain variable region, derived from a first monospecific antibody;
(c) a third variable region, e.g. derived from a heavy chain of a second monospecific antibody; preferably a VH sequence, i.e. a heavy chain variable region, derived from a second monospecific antibody; and
(d) an IgG CH1-CH2-CH3.

Preferably, components (a) and (b) are linked by a long linker, components (b) and (c) are linked by a short linker and components (c) and (d) are directly linked. A light chain of Bs1 comprises (in this order from N to C terminus):
(e) a fourth variable region, forming a second epitope binding site with the third variable region (c), e.g. the corresponding light chain variable region derived from a second monospecific antibody; preferably a VL sequence, i.e. a light chain variable region, derived from a second monospecific antibody; and
(f) an IgG CK or IG CL; preferably an Ig CK.

Preferably, components (e) and (f) are directly linked. Since Bs1 is based on IgG, Bs1 comprises two identical heavy chains and two identical light chains. As used herein, the position in the antibody, where the CDRs/variable regions forming the first epitope binding site in Bs1 (components (a) and (b)) are arranged, is referred to as "position A" and the position in the antibody, where the CDRs/variable regions forming the second epitope binding site in Bs1 (components (c) and (d)) are arranged, is referred to as "position B" (cf. FIG. 4). In construction, a (second) monospecific antibody, from which heavy and light chain variable regions are used in the heavy and the light chain, respectively, of the multispecific antibody, may serve as "scaffold". A preferred embodiment of construct type "Bs1" and its construction is described in US 2009/0155275 A1, FIGS. 4E and 4F and the corresponding description.

Construct type "Bs2" is a bispecific, tetravalent antibody format based on IgG, preferably based on IgG1. A heavy chain of Bs2 comprises (in this order from N to C terminus):
(a) a first variable region, e.g. derived from a heavy chain of a first monospecific antibody; preferably a VH sequence, i.e. a heavy chain variable region, derived from a first monospecific antibody; and
(b) an IgG CH1-CH2-CH3.

Preferably, components (a) and (b) are directly linked. A light chain of Bs2 comprises (in this order from N to C terminus):
(c) a second variable region, e.g. derived from a heavy or light chain of a second monospecific antibody; preferably a VH sequence, i.e. a heavy chain variable region, derived from a second monospecific antibody;
(d) a corresponding third variable region forming a first epitope binding site with the second variable region (c), e.g. the corresponding heavy or light chain variable region derived from a second monospecific antibody; preferably a VL sequence, i.e. a light chain variable region, derived from a second monospecific antibody;
(e) a fourth variable region, forming a second epitope binding site with the first variable region (a), e.g. the corresponding light chain variable region derived from a first monospecific antibody; preferably a VL sequence, i.e. a light chain variable region, derived from a first monospecific antibody; and
(f) an IgG CK or IG CL; preferably an Ig CK.

Preferably, components (c) and (d) are linked by a long linker, components (d) and (e) are linked by a short linker and components (e) and (f) are directly linked. Since Bs2 is based on IgG, Bs2 comprises two identical heavy chains and two identical light chains. As used herein, the position in the antibody, where the CDRs/variable regions forming the first epitope binding site in Bs2 (components (c) and (d)) are arranged, is referred to as "position A" and the position in the antibody, where the CDRs/variable regions forming the second epitope binding site in Bs2 (components (a) and (e)) are arranged, is referred to as "position B" (cf. FIG. 4). In construction, a (first) monospecific antibody, from which heavy and light chain variable regions are used in the heavy and the light chain, respectively, of the multispecific antibody, may serve as "scaffold". A preferred embodiment of construct type "Bs2" and its construction is described in US 2009/0155275 A1, FIGS. 4C and 4D and the corresponding description.

Construct type "Bs3" is a bispecific, tetravalent antibody format based on IgG, preferably based on IgG1. A heavy chain of Bs3 comprises (in this order from N to C terminus):
(a) a first variable region, e.g. derived from a heavy chain of a first monospecific antibody;

preferably a VH sequence, i.e. a heavy chain variable region, derived from a first monospecific antibody;

(b) an IgG CH1-CH2-CH3;
(c) a second variable region, e.g. derived from a heavy or light chain of a second monospecific antibody; preferably a VH sequence, i.e. a heavy chain variable region, derived from a second monospecific antibody; and
(d) a corresponding third variable region forming a first epitope binding site with the second variable region (c), e.g. the corresponding heavy or light chain variable region derived from a second monospecific antibody; preferably a VL sequence, i.e. a light chain variable region, derived from a second monospecific antibody.

Preferably, components (a) and (b) are directly linked, components (b) and (c) are linked by a short linker and components (c) and (d) are linked by a long linker. A light chain of Bs3 comprises (in this order from N to C terminus):
(e) a fourth variable region, forming a second epitope binding site with the first variable region (a), e.g. the corresponding light chain variable region derived from a first monospecific antibody; preferably a VL sequence, i.e. a light chain variable region, derived from a first monospecific antibody; and
(f) an IgG CK or IG CL; preferably an Ig CK.

Preferably, components (e) and (f) are directly linked. Since Bs3 is based on IgG, Bs3 comprises two identical heavy chains and two identical light chains. As used herein, the position in the antibody, where the CDRs/variable regions forming the first epitope binding site in Bs3 (components (c) and (d)) are arranged, is referred to as "position C" and the position in the antibody, where the CDRs/variable regions forming the second epitope binding site in Bs3 (components (a) and (e)) are arranged, is referred to as "position B" (cf. FIG. 4). In construction, a (first) monospecific antibody, from which heavy and light chain variable regions are used in the heavy and the light chain, respectively, of the multispecific antibody, may serve as "scaffold". The principle of construct type "Bs3" (but with other "specificities", i.e. epitope binding sites, which are not according to the present invention) and its construction is also described in Dimasi, N., Gao, C., Fleming, R., Woods, R. M., Yao, X.-T., Shirinian, L., Kiener, P. A., and Wu, H. (2009). The design and characterization of oligospecific antibodies for simultaneous targeting of multiple disease mediators. J Mol Biol 393, 672-692: FIG. 1 (*d*) ("Bs3Ab") and the corresponding description.

Construct type "Ts1" is a trispecific, hexavalent antibody format based on IgG, preferably based on IgG1. A heavy chain of Ts1 comprises (in this order from N to C terminus):
(a) a first variable region, e.g. derived from a heavy chain of a first monospecific antibody; preferably a VH sequence, i.e. a heavy chain variable region, derived from a first monospecific antibody;
(b) an IgG CH1-CH2-CH3;
(c) a second variable region, e.g. derived from a heavy or light chain of a second monospecific antibody; preferably a VH sequence, i.e. a heavy chain variable region, derived from a second monospecific antibody;
(d) a corresponding third variable region forming a first epitope binding site with the second variable region (c), e.g. the corresponding heavy or light chain variable region derived from a second monospecific antibody; preferably a VL sequence, i.e. a light chain variable region, derived from a second monospecific antibody;
(e) a fourth variable region, e.g. derived from a heavy or light chain of a third monospecific antibody; preferably a VH sequence, i.e. a heavy chain variable region, derived from a third monospecific antibody; and
(f) a corresponding fifth variable region forming a second epitope binding site with the fourth variable region (e), e.g. the corresponding heavy or light chain variable region derived from a third monospecific antibody; preferably a VL sequence, i.e. a light chain variable region, derived from a third monospecific antibody.

Preferably, components (a) and (b) are directly linked, components (b) and (c) and components (d) and (e) are linked by a short linker and components (c) and (d) and components (e) and (f) are linked by a long linker. A light chain of Ts1 comprises (in this order from N to C terminus):
(g) a sixth variable region, forming a third epitope binding site with the first variable region (a), e.g. the corresponding light chain variable region derived from a first monospecific antibody; preferably a VL sequence, i.e. a light chain variable region, derived from a first monospecific antibody; and
(h) an IgG CK or IG CL; preferably an Ig CK.

Preferably, components (g) and (h) are directly linked. Since Ts1 is based on IgG, Ts1 comprises two identical heavy chains and two identical light chains. As used herein, the position in the antibody, where the CDRs/variable regions forming the first epitope binding site in Ts1 (components (c) and (d)) are arranged, as well as the position in the antibody, where the CDRs/variable regions forming the second epitope binding site in Ts1 (components (e) and (f)) are arranged, is referred to as "position C", and the position in the antibody, where the CDRs/variable regions forming the third epitope binding site in Ts1 (components (a) and (g)) are arranged, is referred to as "position B" (cf. FIG. 4). In construction, a (first) monospecific antibody, from which heavy and light chain variable regions are used in the heavy and the light chain, respectively, of the multispecific antibody, may serve as "scaffold". A preferred embodiment of construct type "Ts1" and its construction is described in US 2009/0155275 A1, FIGS. 3A and 3B and the corresponding description.

Construct type "Ts2" is a trispecific, hexavalent antibody format based on IgG, preferably based on IgG1. A heavy chain of Ts2 comprises (in this order from N to C terminus):
(a) a first variable region, e.g. derived from a heavy or light chain of a first monospecific antibody; preferably a VH sequence, i.e. a heavy chain variable region, derived from a first monospecific antibody;
(b) a corresponding second variable region forming a first epitope binding site with the first variable region (a), e.g. the corresponding heavy or light chain variable region derived from a first monospecific antibody; preferably a VL sequence, i.e. a light chain variable region, derived from a first monospecific antibody;
(c) a third variable region, e.g. derived from a heavy chain of a second monospecific antibody; preferably a VH sequence, i.e. a heavy chain variable region, derived from a second monospecific antibody; and
(d) an IgG CH1-CH2-CH3.

Preferably, components (a) and (b) are linked by a long linker, components (b) and (c) are linked by a short linker and components (c) and (d) are directly linked. A light chain of Ts2 comprises (in this order from N to C terminus):
(e) a fourth variable region, e.g. derived from a heavy or light chain of a third monospecific antibody; preferably a VH sequence, i.e. a heavy chain variable region, derived from a third monospecific antibody;
(f) a corresponding fifth variable region forming a second epitope binding site with the fourth variable region (e), e.g. the corresponding heavy or light chain variable region derived from a third monospecific antibody; preferably a VL sequence, i.e. a light chain variable region, derived from a third monospecific antibody;

(g) a sixth variable region, forming a third epitope binding site with the third variable region (c), e.g. the corresponding light chain variable region derived from a second monospecific antibody; preferably a VL sequence, i.e. a light chain variable region, derived from a second monospecific antibody; and (h) an IgG CK or IG CL; preferably an Ig CK.

Preferably, components (e) and (f) are linked by a long linker, components (f) and (g) are linked by a short linker and components (g) and (h) are directly linked. Since Ts2 is based on IgG, Ts2 comprises two identical heavy chains and two identical light chains. As used herein, the position in the antibody, where the CDRs/variable regions forming the first epitope binding site in Ts2 (components (a) and (b)) are arranged as well as the position in the antibody, where the CDRs/variable regions forming the second epitope binding site in Ts2 (components (e) and (f)) are arranged is referred to as "position A", and the position in the antibody, where the CDRs/variable regions forming the third epitope binding site in Ts2 (components (c) and (g)) are arranged, is referred to as "position B" (cf. FIG. 4). In construction, a (second) monospecific antibody, from which heavy and light chain variable regions are used in the heavy and the light chain, respectively, of the multispecific antibody, may serve as "scaffold". A preferred embodiment of construct type "Ts2" and its construction is described in US 2009/0155275 A1, FIGS. 4G and 4H and the corresponding description.

Construct type "Ts3" is a trispecific, hexavalent antibody format based on IgG, preferably based on IgG1. A heavy chain of Ts3 comprises (in this order from N to C terminus):

(a) a first variable region, e.g. derived from a heavy or light chain of a first monospecific antibody; preferably a VH sequence, i.e. a heavy chain variable region, derived from a first monospecific antibody;

(b) a corresponding second variable region forming a first epitope binding site with the first variable region (a), e.g. the corresponding heavy or light chain variable region derived from a first monospecific antibody; preferably a VL sequence, i.e. a light chain variable region, derived from a first monospecific antibody;

(c) a third variable region, e.g. derived from a heavy chain of a second monospecific antibody; preferably a VH sequence, i.e. a heavy chain variable region, derived from a second monospecific antibody;

(d) an IgG CH1-CH2-CH3;

(e) a fourth variable region, e.g. derived from a heavy or light chain of a third monospecific antibody; preferably a VH sequence, i.e. a heavy chain variable region, derived from a third monospecific antibody; and (f) a corresponding fifth variable region forming a second epitope binding site with the fourth variable region (e), e.g. the corresponding heavy or light chain variable region derived from a third monospecific antibody; preferably a VL sequence, i.e. a light chain variable region, derived from a third monospecific antibody.

Preferably, components (a) and (b) and components (e) and (f) are linked by a long linker, components (b) and (c) and components (d) and (e) are linked by a short linker and components (c) and (d) are directly linked. A light chain of Ts3 comprises (in this order from N to C terminus):

(e) a sixth variable region, forming a third epitope binding site with the third variable region (c), e.g. the corresponding light chain variable region derived from a second monospecific antibody; preferably a VL sequence, i.e. a light chain variable region, derived from a second monospecific antibody; and (f) an IgG CK or IG CL; preferably an Ig CK.

Preferably, components (e) and (f) are directly linked. Since Ts3 is based on IgG, Ts3 comprises two identical heavy chains and two identical light chains. As used herein, the position in the antibody, where the CDRs/variable regions forming the first epitope binding site in Ts3 (components (a) and (b)) are arranged, is referred to as "position A", the position in the antibody, where the CDRs/variable regions forming the second epitope binding site in Ts3 (components (e) and (f)) are arranged, is referred to as "position C", and the position in the antibody, where the CDRs/variable regions forming the third epitope binding site in Ts3 (components (c) and (d)) are arranged, is referred to as "position B" (cf. FIG. 4). In construction, a (second) monospecific antibody, from which heavy and light chain variable regions are used in the heavy and the light chain, respectively, of the multispecific antibody, may serve as "scaffold".

For further information about the construction of construct types Bs1, Bs2, Bs3, Ts1, and Ts2 the documents US 2009/0155275 A1 and Dimasi, N., Gao, C., Fleming, R., Woods, R. M., Yao, X.-T., Shirinian, L., Kiener, P. A., and Wu, H. (2009): The design and characterization of oligospecific antibodies for simultaneous targeting of multiple disease mediators; J Mol Biol 393, 672-692 may be used. Principles of the constructions outlined in these documents may be adapted to, and then applied to, the novel construct type Ts3.

Neutralization

Preferably, the multispecific antibody, or the antigen binding fragment thereof, according the present invention neutralizes the target effect of a cytokine, in particular GM-CSF, (i) under stringent conditions with an $IC_{90}$ of 150 ng/ml or less, preferably with an $IC_{90}$ of 120 ng/ml or less, more preferably with an $IC_{90}$ of 100 ng/ml or less, even more preferably with an $IC_{90}$ of 50 ng/ml or less, and particularly preferably with an $IC_{90}$ of 10 ng/ml or less;

(ii) under less stringent conditions with an $IC_{90}$ of 20 ng/ml or less, preferably with an $IC_{90}$ of 15 ng/ml or less, more preferably with an $IC_{90}$ of 10 ng/ml or less, even more preferably with an $IC_{90}$ of 5 ng/ml or less, and particularly preferably with an $IC_{90}$ of 1 ng/ml or less;

(iii) under more stringent conditions with an $IC_{90}$ of 160 ng/ml or less, preferably with an $IC_{90}$ of 130 ng/ml or less, more preferably with an $IC_{90}$ of 100 ng/ml or less, even more preferably with an $IC_{90}$ of 50 ng/ml or less, and particularly preferably with an $IC_{90}$ of 10 ng/ml or less; and/or (iv) under very stringent conditions with an $IC_{90}$ of 1000 ng/ml or less, preferably with an $IC_{90}$ of 500 ng/ml or less, more preferably with an $IC_{90}$ of 250 ng/ml or less, even more preferably with an $IC_{90}$ of 100 ng/ml or less, and particularly preferably with an $IC_{90}$ of 50 ng/ml or less.

Thereby, an "$IC_{90}$ of x ng/ml or less" refers to the concentration (x ng/ml or less) of the antibody, or the antigen binding fragment thereof, according to the present invention, which is required for 90% neutralization ($IC_{90}$) of the target effect of a cytokine (e.g. GM-CSF).

In general, the functionality of an antibody is assessed by its ability to neutralize an important effect ("target effect") of a cytokine (e.g. GM-CSF). In a neutralization assay, the concentration of an antibody required for neutralization, e.g. of a target effect of a cytokine (e.g. GM-CSF) or of infectivity of a virus, can be determined. Various neutralization assays are known to the person skilled in the art, whereby the skilled person typically selects a neutralization assay depending on the cytokine (e.g. GM-CSF) and its target effect. Cytokine (e.g. GM-CSF) target effects which are useful in a neutralization assay include for example cytokine-induced proliferation, e.g. of indicator cell lines, cytokine-induced cytokine production, TNF-α-induced killing of L929 cell line, and IFN-γ-protection from viral infection of L929 and A549 cell lines.

In the following a non-limiting example of a neutralization assay is given to illustrate the principle of a neutralization assay:

(1) different concentrations of the antibody to be tested, e.g. serial dilutions, are prepared for example in a microtiter plate or any other suitable format;
(2) a target dose of a cytokine (i.e. a given amount of cytokine, e.g. GM-CSF) is added to the antibody and co-incubated under appropriate conditions, e.g. for 1 hour at room temperature or at 37° C.;
(3) the co-incubated antibody-cytokine (e.g. the co-incubated antibody-GM-CSF) is transferred to an appropriate target cell culture, e.g. in wells containing (e.g. monolayers of) target cells, and incubation is allowed, e.g. at room temperature or 37° C. for a predetermined amount of time, e.g. 1, 2, 3, 4, 5, 6, or 7 days; and
(4) thereafter the target effect is analyzed and the $IC_{90}$ can be determined.

The effects measured are usually dose-dependent: The higher the antibody titer, the stronger the neutralization of the target effect. Depending on the neutralizing character of the antibody, the $IC_{90}$ values vary, e.g. an antibody of significant neutralizing character will require lower amounts (of the antibody) to be added for, e.g., achieving the same amount of neutralization of the target effect in the assay.

As used herein, "less stringent conditions" refer to a final cytokine (e.g. GM-CSF) concentration of about 50 pg/ml and about 1000 cells/well. "Stringent conditions" refer to a final cytokine (e.g. GM-CSF) concentration of about 50 pg/ml and about 10000 cells/well. "More stringent conditions" refer to a final cytokine (e.g. GM-CSF) concentration of about 500 pg/ml and about 1000 cells/well. "Very stringent conditions" refer to a final cytokine (e.g. GM-CSF) concentration of about 500 pg/ml and about 10000 cells/well.

Examples of suitable indicator cell lines for assessing neutralization of cytokine-induced proliferation or neutralization of cytokine-induced cytokine production include TF-1, MC/9, L929, D10, CTLL-2, B9, splenocytes, NIH/3T3, COL0205, A549, hPBMC, NHDF and Nag 7/8, whereby TF-1 cells are preferably used in neutralization of the cytokines GM-CSF, IL-13, IL-4, and IL-5, MC/9 cells are preferably used in neutralization of the cytokines GM-CSF, IL-5, and IL-10, L929 cells are preferably used in neutralization of the cytokines IFN-gamma and TNF-alpha, D10 cells are preferably used in neutralization of the cytokines IL-1alpha und IL-1beta, CTLL-2 cells are preferably used in neutralization of the cytokines 11-2, IL-4, and IL-15, B9 cells are preferably used in neutralization of the cytokines IL-6 and IL-21, splenocytes are preferably used in neutralization of the cytokines IL-12/IL-23 p40 and IL-23, NIH/3T3 cells are preferably used in neutralization of the cytokine IL-17A, COLO205 cells are preferably used in neutralization of the cytokine IL-22, A549 cells are preferably used in neutralization of the cytokines IFN-gamma und IFN-beta, hPBMC are preferably used in neutralization of the cytokine IL-12/IL-23 p40, NHDF cells are preferably used in neutralization of the cytokine IL-17A, and Nag7/8 cells are preferably used in neutralization of the cytokine TSLP.

If the ability of an antibody to neutralize the cytokine GM-CSF, in particular GM-CSF-induced proliferation, is assessed, the preferred cells to be used are TF-1 cells. A preferred GM-CSF neutralization assay comprises the following steps:

(1) different concentrations of the antibody to be tested, e.g. serial dilutions, are prepared for example in a microtiter plate or any other suitable format;
(2) a target dose of a GM-CSF, e.g. 100 pg/ml, is added to the antibody and co-incubated under appropriate conditions, in particular for 1 hour at 37° C.;
(3) the co-incubated antibody-GM-CSF is transferred to TF-1 cells, in particular to wells containing 1000 or 10000 TF-1 cells/well, and incubation is allowed, e.g. at 37° C. for 3-4 days, e.g. 72 h; and
(4) thereafter the neutralization of proliferation is analyzed and the $IC_{90}$ can be determined, for example GM-CSF neutralization may be calculated as percentage of inhibition of TF-1 growth with the following formula: [1-(CCPM of a single well–average CCPM of control cells grown without GM-CSF)/(average CCPM of control cells grown with GM-CSF–average CCPM of control cells grown without GM-CSF)]×100 (CCPM=corrected counts per minute) and $IC_{90}$ (μg/ml) may be calculated for every sample by a nonlinear regression analysis, e.g. using GraphPad Prism 5 software.

In this assay, less stringent conditions refer to a final GM-CSF concentration of about 50 pg/ml and about 1000 TF-1 cells/well. Stringent conditions refer to a final GM-CSF concentration of about 50 pg/ml and about 10000 TF-1 cells/well. More stringent conditions refer to a final GM-CSF concentration of about 500 pg/ml and about 1000 TF-1 cells/well. Very stringent conditions refer to a final GM-CSF concentration of about 500 pg/ml and about 10000 TF-1 cells/well.

Variable Regions and CDRs

Preferably, the antibody according to the present invention, or the antigen binding fragment thereof, comprises one or more complementarity determining regions (CDRs). In general, complementarity determining regions (CDRs) are the hypervariable regions present in heavy chain variable domains and light chain variable domains of an antibody. Preferably, the antibody according to the present invention, or the antigen binding fragment, thereof, comprises at least three CDRs on the heavy chain and at least three CDRs on the light chain. More preferably, the antibody according to the present invention, or the antigen binding fragment thereof, comprises at least six CDRs on the heavy chain and at least three CDRs on the light chain. Even more preferably, the antibody according to the present invention, or the antigen binding fragment thereof, comprises either at least nine CDRs on the heavy chain and at least three CDRs on the light chain or at least six CDRs on the heavy chain and at least six CDRs on the light chain.

Typically, the domain of an antibody, which specifically binds to an epitope of an antigen—e.g. to a certain site in a cytokine molecule, in particular GM-CSF, is also referred to as "antigen receptor" or "epitope binding site". This domain of the antibody, i.e. the antigen receptor/epitope binding site, is usually, in particular in native monospecific IgG antibodies, formed by the three CDRs of a heavy chain and the three CDRs of the connected light chain. In other words, since in particular in native monospecific IgG antibodies antigen receptors/epitope binding sites are typically composed of two variable domains, there are six CDRs for each antigen receptor (heavy chain: CDRH1, CDRH2, and CDRH3; light chain: CDRL1, CDRL2, and CDRL3). A single antibody, in particular a single native monospecific IgG antibody, usually has two (identical) antigen receptors and therefore contains twelve CDRs (i.e. 2×six CDRs).

However, the multispecific antibody, or antigen binding fragment thereof, according to the present invention comprises at least two different domains specifically binding to at least two different non-overlapping sites of a cytokine, in particular GM-CSF. Preferably, a single molecule of the multispecific antibody, or antigen binding fragment thereof, according to the present invention comprises two identical domains of each different domain specifically binding to at least two different non-overlapping sites of a cytokine. It is also preferred that a single molecule of the multispecific antibody, or antigen binding fragment thereof, according to the present invention comprises two heavy chains and two light chains. More preferably, a single molecule of the multispecific antibody, or antigen binding fragment thereof, according to the present invention comprises two heavy chains and two light chains whereby the two heavy chains share at least 80%, preferably 85%, more preferably 90%, even more preferably 95%, and particularly preferably 100% sequence identity and/or the two light chains share at least 80%, preferably 85%, more preferably 90%, even more preferably 95%, and particularly preferably 100% sequence identity. Thus, if a single molecule of the multispecific antibody, or antigen binding fragment thereof, according to the present invention comprises two identical domains of each different domain specifically binding to at least two different non-overlapping sites of a cytokine (e.g. GM-CSF), one of said identical domains is preferably comprised by the first heavy and light chains and the other is preferably comprised by the second heavy and light chains of the multispecific antibody.

Due to their "multispecificity", i.e. the different epitope binding sites, the heavy chain and/or the light chain of the multispecific antibodies, or antigen binding fragments thereof, according to the present invention may (each) comprise more than three CDRs, in particular more than three different CDRs. For example, the multispecific antibody, or antigen binding fragments thereof, according to the present invention may comprise at least two different domains specifically binding to at least two different non-overlapping sites of a cytokine, in particular GM-CSF, wherein each of said at least two different domains is derived from a different monospecific antibody, e.g. of the IgG-type. Since such a monospecific antibody typically comprises three CDRs in the heavy chain and three CDRs in the light chain forming the antigen receptor/epitope binding site, a multispecific antibody according to the present invention may in particular comprise three CDRs of a heavy chain of a first antibody and three CDRs of a light chain of a first antibody, three CDRs of a heavy chain of a second antibody and three CDRs of a light chain of a second antibody, optionally three CDRs of a heavy chain of a third antibody and three CDRs of a light chain of a third antibody etc. Thus, the number of CDRs comprised by a heavy chain and/or a light chain of a multispecific antibody according to the present invention is preferably a multiple of three, for example three, six, nine, twelve, etc. It is thereby also preferred that the sum of the CDRs comprised by both, heavy chain and light chain of a multispecific antibody according to the present invention is a multiple of six, for example six, twelve, eighteen etc.

In particular, in the multispecific antibody, or antigen binding fragment thereof, according to the present invention the heavy chain may also comprise CDRs or variable regions derived from a light chain of a monospecific antibody. For example, in a multispecific antibody according to the present invention the heavy chain may comprise the heavy chain variable region (VH) and the light chain variable region (VL) derived from a first monospecific antibody and the heavy chain variable region (VH) derived from a second monospecific antibody different from the first monospecific antibody, whereas the light chain variable region (VL) derived from the second monospecific antibody is comprised by the light chain of the multispecific antibody according to the present invention. In such a multispecific antibody, the second monospecific antibody may be used in particular as "scaffold". Accordingly, in a multispecific antibody according to the present invention the heavy chain may comprise one or more, preferably all three, heavy chain CDRs and one or more, preferably all three, light chain CDRs derived from a first monospecific antibody and one or more, preferably all three, heavy chain CDRs derived from a second monospecific antibody different from the first monospecific antibody, whereas one or more, preferably all three, light chain CDRs derived from the second monospecific antibody is comprised by the light chain of the multispecific antibody according to the present invention. In such multispecific antibodies, the second monospecific antibody may be used in particular as "scaffold".

Typically, in particular in native monospecific IgG antibodies, the three CDRs (CDR1, CDR2, and CDR3) are arranged non-consecutively in the variable domain. In other words, the CDRs on the heavy and/or light chain may be separated for example by framework regions, whereby a framework region (FR) is a region in the variable domain which is less "variable" than the CDR. For example, in an antibody according to the present invention a variable region (or each variable region, respectively) may preferably comprise four framework regions, separated by three CDRs.

As described above, in the multispecific antibodies according to the present invention, a single chain, preferably a heavy chain, may comprise more than three CDRs (CDR1, CDR2, and CDR3) and/or more than one variable region as described above. Since an "antigen receptor" is typically characterized by the CDRs, i.e. CDRH1, CDRH2, and CDRH3 as well as CDRL1, CDRL2, and CDRL3, it is preferred in the multispecific antibodies according to the present invention that the CDRs are arranged such, that the order (e.g. CDRH1, CDRH2, and CDRH3 and/or CDRL1, CDRL2, and CDRL3 derived from the same monospecific antibody) is maintained to preserve the "antigen receptor", i.e. to preserve to ability to specifically bind to a certain site in the antigen (e.g. the cytokine, in particular GM-CSF). This means that for example the order of CDRH1, CDRH2, and CDRH3 derived from a first monospecific antibody in an amino acid stretch is preferably not interrupted by any CDR derived from a second monospecific antibody. Moreover, if a single chain, preferably a heavy chain, of a multispecific antibody according to the present invention comprises CDRs derived from a heavy chain and from a light chain of a first monospecific antibody, the heavy chain CDR(s) are preferably arranged next to the light chain CDR(s) derived from the same monospecific antibody. For example, such an arrangement may be -CDRH1(a)-CDRH2(a)-CDRH3(a)-CDRL1(a)-CDRL2(a)-CDRL3(a)-CDRH1(b)-CDRH2(b)-CDRH3(b)-, whereby (a) and (b) refers to different monospecific antibodies from which the respective CDR is derived and the CDRs are usually arranged in a non-consecutive manner, i.e. the CDRs may be separated by any amino acid sequence which is not a CDR, e.g. a framework region and/or a linker.

Importantly, if the multipecific antibody according to the present invention comprises epitope binding sites (antigen receptors) derived from at least two different monospecific antibodies, the CDRs or variable regions of these monospecific antibodies are arranged in the multipecific antibody according to the present invention such that the "antigen receptor" of each monospecific antibody from which the CDRs (or variable regions) are derived, is preserved, i.e. its ability to specifically bind to a certain site in the antigen (e.g. the cytokine, in particular GM-CSF), is preserved.

The position of the CDR amino acids are defined herein according to the IMGT numbering system (IMGT: http://www.imgt.org/; cf. Lefranc, M.-P. et al. (2009) Nucleic Acids Res. 37, D1006-D1012). Example sequences of CDRs, heavy chains, light chains as well as the sequences of the nucleic acid molecules encoding the CDRs, heavy chains, light chains of the antibodies of the invention, i.e. of several antibodies according to the invention, are disclosed in the sequence listing. The CDRs of a multispecific antibody according to the present invention, which are derived from a heavy chain CDR of a monospecific antibody are also referred to as CDRH1, CDRH2 and CDRH3, respectively. Similarly, the CDRs of a multispecific antibody according to the present invention, which are derived from a light chain CDR of a monospecific antibody are also referred to as CDRL1, CDRL2 and CDRL3, respectively. Thus, for example CDRL1, CDRL2 and CDRL3 may also be present on a heavy chain of a multispecific antibody according to the present invention. Accordingly, the variable regions of a multispecific antibody according to the present invention, which are derived from a heavy chain variable region of a monospecific antibody are also referred to as VH and the variable regions of a multispecific antibody according to the present invention, which are derived from a light chain variable region of a monospecific antibody are also referred to as VL. Thus, for example VL may also be present on a heavy chain of a multispecific antibody according to the present invention.

Preferably, the antibody according to the present invention, or the antigen binding fragment thereof, comprises a heavy chain comprising at least one CDRH1, at least one CDRH2 and at least one CDRH3 and a light chain comprising at least one CDRL1, at least one CDRL2 and at least one CDRL3, wherein the at least one heavy chain CDRH3 comprises an amino acid sequence according to SEQ ID NOs: 3, 51, 69, or 107 or functional sequence variants thereof, preferably the at least one heavy chain CDRH3 comprises an amino acid sequence according to SEQ ID NOs: 3 or 69 or functional sequence variants thereof. It is also preferred that the heavy chain comprises at least two CDRH1, at least two CDRH2 and at least two CDRH3, wherein one CDRH1, CDRH2 and CDRH3 is derived from a first monospecific antibody and one CDRH1, CDRH2 and CDRH3 is derived from a second monospecific antibody different from the first monospecific antibody.

It is also preferred that, the multispecific antibody of the invention, or the antigen binding fragment thereof, comprises a heavy chain comprising at least one CDRH1, at least one CDRH2 and at least one CDRH3 and a light chain comprising at least one CDRL1, at least one CDRL2 and at least one CDRL3, wherein the at least one heavy chain CDRH3 comprises an amino acid sequence that is at least 90%, for example, 90%, 91%, 92%, 93%, 94%, 95%, 96%, 97%, 98%, 99% or 100% identical to SEQ ID NOs: 3, 51, 69, or 107, preferably to SEQ ID NOs: 3 or 69.

Table 1 provides the SEQ ID numbers for the amino acid sequences of the six CDRs, which are derived from exemplary monosprecific antibodies and used in the exemplary multispecific antibodies of the invention.

TABLE 1

SEQ ID Numbers for CDR peptides derived from exemplary monospecific antibodies.

| Origin (mono-Specific AB) | SEQ ID NOs. for CDR peptides CDRH1 | CDRH2 | CDRH3 | CDRL1 | CDRL2 | CDRL3 |
|---|---|---|---|---|---|---|
| GCA7 | 1 | 2 | 3 | 4 | 5/6 | 7 |
| GCA21 | 49 | 50 | 51 | 52 | 53/54 | 55 |
| GCB59 | 67 | 68 | 69 | 70 | 71/72 | 73 |
| GCE536 | 105 | 106 | 107 | 108 | 109/110 | 111 |

Variant antibodies are also included within the scope of the invention. Thus, variants of the sequences recited in the application are also included within the scope of the invention. Such variants include natural variants generated by somatic mutation in vivo during the immune response or in vitro upon culture of immortalized B cell clones. Alternatively, variants may arise due to the degeneracy of the genetic code or may be produced due to errors in transcription or translation.

Further variants of the antibody sequences having improved affinity and/or potency may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences of the invention are also within the scope of the invention.

Preferably, variant antibody sequences may share 70% or more (i.e. 75%, 80%, 85%, 88%, 90%, 92%, 95%, 96%, 97%, 98%, 99% or more) amino acid sequence identity with the sequences recited in the application. Such variants usually have a greater homology to the sequences listed herein in the CDRs of the heavy chain variable region ($V_H$) and light chain variable region ($V_L$) than in the framework region. As is known to one of skill in the art, mutations are more tolerated, i.e., limited or no loss of function (e.g., specificity or neutralization ability) in the framework regions than in the CDRs.

The invention thus comprises an antibody, or an antigen binding fragment thereof, wherein the variation from the sequences provided herein is preferably in the framework region(s) of the antibody or in the nucleic acid residues that encode the framework region(s) of the antibody.

In the present invention, such (variant) antibodies are preferred, in which the number of somatic mutations is reduced (i.e. "germlined" antibodies: reverted back to the "germline" configuration). Germline sequences of antibodies may be determined, for example, with reference to IMGT database (e.g., according to the IMGT VDJ and VJ assignments and rearrangement interpretation: http://www.imgt.org/; cf. Lefranc, M.-P. et al. (2009) Nucleic Acids Res. 37, D1006-D1012) and "germlined" antibody variants may be produced, for example, by gene synthesis or by site-directed mutagenesis. A low level of somatic mutations reduces the potential risk of antibody immunogenicity. Preferably, the number of somatic mutations is reduced in the framework regions (FR) (i.e. "framework regions germlined" antibodies, also referred to herein as FR-GL variants). (Variant) antibodies, or an antigen binding fragment thereof, and FR-GL variants, respectively, without any somatic mutations in the framework regions (FR) are more preferred. Particularly preferred are such (variant) antibodies, or an antigen binding fragment thereof, and FR-GL variants, respectively, with as few somatic mutations as possible, whereby on the other hand the neutralizing activity is not impaired (as compared to the reference antibody/fragment containing (more) somatic mutations). Such antibodies are on the one hand not impaired in their neutralizing activities, thus showing a very high potency and breadth. On the other hand, a potential risk of antibody immunogenicity is significantly reduced.

In a preferred embodiment, the multispecific antibody or antibody fragment of the invention comprises at least one CDR with a sequence that has at least 95% sequence identity to any one of SEQ ID NOs: 1-7, 49-55, 67-73 and 105-111.

Preferably, the multispecific antibody or antibody fragment of the invention comprises more than one CDR with a sequence that has at least 95% sequence identity to any one of SEQ ID NOs: 1-7, 49-55, 67-73 and 105-111.

Preferably, the antibody, or antigen binding fragment thereof, comprises two CDRs with a sequence that has at least 95% sequence identity to any one of SEQ ID NOs: 1-7, 49-55, 67-73 and 105-111. Thereby it is preferred that the antibody, or antigen binding fragment thereof, comprises (i) a CDRH1 that has at least 95% sequence identity to any one of SEQ ID NOs: 1, 49, 67 and 105 and a CDRL1 that has at least 95% sequence identity to any one of SEQ ID NOs: 4, 52, 70 and 108; (ii) a CDRH2 that has at least 95% sequence identity to any one of SEQ ID NOs: 2, 50, 68 and 106, and a CDRL2 that has at least 95% sequence identity to any one of SEQ ID NOs: 5, 6, 53, 54, 71, 72, 109 and 110; or (iii) a CDRH3 that has at least 95% sequence identity to any one of SEQ ID NOs: 3, 51, 69 and 107, and a CDRL3 that has at least 95% sequence identity to any one of SEQ ID NOs: 7, 55, 73 and 111.

Preferably, the antibody, or antigen binding fragment thereof, comprises three CDRs with a sequence that has at least 95% sequence identity to any one of SEQ ID NOs: 1-7, 49-55, 67-73 and 105-111. Thereby it is preferred that the antibody, or antigen binding fragment thereof, comprises (i) a CDRH1 that has at least 95% sequence identity to any one of SEQ ID NOs: 1, 49, 67 and 105, a CDRH2 that has at least 95% sequence identity to any one of SEQ ID NOs: 2, 50, 68 and 106, and a CDRH3 that has at least 95% sequence identity to any one of SEQ ID NOs: 3, 51, 69 and 107; or (ii) a CDRL1 that has at least 95% sequence identity to any one of SEQ ID NOs: 4, 52, 70 and 108, a CDRL2 that has at least 95% sequence identity to any one of SEQ ID NOs: 5, 6, 53, 54, 71, 72, 109 and 110, and a CDRL3 that has at least 95% sequence identity to any one of SEQ ID NOs: 7, 55, 73 and 111.

Preferably, the antibody, or antigen binding fragment thereof, comprises four CDRs with a sequence that has at least 95% sequence identity to any one of SEQ ID NOs: 1-7, 49-55, 67-73 and 105-111. Thereby it is preferred that the antibody, or antigen binding fragment thereof, comprises (i) a CDRH1 that has at least 95% sequence identity to any one of SEQ ID NOs: 1, 49, 67 and 105, a CDRH2 that has at least 95% sequence identity to any one of SEQ ID NOs: 2, 50, 68 and 106, a CDRH3 that has at least 95% sequence identity to any one of SEQ ID NOs: 3, 51, 69 and 107, and a CDRL that has at least 95% sequence identity to any one of SEQ ID NOs: 4-7, 52-55, 70-73, or 108-111; (ii) a CDRL1 that has at least 95% sequence identity to any one of SEQ ID NOs: 4, 52, 70 and 108, a CDRL2 that has at least 95% sequence identity to any one of SEQ ID NOs: 5, 6, 53, 54, 71, 72, 109 and 110, a CDRL3 that has at least 95% sequence identity to any one of SEQ ID NOs: 7, 55, 73 and 111, and a CDRH that has at least 95% sequence identity to any one of SEQ ID NOs: 1-3, 49-51, 67-69, and 105-107, whereby a CDRH3 that has at least 95% sequence identity to any one of SEQ ID NOs: 3, 51, 69 and 107 is particularly preferred; (iii) a CDRH1 that has at least 95% sequence identity to any one of SEQ ID NOs: 1, 49, 67 and 105, a CDRL1 that has at least 95% sequence identity to any one of SEQ ID NOs: 4, 52, 70 and 108, a CDRH2 that has at least 95% sequence identity to any one of SEQ ID NOs: 2, 50, 68 and 106, and a CDRL2 that has at least 95% sequence identity to any one of SEQ ID NOs: 5, 6, 53, 54, 71, 72, 109 and 110; (iv) a CDRH1 that has at least 95% sequence identity to any one of SEQ ID NOs: 1, 49, 67 and 105, a CDRL1 that has at least 95% sequence identity to any one of SEQ ID NOs: 4, 52, 70 and 108, a CDRH3 that has at least 95% sequence identity to any one of SEQ ID NOs: 3, 51, 69 and 107, and a CDRL3 that has at least 95% sequence identity to any one of SEQ ID NOs: 7, 55, 73 and 111; or (v) a CDRH2 that has at least 95% sequence identity to any one of SEQ ID NOs: 2, 50, 68 and 106, a CDRL2 that has at least 95% sequence identity to any one of SEQ ID NOs: 5, 6, 53, 54, 71, 72, 109 and 110, a CDRH3 that has at least 95% sequence identity to any one of SEQ ID NOs: 3, 51, 69 and 107, and a CDRL3 that has at least 95% sequence identity to any one of SEQ ID NOs: 7, 55, 73 and 111.

Preferably, the antibody, or antigen binding fragment thereof, comprises five CDRs with a sequence that has at least 95% sequence identity to any one of SEQ ID NOs: 1-7, 49-55, 67-73 and 105-111. Thereby it is preferred that the antibody, or antigen binding fragment thereof, comprises five CDRs selected from the group of a CDRH1 that has at least 95% sequence identity to any one of SEQ ID NOs: 1, 49, 67 and 105, a CDRH2 that has at least 95% sequence identity to any one of SEQ ID NOs: 2, 50, 68 and 106, a CDRH3 that has at least 95% sequence identity to any one of SEQ ID NOs: 3, 51, 69 and 107, a CDRL1 that has at least 95% sequence identity to any one of SEQ ID NOs: 4, 52, 70 and 108, a CDRL2 that has at least 95% sequence identity to any one of SEQ ID NOs: 5, 6, 53, 54, 71, 72, 109 and 110, and a CDRL3 that has at least 95% sequence identity to any one of SEQ ID NOs: 7, 55, 73 and 111.

Preferably, the antibody, or antigen binding fragment thereof, comprises six CDRs with a sequence that has at least 95% sequence identity to any one of SEQ ID NOs: 1-7, 49-55, 67-73 and 105-111. Thereby it is preferred that the antibody, or antigen binding fragment thereof, comprises six CDRs selected from the group of a CDRH1 that has at least 95% sequence identity to any one of SEQ ID NOs: 1, 49, 67 and 105, a CDRH2 that has at least 95% sequence identity to any one of SEQ ID NOs: 2, 50, 68 and 106, a CDRH3 that has at least 95% sequence identity to any one of SEQ ID NOs: 3, 51, 69 and 107, a CDRL1 that has at least 95% sequence identity to any one of SEQ ID NOs: 4, 52, 70 and 108, a CDRL2 that has at least 95% sequence identity to any one of SEQ ID NOs: 5, 6, 53, 54, 71, 72, 109 and 110, and a CDRL3 that has at least 95% sequence identity to any one of SEQ ID NOs: 7, 55, 73 and 111. More preferably, the antibody, or antigen binding fragment thereof, comprises:

(i) heavy chain CDRH1, CDRH2, and CDRH3 amino acid sequences and light chain CDRL1, CDRL2, and CDRL3 amino acid sequences according to SEQ ID NOs: 1-5 and 7, or functional sequence variants thereof, or according to SEQ ID NOs: 1-4 and 6-7, respectively, or functional sequence variants thereof;

(ii) heavy chain CDRH1, CDRH2, and CDRH3 amino acid sequences and light chain CDRL1, CDRL2, and CDRL3 amino acid sequences according to SEQ ID NOs: 49-53 and 55, or functional sequence variants thereof, or according SEQ ID NOs: 49-52 and 54-55, respectively, or functional sequence variants thereof;

(iii) heavy chain CDRH1, CDRH2, and CDRH3 amino acid sequences and light chain CDRL1, CDRL2, and CDRL3 amino acid sequences according to SEQ ID NOs: 67-71 and 73, or functional sequence variants thereof, or according to SEQ ID NOs: 67-70 and 72-73, respectively, or functional sequence variants thereof; and/or (iv) heavy chain CDRH1, CDRH2, and CDRH3 amino acid sequences and light chain CDRL1, CDRL2, and CDRL3 amino acid sequences according to SEQ ID NOs: 105-109 and 111, or functional sequence variants thereof, or according to SEQ ID NOs: 105-108 and 110-111, respectively, or functional sequence variants thereof.

Among the embodiments described above of the antibody, or antigen binding fragment thereof, of the invention having at least one CDR, i.e. one, two, three, four, five, six or more CDRs as described above, such an embodiment of the antibody, or antigen binding fragment thereof, is preferred, which comprises a CDRH3 that has at least 95% sequence identity to any one of SEQ ID NOs: 3, 51, 69 and 107.

It is also preferred that, the isolated antibody or antigen binding fragment of the invention comprises a heavy chain CDR1 with the amino acid sequence of SEQ ID NOs: 1, 49, 67 and 105 or functional sequence variants thereof; a heavy chain CDR2 with the amino acid sequence of SEQ ID NOs: 2, 50, 68 and 106 or functional sequence variants thereof; and a heavy chain CDR3 with the amino acid sequence of SEQ ID NOs: 3, 51, 69 and 107 or functional sequence variants thereof. In certain embodiments, an antibody or antibody fragment as provided herein comprises a heavy chain comprising the amino acid sequence of (i) SEQ ID NO: 1 for CDRH1, SEQ ID NO: 2 for CDRH2 and SEQ ID NO: 3 for CDRH3, (ii) SEQ ID NO: 49 for CDRH1, SEQ ID NO: 50 for CDRH2, and SEQ ID NO: 21 for CDRH3, (iii) SEQ ID NO: 67 for CDRH1, SEQ ID NO: 68 for CDRH2, and SEQ ID NO: 69 for CDRH3, and/or (iv) SEQ ID NO: 105 for CDRH1, SEQ ID NO: 106 for CDRH2, and SEQ ID NO: 107 for CDRH3.

Preferably, the antibody or antigen binding fragment of the invention comprises a light chain CDR1 with an amino acid sequence according to any of SEQ ID NOs: 4, 52, 70 and 108 or functional sequence variants thereof; a light chain CDR2 with an amino acid sequence according to any of SEQ ID NOs: 5, 6, 53, 54, 71, 72, 109 and 110 or functional sequence variants thereof; and/or a light chain CDR3 with an amino acid sequence according to any of SEQ ID NO: 7, 55, 73 and 111 or functional sequence variants thereof. In certain embodiments, an antibody or antibody fragment as provided herein comprises a light chain comprising the amino acid sequence of (i) SEQ ID NO: 4 for CDRL1, SEQ ID NO: 5 or 6 for CDRL2, and SEQ ID NO: 7 for CDRL3; (ii) SEQ ID NO: 52 for CDRL1, SEQ ID NO: 53 or 54 for CDRL2, and SEQ ID NO: 55 for CDRL3; (iii) SEQ ID NO: 70 for CDRL1, SEQ ID NO: 71 or 72 for CDRL2, and SEQ ID NO: 73 for CDRL3; and/or (iv) SEQ ID NO: 108 for CDRL1, SEQ ID NO: 109 or 110 for CDRL2, and SEQ ID NO: 111 for CDRL3.

In another embodiment of the invention, the invention comprises an isolated antibody or antigen binding fragment thereof, comprising heavy chain CDR1, CDR2 and CDR3 and light chain CDR1, CDR2, and CDR3 amino acid sequences that are at least 80%, for example, 80%, 81%, 82%, 83%, 84%, 85%, 86%, 87%, 88%, 89%, 90%, 91%, 92%, 93%, 94%, 95%, 96%, 97%, 98%, 99% or 100% identical to any six amino acid sequences of SEQ ID NOs: 1-7, 49-55, 67-73, and 105-111, respectively.

Table 2 provides the SEQ ID numbers for the amino acid sequences, as well as the nucleic acid sequences which encode them, of the heavy and light chain variable regions, which are derived from exemplary monospecific antibodies and used in the exemplary multispecific antibodies of the invention.

TABLE 2

SEQ ID Numbers for VH and VL peptides derived from exemplary monospecific antibodies.

| Origin (mono-Specific AB) | VH amino acid | VL amino acid | VH nucleic acid | VL nucleic acid |
|---|---|---|---|---|
| GCA7 | 37 | 38 | 39-43 | 44-48 |
| GCA21 | 63 | 64 | 65 | 66 |
| GCB59 | 95 | 96 | 97-100 | 101-104 |
| GCE536 | 130 | 131 | 132-135 | 136-139 |

These sequences are referred to as "VH sequence" or "VL sequence", respectively, depending whether they are derived from a heavy chain of a monospecific antibody (e.g. GCA7, GCA21, GCB59, or GCE536) or from a light chain of a monospecific antibody (e.g. GCA7, GCA21, GCB59, or GCE536). Thus, in the multispecific antibody according to the present invention, for example the heavy chain may also (e.g. in addition to one or more VH sequences) comprise one or more VL sequences (which were comprised by the light chain of the monospecific antibody from which they are derived).

Preferably, the isolated antibody or antigen binding fragment according to the present invention comprises a VH sequence having an amino acid sequence that is about 70%, 75%, 80%, 85%, 88%, 90%, 92%, 95%, 96%, 97%, 98%, 99% or 100% identical to any one of the sequences according to SEQ ID NOs: 37, 63, 95 and 130. In another embodiment, the antibody or antibody fragment comprises a VL sequence having an amino acid sequence that is about 70%, 75%, 80%, 85%, 90%, 85%, 88%, 90%, 92%, 95%, 96%, 97%, 98%, 99% or 100% identical to any one of the sequences according to SEQ ID NOs: 38, 64, 96, 131.

Preferably, the antibody or antigen binding fragment according to the present invention comprises:

(i) a VH amino acid sequence according to SEQ ID NO: 37 or a functional sequence variant thereof and a VL amino acid sequence according to SEQ ID NO: 38 or a functional sequence variant thereof; and/or (ii) a VH amino acid sequence according to SEQ ID NO: 63 or a functional sequence variant thereof and a VL amino acid sequence according to SEQ ID NO: 64 or a functional sequence variant thereof; and/or (iii) a VH amino acid sequence according to SEQ ID NO: 95 or a functional sequence variant thereof and a VL amino acid sequence according to SEQ ID NO: 96 or a functional sequence variant thereof; and/or (iv) a VH amino acid sequence according to SEQ ID NO: 130 or a functional sequence variant thereof and a VL amino acid sequence according to SEQ ID NO: 131 or a functional sequence variant thereof.

Moreover, the heavy chain of the antibody, or the antigen binding fragment thereof, according to the present invention preferably comprises a VL amino acid sequence selected from the amino acids sequences according to SEQ ID NOs: 38, 64, 96 and 131 or functional sequence variants thereof. More preferably the heavy chain of the antibody or antigen binding fragment comprises a VL amino acid sequence selected from the amino acids sequences according to SEQ ID NOs: 38 and 96 or functional sequence variants thereof and even more preferably the heavy chain of the antibody or antigen binding fragment comprises a VL amino acid sequence according to SEQ ID NO: 96 or functional sequence variants thereof.

In the multispecific antibody, or antigen binding fragment thereof, according to the present invention, it is preferred that (i) the antibody or antigen binding fragment is of a construct type select from the group consisting of the construct types Bs1, Bs2, Bs3, Ts1, Ts2 and Ts3; and (ii) the antibody or antigen binding fragment comprises a CDRH1 amino acid sequence, a CDRH2 amino acid sequence, a CDRH3 amino acid sequence, a CDRL1 amino acid sequence, a CDRL2 amino acid sequence and a CDRL3 amino acid sequence selected from the group consisting of (a) amino acid sequences according to SEQ ID NOs: 1-5 and 7 or functional sequence variants thereof; (b) amino acid sequences according to SEQ ID NOs: 1-4 and 6-7 or functional sequence variants thereof; (c) amino acid sequences according to SEQ ID NOs: 67-71 and 73 or functional sequence variants thereof; (d) amino acid sequences according to SEQ ID NOs: 67-70 and 72-73 or functional sequence variants thereof; (e) amino acid sequences according to SEQ ID NOs: 49-53 and 55 or functional sequence variants thereof; (f) amino acid sequences according to SEQ ID NOs: 49-52 and 54-55 or functional sequence variants thereof; (g) amino acid sequences according to SEQ ID NOs: 105-109 and 111 or functional sequence variants thereof; and (h) amino acid sequences according to SEQ ID NOs: 105-108 and 110-111 or functional sequence variants thereof.

More preferably, the multispecific antibody, or antigen binding fragment thereof, according to the present invention (i) is of a construct type select from the group consisting of the construct types Bs1, Bs2, Bs3, Ts1, Ts2 and Ts3; and (ii) comprises at any of the positions A and/or C a CDRH1 amino acid sequence, a CDRH2 amino acid sequence, a CDRH3 amino acid sequence, a CDRL1 amino acid sequence, a CDRL2 amino acid sequence and a CDRL3 amino acid sequence selected from the group consisting of (a) amino acid sequences according to SEQ ID NOs: 1-5 and 7 or functional sequence variants thereof; (b) amino acid sequences according to SEQ ID NOs: 1-4 and 6-7 or functional sequence variants thereof; (c) amino acid sequences according to SEQ ID NOs: 67-71 and 73 or functional sequence variants thereof; and (d) amino acid sequences according to SEQ ID NOs: 67-70 and 72-73 or functional sequence variants thereof.

Even more preferably, the multispecific antibody, or antigen binding fragment thereof, according to the present invention (i) is of a construct type select from the group consisting of the construct types Bs1, Bs2, Bs3, Ts1, Ts2 and Ts3; and (ii) comprises at any of the positions A and/or C a CDRH1 amino acid sequence, a CDRH2 amino acid sequence, a CDRH3 amino acid sequence, a CDRL1 amino acid sequence, a CDRL2 amino acid sequence and a CDRL3 amino acid sequence according to SEQ ID NOs: 67-71 and 73 or functional sequence variants thereof or according to SEQ ID NOs: 67-70 and 72-73 or functional sequence variants thereof.

Particularly preferably, the multispecific antibody, or antigen binding fragment thereof, according to the present invention (i) is of a construct type select from the group consisting of the construct types Bs1, Bs2, Bs3, Ts1, Ts2 and Ts3; and (ii) comprises at position A a CDRH1 amino acid sequence, a CDRH2 amino acid sequence, a CDRH3 amino acid sequence, a CDRL1 amino acid sequence, a CDRL2 amino acid sequence and a CDRL3 amino acid sequence according to SEQ ID NOs: 67-71 and 73 or functional sequence variants thereof or according to SEQ ID NOs: 67-70 and 72-73 or functional sequence variants thereof.

Preferably, the multispecific antibody, or the antigen binding fragment thereof, according to the present invention is according to gTs1GC1, gTs1GC2a, gTs2GC2b, gTs2GC2c, gTs3GC2d, gTs3GC2e, gBs3GC1a, gBs3GC1b, gBs2GC1c, gBs2GC1d, gBs1GC2a, gBs3GC2b, gBs1GC3a, gBs3GC3b, gBs3GC4, and gBs3GC5, preferably it is according to gTs3GC2d or gBs1GC3a. More preferably, the antibody, or the antigen binding fragment thereof, is Ts1GC1, Ts1GC2a, Ts2GC2b, Ts2GC2c, Ts3GC2d, Ts3GC2e, Bs3GC1a, Bs3GC1b, Bs2GC1c, Bs2GC1d, Bs1GC2a, Bs3GC2b, Bs1GC3a, Bs3GC3b, Bs3GC4, and Bs3GC5, preferably Ts3GC2d or Bs1 GC3a.

The present inventors have designed and constructed sixteen multispecific antibodies, which are referred to herein as Ts1GC1, Ts1GC2a, Ts2GC2b, Ts2GC2c, Ts3GC2d, Ts3GC2e, Bs3GC1a, Bs3GC1b, Bs2GC1c, Bs2GC1d, Bs1GC2a, Bs3GC2b, Bs1GC3a, Bs3GC3b, Bs3GC4, and Bs3GC5 (cf. Example 5; Table 7). Based on the antibodies Ts1GC1, Ts1GC2a, Ts2GC2b, Ts2GC2c, Ts3GC2d, Ts3GC2e, Bs3GC1a, Bs3GC1b, Bs2GC1c, Bs2GC1d, Bs1GC2a, Bs3GC2b, Bs1GC3a, Bs3GC3b, Bs3GC4, and Bs3GC5, in particular on the combination of VH and VL sequences derived from four monospecific antibodies (GCA7, GCA21, GCB59, GCE536), the terms gTs1GC1, gTs1GC2a, gTs2GC2b, gTs2GC2c, gTs3GC2d, gTs3GC2e, gBs3GC1a, gBs3GC1b, gBs2GC1c, gBs2GC1d, gBs1GC2a, gBs3GC2b, gBs1GC3a, gBs3GC3b, gBs3GC4, and gBs3GC5, as used herein, refer to respective "generic" antibodies, or antigen binding fragments thereof, comprising the specific VH and VL amino acid sequences, encoded by the specific nucleotide sequences, as outlined below.

Table 7 (Example 5) shows the SEQ ID NOs for the amino acid sequences of the heavy chains as well as the SEQ ID NOs for the amino acid sequences of light chains of antibodies Ts1GC1, Ts1GC2a, Ts2GC2b, Ts2GC2c, Ts3GC2d, Ts3GC2e, Bs3GC1a, Bs3GC1b, Bs2GC1c, Bs2GC1d, Bs1GC2a, Bs3GC2b, Bs1GC3a, Bs3GC3b, Bs3GC4, and Bs3GC5, respectively (referred to as "complete sequence" in Table 7), as well as the nucleic acid sequences that encode them. The respective sequences are shown in the "Table of Sequences and SEQ ID Numbers" following the "Examples".

As used herein, "gTs1GC1" refers to a trispecific antibody, or antigen binding fragment thereof, comprising:

(i) a heavy chain comprising a VH amino acid sequence according to SEQ ID NO: 63, a VH amino acid sequence according to SEQ ID NO: 37, a VL amino acid sequence according to SEQ ID NO: 38, a VH amino acid sequence according to SEQ ID NO: 95 and a VL amino acid sequence according to SEQ ID NO: 96; and (ii) a light chain comprising a VL amino acid sequence according to SEQ ID NO: 64.

Preferably gTs1GC1 is of the IgG1 type, whereby the light chain of gTs1GC1 further comprises an IgG1 CK sequence according to SEQ ID NO: 141 and the heavy chain of gTs1GC1 further comprises an IgG1 CH1-CH2-CH3 sequence according to SEQ ID NO: 140 and, optionally one or more linker sequences, e.g. according to SEQ ID NOs: 143 or 144, whereby a short linker may be preferably arranged between the IgG1 CH1-CH2-CH3 sequence according to SEQ ID NO: 140 and the VH amino acid sequence according to SEQ ID NO: 37 as well as between the VL amino acid sequence according to SEQ ID NO: 38 and the VH amino acid sequence according to SEQ ID NO: 95 and a long linker may be preferably arranged between the VH amino acid sequence according to SEQ ID NO: 37 and the VL amino acid sequence according to SEQ ID NO: 38 as well as between the VH amino acid sequence according to SEQ ID NO: 95 and the VL amino acid sequence according to SEQ ID NO: 96. Preferably, the construct type of gTs1GC1 is Ts1.

As used herein, "gTs1GC2a" refers to a trispecific antibody, or antigen binding fragment thereof, comprising:

(i) a heavy chain comprising a VH amino acid sequence according to SEQ ID NO: 130, a VH amino acid sequence according to SEQ ID NO: 37, a VL amino acid sequence according to SEQ ID NO: 38, a VH amino acid sequence according to SEQ ID NO: 95 and a VL amino acid sequence according to SEQ ID NO: 96; and (ii) a light chain comprising a VL amino acid sequence according to SEQ ID NO: 131.

Preferably gTs1GC2a is of the IgG1 type, whereby the light chain of gTs1GC2a further comprises an IgG1 CK sequence according to SEQ ID NO: 141 and the heavy chain of gTs1GC2a further comprises an IgG1 CH1-CH2-CH3 sequence according to SEQ ID NO: 140 and, optionally one or more linker sequences, e.g. according to SEQ ID NOs: 143 or 144, whereby a short linker may be preferably arranged between the IgG1 CH1-CH2-CH3 sequence according to SEQ ID NO: 140 and the VH amino acid sequence according to SEQ ID NO: 37 as well as between the VL amino acid sequence according to SEQ ID NO: 38 and the VH amino acid sequence according to SEQ ID NO: 95 and a long linker may be preferably arranged between the VH amino acid sequence according to SEQ ID NO: 37 and the VL amino acid sequence according to SEQ ID NO: 38 as well as between the VH amino acid sequence according to SEQ ID NO: 95 and the VL amino acid sequence according to SEQ ID NO: 96. Preferably, the construct type of gTs1GC2a is Ts1.

As used herein, "gTs2GC2b" refers to a trispecific antibody, or antigen binding fragment thereof, comprising:

(i) a heavy chain comprising a VH amino acid sequence according to SEQ ID NO: 95, a VL amino acid sequence according to SEQ ID NO: 96, and a VH amino acid sequence according to SEQ ID NO: 130; and (ii) a light chain comprising a VH amino acid sequence according to SEQ ID NO: 37, a VL amino acid sequence according to SEQ ID NO: 38, and a VL amino acid sequence according to SEQ ID NO: 131.

Preferably gTs2GC2b is of the IgG1 type, whereby the light chain of gTs2GC2b further comprises an IgG1 CK sequence according to SEQ ID NO: 141 and, optionally one or more linker sequences, e.g. according to SEQ ID NOs: 143 or 144, whereby a short linker may be preferably arranged between the VL amino acid sequence according to SEQ ID NO: 38 and the VL amino acid sequence according to SEQ ID NO: 131 and a long linker may be preferably arranged between the VH amino acid sequence according to SEQ ID NO: 37 and the VL amino acid sequence according to SEQ ID NO: 38 and the heavy chain of gTs2GC2b further comprises an IgG1 CH1-CH2-CH3 sequence according to SEQ ID NO: 140 and, optionally one or more linker sequences, e.g. according to SEQ ID NOs: 143 or 144, whereby a short linker may be preferably arranged the VL amino acid sequence according to SEQ ID NO: 96 and the VH amino acid sequence according to SEQ ID NO: 130 and a long linker may be preferably arranged between the VH amino acid sequence according to SEQ ID NO: 95 and the VL amino acid sequence according to SEQ ID NO: 96. Preferably, the construct type of gTs2GC2b is Ts2.

As used herein, "gTs2GC2c" refers to a trispecific antibody, or antigen binding fragment thereof, comprising:

(i) a heavy chain comprising a VH amino acid sequence according to SEQ ID NO: 95, a VL amino acid sequence according to SEQ ID NO: 96, and a VH amino acid sequence according to SEQ ID NO: 37; and (ii) a light chain comprising a VH amino acid sequence according to SEQ ID NO: 130, a VL amino acid sequence according to SEQ ID NO: 131, and a VL amino acid sequence according to SEQ ID NO: 38.

Preferably gTs2GC2c is of the IgG1 type, whereby the light chain of gTs2GC2c further comprises an IgG1 CK sequence according to SEQ ID NO: 141 and, optionally one or more linker sequences, e.g. according to SEQ ID NOs: 143 or 144, whereby a short linker may be preferably arranged between the VL amino acid sequence according to SEQ ID NO: 131 and the VL amino acid sequence according to SEQ ID NO: 38 and a long linker may be preferably arranged between the VH amino acid sequence according to SEQ ID NO: 130 and the VL amino acid sequence according to SEQ ID NO: 131 and the heavy chain of gTs2GC2c further comprises an IgG1 CH1-CH2-CH3 sequence according to SEQ ID NO: 140 and, optionally one or more linker sequences, e.g. according to SEQ ID NOs: 143 or 144, whereby a short linker may be preferably arranged the VL amino acid sequence according to SEQ ID NO: 96 and the VH amino acid sequence according to SEQ ID NO: 37 and a long linker may be preferably arranged between the VH amino acid sequence according to SEQ ID NO: 95 and the VL amino acid sequence according to SEQ ID NO: 96. Preferably, the construct type of gTs2GC2c is Ts2.

As used herein, "gTs3GC2d" refers to a trispecific antibody, or antigen binding fragment thereof, comprising:

(i) a heavy chain comprising a VH amino acid sequence according to SEQ ID NO: 95, a VL amino acid sequence according to SEQ ID NO: 96, a VH amino acid sequence according to SEQ ID NO: 130, a VH amino acid sequence according to SEQ ID NO: 37 and a VL amino acid sequence according to SEQ ID NO: 38; and (ii) a light chain comprising a VL amino acid sequence according to SEQ ID NO: 131.

Preferably gTs3GC2d is of the IgG1 type, whereby the light chain of gTs3GC2d further comprises an IgG1 CK sequence according to SEQ ID NO: 141 and the heavy chain of gTs3GC2d further comprises an IgG1 CH1-CH2-CH3 sequence according to SEQ ID NO: 140 and, optionally one or more linker sequences, e.g. according to SEQ ID NOs: 143 or 144, whereby a short linker may be preferably arranged between the IgG1 CH1-CH2-CH3 sequence according to SEQ ID NO: 140 and the VH amino acid sequence according to SEQ ID NO: 37 as well as between the VL amino acid sequence according to SEQ ID NO: 96 and the VH amino acid sequence according to SEQ ID NO: 130 and a long linker may be preferably arranged between the VH amino acid sequence according to SEQ ID NO: 37 and the VL amino acid sequence according to SEQ ID NO: 38 as well as between the VH amino acid sequence according to SEQ ID NO: 95 and the VL amino acid sequence according to SEQ ID NO: 96. Preferably, the construct type of gTs3GC2d is Ts3.

As used herein, "gTs3GC2e" refers to a trispecific antibody, or antigen binding fragment thereof, comprising:

(i) a heavy chain comprising a VH amino acid sequence according to SEQ ID NO: 95, a VL amino acid sequence according to SEQ ID NO: 96, a VH amino acid sequence according to SEQ ID NO: 37, a VH amino acid sequence according to SEQ ID NO: 130 and a VL amino acid sequence according to SEQ ID NO: 131; and (ii) a light chain comprising a VL amino acid sequence according to SEQ ID NO: 38.

Preferably gTs3GC2e is of the IgG1 type, whereby the light chain of gTs3GC2e further comprises an IgG1 CK sequence according to SEQ ID NO: 141 and the heavy chain of gTs3GC2e further comprises an IgG1 CH1-CH2-CH3 sequence according to SEQ ID NO: 140 and, optionally one or more linker sequences, e.g. according to SEQ ID NOs: 143 or 144, whereby a short linker may be preferably arranged between the IgG1 CH1-CH2-CH3 sequence according to SEQ ID NO: 140 and the VH amino acid sequence according to SEQ ID NO: 130 as well as between the VL amino acid sequence according to SEQ ID NO: 96 and the VH amino acid sequence according to SEQ ID NO: 37 and a long linker may be preferably arranged between the VH amino acid sequence according to SEQ ID NO: 130 and the VL amino acid sequence according to SEQ ID NO: 131 as well as between the VH amino acid sequence according to SEQ ID NO: 95 and the VL amino acid sequence according to SEQ ID NO: 96. Preferably, the construct type of gTs3GC2e is Ts3.

As used herein, "gBs3GC1a" refers to a bispecific antibody, or antigen binding fragment thereof, comprising:

(i) a heavy chain comprising a VH amino acid sequence according to SEQ ID NO: 130, a VH amino acid sequence according to SEQ ID NO: 37, and a VL amino acid sequence according to SEQ ID NO: 38; and (ii) a light chain comprising a VL amino acid sequence according to SEQ ID NO: 131.

Preferably gBs3GC1a is of the IgG1 type, whereby the light chain of gBs3GC1a further comprises an IgG1 CK sequence according to SEQ ID NO: 141 and the heavy chain of gBs3GC1a further comprises an IgG1 CH1-CH2-CH3 sequence according to SEQ ID NO: 140 and, optionally one or more linker sequences, e.g. according to SEQ ID NOs: 143 or 144, whereby a short linker may be preferably arranged between the IgG1 CH1-CH2-CH3 sequence according to SEQ ID NO: 140 and the VH amino acid sequence according to SEQ ID NO: 37 and a long linker may be preferably arranged between the VH amino acid sequence according to SEQ ID NO: 37 and the VL amino acid sequence according to SEQ ID NO: 38. Preferably, the construct type of gBs3GC1a is Bs3.

As used herein, "gBs3GC1b" refers to a bispecific antibody, or antigen binding fragment thereof, comprising:

(i) a heavy chain comprising a VH amino acid sequence according to SEQ ID NO: 37, a VH amino acid sequence according to SEQ ID NO: 130, and a VL amino acid sequence according to SEQ ID NO: 131; and (ii) a light chain comprising a VL amino acid sequence according to SEQ ID NO: 38.

Preferably gBs3GC1b is of the IgG1 type, whereby the light chain of gBs3GC1b further comprises an IgG1 CK sequence according to SEQ ID NO: 141 and the heavy chain of gBs3GC1b further comprises an IgG1 CH1-CH2-CH3 sequence according to SEQ ID NO: 140 and, optionally one or more linker sequences, e.g. according to SEQ ID NOs: 143 or 144, whereby a short linker may be preferably arranged between the IgG1 CH1-CH2-CH3 sequence according to SEQ ID NO: 140 and the VH amino acid sequence according to SEQ ID NO: 130 and a long linker may be preferably arranged between the VH amino acid sequence according to SEQ ID NO: 130 and the VL amino acid sequence according to SEQ ID NO: 131. Preferably, the construct type of gBs3GC1b is Bs3.

As used herein, "gBs2GC1c" refers to a bispecific antibody, or antigen binding fragment thereof, comprising:

(i) a heavy chain comprising a VH amino acid sequence according to SEQ ID NO: 130; and (ii) a light chain comprising a VH amino acid sequence according to SEQ ID NO: 37, a VL amino acid sequence according to SEQ ID NO: 38, and a VL amino acid sequence according to SEQ ID NO: 131.

Preferably gBs2GC1c is of the IgG1 type, whereby the light chain of gBs2GC1c further comprises an IgG1 CK sequence according to SEQ ID NO: 141 and, optionally one or more linker sequences, e.g. according to SEQ ID NOs: 143 or 144, whereby a short linker may be preferably arranged between the VL amino acid sequence according to SEQ ID NO: 38 and the VL amino acid sequence according to SEQ ID NO: 131 and a long linker may be preferably arranged between the VH amino acid sequence according to SEQ ID NO: 37 and the VL amino acid sequence according to SEQ ID NO: 38, and the heavy chain of gBs2GC1c further comprises an IgG1 CH1-CH2-CH3 sequence according to SEQ ID NO: 140. Preferably, the construct type of gBs2GC1c is Bs2.

As used herein, "gBs2GC1d" refers to a bispecific antibody, or antigen binding fragment thereof, comprising:

(i) a heavy chain comprising a VH amino acid sequence according to SEQ ID NO: 37; and (ii) a light chain comprising a VH amino acid sequence according to SEQ ID NO: 130, a VL amino acid sequence according to SEQ ID NO: 131, and a VL amino acid sequence according to SEQ ID NO: 38.

Preferably gBs2GC1d c is of the IgG1 type, whereby the light chain of gBs2GC1d further comprises an IgG1 CK sequence according to SEQ ID NO: 141 and, optionally one or more linker sequences, e.g. according to SEQ ID NOs: 143 or 144, whereby a short linker may be preferably arranged between the VL amino acid sequence according to SEQ ID NO: 131 and the VL amino acid sequence according to SEQ ID NO: 38 and a long linker may be preferably arranged between the VH amino acid sequence according to SEQ ID NO: 130 and the VL amino acid sequence according to SEQ ID NO: 131, and the heavy chain of gBs2GC1d further comprises an IgG1 CH1-CH2-CH3 sequence according to SEQ ID NO: 140. Preferably, the construct type of gBs2GC1d is Bs2.

As used herein, "gBs1GC2a" refers to a bispecific antibody, or antigen binding fragment thereof, comprising:

(i) a heavy chain comprising a VH amino acid sequence according to SEQ ID NO: 95, a VL amino acid sequence according to SEQ ID NO: 96, and a VH amino acid sequence according to SEQ ID NO: 130; and (ii) a light chain comprising a VL amino acid sequence according to SEQ ID NO: 131.

Preferably gBs1GC2a is of the IgG1 type, whereby the light chain of gBs1GC2a further comprises an IgG1 CK sequence according to SEQ ID NO: 141 and the heavy chain of gBs1GC2a further comprises an IgG1 CH1-CH2-CH3 sequence according to SEQ ID NO: 140 and, optionally, one or more linker sequences, e.g. according to SEQ ID NOs: 143 or 144, whereby a short linker may be preferably arranged between the VL amino acid sequence according to SEQ ID NO: 96 and the VH amino acid sequence according to SEQ ID NO: 130 and a long linker may be preferably arranged between the VH amino acid sequence according to SEQ ID NO: 95 and the VL amino acid sequence according to SEQ ID NO: 96. Preferably, the construct type of gBs1GC2a is Bs1.

As used herein, "gBs3GC2b" refers to a bispecific antibody, or antigen binding fragment thereof, comprising:

(i) a heavy chain comprising a VH amino acid sequence according to SEQ ID NO: 95, a VH amino acid sequence according to SEQ ID NO: 130, and a VL amino acid sequence according to SEQ ID NO: 131; and
(ii) a light chain comprising a VL amino acid sequence according to SEQ ID NO: 96.

Preferably gBs3GC2b is of the IgG1 type, whereby the light chain of gBs3GC2b further comprises an IgG1 CL sequence according to SEQ ID NO: 142 and the heavy chain of gBs3GC2b further comprises an IgG1 CH1-CH2-CH3 sequence according to SEQ ID NO: 140 and, optionally one or more linker sequences, e.g. according to SEQ ID NOs: 143 or 144, whereby a short linker may be preferably arranged between the IgG1 CH1-CH2-CH3 sequence according to SEQ ID NO: 140 and the VH amino acid sequence according to SEQ ID NO: 130 and a long linker may be preferably arranged between the VH amino acid sequence according to SEQ ID NO: 130 and the VL amino acid sequence according to SEQ ID NO: 131. Preferably, the construct type of gBs3GC2b is Bs3.

As used herein, "gBs1GC3a" refers to a bispecific antibody, or antigen binding fragment thereof, comprising:

(i) a heavy chain comprising a VH amino acid sequence according to SEQ ID NO: 95, a VL amino acid sequence according to SEQ ID NO: 96, and a VH amino acid sequence according to SEQ ID NO: 37; and
(ii) a light chain comprising a VL amino acid sequence according to SEQ ID NO: 38.

Preferably gBs1GC3a is of the IgG1 type, whereby the light chain of gBs1GC3a further comprises an IgG1 CK sequence according to SEQ ID NO: 141 and the heavy chain of gBs1GC3a further comprises an IgG1 CH1-CH2-CH3 sequence according to SEQ ID NO: 140 and, optionally, one or more linker sequences, e.g. according to SEQ ID NOs: 143 or 144, whereby a short linker may be preferably arranged between the VL amino acid sequence according to SEQ ID NO: 96 and the VH amino acid sequence according to SEQ ID NO: 37 and a long linker may be preferably arranged between the VH amino acid sequence according to SEQ ID NO: 95 and the VL amino acid sequence according to SEQ ID NO: 96. Preferably, the construct type of gBs1GC3a is Bs1.

As used herein, "gBs3GC3b" refers to a bispecific antibody, or antigen binding fragment thereof, comprising:

(i) a heavy chain comprising a VH amino acid sequence according to SEQ ID NO: 95, a VH amino acid sequence according to SEQ ID NO: 37, and a VL amino acid sequence according to SEQ ID NO: 38; and
(ii) a light chain comprising a VL amino acid sequence according to SEQ ID NO: 96.

Preferably gBs3GC3b is of the IgG1 type, whereby the light chain of gBs3GC3b further comprises an IgG1 CL sequence according to SEQ ID NO: 142 and the heavy chain of gBs3GC3b further comprises an IgG1 CH1-CH2-CH3 sequence according to SEQ ID NO: 140 and, optionally one or more linker sequences, e.g. according to SEQ ID NOs: 143 or 144, whereby a short linker may be preferably arranged between the IgG1 CH1-CH2-CH3 sequence according to SEQ ID NO: 140 and the VH amino acid sequence according to SEQ ID NO: 37 and a long linker may be preferably arranged between the VH amino acid sequence according to SEQ ID NO: 37 and the VL amino acid sequence according to SEQ ID NO: 38. Preferably, the construct type of gBs3GC3b is Bs3.

As used herein, "gBs3GC4" refers to a bispecific antibody, or antigen binding fragment thereof, comprising:

(i) a heavy chain comprising a VH amino acid sequence according to SEQ ID NO: 63, a VH amino acid sequence according to SEQ ID NO: 130, and a VL amino acid sequence according to SEQ ID NO: 131; and
(ii) a light chain comprising a VL amino acid sequence according to SEQ ID NO: 64.

Preferably gBs3GC4 is of the IgG1 type, whereby the light chain of gBs3GC4 further comprises an IgG1 CK sequence according to SEQ ID NO: 141 and the heavy chain of gBs3GC4 further comprises an IgG1 CH1-CH2-CH3 sequence according to SEQ ID NO: 140 and, optionally one or more linker sequences, e.g. according to SEQ ID NOs: 143 or 144, whereby a short linker may be preferably arranged between the IgG1 CH1-CH2-CH3 sequence according to SEQ ID NO: 140 and the VH amino acid sequence according to SEQ ID NO: 130 and a long linker may be preferably arranged between the VH amino acid sequence according to SEQ ID NO: 130 and the VL amino acid sequence according to SEQ ID NO: 131. Preferably, the construct type of gBs3GC4 is Bs3.

As used herein, "gBs3GC5" refers to a bispecific antibody, or antigen binding fragment thereof, comprising:

(i) a heavy chain comprising a VH amino acid sequence according to SEQ ID NO: 63, a VH amino acid sequence according to SEQ ID NO: 37, and a VL amino acid sequence according to SEQ ID NO: 38; and
(ii) a light chain comprising a VL amino acid sequence according to SEQ ID NO: 64.

Preferably gBs3GC5 is of the IgG1 type, whereby the light chain of gBs3GC5 further comprises an IgG1 CK sequence according to SEQ ID NO: 141 and the heavy chain of gBs3GC5 further comprises an IgG1 CH1-CH2-CH3 sequence according to SEQ ID NO: 140 and, optionally one or more linker sequences, e.g. according to SEQ ID NOs: 143 or 144, whereby a short linker may be preferably arranged between the IgG1 CH1-CH2-CH3 sequence according to SEQ ID NO: 140 and the VH amino acid sequence according to SEQ ID NO: 37 and a long linker may be preferably arranged between the VH amino acid sequence according to SEQ ID NO: 37 and the VL amino acid sequence according to SEQ ID NO: 38. Preferably, the construct type of gBs3GC5 is Bs3.

Preferably, the isolated multispecific antibody or antigen binding fragment according to the present invention comprises all of the CDRs comprised by all of the respective VH and VL sequences of gTs3GC2d or the isolated multispecific antibody or antigen binding fragment according to the present invention comprises all of the CDRs comprised by all of the respective VH and VL sequences of gBs1GC3a. Table 3 below shows which VH or VL sequences (SEQ ID numbers of amino acid sequences) comprise which CDRs (SEQ ID numbers of amino acid sequences), as well as the exemplary monospecific antibodies from which they are derived. Alternatively, the isolated multispecific antibody or antigen binding fragment according to the present invention comprises all of the CDRs comprised by all of the respective VH and VL sequences of gTs1GC1. Alternatively, the isolated multispecific antibody or antigen binding fragment according to the present invention comprises all of the CDRs comprised by all of the respective VH and VL sequences of gTs1GC2a. Alternatively, the isolated multispecific antibody or antigen binding fragment according to the present invention comprises all of the CDRs comprised by all of the respective VH and VL sequences of gTs2GC2b. Alternatively, the isolated multispecific antibody or antigen binding fragment according to the present invention comprises all of the CDRs comprised by all of the respective VH and VL sequences of gTs2GC2c. Alternatively, the isolated multispecific antibody or antigen binding fragment according to the present invention comprises all of the CDRs comprised by all of the respective VH and VL sequences of gTs2GC2c. Alternatively, the isolated multispecific antibody or antigen binding fragment according to the present invention comprises all of the CDRs comprised by all of the respective VH and VL sequences of gTs3GC2d. Alternatively, the isolated multispecific antibody or antigen binding fragment according to the present invention comprises all of the CDRs comprised by all of the respective VH and VL sequences of gTs3GC2d. Alternatively, the isolated multispecific antibody or antigen binding fragment according to the present invention comprises all of the CDRs comprised by all of the respective VH and VL sequences of gTs3GC2e. Alternatively, the isolated multispecific antibody or antigen binding fragment according to the present invention comprises all of the CDRs comprised by all of the respective VH and VL sequences of gBs3GC1a. Alternatively, the isolated multispecific antibody or antigen binding fragment according to the present invention comprises all of the CDRs comprised by all of the respective VH and VL sequences of gBs3GC1b. Alternatively, the isolated multispecific antibody or antigen binding fragment according to the present invention comprises all of the CDRs comprised by all of the respective VH and VL sequences of gBs2GC1c. Alternatively, the isolated multispecific antibody or antigen binding fragment according to the present invention comprises all of the CDRs comprised by all of the respective VH and VL sequences of gBs2GC1d. Alternatively, the isolated multispecific antibody or antigen binding fragment according to the present invention comprises all of the CDRs comprised by all of the respective VH and VL sequences of gBs1GC2a. Alternatively, the isolated multispecific antibody or antigen binding fragment according to the present invention comprises all of the CDRs comprised by all of the respective VH and VL sequences of gBs3GC2b. Alternatively, the isolated multispecific antibody or antigen binding fragment according to the present invention comprises all of the CDRs comprised by all of the respective VH and VL sequences of gBs1GC3a. Alternatively, the isolated multispecific antibody or antigen binding fragment according to the present invention comprises all of the CDRs comprised by all of the respective VH and VL sequences of gBs3GC3b. Alternatively, the isolated multispecific antibody or antigen binding fragment according to the present invention comprises all of the CDRs comprised by all of the respective VH and VL sequences of gBs3GC4. Alternatively, the isolated multispecific antibody or antigen binding fragment according to the present invention comprises all of the CDRs comprised by all of the respective VH and VL sequences of gBs3GC5.

TABLE 3

SEQ ID numbers of CDR amino acid sequences comprised by the VH or VL amino acid sequences as indicated in the table.

| VL or VH sequence and origin (monospecific AB) | CDR1 | CDR2 | CDR3 |
|---|---|---|---|
| GCA7 VH (SEQ ID NO: 37) | 1 | 2 | 3 |
| GCA7 VL (SEQ ID NO: 38) | 4 | 5, 6 | 7 |
| GCA21 VH (SEQ ID NO: 63) | 49 | 50 | 51 |
| GCA21 VL (SEQ ID NO: 64) | 52 | 53, 54 | 55 |
| GCB59 VH (SEQ ID NO: 95) | 67 | 68 | 69 |
| GCB59 VL (SEQ ID NO: 96) | 70 | 71, 72 | 73 |
| GCE 536 VH (SEQ ID NO: 130) | 105 | 10 | 107 |
| GCE536 VL (SEQ ID NO: 131) | 108 | 109, 110 | 111 |

The multispecific antibody, or the antigen binding fragment thereof, according to the present invention may be used as a medicament. In particular, the multispecific antibody, or the antigen binding fragment thereof, according to the present invention may be used in the prophylaxis, treatment or attenuation of an inflammatory and/or an autoimmune disease. Further details for this use are described below, e.g. in the context of a pharmaceutical composition and of a medical use.

The invention further comprises an antibody, or fragment thereof, that binds to the same epitopes, i.e. to the same at least two different non-overlapping sites in a cytokine, in particular GM-CSF, as an antibody or antigen binding fragment of the invention, or an antibody that competes with an antibody or antigen binding fragment of the invention.

Preferably, the antibody, or the antigen binding fragment thereof, according to the present invention that binds to the same epitope as the antibody as described above, also comprises an Fc moiety. Preferred embodiments described above for the multispecific antibody, or the antigen binding fragment thereof, according to the present invention that comprises:

(a) at least two different domains specifically binding to at least two different, non-overlapping sites in a cytokine; and
(b) an Fc moiety also apply to the antibody, or the antigen binding fragment thereof, according to the present invention that binds to the same epitope as the antibody as described above.

Antibodies of the invention also include hybrid multispecific antibody molecules comprising:

(a) at least two different domains specifically binding to at least two different, non-overlapping sites in a cytokine; and
(b) an Fc moiety as described above, which comprise one or more CDRs from an antibody of the invention and one or more CDRs from another antibody, in particular to the same epitopes or to further epitopes on the same cytokine, in particular GM-CSF, or on another antigen, e.g. another cytokine, a tumor associated epitope, a T cell epitope, a B cell epitope etc. In one embodiment, such hybrid antibodies comprise three CDRs from an antibody of the invention and three CDRs from another antibody, e.g. to the same or other epitopes as described above. Exemplary hybrid antibodies comprise (i) the three heavy chain CDRs from an antibody of the invention and the three light chain CDRs from another antibody to the same or other epitopes as described above, or (ii) the three light chain CDRs from an antibody of the invention and the three heavy chain CDRs from another antibody to the same or other epitopes as described above.

Nucleic Acid Molecule

In another aspect, the invention also provides a nucleic acid molecule comprising a polynucleotide encoding the antibody, or the antigen binding fragment thereof, according to the present invention as described above. Nucleic acid sequences encoding part or all of the light and heavy chains and CDRs of the antibodies of the present invention are preferred. Preferably provided herein are thus nucleic acid sequences encoding part or all of the light and heavy chains, in particular VH and VL sequences and CDRs of the exemplary antibodies of the invention. The SEQ ID numbers for the nucleic acid sequences encoding the VH and VL sequences derived from monospecific antibodies and used in some examples of antibodies of the invention may be derived from Table 7. Table 4 below provides the SEQ ID numbers for the nucleic acid sequences encoding the CDRs of some examples of the antibodies of the invention. Due to the redundancy of the genetic code, the present invention also comprises variants of these nucleic acid sequences encoding the same amino acid sequences.

Thus, the present invention also comprises a nucleic acid molecule comprising a polynucleotide encoding the antibody, or the antigen binding fragment thereof, according to the present invention.

A nucleic acid molecule is a molecule comprising, preferably consisting of nucleic acid components. The term nucleic acid molecule preferably refers to DNA or RNA molecules. In particular, it is used synonymous with the term "polynucleotide". Preferably, a nucleic acid molecule is a polymer comprising or consisting of nucleotide monomers which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

TABLE 4

SEQ ID Numbers for CDR polynucleotides derived from monospecific antibodies as indicated and used in some exemplary antibodies according to the present invention.

| Origin (mono- | SEQ ID NOs. for CDR polynucleotides | | | | | |
|---|---|---|---|---|---|---|
| Specific AB) | CDRH1 | CDRH2 | CDRH3 | CDRL1 | CDRL2 | CDRL3 |
| GCA7 | 8-12 | 13-15 | 16-20 | 21-25 | 26-31 | 32-36 |
| GCA21 | 56 | 57 | 58 | 59 | 60/61 | 62 |
| GCB59 | 74-76 | 77-79 | 80-82 | 83-85 | 86-91 | 92-94 |
| GCE536 | 112-114 | 115 | 116-118 | 119-121 | 122-125 | 126-129 |

Preferably, the sequence of the nucleic acid molecule according to the present invention comprises or consists of a nucleic acid sequence according to any one of SEQ ID NOs: 8-36, 39-48, 56-62, 65-66, 74-94, 97-104, 112-129, 132-139, 152, 154, 156, 158, 160, 162, 164, 166, 168, 170, 172, 174, 176, 178, 180, 182, 184, 186, 188, and 190 or a functional sequence variant thereof.

It is also preferred that nucleic acid sequences according to the invention include nucleic acid sequences having at least 70%, at least 75%, at least 80%, at least 85%, at least 88%, at least 90%, at least 92%, at least 95%, at least 96%, at least 97%, at least 98% or at least 99% identity to the nucleic acid encoding a VH sequence and/or a VL sequence used in an antibody according to the present invention. Thus a nucleic acid molecule is preferred, wherein the polynucleotide sequence comprises or consists of a nucleic acid sequence according to any one of SEQ ID NOs: 39-48, 65-66, 97-104 and 132-139 or a functional sequence variant thereof. More preferably, a nucleic acid molecule according to the present invention comprises or consists of a nucleic acid sequence encoding a complete heavy chain or complete light chain of one of the exemplary antibodies according to the present invention. Thus, a nucleic acid molecule is preferred, wherein the polynucleotide sequence comprises or consists of a nucleic acid sequence according to any one of SEQ ID NOs: 152, 154, 156, 158, 160, 162, 164, 166, 168, 170, 172, 174, 176, 178, 180, 182, 184, 186, 188, and 190 or a functional sequence variant thereof.

In another embodiment, a nucleic acid sequence of the invention has the sequence of a nucleic acid encoding a heavy or light chain CDR of an exemplary antibody of the invention. For example, a nucleic acid sequence according to the invention comprises or consists of a sequence that is at least 75%, at least 80%, at least 85%, at least 88%, at least 90%, at least 92%, at least 95%, at least 96%, at least 97%, at least 98% or at least 99% identical to the nucleic acid sequences of SEQ ID NOs: 8-36, 39-48, 56-62, 65-66, 74-94, 97-104, 112-129, 132-139, 152, 154, 156, 158, 160, 162, 164, 166, 168, 170, 172, 174, 176, 178, 180, 182, 184, 186, 188, and 190.

In general, the nucleic acid molecule may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the CDR regions, VH sequence or VL sequence, or a heavy or a light chain of an (exemplary) antibody of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

Vector

Further included within the scope of the invention are vectors, for example, expression vectors, comprising a nucleic acid sequence according to the invention. Preferably, a vector comprises a nucleic acid molecule according to the invention, for example a nucleic acid molecule as described above.

The term "vector" refers to a nucleic acid molecule, preferably to an artificial nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule.

Thus, the vector may comprise a sequence corresponding, e.g., to a desired antibody or antibody fragment thereof according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

Cells

Cells transformed with such vectors are also included within the scope of the invention. Examples of such cells include but are not limited to, eukaryotic cells, e.g., yeast cells, animal cells or plant cells. In one embodiment the cells are mammalian, e.g., human, CHO, HEK293T, PER.C6, NSO, myeloma or hybridoma cells. Accordingly, the present invention also provides a cell expressing the antibody, or the antigen binding fragment thereof, according to the present invention; or comprising the vector according to the present invention.

In particular, the cell may be transfected with a vector according to the present invention, preferably with an expression vector. The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Polypeptides

The present invention also relates to a polypeptide, e.g. an isolated or purified immunogenic polypeptide, comprising at least two epitopes that specifically bind to the antibody, or the antigen binding fragment thereof, according to the present invention. For example, an (immunogenic) polypeptide according to the present invention may be used for a vaccine, in diagnosis of a disease as described herein and/or during production, purification and/or validation processes and/or during quality controls of an antibody according to the present invention. Preferably, the (immunogenic) polypeptide according to the present invention, which comprises at least two epitopes that specifically bind to the antibody, or the antigen binding fragment thereof, according to the present invention, is a recombinant polypeptide, i.e. a polypeptide which does not occur naturally.

Monoclonal and recombinant antibodies are particularly useful in identification and purification of the individual polypeptides or other antigens against which they are directed. The antibodies of the invention have thus additional utility in that they may be employed as reagents in immunoassays, radioimmunoassays (RIA) or enzyme-linked immunosorbent assays (ELISA). In these applications, the antibodies can be labeled with an analytically-detectable reagent such as a radioisotope, a fluorescent molecule or an enzyme. The antibodies may also be used for the molecular identification and characterization (epitope mapping) of antigens.

The polypeptides that bind to the antibodies of the present invention may thus have a number of uses. The polypeptides and polypeptide variants thereof in purified or synthetic form can be used to raise immune responses (i.e., as a vaccine, or for the production of antibodies for other uses) or for screening sera for antibodies that immunoreact with the epitope or mimotopes thereof. In one embodiment such polypeptides or polypeptide variants, or antigen comprising such polypeptides or polypeptide variants may be used as a vaccine for raising an immune response that comprises antibodies of the same quality as those described in the present invention.

The polypeptides that bind to the antibodies of the present invention may also be useful in screening for ligands that bind to said polypeptides. Such ligands, include but are not limited to antibodies; including those from camels, sharks and other species, fragments of antibodies, peptides, phage display technology products, aptamers, adnectins or fragments of other viral or cellular proteins, may block the epitope and so prevent infection. Such ligands are encompassed within the scope of the invention.

Optional Additional Features of the Antibodies

Antibodies of the invention may be coupled, for example, to a drug for delivery to a treatment site or coupled to a detectable label to facilitate imaging of a site comprising cells of interest. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest on a cytokine, in particular GM-CSF, can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbel liferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include 125I, 131I, 35S, or 3H. Such labeled reagents may be used in a variety of well-known assays, such as radioimmunoassays, enzyme immunoassays, e.g., ELISA, fluorescent immunoassays, and the like. Labeled antibodies according to the present invention may be thus be used in such assays for example as described in U.S. Pat. Nos. 3,766,162; 3,791,932; 3,817,837; and 4,233,402.

An antibody according to the invention may be conjugated to a therapeutic moiety such as a cytotoxin, a therapeutic agent, or a radioactive metal ion or radioisotope.

Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Alternatively, an antibody, or antibody fragment thereof, can be conjugated to a second antibody, or antibody fragment thereof, to form an antibody heteroconjugate as described in U.S. Pat. No. 4,676,980. In addition, linkers may be used between the labels and the antibodies of the invention, e.g., as described in U.S. Pat. No. 4,831,175. Antibodies or, antigen-binding fragments thereof may be directly labeled with radioactive iodine, indium, yttrium, or other radioactive particle known in the art, e.g., as described in U.S. Pat. No. 5,595,721. Treatment may consist of a combination of treatment with conjugated and non-conjugated antibodies administered simultaneously or subsequently e.g., as described in WO00/52031; WO00/52473.

Antibodies of the invention may also be attached to a solid support. Additionally, antibodies of the invention, or functional antibody fragments thereof, can be chemically modified by covalent conjugation to a polymer to, for example, increase their circulating half-life. Examples of polymers, and methods to attach them to peptides, are shown in U.S. Pat. Nos. 4,766,106; 4,179,337; 4,495,285 and 4,609,546. In some embodiments the polymers may be selected from polyoxyethylated polyols and polyethylene glycol (PEG). PEG is soluble in water at room temperature and has the general formula: R(O—CH2-CH2)n O—R where R can be hydrogen, or a protective group such as an alkyl or alkanol group. Preferably, the protective group may have between 1 and 8 carbons. For example, the protective group is methyl. The symbol n is a positive integer. In one embodiment n is between 1 and 1,000. In another embodiment n is between 2 and 500. Preferably, the PEG has an average molecular weight between 1,000 and 40,000, more preferably the PEG has a molecular weight between 2,000 and 20,000, even more preferably the PEG has a molecular weight between 3,000 and 12,000. Furthermore, PEG may have at least one hydroxy group, for example the PEG may have a terminal hydroxy group. For example, it is the terminal hydroxy group which is activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. In one embodiment, POG is used. Without being bound by any theory, because the glycerol backbone of polyoxyethylated glycerol is the same backbone occurring naturally in, for example, animals and humans in mono-, di-, triglycerides, this branching would not necessarily be seen as a foreign agent in the body. POG may have a molecular weight in the same range as PEG. Another drug delivery system that can be used for increasing circulatory half-life is the liposome. Methods of preparing liposome delivery systems are known to one of skill in the art. Other drug delivery systems are known in the art and are described in, for example, referenced in Poznansky et al. (1980) and Poznansky (1984).

Antibodies of the invention may be provided in purified form. Typically, the antibody will be present in a composition that is substantially free of other polypeptides e.g., where less than 90% (by weight), usually less than 60% and more usually less than 50% of the composition is made up of other polypeptides.

Antibodies of the invention may be immunogenic in non-human (or heterologous) hosts e.g., in mice. In particular, the antibodies may have an idiotope that is immunogenic in non-human hosts, but not in a human host. Antibodies of the invention for human use include those that cannot be easily isolated from hosts such as mice, goats, rabbits, rats, non-primate mammals, etc. and cannot generally be obtained by humanization or from xeno-mice.

Production of Antibodies

Antibodies according to the invention can be made by any method known in the art. For example, the general methodology for making monoclonal antibodies using hybridoma technology is well known (Kohler, G. and Milstein, C. 1975; Kozbar et al. 1983). In one embodiment, the alternative EBV immortalization method described in WO2004/076677 is used.

Using the method described in WO 2004/076677, B cells producing the antibody of the invention can be transformed with EBV and a polyclonal B cell activator. Additional stimulants of cellular growth and differentiation may optionally be added during the transformation step to further enhance the efficiency. These stimulants may be cytokines such as IL-2 and IL-15. In one aspect, IL-2 is added during the immortalization step to further improve the efficiency of immortalization, but its use is not essential. The immortalized B cells produced using these methods can then be cultured using methods known in the art and antibodies isolated therefrom.

Using the method described in WO 2010/046775, plasma cells can be cultured in limited numbers, or as single plasma cells in microwell culture plates. Antibodies can be isolated from the plasma cell cultures. Further, from the plasma cell cultures, RNA can be extracted and PCR can be performed using methods known in the art. The VH and VL regions of the antibodies can be amplified by RT-PCR (reverse transcriptase PCR), sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136).

Standard techniques of molecular biology may be used to prepare DNA sequences encoding the antibodies or antibody fragments of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example *E. coli*, and other microbial systems may be used, in part, for expression of antibody fragments such as Fab and F(ab')2 fragments, and especially Fv fragments and single chain antibody fragments, for example, single chain Fvs. Eukaryotic, e.g., mammalian, host cell expression systems may be used for production of larger antibody molecules, including complete antibody molecules. Suitable mammalian host cells include, but are not limited to, CHO, HEK293T, PER.C6, NS0, myeloma or hybridoma cells.

The present invention also provides a process for the production of an antibody molecule according to the present invention comprising culturing a host cell comprising a vector encoding a nucleic acid of the present invention under conditions suitable for expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides. Alternatively, antibodies according to the invention may be produced by (i) expressing a nucleic acid sequence according to the invention in a host cell, and (ii) isolating the expressed antibody product. Additionally, the method may include (iii) purifying the isolated antibody. Transformed B cells and cultured plasma cells may be screened for those producing antibodies of the desired specificity or function.

The screening step may be carried out by any immunoassay, e.g., ELISA, by staining of tissues or cells (including transfected cells), by neutralization assay or by one of a number of other methods known in the art for identifying desired specificity or function. The assay may select on the basis of simple recognition of one or more antigens, or may select on the additional basis of a desired function e.g., to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

Individual transformed B cell clones may then be produced from the positive transformed B cell culture. The cloning step for separating individual clones from the mixture of positive cells may be carried out using limiting dilution, micromanipulation, single cell deposition by cell sorting or another method known in the art.

Nucleic acid from the cultured plasma cells can be isolated, cloned and expressed in HEK293T cells or other known host cells using methods known in the art.

The immortalized B cell clones or the transfected host-cells of the invention can be used in various ways e.g., as a source of monoclonal antibodies, as a source of nucleic acid (DNA or mRNA) encoding a monoclonal antibody of interest, for research, etc.

The invention also provides a composition comprising immortalized B memory cells or transfected host cells that produce antibodies according to the present invention.

The immortalized B cell clone or the cultured plasma cells of the invention may also be used as a source of nucleic acid for the cloning of antibody genes for subsequent recombinant expression. Expression from recombinant sources is more common for pharmaceutical purposes than expression from B cells or hybridomas e.g., for reasons of stability, reproducibility, culture ease, etc.

Thus the invention also provides a method for preparing a recombinant cell, comprising the steps of: (i) obtaining one or more nucleic acids (e.g., heavy and/or light chain mRNAs) from the B cell clone or the cultured plasma cells that encodes the antibody of interest; (ii) inserting the nucleic acid into an expression vector and (iii) transfecting the vector into a host cell in order to permit expression of the antibody of interest in that host cell.

Similarly, the invention provides a method for preparing a recombinant cell, comprising the steps of: (i) sequencing nucleic acid(s) from the B cell clone or the cultured plasma cells that encodes the antibody of interest; and (ii) using the sequence information from step (i) to prepare nucleic acid(s) for insertion into a host cell in order to permit expression of the antibody of interest in that host cell. The nucleic acid may, but need not, be manipulated between steps (i) and (ii) to introduce restriction sites, to change codon usage, and/or to optimize transcription and/or translation regulatory sequences.

Furthermore, the invention also provides a method of preparing a transfected host cell, comprising the step of transfecting a host cell with one or more nucleic acids that encode an antibody of interest, wherein the nucleic acids are nucleic acids that were derived from an immortalized B cell clone or a cultured plasma cell of the invention. Thus the procedures for first preparing the nucleic acid(s) and then using it to transfect a host cell can be performed at different times by different people in different places (e.g., in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture technique can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from B cells or plasma cells are well known in the art (e.g., see Chapter 4 of Kuby Immunology, 4th edition, 2000).

The transfected host cell may be a eukaryotic cell, including yeast and animal cells, particularly mammalian cells (e.g., CHO cells, NSO cells, human cells such as PER.C6 or HKB-11 cells, myeloma cells), as well as plant cells. Preferred expression hosts can glycosylate the antibody of the invention, particularly with carbohydrate structures that are not themselves immunogenic in humans. In one embodiment the transfected host cell may be able to grow in serum-free media. In a further embodiment the transfected host cell may be able to grow in culture without the presence of animal-derived products. The transfected host cell may also be cultured to give a cell line.

The invention also provides a method for preparing one or more nucleic acid molecules (e.g., heavy and light chain genes) that encode an antibody of interest, comprising the steps of: (i) preparing an immortalized B cell clone or culturing plasma cells according to the invention; (ii) obtaining from the B cell clone or the cultured plasma cells nucleic acid that encodes the antibody of interest. Further, the invention provides a method for obtaining a nucleic acid sequence that encodes an antibody of interest, comprising the steps of: (i) preparing an immortalized B cell clone or culturing plasma cells according to the invention; (ii) sequencing nucleic acid from the B cell clone or the cultured plasma cells that encodes the antibody of interest.

The invention further provides a method of preparing nucleic acid molecule(s) that encode an antibody of interest, comprising the step of obtaining the nucleic acid that was obtained from a transformed B cell clone or cultured plasma cells of the invention. Thus the procedures for first obtaining the B cell clone or the cultured plasma cell, and then obtaining nucleic acid(s) from the B cell clone or the cultured plasma cells can be performed at different times by different people in different places (e.g., in different countries).

The invention also comprises a method for preparing an antibody (e.g., for pharmaceutical use) according to the present invention, comprising the steps of: (i) obtaining and/or sequencing one or more nucleic acids (e.g., heavy and light chain genes) from the selected B cell clone or the cultured plasma cells expressing the antibody of interest; (ii) inserting the nucleic acid(s) into or using the nucleic acid(s) sequence(s) to prepare an expression vector; (iii) transfecting a host cell that can express the antibody of interest; (iv) culturing or sub-culturing the transfected host cells under conditions where the antibody of interest is expressed; and, optionally, (v) purifying the antibody of interest.

The invention also provides a method of preparing an antibody comprising the steps of: culturing or sub-culturing a transfected host cell population under conditions where the antibody of interest is expressed and, optionally, purifying the antibody of interest, wherein said transfected host cell population has been prepared by (i) providing nucleic acid(s) encoding a selected antibody of interest that is produced by a B cell clone or cultured plasma cells prepared as described above, (ii) inserting the nucleic acid(s) into an expression vector, (iii) transfecting the vector in a host cell that can express the antibody of interest, and (iv) culturing or sub-culturing the transfected host cell comprising the inserted nucleic acids to produce the antibody of interest. Thus the procedures for first preparing the recombinant host cell and then culturing it to express antibody can be performed at very different times by different people in different places (e.g., in different countries).

Pharmaceutical Compositions

The present invention also provides a pharmaceutical composition comprising one or more of:

(i) the antibody, or antibody fragments according to the present invention;
(ii) the nucleic acid encoding the antibody, or antibody fragments according to the present invention;
(iii) the vector encoding the nucleic acid according to the present invention;
(iv) the cell expressing the antibody according to the present invention or comprising the vector according to the present invention; or
(v) the immunogenic polypeptide recognized by the antibodies or antigen binding fragment thereof according to the present invention.

The pharmaceutical composition may also contain a pharmaceutically acceptable carrier, diluent and/or excipient. Preferably, the pharmaceutical composition according to the present invention comprises one or more of:

(i) the antibody, or antibody fragments according to the present invention;
(ii) the nucleic acid encoding the antibody, or antibody fragments according to the present invention;
(iii) the vector encoding the nucleic acid according to the present invention;
(iv) the cell expressing the antibody according to the present invention or comprising the vector according to the present invention; or
(v) the immunogenic polypeptide recognized by the antibodies or antigen binding fragment thereof according to the present invention; and a pharmaceutically acceptable excipient, diluent and/or carrier.

Although the carrier or excipient may facilitate administration, it should not itself induce the production of antibodies harmful to the individual receiving the composition. Nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Compositions of the invention may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, like Synagis™ and Herceptin™, for reconstitution with sterile water containing a preservative). The composition may be prepared for topical administration e.g., as an ointment, cream or powder. The composition may be prepared for oral administration e.g., as a tablet or capsule, as a spray, or as a syrup (optionally flavored). The composition may be prepared for pulmonary administration e.g., as an inhaler, using a fine powder or a spray. The composition may be prepared as a suppository or pessary. The composition may be prepared for nasal, aural or ocular administration e.g., as drops. The composition may be in kit form, designed such that a combined composition is reconstituted just prior to administration to a subject. For example, a lyophilized antibody can be provided in kit form with sterile water or a sterile buffer.

It is preferred that the active ingredient in the composition is an antibody molecule, an antibody fragment or variants and derivatives thereof, in particular the active ingredient in the composition is an antibody, an antibody fragment or variants and derivatives thereof, according to the present invention. As such, it may be susceptible to degradation in the gastrointestinal tract. Thus, if the composition is to be administered by a route using the gastrointestinal tract, the composition may contain agents which protect the antibody from degradation but which release the antibody once it has been absorbed from the gastroi ntesti nal tract.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in other embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Within the scope of the invention are compositions present in several forms of administration; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid.A vehicle is typically understood to be a material that is suitable for storing, transporting, and/or administering a compound, such as a pharmaceutically active compound, in particular the antibodies according to the present invention. For example, the vehicle may be a physiologically acceptable liquid, which is suitable for storing, transporting, and/or administering a pharmaceutically active compound, in particular the antibodies according to the present invention. Once formulated, the compositions of the invention can be administered directly to the subject. In one embodiment the compositions are adapted for administration to mammalian, e.g., human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Preferably, the pharmaceutical composition may be prepared for oral administration, e.g. as tablets, capsules and the like, for topical administration, or as injectable, e.g. as liquid solutions or suspensions. Solid forms suitable for solution in, or suspension in, liquid vehicles prior to injection may also be prepared.

For injection, e.g. intravenous, cutaneous or subcutaneous injection, or injection at the site of affliction, the active ingredient will preferably be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount" or a "therapeutically effective amount" (as the case may be), this being sufficient to show benefit to the individual. The actual amount administered, and rate and time-course of administration, will depend on the nature and severity of what is being treated. For injection, the pharmaceutical composition according to the present invention may be provided for example in a pre-filled syringe.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the inventive transporter cargo conjugate molecule as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive pharmaceutical composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

Dosage treatment may be a single dose schedule or a multiple dose schedule, whereby in the context of the present invention a multiple dose schedule is preferred. Known antibody-based pharmaceuticals, in particular anti-cytokine, e.g. anti-GM-CSF, based pharmaceuticals provide guidance relating to frequency of administration e.g., whether a pharmaceutical should be delivered daily, weekly, monthly, etc. Frequency and dosage may also depend on the severity of symptoms.

For example, the pharmaceutical composition according to the present invention may be administered daily, e.g. once or several times per day, e.g. once, twice, three times or four times per day, preferably once or twice per day, more preferable once per day, for 1, 2, 3, 4, 5, 6, 7, 8, 9, 10, 11, 12, 13, 14, 15, 16, 17, 18, 19, 20 or 21 or more days, e.g. daily for 1, 2, 3, 4, 5, 6 months. Preferably, the pharmaceutical composition according to the present invention may be administered weekly, e.g. once or twice, preferably once per week, for 1, 2, 3, 4, 5, 6, 7, 8, 9, 10, 11, 12, 13, 14, 15, 16, 17, 18, 19, 20 or 21 or more weeks, e.g. weekly 1, 2, 3, 4, 5, 6, 7, 8, 9, 10, 11, or 12 months or weekly for 2, 3, 4, or 5 years.

In particular, it is preferred that for a single dose, e.g. a daily, weekly or monthly dose, preferably for a weekly dose, the amount of the antibody, or the antigen binding fragment thereof, in the pharmaceutical composition according to the present invention, does not exceed 150 mg, preferably does not exceed 100 mg, more preferably does not exceed 50 mg, even more preferably does not exceed 20 mg, and particularly preferably does not exceed 10 mg. This amount of antibody preferably refers to a single dose as described above, which is for example administered daily, weekly etc. as described above. Such a low amount of the antibody according to the present invention could be produced and formulated in a stable form (e.g., in a lyophilized formulation, where for instance previous studies have shown that monoclonal antibodies preserved by lyophilization are stable for 33 months at 40° C. and 5 months at 50° C.) and at an affordable cost.

Pharmaceutical compositions typically include an effective amount of one or more antibodies of the invention and/or a polypeptide comprising an epitope that binds an antibody of the invention i.e., an amount that is sufficient to treat, ameliorate, attenuate or prevent a desired disease or condition, or to exhibit a detectable therapeutic effect. Therapeutic effects also include reduction or attenuation in pathogenic potency or physical symptoms. The precise effective amount for any particular subject will depend upon their size, weight, and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.005 to about 100 mg/kg, preferably from about 0.0075 to about 50 mg/kg, more preferably from about 0.01 to about 10 mg/kg, even more preferably from about 0.02 to about 5 mg/kg, and particularly preferably from about 0.03 to about 1 mg/kg of the antibody of the present invention (e.g. amount of the antibody in the pharmaceutical composition) in relation to the bodyweight (e.g., in kg) of the individual to which it is administered.

Moreover, the pharmaceutical composition according to the present invention may also comprises at least two antibodies or antigen binding fragments thereof, according to the present invention, wherein the two antibodies, or the antigen binding fragments thereof, specifically bind to a different set of non-overlapping epitopes on the cytokine, in particular on GM-CSF. For example, the pharmaceutical composition according to the present invention comprises a first antibody or an antigen binding fragment thereof, according to the present invention, and a second antibody, or an antigen binding fragment thereof, according to the present invention, wherein the first antibody, or the antigen binding fragment thereof, specifically binds to a first set of non-overlapping epitopes on the cytokine, in particular on GM-CSF, which is different from the set of non-overlapping epitopes on the cytokine, in particular on GM-CSF to which the second antibody or the second antigen binding fragment thereof binds. "Different sets of non-overlapping epitopes on the cytokine, in particular on. GM-CSF" means herein that for example a first set includes an epitope I and an epitope II on a cytokine and a second (different) set includes an epitope I and an epitope III on a cytokine. Thus, the different sets may be overlapping, i.e. comprise the same epitopes, however they usually differ in at least one epitope. Preferably, however, the different sets of epitopes are non-overlapping, i.e. the first antibody binds to at least two different sites on a cytokine, e.g. GM-CSF, wherein each of the at least two different sites is different from the at least two different sites on a cytokine, e.g. GM-CSF, to which the second antibody binds. For example, if the pharmaceutical composition according to the present invention comprises two antibodies or antigen binding fragments thereof, according to the present invention, and the first antibody, or the antigen binding fragment thereof, specifically binds to non-overlapping sites I and II on the cytokine, in particular on GM-CSF, the second antibody, or the antigen binding fragment thereof, may specifically bind to non-overlapping sites III and IV on the cytokine, in particular GM-CSF. In such a way all (non-overlapping) sites on a cytokine, e.g. GM-CSF, may be covered by antibodies according to the present invention.

Moreover, the pharmaceutical composition may also contain more than two, e.g. 3, 4, 5, 6, etc., antibodies according to the present invention, whereby at least two, preferably more than two, more preferably all antibodies contained, bind to different sets of epitopes on the cytokine, e.g. GM-CSF.

Preferably, the two antibodies according to the present invention are present in the pharmaceutical composition at equimolar amounts, preferably as an equimolar mixture.

Preferably, compositions can include two or more (e.g., 2, 3, 4, 5 etc.) antibodies of the invention to provide an additive or synergistic therapeutic effect. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

In another embodiment, the composition may comprise one or more (e.g., 2, 3, etc.) antibodies according the invention and one or more (e.g., 2, 3, etc.) additional antibodies against the cytokine, in particular GM-CSF. Further, the administration of antibodies of the invention together with antibodies specific to other cytokines or, more generally, to other antigens, are within the scope of the invention. The antibodies of the invention can be administered either combined/simultaneously or at separate times from antibodies specific to other cytokines or, more generally, to other antigens.

Examples of antibodies of the invention against a cytokine, in particular against GM-CSF, include, but are not limited to, Ts1GC1, Ts1GC2a, Ts2GC2b, Ts2GC2c, Ts3GC2d, Ts3GC2e, Bs3GC1a, Bs3GC1b, Bs2GC1c, Bs2GC1d, Bs1GC2a, Bs3GC2b, Bs1GC3a, Bs3GC3b, Bs3GC4, and Bs3GC5.

Moreover, a pharmaceutical composition comprising the antibody according to gTs1GC1 or an antigen binding fragment thereof, and a pharmaceutically acceptable carrier is also preferred. A pharmaceutical composition comprising the antibody according to gTs1GC2a or an antigen binding fragment thereof, and a pharmaceutically acceptable carrier is also preferred. A pharmaceutical composition comprising the antibody according to gTs2GC2b or an antigen binding fragment thereof, and a pharmaceutically acceptable carrier is also preferred. A pharmaceutical composition comprising the antibody according to gTs2GC2c or an antigen binding fragment thereof, and a pharmaceutically acceptable carrier is also preferred. A pharmaceutical composition comprising the antibody according to gTs3GC2d or an antigen binding fragment thereof, and a pharmaceutically acceptable carrier is also preferred. A pharmaceutical composition comprising the antibody according to gTs3GC2e or an antigen binding fragment thereof, and a pharmaceutically acceptable carrier is also preferred. A pharmaceutical composition comprising the antibody according to gBs3GC1 a or an antigen binding fragment thereof, and a pharmaceutically acceptable carrier is also preferred. A pharmaceutical composition comprising the antibody according to gBs3GC1b or an antigen binding fragment thereof, and a pharmaceutically acceptable carrier is also preferred. A pharmaceutical composition comprising the antibody according to gBs2GC1c or an antigen binding fragment thereof, and a pharmaceutically acceptable carrier is also preferred. A pharmaceutical composition comprising the antibody according to gBs2GC1d or an antigen binding fragment thereof, and a pharmaceutically acceptable carrier is also preferred. A pharmaceutical composition comprising the antibody according to gBs1GC2a or an antigen binding fragment thereof, and a pharmaceutically acceptable carrier is also preferred. A pharmaceutical composition comprising the antibody according to gBs3GC2b or an antigen binding fragment thereof, and a pharmaceutically acceptable carrier is also preferred. A pharmaceutical composition comprising the antibody according to gBs1GC3a or an antigen binding fragment thereof, and a pharmaceutically acceptable carrier is also preferred. A pharmaceutical composition comprising the antibody according to gBs3GC3b or an antigen binding fragment thereof, and a pharmaceutically acceptable carrier is also preferred. A pharmaceutical composition comprising the antibody according to gBs3GC4 or an antigen binding fragment thereof, and a pharmaceutically acceptable carrier is also preferred. A pharmaceutical composition comprising the antibody according to gBs3GC5 or an antigen binding fragment thereof, and a pharmaceutically acceptable carrier is also preferred.

In addition, a pharmaceutical composition comprising the antibody Ts1GC1 or an antigen binding fragment thereof, and a pharmaceutically acceptable carrier is also preferred. A pharmaceutical composition comprising the antibody Ts1GC2a or an antigen binding fragment thereof, and a pharmaceutically acceptable carrier is also preferred. A pharmaceutical composition comprising the antibody Ts2GC2b or an antigen binding fragment thereof, and a pharmaceutically acceptable carrier is also preferred. A pharmaceutical composition comprising the antibody Ts2GC2c or an antigen binding fragment thereof, and a pharmaceutically acceptable carrier is also preferred. A pharmaceutical composition comprising the antibody Ts3GC2d or an antigen binding fragment thereof, and a pharmaceutically acceptable carrier is also preferred. A pharmaceutical composition comprising the Ts3GC2e or an antigen binding fragment thereof, and a pharmaceutically acceptable carrier is also preferred. A pharmaceutical composition comprising the antibody Bs3GC1a or an antigen binding fragment thereof, and a pharmaceutically acceptable carrier is also preferred. A pharmaceutical composition comprising the antibody Bs3GC1b or an antigen binding fragment thereof, and a pharmaceutically acceptable carrier is also preferred. A pharmaceutical composition comprising the antibody Bs2GC1c or an antigen binding fragment thereof, and a pharmaceutically acceptable carrier is also preferred. A pharmaceutical composition comprising the antibody Bs2GC1d or an antigen binding fragment thereof, and a pharmaceutically acceptable carrier is also preferred. A pharmaceutical composition comprising the antibody Bs1GC2a or an antigen binding fragment thereof, and a pharmaceutically acceptable carrier is also preferred. A pharmaceutical composition comprising the antibody Bs3GC2b or an antigen binding fragment thereof, and a pharmaceutically acceptable carrier is also preferred. A pharmaceutical composition comprising the antibody Bs1GC3a or an antigen binding fragment thereof, and a pharmaceutically acceptable carrier is also preferred. A pharmaceutical composition comprising the antibody Bs3GC3b or an antigen binding fragment thereof, and a pharmaceutically acceptable carrier is also preferred. A pharmaceutical composition comprising the antibody Bs3GC4 or an antigen binding fragment thereof, and a pharmaceutically acceptable carrier is also preferred. A pharmaceutical composition comprising the antibody Bs3GC5 or an antigen binding fragment thereof, and a pharmaceutically acceptable carrier is also preferred.

In one embodiment, a composition of the invention may include antibodies of the invention, wherein the antibodies may make up at least 50% by weight (e.g., 60%, 70%, 75%, 80%, 85%, 90%, 95%, 97%, 98%, 99% or more) of the total protein in the composition. In such a composition, the antibodies are preferably in purified form.

The present invention also provides a method of preparing a pharmaceutical composition comprising the steps of: (i) preparing an antibody of the invention; and (ii) admixing the purified antibody with one or more pharmaceutically-acceptable carriers.

In another embodiment, a method of preparing a pharmaceutical composition comprises the step of: admixing an antibody with one or more pharmaceutically-acceptable carriers, wherein the antibody is a monoclonal antibody that was obtained from a transformed B cell or a cultured plasma cell of the invention. Thus the procedures for first obtaining the monoclonal antibody and then preparing the pharmaceutical can be performed at very different times by different people in different places (e.g., in different countries).

As an alternative to delivering antibodies or B cells for therapeutic purposes, it is possible to deliver nucleic acid (typically DNA) that encodes the monoclonal antibody (or active fragment thereof) of interest derived from the B cell or the cultured plasma cells to a subject, such that the nucleic acid can be expressed in the subject in situ to provide a desired therapeutic effect. Suitable gene therapy and nucleic acid delivery vectors are known in the art.

Compositions may include an antimicrobial, particularly if packaged in a multiple dose format. They may comprise detergent e.g., a Tween (polysorbate), such as Tween 80. Detergents are generally present at low levels e.g., less than 0.01%. Compositions may also include sodium salts (e.g., sodium chloride) to give tonicity. For example, a concentration of 10±2 mg/ml NaCl is typical.

Further, compositions may comprise a sugar alcohol (e.g., mannitol) or a disaccharide (e.g., sucrose or trehalose) e.g., at around 15-30 mg/ml (e.g., 25 mg/ml), particularly if they are to be lyophilized or if they include material which has been reconstituted from lyophilized material. The pH of a composition for lyophilisation may be adjusted to between 5 and 8, or between 5.5 and 7, or around 6.1 prior to lyophilisation.

The compositions of the invention may also comprise one or more immunoregulatory agents. In one embodiment, one or more of the immunoregulatory agents include(s) an adjuvant.

Medical Treatments and Uses

In a further aspect, the present invention provides the use of an antibody, or an antigen binding fragment thereof, according to the present invention, the nucleic acid according to the present invention, the vector according to the present invention, the cell according to the present invention, the immunogenic polypeptide according to the present invention, or the pharmaceutical composition according to the present invention in (i) prophylaxis, treatment or attenuation of inflammatory and/or autoimmune diseases; or in (ii) diagnosis of inflammatory and/or autoimmune diseases.

Inflammatory diseases may be due to a variety of causes. In the context of the present invention preferably such inflammatory diseases may be treated, attenuated and/or prevented, which are due to physical causes, e.g. burns, frostbite, physical injury, blunt or penetrating, foreign bodies including splinters, dirt and debris, trauma and ionizing radiation; biological causes, e.g. infection by pathogens, immune reactions due to hypersensitivity, and stress; and chemical causes, e.g. chemical irritants, toxins, and alcohol.

Inflammatory diseases (also referred to as inflammatory disorders) include the following diseases and, thus, in the context of the present invention an inflammatory disease may be preferably selected from the group consisting of appendicitis, bursitis, colitis, cystitis, dermatitis, phlebitis, RSD/CRPS, rhinitis, tendonitis, tonsillitis, vasculitis, Alzheimer's disease, ankylosing spondylitis, arthritis (osteoarthritis, rheumatoid arthritis (RA), psoriatic arthritis, asthma, atherosclerosis, Crohn's disease, colitis, dermatitis, diverticulitis, fibromyalgia, hepatitis, irritable bowel syndrome (IBS), systemic lupus erythematous (SLE), nephritis, Parkinson's disease, ulcerative colitis, Acne vulgaris, autoinflammatory diseases, celiac disease, prostatitis, pulmonary alveolar proteinosis, glomerulonephritis, hypersensitivities, inflammatory bowel diseases, pelvic inflammatory disease, reperfusion injury, sarcoidosis, transplant rejection, vasculitis, interstitial cystitis, inflammatory myopathies, encephalomyelitis, in particular acute disseminated encephalomyelitis, spondylitis, in particular ankylosing spondylitis, antisynthetase syndrome, dermatitis, in particular atopic dermatitis or contact dermatitis, hepatitis, in particular autoimmune hepatitis, autoimmune peripheral neuropathy, pancreatitis, in particular autoimmune pancreatitis, Behcet's disease, Bickerstaff's, encephalitis, Blau syndrome, Coeliac disease, Chagas disease, polyneuropathy, in particular chronic inflammatory demyelinating polyneuropathy, osteomyelitis, in particular chronic recurrent multifocal osteomyelitis, Churg-Strauss syndrome, Cogan syndrome, giant-cell arteritis, CREST syndrome, vasculitis, in particular cutaneous small-vessel vasculitis and urticarial vasculitis, dermatitis herpetiformis, dermatomyositis, systemic scleroderma, Dressler's syndrome, drug-induced lupus erythematosus, discoid lupus erythematosus, enthesitis, eosinophilic fasciitis, eosinophilic gastroenteritis, erythema nodosum, Idiopathic pulmonary fibrosis, gastritis, Grave's disease, Guillain-barre syndrome, Hashimoto's thyroiditis, Henoch-Schonlein purpura, Hidradenitis suppurativa, Idiopathic inflammatory demyelinating diseases, myositis, in particular inclusion body myositis, cystitis, in particular interstitial cystitis, Kawasaki disease, Lichen planus, lupoid hepatitis, Majeed syndrome, Ménière's disease, microscopic polyangiitis, mixed connective tissue disease, myelitis, in particular neuromyelitis optica, thyroiditis, in particular Ord's thyroiditis, rheumatism, in particular palindromic rheumatism, Parsonage-Turner syndrome, pemphigus vulgaris, perivenous encephalomyelitis, polyarteritis nodosa, polymyalgia, in particular polymyalgia rheumatica, polymyositis, cirrhosis, in particular primary biliary cirrhosis, cholangitis, in particular primary sclerosing cholangitis, progressive inflammatory neuropathy, Rasmussen's encephalitis, relapsing polychondritis, arthritis, in particular reactive arthritis (Reiter disease) and rheumatoid arthritis, rheumatic fever, sarcoidosis, Schnitzler syndrome, serum sickness, spondyloarthropathy, Takayasu's arteritis, Tolosa-Hunt syndrome, transverse myelitis, and Wegener's granulomatosis.

Autoimmune disorders (also referred to as autoimmune diseases) include the following diseases and, thus, in the context of the present invention an autoimmune disease may be preferably selected from the group consisting of autoimmune diseases of the CNS, auto-inflammatory diseases, Celiac disease; Sjogren's syndrome, systemic lupus erythematosus, Blau syndrome, Bullous pemphigoid, Cancer, Castleman's disease, Celiac disease, Chagas disease, Chronic inflammatory demyelinating polyneuropathy, Chronic recurrent multifocal osteomyelitis, chronic obstructive pulmonary disease, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Dercum's disease, Dermatitis herpetiformis, Dermatomyositis, Diabetes mellitus type 1, Diffuse cutaneous systemic sclerosis, Dressler's syndrome, lupus, Discoid lupus erythematosus, Eczema, Acute disseminated encephalomyelitis (ADEM), Addison's disease, Agammaglobulinemia, Amyotrophic lateral sclerosis (Also Lou Gehrig's disease; Motor Neuron Disease), Ankylosing Spondylitis Antiphospholipid syndrome, Antisynthetase syndrome, Atopic dermatitis, Autoimmune aplastic anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune urticarial, Autoimmune uveitis, Balo disease/Balo concentric sclerosis, Behcet's disease, Berger's disease, Bickerstaff's encephalitis, Endometriosis, Enthesitis-related arthritis, Eosinophilic gastroenteritis, Epidermolysis bullosa acquisita, Erythroblastosis fetalis, Evan's syndrome, Fibrodysplasia ossificans, Fibrosing alveolitis (or Idiopathic pulmonary fibrosis), Gastritis, Glomerulonephritis, Goodpasture's syndrome, Graves' disease, Guillain-Barre syndrome, Hashimoto's encephelopathy, Hashimoto's thyroiditis, Gestational Pemphigoid, Hidradenitis suppurativa, Hypogannmaglobulinennia, Idiopathic thrombocytopenic purpura (Autoimmune thrombocytopenic purpura), IgA nephropathy, Occular cicatricial pemphigoid, Inclusion body myositis, Rheumatoid arthritis, Chronic inflammatory Rheumatic fever, demyelinating polyneuropathy, Sarcoidosis, Palindromic rheumatism, Interstitial cystitis, Juvenile idiopathic Schizophrenia, PANDAS (pediatric arthritis aka Juvenile autoimmune rheumatoid arthritis), Schmidt syndrome, neuropsychiatric Kawasaki's disease another form of APS, Schnitzler syndrome, Paraneoplastic cerebellar myasthenic syndrome, Leukocytoclastic Serum Sickness, Lichen planus, Sjogren's syndrome, Lichen sclerosus, Parsonage-Turner, Linear IgA disease, Still's disease, Pemphigus vulgaris, Lupoid hepatitis, Autoimmune hepatitis, Stiff person syndrome, Pernicious anaemia, Subacute bacterial endocarditis (SBE), POEMS syndrome, Lupus erythematosus, Sweet's syndrome, Sympathetic ophthalmia, Meniere's disease, Systemic lupus, Primary biliary cirrhosis, Miller-Fisher syndrome, Takayasu's arteritis, cholangitis, Progressive inflammatory neuropathy, Mucha-Habermann disease, Psoriasis, Psoriatic arthritis, Pyoderma gangrenosum, Multiple sclerosis, Pure red cell aplasia, Rasmussen's encephalitis, Myasthenia gravis, Transverse myelitis, Raynaud phenomenon, Microscopic colitis, Ulcerative colitis, Myositis, idiopathic inflammatory bowel disease (IBD), Neuromyelitis optica, Devic's disease, and Neuromyotonia.

Typically, autoimmune diseases arise from an abnormal immune response of the body against substances and tissues normally present in the body (autoimmunity). This may be restricted to certain organs (e.g. in autoimmune thyroiditis) or may involve a particular tissue in different places (e.g. Goodpasture's disease which may affect the basement membrane in both the lung and the kidney). Autoimmune diseases may be classified by corresponding type of hypersensitivity: type I (i.e. urticaria induced by autologous serum), type II, type III, or type IV.

In particular, at least some autoimmune disorders may also be inflammatory diseases and vice versa.

Autoimmune diseases and/or inflammatory diseases, which are preferably treated, prevented and/or attenuated in the context of the present invention, include multiple sclerosis, pulmonary alveolar proteinosis, arthritis, in particular rheumatoid arthritis, and asthma.

Within the scope of the invention are several forms and routes of administration of the antibody, or the antigen binding fragment thereof, the nucleic acid, the vector, the cell, the immunogenic polypeptide, or the pharmaceutical composition, as described above, in respect to the pharmaceutical composition. This applies also in the context of the use of the antibody, or the antigen binding fragment thereof, the nucleic acid, the vector, the cell, the immunogenic polypeptide as described herein, in particular regarding preferred forms and routes of administration.

Methods of diagnosis may include contacting an antibody or an antibody fragment with a sample. Such samples may be isolated from a subject, for example an isolated tissue sample taken from, for example, nasal passages, sinus cavities, salivary glands, lung, liver, pancreas, kidney, ear, eye, placenta, alimentary tract, heart, ovaries, pituitary, adrenals, thyroid, brain, skin or blood, preferably serum. The methods of diagnosis may also include the detection of an antigen/antibody complex, in particular following the contacting of an antibody or an antibody fragment with a sample. Such a detection step is typically performed at the bench, i.e. without any contact to the human or animal body. Examples of detection methods include e.g. ELISA (enzyme-linked immunosorbent assay).

The invention also provides the use of (i) an antibody, an antibody fragment, or variants and derivatives thereof according to the invention, (ii) an immortalized B cell clone according to the invention, (iii) a nucleic acid or a vector according to the present invention or (iv) a pharmaceutical composition of the invention in (a) the manufacture of a medicament for the treatment or attenuation of inflammatory and/or autoimmune diseases or (b) diagnosis of inflammatory and/or autoimmune diseases.

The invention also provides a composition of the invention for use as a medicament for the prevention or treatment of inflammatory and/or autoimmune diseases. It also provides the use of an antibody of the invention and/or a protein comprising an epitope to which such an antibody binds in the manufacture of a medicament for treatment of a subject and/or diagnosis in a subject. It also provides a method for treating a subject, comprising the step of administering to the subject a composition of the invention. In some embodiments the subject may be a human. One way of checking efficacy of therapeutic treatment involves monitoring disease symptoms after administration of the composition of the invention. Treatment can be a single dose schedule or a multiple dose schedule.

In one embodiment, an antibody, antibody fragment, immortalized B cell clone, or pharmaceutical composition according to the invention is administered to a subject in need of such treatment. Such a subject includes, but is not limited to, one who is particularly at risk of or susceptible to inflammatory and/or autoimmune diseases.

Antibodies and fragments thereof as described in the present invention may also be used in a kit for the diagnosis of inflammatory and/or autoimmune diseases. Further, at least two epitopes, in particular of a cytokine, e.g. GM-CSF, capable of binding an antibody of the invention may be used in a kit for monitoring the efficacy of application procedures by detecting the presence or determining the titer of the protective anti-cytokine, in particular anti-GM-CSF, antibodies.

The invention also provides a method of preparing a pharmaceutical, comprising the step of admixing a monoclonal antibody with one or more pharmaceutically-acceptable carriers, wherein the monoclonal antibody is a monoclonal antibody that was obtained from a transfected host cell of the invention. Thus the procedures for first obtaining the monoclonal antibody (e.g., expressing it and/or purifying it) and then admixing it with the pharmaceutical carrier(s) can be performed at very different times by different people in different places (e.g., in different countries).

Starting with a transformed B cell or a cultured plasma cell of the invention, various steps of culturing, sub-culturing, cloning, sub-cloning, sequencing, nucleic acid preparation etc. can be performed in order to perpetuate the antibody expressed by the transformed B cell or the cultured plasma cell, with optional optimization at each step. In one embodiment, the above methods further comprise techniques of optimization (e.g., affinity maturation or optimization) applied to the nucleic acids encoding the antibody. The invention encompasses all cells, nucleic acids, vectors, sequences, antibodies etc. used and prepared during such steps.

In all these methods, the nucleic acid used in the expression host may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the CDR regions, heavy chain variable regions or light chain variable regions of antibodies of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

The present invention is not to be limited in scope by the specific embodiments described herein. Indeed, various modifications of the invention in addition to those described herein will become apparent to those skilled in the art from the description and accompanying figures. Such modifications fall within the scope of the appended claims.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated by reference in their entirety. In the case of conflict, the present specification, including definitions, will control.

The following Figures, Sequences and Examples are intended to illustrate the invention further. They are not intended to limit the subject matter of the invention thereto.

DESCRIPTION OF FIGURES

FIG. 6 shows the extremely potent neutralization of GM-CSF by TsgC2d and BsGC3a as compared to single antibodies or combinations of antibodies forming TsgC2d and BsGC3a.

EXAMPLES

Figure 1:
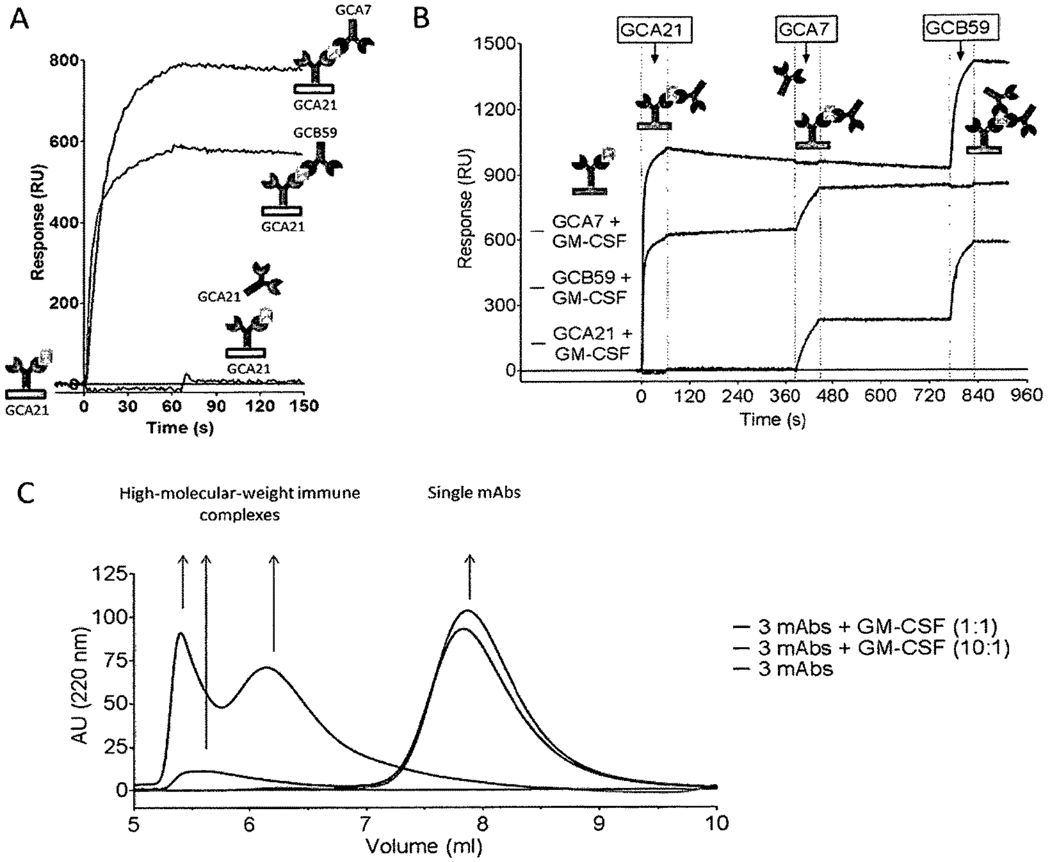
FIG. 1 shows (A) SPR cross-competition between GCA21, GCA7 and GCB59, (B) A multichannel chip coated with GCA21, GCA7 or site IV GCB59 was saturated with GM-CSF and serially exposed to an excess of the same antibodies. (C) SEC-HPLC profile of samples containing the three non-cross-competing antibodies, alone or with GM-CSF added in equimolar concentrations (1:1) or in 10-fold antibody excess (10:1).

Exemplary embodiments of the present invention are provided in the following examples. The following examples are presented only by way of illustration and to assist one of ordinary skill in using the invention. The examples are not intended in any way to otherwise limit the scope of the invention.

Example 1

Isolation and Characterization GM-CSF-Specific Antibodies

Peripheral blood samples were collected from five pulmonary alveolar proteinosis (PAP) patients. IgG memory B cells were isolated from cryopreserved or fresh PBMCs by a combination of magnetic and fluorescence-activated cell sorting, in particular using anti-FITC microbeads (Miltenyi Biotec) following staining of PBMCs with CD22-FITC (BD Phamingen). IgG memory B cells were then immortalized in clonal conditions with EBV (Epstein-Barr virus) and CpG in 384 well micro-plates in the presence of feeder cells as described by Traggiai E. et al. (2004) Nat Med. 10(8):871-5 and WO 2004/076677 A2. The culture supernatants were screened for the presence of GM-CSF-specific IgG antibodies by ELISA. Four immortalized B cell clones that produced GM-CSF monoclonal antibodies were identified. cDNA was synthesized from positive cultures and the antibody V genes (heavy chain and light chain variable regions) were sequenced and analyzed using the IMGT database (http://www.imgt.org/). The V(D)J gene usage of the four PAP autoantibodies is shown in Table 5.

TABLE 5

V(D)J gene usage of the 4 PAP autoantibodies. The antibodies use different V, D and J genes and are somatically mutated. The load of somatic mutations was comparable to that characteristic of T-cell-dependent responses against non-self-antigens, ranging from 8.8% to 16.7% in the VH gene segment and from 0% to 8.6% in the VL gene segment.

| mAb | Heavy chain VDJ genes (% identity to GL) | | | | | Light chain VJ genes (% identity to GL) | | | |
|---|---|---|---|---|---|---|---|---|---|
| GCA7 | VH3-66 | (91.2) | D3-10 | JH4 | (93.8) | VK4-1 | (96) | JK3 | (100) |
| GCA21 | VH3-30-3 | (83.3) | D2-15 | JH2 | (84.9) | VK1-5 | (92.8) | JK4 | (97.2) |
| GCB59 | VH3-21 | (86.8) | D2-15 | JH6 | (77.4) | VL3-21 | (92.1) | JL2 | (91.9) |
| GCE536 | VH1-46 | (87.9) | D2-2 | JH6 | (85.5) | VK3-20 | (91.5) | JK2 | (92.1) |

All antibodies were recombinantly produced as IgG1 by transient transfection of HEK 293 Freestyle Cells (Invitrogen) using polyethylenimine (PEI). The antibodies were then tested for binding to human GM-CSF by ELISA. Binding properties and V-gene usage is shown in Table 5. The antibodies showed high affinities comparable to the antibodies MOR103 and namilumab, which are GM-CSF neutralizing monoclonal antibodies under clinical development, which serve herein as reference antibodies. The EC50 values (ng/ml) were determined by ELISA and calculated for every sample by nonlinear regression analysis using GraphPad Prism 5 software. The EC50 values ranged from 61.4 to 307.6 ng/ml. Interestingly, the antibodies did not cross-react with both mouse and rat GM-CSF.

The kinetics of binding was determined by surface plasmon resonance (SPR). Briefly, for SPR Protein A (450 nM) was stabilized in 10 mM acetate buffer, pH 4.5, and immobilized onto a EDC/NHS pre-activated ProteOn sensor chip (Biorad) through amine coupling; unreacted groups were blocked by injection of ethanolamine HCl (1 M). HEPES buffered saline (HBS) (10 mM HEPES, pH 7.4, 150 mM NaCl, 3 mM EDTA, 0.005% surfactant Tween-20) was used as running buffer. All injections were made at flow rate of 100 µl/min. Monoclonal antibodies were diluted in HBS (200 nM) and injected onto the protein A coated chip for capturing, followed by injection of different concentrations of human GM-CSF (400 nM, 200 nM, 100 nM, 50 nM, 25 nM); one channel of the chip was injected with HBS and used as reference for the analysis. Injection time and dissociation time were 120 s and 600 s, respectively. Each binding interaction of mAbs with GM-CSF was assessed using a ProteON XPR36 instrument (Biorad) and data processed with ProteOn Manager Software. Ka, Kd and KD were calculated applying the Langmuir fit model. The KD determined ranged from 0.18 to 0.69 nM, consistent with the high affinity binding. However, the kinetic values were highly heterogeneous. For instance, antibodies GCA7 and GCB59 had comparable KD values (0.38 and 0.68 nM, respectively), but showed different kinetics with GCA7 being characterized by a slow on-/slow off-rate and GCB59 by a high on-/high off-rate (Table 6).

TABLE 6

Binding properties and V-gene usage of GM-CSF autoantibodies from PAP patients. Human monoclonal antibodies from PAP patients show high affinities comparable to reference monoclonal antibodies. The table shows EC50 values determined by ELISA and Ka, Kd and KD values determined by SPR; reference monoclonal antibodies are highlighted in bold.

| mAb | EC50 (ng/ml) | Ka (1/Ms) | Kd (1/s) | KD (M) |
|---|---|---|---|---|
| GCA7 | 186.8 | 2.4E+05 | 6.0E−05 | 3.8E−10 |
| GCA21 | 59.4 | 9.5E+05 | 6.5E−04 | 6.9E−10 |
| GCB59 | 307.6 | 1.7E+06 | 1.2E−03 | 6.8E−10 |
| GCE536 | 61.4 | 6.6E+05 | 1.1E−04 | 1.8E−10 |

TABLE 6-continued

Binding properties and V-gene usage of GM-CSF autoantibodies from PAP patients. Human monoclonal antibodies from PAP patients show high affinities comparable to reference monoclonal antibodies. The table shows EC50 values determined by ELISA and Ka, Kd and KD values determined by SPR; reference monoclonal antibodies are highlighted in bold.

| mAb | EC50 (ng/ml) | Ka (1/Ms) | Kd (1/s) | KD (M) |
|---|---|---|---|---|
| Clone 3092 | 61.0 | 5.9E+05 | 3.4E−04 | 5.7E−10 |
| Clone 1089 | 1080.0 | 1.8E+05 | 7.9E−05 | 4.4E−10 |
| MOR103 | 90.0 | 2.7E+05 | 1.5E−05 | 1.9E−10 |
| Namilumab | 75.3 | 3.1E+05 | 7.7E−05 | 2.4E−10 |

Example 2

The Four PAP Autoantibodies Recognize Distinct Sites on GM-CSF and Can Form High-Molecular-Weight Immune Complexes To assess simultaneous binding of the different mABs to GM-CSF, SPR cross competition experiments were performed by SPR as described above (Example 1) whereby the different mAbs (200 nM each) were serially injected after GM-CSF capture (50 nM). Injection time and dissociation time were 60 s and 20 s, respectively. Thereby, it was found that GCA7, GCA21, GCB59 and GCE536 do not cross-compete between them for binding to GM-CSF (FIG. 1A). Interestingly, SPR experiments show that three non-cross-competing autoantibodies can bind simultaneously to a single molecule of GM-CSF (FIG. 1B). Furthermore, when GM-CSF was incubated with an excess of three antibodies, formation of high-molecular-weight immune complexes could be detected by size-exclusion chromatography (SEC-HPLC) (FIG. 1C). In the SEC-HPLC experiment three non-cross competing mAbs were diluted in PBS singularly or as a three-antibody-combination (10 μg of total antibody amount), and mixed with GM-CSF (1:1 or 10:1 molar ratios) for 1 hour, RT. Samples were analyzed by Agilent 1100 HPLC machine using TSK-GEL G3000SW columns (Tosoh, bed volume: 13 ml, void volume: 4.6 ml) with PBS as mobile phase (flow rate: 1 ml/min). A universal solvent 2 μm filter (Agilent) was put between injector and column. Detection was performed by a Variable Wavelength Detector (VWD, Agilent) with ultraviolet absorption at 220 nm.

Example 3

Figure 2:
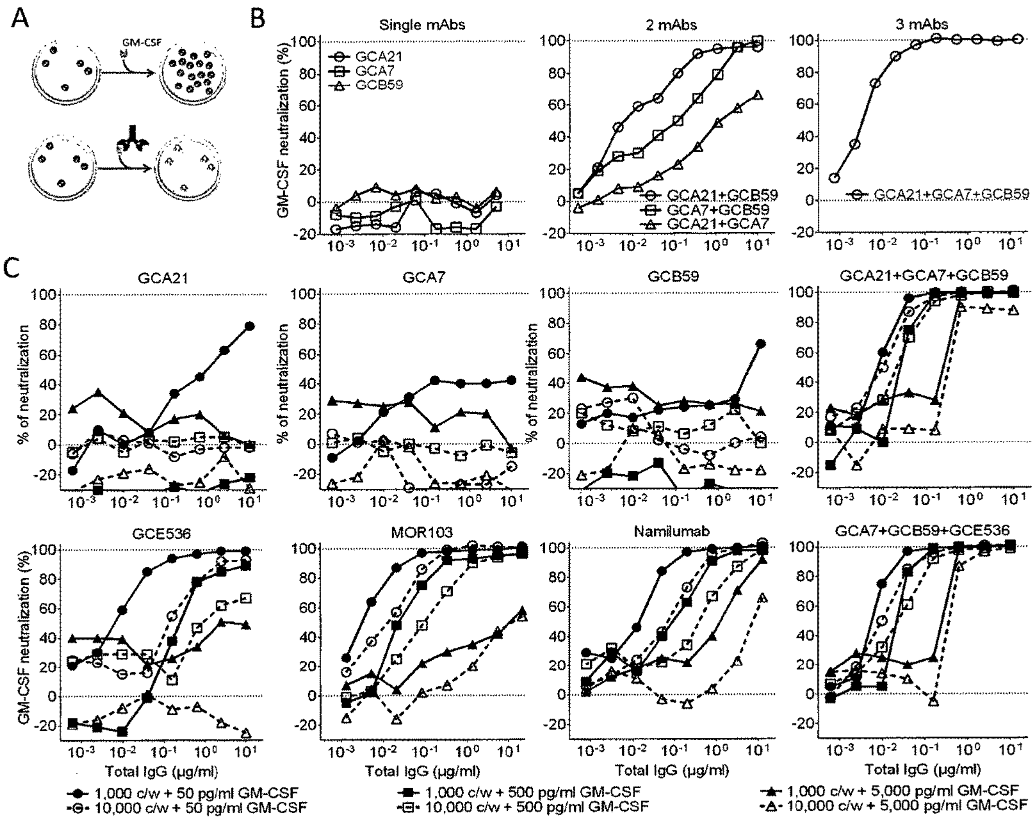
FIG. 2 shows the potent in vitro neutralization of GM-CSF by a combination of three antibodies. A fixed amount of GM-CSF (final concentration 50 pg ml-1) was incubated with serial dilutions of one or more antibodies, added to TF1 cells (10,000 per well) and cell proliferation was measured on day 3 by thymidine incorporation. (A) Scheme of the TF-1 bioassay. (B) Serial dilutions of single monoclonal antibodies or mixtures of two and three non-cross-competing antibodies were tested for their capacity to neutralize GM-CSF. (C) The sensitivity of the test was changed by varying the number of cells and the concentration of GM-CSF as indicated. Shown is for each experimental condition the inhibition obtained using single antibodies or a combination of three non-cross-competing antibodies.

Potent In Vitro Neutralization of GM-CSF Requires Combinations of 3 Antibodies Binding to Non-Overlapping Sites The neutralizing activity of the autoantibodies was assessed by measuring their ability to inhibit the proliferation of TF-1 cells in response to recombinant GM-CSF (FIG. 2A). To this end, TF-1 cells (CLS, Cell Lines Service) were maintained in RPMI 1640 medium supplemented with 10% Fetal Bovine Serum (Hyclone), 1% GlutaMAX, 1% Penicillin/Streptavidin, 1% non-essential amino acids, 1% sodium pyruvate, 1% 2-mercaptoethanol (all from GIBCO), 5 ng/ml human GM-CSF (Gentaur), 10 ng/ml human IL-3 (ImmunoTools). Cells were grown at 37° C. in a humidified incubator with 5% CO2. A GM-CSF neutralization assay was performed by serially diluting mAbs (or combination of mAbs, total IgG, or affinity-purified antibodies) in growth medium with neither GM-CSF nor IL-3, adding GM-CSF at a concentration of 100 pg/ml, and preincubating in 96-well flat-bottom cell culture plates (Costar) at 37° C. for 1 hour. TF-1 cells were washed 5 times, diluted in growth medium with neither GM-CSF nor IL-3, and 10,000 cells per well were seeded (final GM-CSF concentration equal to 50 pg/ml). In other tests, GM-CSF was used at final concentration of 500 and 5,000 pg/ml, and 1,000 cells per wells were seeded. Cells with or without GM-CSF in absence of antibodies were used as control to determine maximum and minimum levels of cell proliferation. Plates were incubated at 37° C. in a humidified incubator with 5% CO2 for 72 hours, and cell proliferation was measured after 6-hour incubation with 0.2 μCi/well of [3H]-thymidine (PerkinElmer). GM-CSF neutralization was calculated as percentage of inhibition of TF-1 growth with the following formula: [1-(CCPM of a single well—average CCPM of control cells grown without GM-CSF)/(average CCPM of control cells grown with GM-CSF—average CCPM of control cells grown without GM-CSF)]×100 (CCPM=corrected counts per minute). $IC_{90}$ (μg/ml) was calculated for every sample by a nonlinear regression analysis using GraphPad Prism 5 software. In some experiments mouse sera were titrated in TF-1 growth medium and preincubated at 37° C. for 30 min. TF-1 cells were washed and seeded (1,000 cells per well). A titration of GM-CSF (60,000 to 0.3 ng/ml) was added as growth control. CCPM of each single well were plotted against the serum titration.

Surprisingly, using this bioassay, GCA21, GCA7 and GCB59 failed to neutralize GM-CSF (FIG. 2B), even when tested at the concentration of 1 mg/ml (data not shown). The only exception was GCE536 which neutralized GM-CSF activity with an $IC_{90}$ value of 2.43 μg/ml, while the therapeutic antibodies Namilumab and MOR103 showed $IC_{90}$ values of 0.80 and 0.16, respectively. Interestingly, when combined together, two non-cross-competing antibodies showed enhanced neutralizing activity both in terms of dose-response and percent inhibition, the combination of GCA21 and GCB59 being the most effective (FIG. 2B). Strikingly, a combination of three non-cross-competing antibodies (GCA21, GCA7 and GCB59) led to a complete inhibition of proliferation with an $IC_{90}$ value of 0.08 μg/ml (expressed as the total concentration of the three mAbs), which was lower than that of the therapeutic antibodies MOR103 and Namilumab (FIG. 2B).

As expected from the law of mass action, it was found that by varying the cell number and the GM-CSF concentration the sensitivity of the assay was dramatically affected. In particular, lowering the number of TF-1 cells and the concentration of GM-CSF led to a more sensitive test that showed increased neutralization by single and multiple antibodies (FIG. 2C). In contrast, when high number of TF-1 cells and high doses of GM-CSF were used, even the most potent neutralizing antibodies MOR103 and Namilumab, failed to neutralize GM-CSF, even when present in a 400-fold molar excess. Strikingly, in all conditions, a combination of three non-cross-competing antibodies was capable of completely neutralizing GM-CSF (FIG. 2C).

Example 4

FcR-Dependent Clearance of GM-CSF Immune Complexes In Vivo

Figure 3:
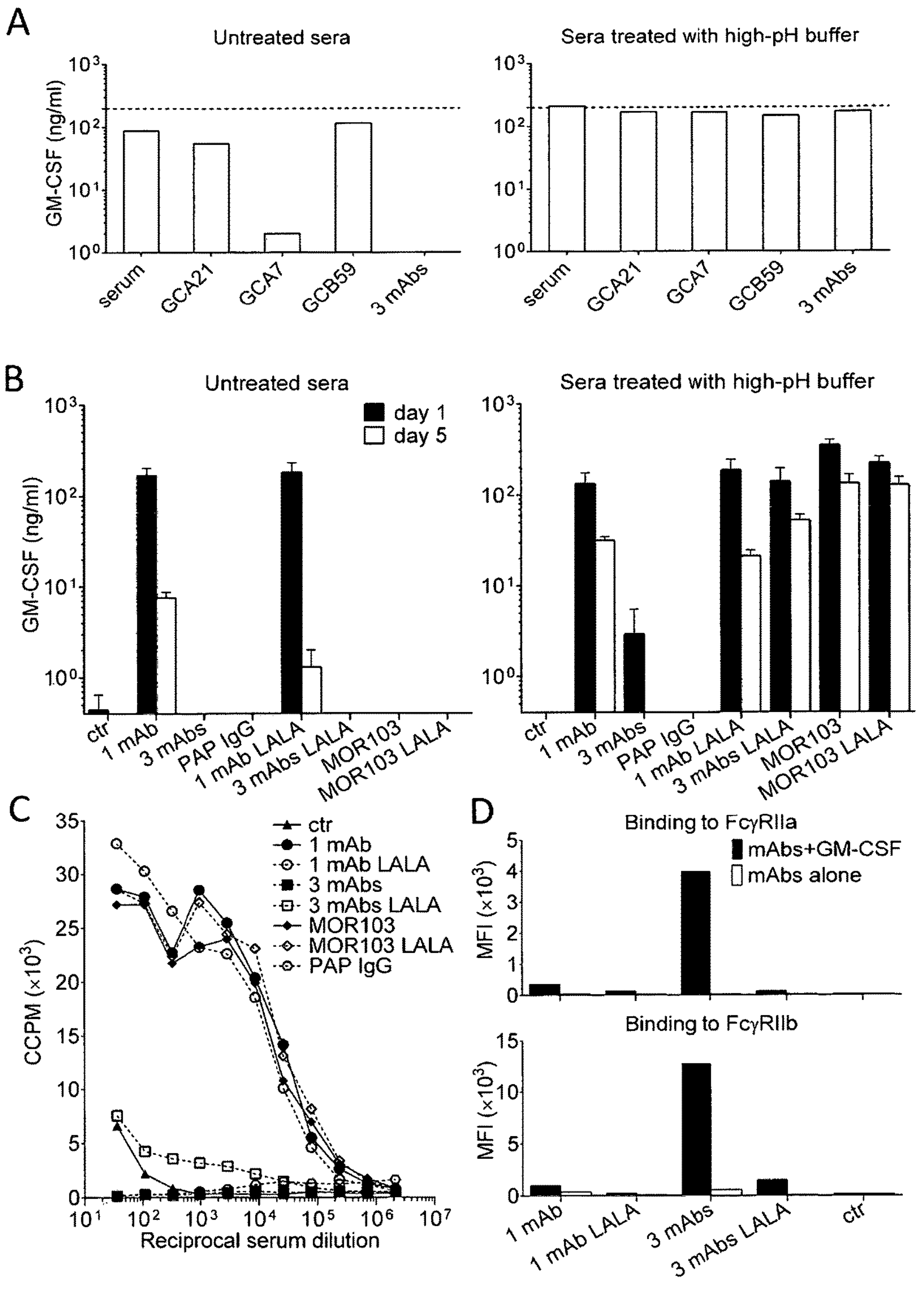
FIG. 3 shows the Fc-dependent clearance of GM-CSF immune complexes in vivo. (A) A sandwich ELISA to detect GM-CSF in the presence of specific antibodies. A fixed amount of GM-CSF was added to mouse serum together with three monoclonal antibodies (GCA21, GCA7, GCB59) added separately or in combination. The quantification of GM-CSF was performed by a sandwich ELISA using an antibody specific for site II for capture and site I for detection. Serial dilutions of serum in neutral (left) or alkaline buffer (right) were added and GM-CSF concentration was determined with reference to a GM-CSF standard. The dotted line represents the concentration of GM-CSF measured in the absence of antibodies. (B) Female Balb/c mice (5 per group) were injected with 100 μg of monoclonal antibody, either GCA21 (1 mAb) or GCA21+GCA7+GCB59 (3 mAbs) in the IgG or IgG-LALA format, or with 2 mg total IgG from a PAP patient, followed by 2 μg GM-CSF after 16 hours. Sera were collected after 1 or 5 days and GM-CSF concentrations were measured by ELISA in untreated serum and in serum treated at pH 11.6 to dissociate immune complexes. Shown is the GM-CSF concentration on day 1 and on day 5 in untreated serum (left) or alkaline-treated serum (right). (C) Proliferation of TF-1 cells in response to different dilutions of serum of mice injected 24 hours before with GM-CSF and the indicated antibodies. (D) Binding of GM-CSF immune complexes formed by one or three antibodies (in the IgG1 or IgG1-LALA format) to TZM-bl cells expressing Fc RIIa or Fc RIIb, as measured by flow cytometry using an anti-IgG Fc specific antibody.

Having established that GM-CSF can form complexes with three antibodies resulting in efficient in vitro neutralization of the cytokine biological activity, the effect of single versus multiple autoantibodies in vivo was investigated. To this end, groups of 6-8 week-old female BALB/c mice were injected intravenously with 100 μg of purified mAbs or 2 mg of total IgG purified from PA96 patient. After 16 hours, 2 μg of human GM-CSF were injected. Sera samples were collected on day 1 and day 5. GM-CSF was quantified by a sandwich ELISA. Briefly, 10 μg/ml of an antibody that bound to site II of GM-CSF was used to coat 96-well Maxisorp plates (Nunc), which were then blocked with PBS+10% FBS (Gibco). All sera and GM-CSF, which was used as standard (range 3.4-600,000 pg/ml), were titrated and tested in parallel under different conditions (either untreated or after alkaline treatment to dissociate the immune complexes; FIG. 3A): in one plate all samples were supplemented with 25% (vol/vol) of an alkaline dissociation buffer (2.5% Triton X100, 2 M ethanolamine, 0.15 M NaCl, pH 11.6), in the other plate all samples were supplemented with 25% (vol/vol) of PBS+10% FBS. Plates were left overnight at RT. Detection of captured GM-CSF was made with 1 μg/ml of a biotinylated antibody that bound to site I of GM-CSF for 1 h, RT, followed by binding of 0.5 μg/ml streptavidin-AP (Jackson ImmunoResearch) for 1 h, RT. Plates were then washed, substrate (p-NPP, Sigma) was added and plates were read at 405 nm.

In the absence of antibodies, the injected GM-CSF disappeared rapidly from the serum and was undetectable after 24 hours (FIG. 3B). In contrast, when single antibodies (GCA21 or MOR103) were used, high levels of GM-CSF were recovered from serum on day 1 and were still present on day 5. Of note, GM-CSF detection required alkaline dissociation in the case of MOR103 but not for GCA21, consistent with the different dissociation rates of the two antibodies (Table 6). In striking contrast, when mice received three non-cross-competing antibodies (GCA21, GCA7 and GCB59) or PAP IgG, GM-CSF was rapidly cleared since only low or undetectable amounts of the cytokine could be detected in the day-1 and day-5 sera, respectively, after alkaline dissociation.

To address the possible role of Fc receptors in the clearance of GM-CSF, the same antibodies were tested in a variant form, called LALA, which does not bind to C1q or to Fc-γ receptors. Similarly to the wild-type antibodies, single LALA antibodies led to an increase in GM-CSF levels in serum. However, in contrast to what was observed for three wild-type antibodies, three LALA antibodies failed to clear GM-CSF, which was quantitatively recovered in the sera following alkaline dissociation even on day 5 (FIG. 3B).

To ask whether the antibody-bound GM-CSF would be bioavailable, the sera of mice were tested for their ability to support TF-1 proliferation (FIG. 3C). Sera of mice receiving GCA21 or MOR103 led to a robust proliferation of TF-1 cells, consistent with a GM-CSF dissociation rate sufficient to engage the cytokine receptor. In contrast, sera of mice receiving three wild-type antibodies or PAP IgG were not able to stimulate proliferation, consistent with clearance of the immune complexes in vivo. In addition, although containing high level of GM-CSF, sera of mice receiving three LALA antibodies were not stimulatory, a finding consistent with irreversible sequestration of GM-CSF in stable immune complexes.

To further address the role of Fcγ-receptors, immune complexes formed between GM-CSF and wild-type or LALA antibodies were tested for their capacity to bind to TZM-bl cells expressing different Fey-receptors. To this end, four TZM-bI cell lines (NIH AIDS Research & Reference Reagent Program) each transfected with a specific Fcγ receptor (FcγRI, FcγRIIa, FcγRIIb or FcγRIIIa) were maintained in DMEM medium supplemented with 10% Fetal Bovine Serum (Hyclone), 0.025 M Hepes, 10 μg/ml Gentamicin and 20 μg/ml Blasticidin. Untransfected TZM-bl cells were used as negative control and were maintained in DMEM medium supplemented with 10% Fetal Bovine Serum (Hyclone) and 2% Penicillin/Streptavidin. Cells were grown at 37° C. in a humidified incubator with 5% CO2. Expression of specific FcγRs was assessed by staining TZM-bl cells with FITC-conjugated anti-CD64 (anti-FcγRI), anti-CD32 (anti-FcγRIIa and anti-FcγRIIb) and anti-CD16 (anti-FcγRIIIa) antibodies (all from BD Pharmingen). Untrasfected and transfected TZM-bl cells were washed with staining buffer (PBS with 10% Fetal Bovine Serum and 2 mM EDTA) and seeded in 96-well-plates at a density of 50,000 cells per well. A single anti-GM-CSF mAb (GCA21) or a combination of three non-cross-competing mAbs (GCA21, GCA7 and GCB59) at final concentration of 2.5 μg/ml were mixed with 0.05 μg/ml GM-CSF, or staining buffer (PBS with 10% Fetal Bovine Serum and 2 mM EDTA). The LALA versions of all antibodies and a mAb with a different specificity were included as controls. Samples were incubated at 37° C. for 30 min to allow the formation of immune complexes and then cooled down to 4° C. before adding them to TZM-bl cells for 30 min. Cells were washed twice and stained with anti-human IgG Fcγ fragment specific F(ab')2 fragment (Jackson ImmunoResearch). Samples were analyzed on BD FACSCanto (BD Biosciences) and median intensity fluorescence was analyzed and compared between samples.

Strong binding was observed only on FcγRIIa- and FcγRIIb-expressing cells and when immune complexes were formed by three wild-type, but not LALA, antibodies (FIG. 3D). Taken together, the above results indicate that single antibodies, even when potently neutralizing in vitro, increase the half-life of GM-CSF and build up a circulating pool of bioavailable cytokine. In contrast, three or more antibodies lead to the formation of immune complexes that are efficiently cleared through an Fc-dependent mechanism.

Example 5

Figure 4:
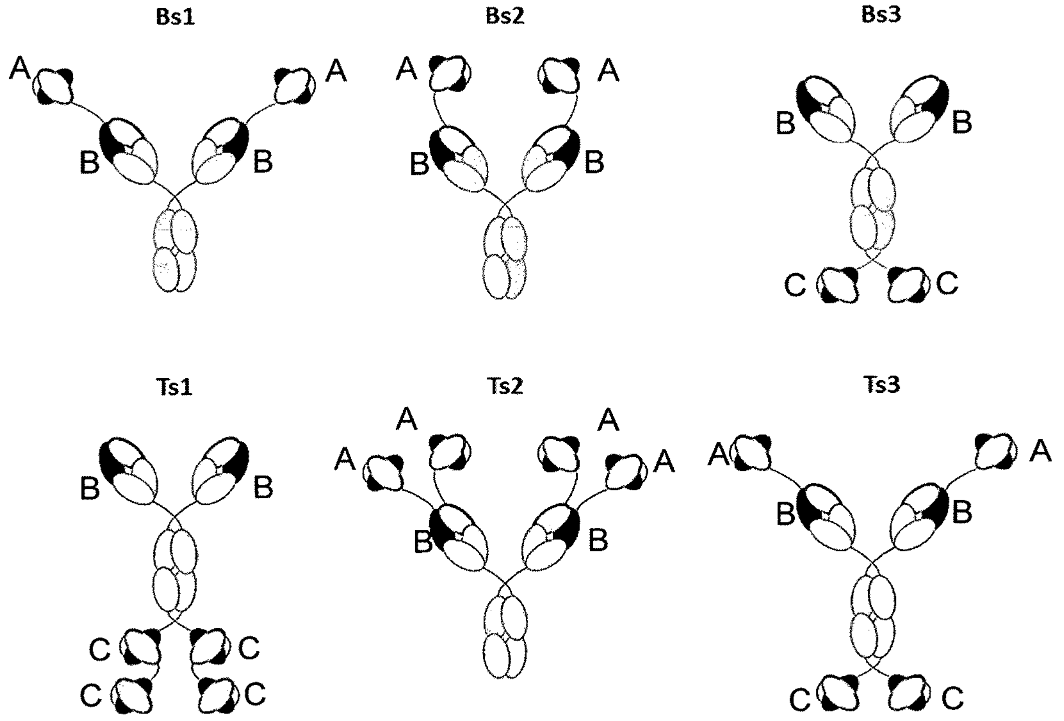
FIG. 4 shows the scheme of three bispecific construct types Bs1, Bs2 and Bs3 and of the three trispecific construct types Ts1, Ts2 and Ts3. Positions A, B, and/or C (if applicable) are shown for each of the construct types. Single chain variable domains (ScVd) of both heavy chain and light chain of different GM-CSF antibodies are added at the N-terminus and/or at the C-terminus of the heavy chain or the light chain of one GM-CSF antibody used as scaffold. Black ovals represent VH domains while dark grey ovals represent VL domains. The VH and VL of the different ScVds are joined together through specific linkers. Other linkers are used to join the ScVds between one another and to the full antibody used as scaffold. Light gray ovals represent IgG1 CH and CL domains.

Engineering of Multispecific Antibodies with the Highest GM-CSF Neutralizing Activity In view of the need of targeting multiple independent sites on GM-CSF to achieve efficient in vivo neutralization and clearance of the cytokine, bispecific and trispecific antibodies carrying the GCA21, GCA7, GCB59 and GCE536 epitope binding sites, specific linkers and an intact human IgG1 Fc were designed and produced (Table 7). Six different construct types were used to produce the multispecific antibodies (FIG. 4). In particular the three construct types Ts1, Ts2 and Ts3 were used to produce 6 different trispecific hexavalent antibodies, while the three construct types Bs1, Bs2 and Bs3 were used to produce 10 different bispecific tetravalent antibodies (FIG. 4 and Table 7). The construct types Bs1, Bs2, Bs3, Ts1 and Ts2 were designed according to US 2009/0155275 A1.

TABLE 7

| Description of GM-CSF multispecific antibodies | | | |
|---|---|---|---|
| Ts1GC1 trispecific antibody | | | |
| Construct type | Ts1 | | |
| Specificities[1] | GCA21 + GCA7 + GCB59 | | |
| | Domain/Linker | SEQ ID NO. aa | SEQ ID NO. nucl |
| Heavy chain[2] | GCA21 VH | 63 | 65 |
| | IgG1 CH1—CH2—CH3 | 140 | 146 |
| | Short linker | 143 | 149 |
| | GCA7 VH | 37 | 42 |
| | Long linker | 144 | 150 |
| | GCA7 VL | 38 | 47 |
| | Short linker | 143 | 149 |
| | GCB59 VH | 95 | 100 |
| | Long linker | 144 | 150 |
| | GCB59 VL | 96 | 104 |
| | Complete sequence | 151 | 152 |
| Light chain[2] | GCA21 VL | 64 | 66 |
| | IgG CK | 141 | 147 |
| | Complete sequence | 183 | 184 |

TABLE 7-continued

Description of GM-CSF multispecific antibodies

Ts1GC2a trispecific antibody

| | | | |
|---|---|---|---|
| Construct type | Ts1 | | |
| Specificities[1] | GCE536 + GCA7 + GCB59 | | |
| | Domain/Linker | SEQ ID NO. aa | SEQ ID NO. nucl |
| Heavy chain[2] | GCE536 VH | 130 | 132 |
| | IgG1 CH1—CH2—CH3 | 140 | 146 |
| | Short linker | 143 | 149 |
| | GCA7 VH | 37 | 42 |
| | Long linker | 144 | 150 |
| | GCA7 VL | 38 | 47 |
| | Short linker | 143 | 149 |
| | GCB59 VH | 95 | 100 |
| | Long linker | 144 | 150 |
| | GCB59 VL | 96 | 104 |
| | Complete sequence | 153 | 154 |
| Light chain[2] | GCE536 VL | 131 | 136 |
| | IgG CK | 141 | 147 |
| | Complete sequence | 189 | 190 |

Ts2GC2b trispecific antibody

| | | | |
|---|---|---|---|
| Construct type | Ts2 | | |
| Specificities[1] | GCE536 + GCA7 + GCB59 | | |
| | Domain/Linker | SEQ ID NO. aa | SEQ ID NO. nucl |
| Heavy chain[2] | GCB59 VH | 95 | 98 |
| | Long linker | 144 | 150 |
| | GCB59 VL | 96 | 102 |
| | Short linker | 143 | 149 |
| | GCE536 VH | 130 | 133 |
| | IgG1 CH1—CH2—CH3 | 140 | 145 |
| | Complete sequence | 155 | 156 |
| Light chain[2] | GCA7 VH | 37 | 41 |
| | Long linker | 144 | 150 |
| | GCA7 VL | 38 | 46 |
| | Short linker | 143 | 149 |
| | GCE536 VL | 131 | 137 |
| | IgG CK | 141 | 147 |
| | Complete sequence | 157 | 158 |

Ts2GC2c trispecific antibody

| | | | |
|---|---|---|---|
| Construct type | Ts2 | | |
| Specificities[1] | GCE536 + GCA7 + GCB59 | | |
| | Domain/Linker | SEQ ID NO. aa | SEQ ID NO. nucl |
| Heavy chain[2] | GCB59 VH | 95 | 99 |
| | Long linker | 144 | 150 |
| | GCB59 VL | 96 | 103 |
| | Short linker | 143 | 149 |
| | GCA7 VH | 37 | 40 |
| | IgG1 CH1—CH2—CH3 | 140 | 145 |
| | Complete sequence | 159 | 160 |
| Light chain[2] | GCE536 VH | 130 | 134 |
| | Long linker | 144 | 150 |
| | GCE536 VL | 131 | 138 |
| | Short linker | 143 | 149 |
| | GCA7 VL | 38 | 45 |
| | IgG CK | 141 | 147 |
| | Complete sequence | 161 | 162 |

Ts3GC2d trispecific antibody

| | | | |
|---|---|---|---|
| Construct type | Ts3 | | |
| Specificities[1] | GCE536 + GCA7 + GCB59 | | |
| | Domain/Linker | SEQ ID NO. aa | SEQ ID NO. nucl |
| Heavy chain[2] | GCB59 VH | 95 | 98 |
| | Long linker | 144 | 150 |
| | GCB59 VL | 96 | 102 |
| | Short linker | 143 | 149 |
| | GCE536 VH | 130 | 133 |
| | IgG1 CH1—CH2—CH3 | 140 | 146 |
| | Short linker | 143 | 149 |
| | GCA7 VH | 37 | 43 |
| | Long linker | 144 | 150 |
| | GCA7 VL | 38 | 48 |
| | Complete sequence | 163 | 164 |
| Light chain[2] | GCE536 VL | 131 | 136 |
| | IgG CK | 141 | 147 |
| | Complete sequence | 189 | 190 |

Ts3GC2e trispecific antibody

| | | | |
|---|---|---|---|
| Construct type | Ts3 | | |
| Specificities[1] | GCE536 + GCA7 + GCB59 | | |
| | Domain/Linker | SEQ ID NO. aa | SEQ ID NO. nucl |
| Heavy chain[2] | GCB59 VH | 95 | 99 |
| | Long linker | 144 | 150 |
| | GCB59 VL | 96 | 103 |
| | Short linker | 143 | 149 |
| | GCA7 VH | 37 | 40 |
| | IgG1 CH1—CH2—CH3 | 140 | 146 |
| | Short linker | 143 | 149 |
| | GCE536 VH | 130 | 135 |
| | Long linker | 144 | 150 |
| | GCE536 VL | 131 | 139 |
| | Complete sequence | 165 | 166 |
| Light chain[2] | GCA7 VL | 38 | 44 |
| | IgG CK | 141 | 147 |
| | Complete sequence | 181 | 182 |

Bs3GC1a bispecific antibody

| | | | |
|---|---|---|---|
| Construct type | Bs3 | | |
| Specificities[1] | GCE536 + GCA7 | | |
| | Domain/Linker | SEQ ID NO. aa | SEQ ID NO. nucl |
| Heavy chain[2] | GCE536 VH | 130 | 132 |
| | IgG1 CH1—CH2—CH3 | 140 | 146 |
| | Short linker | 143 | 149 |
| | GCA7 VH | 37 | 43 |
| | Long linker | 144 | 150 |
| | GCA7 VL | 38 | 48 |
| | Complete sequence | 167 | 168 |
| Light chain[2] | GCE536 VL | 131 | 136 |
| | IgG CK | 141 | 147 |
| | Complete sequence | 189 | 190 |

Bs3GC1b bispecific antibody

| | | | |
|---|---|---|---|
| Construct type | Bs3 | | |
| Specificities[1] | GCE536 + GCA7 | | |
| | Domain/Linker | SEQ ID NO. aa | SEQ ID NO. nucl |
| Heavy chain[2] | GCA7 VH | 37 | 39 |
| | IgG1 CH1—CH2—CH3 | 140 | 146 |
| | Short linker | 143 | 149 |
| | GCE536 VH | 130 | 135 |
| | Long linker | 144 | 150 |
| | GCE536 VL | 131 | 139 |
| | Complete sequence | 169 | 170 |
| Light chain[2] | GCA7 VL | 38 | 44 |
| | IgG CK | 141 | 147 |
| | Complete sequence | 181 | 182 |

TABLE 7-continued

Description of GM-CSF multispecific antibodies

Bs2GC1c bispecific antibody

Construct type: Bs2
Specificities[1]: GCE536 + GCA7

| | Domain/Linker | SEQ ID NO. aa | SEQ ID NO. nucl |
|---|---|---|---|
| Heavy chain[2] | GCE536 VH | 130 | 132 |
| | IgG1 CH1—CH2—CH3 | 140 | 145 |
| | Complete sequence | 187 | 188 |
| Light chain[2] | GCA7 VH | 37 | 41 |
| | Long linker | 144 | 150 |
| | GCA7 VL | 38 | 46 |
| | Short linker | 143 | 149 |
| | GCE536 VL | 131 | 137 |
| | IgG CK | 141 | 147 |
| | Complete sequence | 157 | 158 |

Bs2GC1d bispecific antibody

Construct type: Bs2
Specificities[1]: GCE536 + GCA7

| | Domain/Linker | SEQ ID NO. aa | SEQ ID NO. nucl |
|---|---|---|---|
| Heavy chain[2] | GCA7 VH | 37 | 39 |
| | IgG1 CH1—CH2—CH3 | 140 | 145 |
| | Complete sequence | 179 | 180 |
| Light chain[2] | GCE536 VH | 130 | 134 |
| | Long linker | 144 | 150 |
| | GCE536 VL | 131 | 138 |
| | Short linker | 143 | 149 |
| | GCA7 VL | 38 | 45 |
| | IgG CK | 141 | 147 |
| | Complete sequence | 161 | 162 |

Bs1GC2a bispecific antibody

Construct type: Bs1
Specificities[1]: GCE536 + GCB59

| | Domain/Linker | SEQ ID NO. aa | SEQ ID NO. nucl |
|---|---|---|---|
| Heavy chain[2] | GCB59 VH | 95 | 98 |
| | Long linker | 144 | 150 |
| | GCB59 VL | 96 | 102 |
| | Short linker | 143 | 149 |
| | GCE536 VH | 130 | 133 |
| | IgG1 CH1—CH2—CH3 | 140 | 145 |
| | Complete sequence | 155 | 156 |
| Light chain[2] | GCE536 VL | 131 | 136 |
| | IgG CK | 141 | 147 |
| | Complete sequence | 189 | 190 |

Bs3GC2b bispecific antibody

Construct type: Bs3
Specificities[1]: GCE536 + GCB59

| | Domain/Linker | SEQ ID NO. aa | SEQ ID NO. nucl |
|---|---|---|---|
| Heavy chain[2] | GCB59 VH | 95 | 97 |
| | IgG1 CH1—CH2—CH3 | 140 | 146 |
| | Short linker | 143 | 149 |
| | GCE536 VH | 130 | 135 |
| | Long linker | 144 | 150 |
| | GCE536 VL | 131 | 139 |
| | Complete sequence | 171 | 172 |
| Light chain[2] | GCB59 VL | 96 | 101 |
| | IgG CL | 142 | 148 |
| | Complete sequence | 185 | 186 |

TABLE 7-continued

Description of GM-CSF multispecific antibodies

Bs1GC3a bispecific antibody

Construct type: Bs1
Specificities[1]: GCA7 + GCB59

| | Domain/Linker | SEQ ID NO. aa | SEQ ID NO. nucl |
|---|---|---|---|
| Heavy chain[2] | GCB59 VH | 95 | 99 |
| | Long linker | 144 | 150 |
| | GCB59 VL | 96 | 103 |
| | Short linker | 143 | 149 |
| | GCA7 VH | 37 | 40 |
| | IgG1 CH1—CH2—CH3 | 140 | 145 |
| | Complete sequence | 159 | 160 |
| Light chain[2] | GCA7 VL | 38 | 44 |
| | IgG CK | 141 | 147 |
| | Complete sequence | 181 | 182 |

Bs3GC3b bispecific antibody

Construct type: Bs3
Specificities[1]: GCA7 + GCB59

| | Domain/Linker | SEQ ID NO. aa | SEQ ID NO. nucl |
|---|---|---|---|
| Heavy chain[2] | GCB59 VH | 95 | 97 |
| | IgG1 CH1—CH2—CH3 | 140 | 146 |
| | Short linker | 143 | 149 |
| | GCA7 VH | 37 | 43 |
| | Long linker | 144 | 150 |
| | GCA7 VL | 38 | 48 |
| | Complete sequence | 173 | 174 |
| Light chain[2] | GCB59 VL | 96 | 101 |
| | IgG CL | 142 | 148 |
| | Complete sequence | 185 | 186 |

Bs3GC4 bispecific antibody

Construct type: Bs3
Specificities[1]: GCA21 + GCE536

| | Domain/Linker | SEQ ID NO. aa | SEQ ID NO. nucl |
|---|---|---|---|
| Heavy chain[2] | GCA21 VH | 63 | 65 |
| | IgG1 CH1—CH2—CH3 | 140 | 146 |
| | Short linker | 143 | 149 |
| | GCE536 VH | 130 | 135 |
| | Long linker | 144 | 150 |
| | GCE536 VL | 131 | 139 |
| | Complete sequence | 175 | 176 |
| Light chain[2] | GCA21 VL | 64 | 66 |
| | IgG CK | 141 | 147 |
| | Complete sequence | 183 | 184 |

Bs3GC5 bispecific antibody

Construct type: Bs3
Specificities[1]: GCA21 + GCA7

| | Domain/Linker | SEQ ID NO. aa | SEQ ID NO. nucl |
|---|---|---|---|
| Heavy chain[2] | GCA21 VH | 63 | 65 |
| | IgG1 CH1—CH2—CH3 | 140 | 146 |
| | Short linker | 143 | 149 |
| | GCA7 VH | 37 | 43 |
| | Long linker | 144 | 150 |
| | GCA7 VL | 38 | 48 |
| | Complete sequence | 177 | 178 |
| Light chain[2] | GCA21 VL | 64 | 66 |
| | IgG CK | 141 | 147 |
| | Complete sequence | 183 | 184 |

[1]The antibody used as scaffold is underlined.

[2]From N-terminus to C-terminus.

Example 6

Evaluation of Productivity and Aggregation of Multispecific Antibodies

The anti GM-CSF multispecific antibodies were produced in 293F cells and purified on protein A. Quantification was performed by Pierce bicinchoninic acid (BCA) protein assay according to the manufacturer's instructions (Thermo Scientific). The assay is a detergent-compatible formulation based on BCA for the colorimetric detection and quantitation of total protein. Productivity varied according to the different antibodies with Bs3GC1a, Bs1GC2a, Bs1GC3a, Bs3GC3b, Bs3GC5 being produced at a concentration greater than 30 μg/ml. Aggregation of multispecific antibodies (final concentration: 1 mg/ml) was analyzed by measuring their turbidity at OD 340 nm in absence or presence of GM-CSF (final concentration: 0.1 mg/ml) (Table 8).

TABLE 8

Productivity (μg/ml) of multispecific mAbs by 293F cells and their aggregation measured by turbidity at OD 340 nm in absence or presence of GM-CSF. Low OD values indicates lower level of turbidity.

| Name | Concentration (μg/ml) | Turbidity (OD 340) | Turbidity (OD 340) w/ GM-CSF |
|---|---|---|---|
| Ts1GC1 | 3.2 | 0.345 | 0.369 |
| Ts1GC2a | 3 | 0.292 | 0.424 |
| Ts2GC2b | 7.2 | 0.076 | 0.169 |
| Ts2GC2c | 7.7 | 0.068 | 0.209 |
| Ts3GC2d | 13.5 | 0.012 | 0.197 |
| Ts3GC2e | 11.1 | 0.108 | 0.246 |
| Bs3GC1a | 30.6 | 0.084 | 0.121 |
| Bs3GC1b | 17.5 | 0.051 | 0.093 |
| Bs2GC1c | 7 | 0.058 | 0.133 |
| Bs2GC1d | 5 | 0 | 0.025 |
| Bs1GC2a | 41.8 | 0 | 0 |
| Bs3GC2b | 26 | 0.044 | 0.067 |
| Bs1GC3a | 61.5 | 0 | 0 |
| Bs3GC3b | 31.7 | 0 | 0 |
| Bs3GC4 | 20.9 | 0.553 | 0.396 |
| Bs3GC5 | 42 | 0.224 | 0.245 |

Example 7

Multispecific Antibodies Bind to GM-CSF with High Affinity

Figure 5:
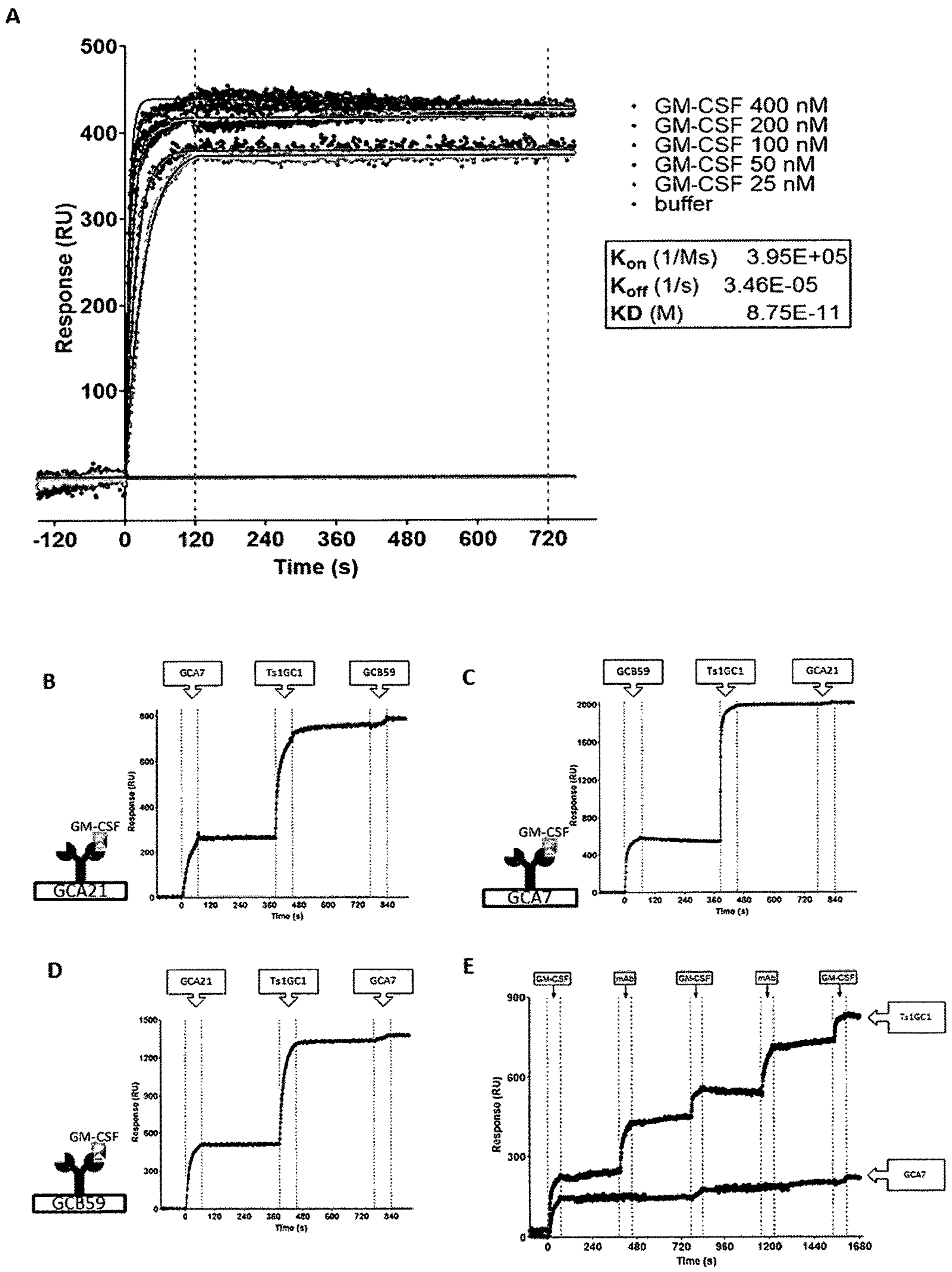
FIG. 5 shows that TsGC1binds to GM-CSF with very high affinity with a very slow off-rate (A). (B-C) TsGC1can use all the 3 different specificities for binding to GM-CSF. GCA21, GCA7 and GCB59 were immobilized on a SPR chip and were serially exposed to GM-CSF followed by GCA7, GCB59 and GCA21, respectively, and finally by TsGC1. (E) TsGC1can form high molecular weight complexes with GM-CSF. TsGC1 was immobilized on an SPR chip and serially exposed for 3 rounds to GM-CSF followed by soluble TsGC1. Shown is the same experiment performed with GCA7 as control.

All multispecific antibodies were tested for binding to GM-CSF by ELISA. The binding was highly specific with a high affinity for GM-CSF as shown by EC50 values in Table 9 below. The use of the different binding sites of the multispecific antibodies was tested by SPR experiments using Ts1GC1 as model. In this experiment GM-CSF was bound by an excess of 2 of the 3 antibodies forming Ts1GC1 and subsequent binding of Ts1GC1 to GM-CSF through the $3^{rd}$ specificity was revealed. Ts1GC1 has a very high affinity, with very low KD as shown in FIG. 5A. In different SPR experiments GM-CSF was complexed with 2 antibodies out of the 3 antibodies composing Ts1GC1, so that only one of the 3 GM-CSF epitopes was left free for binding by Ts1GC1 (FIG. 5B-D). In addition, when immobilized on the SPR chip, Ts1GC1, unlike conventional antibodies such as GCA7, was able to form high molecular weight complexes when the chip was sequentially exposed to multiple rounds of soluble GM-CSF and Ts1GC1 (FIG. 5E).

TABLE 9

Binding of multispecific mAbs to GM-CSF as determined by ELISA.

| Name | EC50 (ng/ml) |
|---|---|
| Ts1GC1 | 27.04 |
| Ts1GC2a | 33.48 |
| Ts2GC2b | 18.38 |
| Ts2GC2c | 20.71 |
| Ts3GC2d | 29.55 |
| Ts3GC2e | 40.67 |
| Bs3GC1a | 74.33 |
| Bs3GC1b | 71.6 |
| Bs2GC1c | 12 |
| Bs2GC1d | 22.56 |
| Bs1GC2a | 16.19 |
| Bs3GC2b | 48.55 |
| Bs1GC3a | 46.8 |
| Bs3GC3b | 586.7 |
| Bs3GC4 | 32.27 |
| Bs3GC5 | 41.75 |

Example 8

Extremely Potent Neutralization of GM-CSF by Multispecific Antibodies

Figure 6:
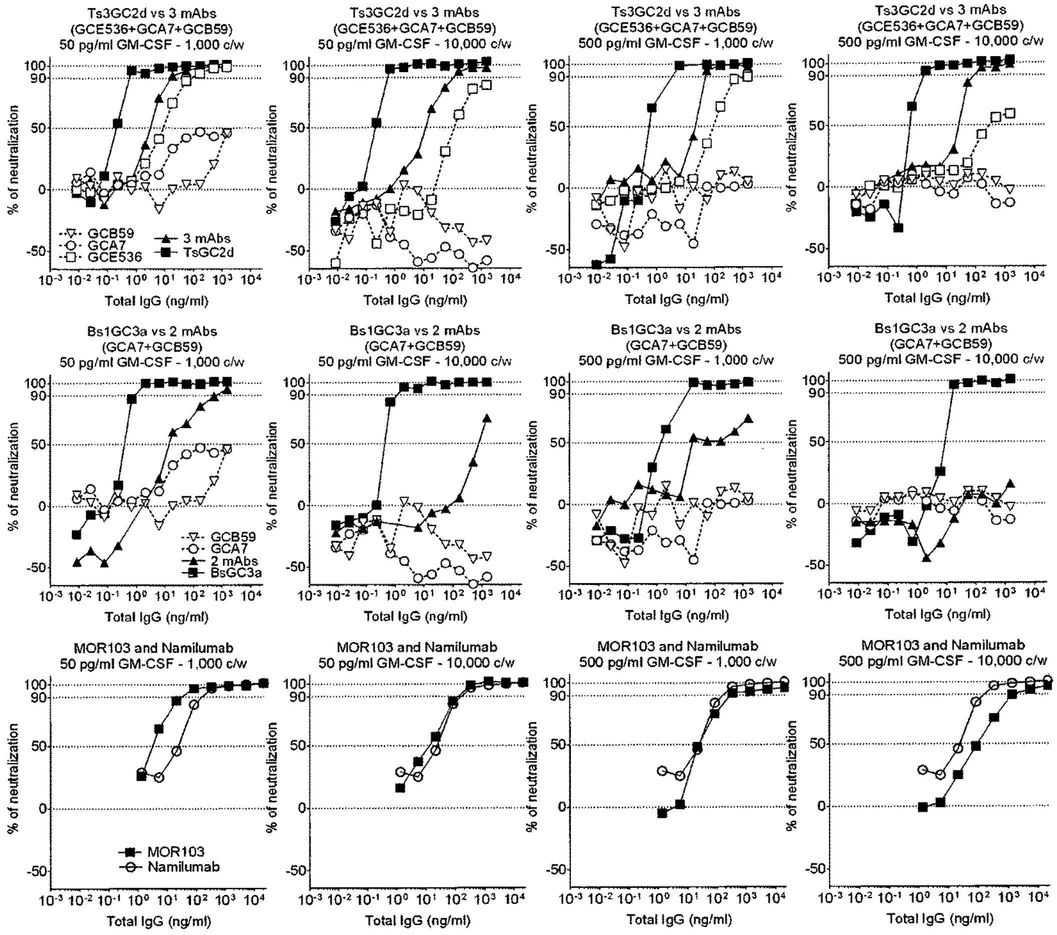

GM-CSF neutralization was tested using the in vitro bioassay based on TF-1 cells as described above (Example 3), whereby 2 different GM-CSF concentrations (50 and 500 pg/ml) and 2 different number of cells per well (1,000 and 10,000) were tested. IC90 values are reported in Table 10. Interestingly, all multispecific antibodies completely inhibited TF-1 proliferation in all conditions tested at very low concentrations (lower than 1 ng/ml for most multispecific antibodies). Of note, using less stringent conditions MOR103 and Namilumab required a 100-fold and 690-fold greater concentration, respectively, as compared to the best multispecific antibody (Ts1GC2a). Under stringent conditions, most multispecific antibodies could neutralize GM-CSF at concentrations lower than 10 ng/ml, while MOR103 and Namilumab required concentrations greater than 1 mg/ml. Two multispecific antibodies, Ts3GC2d and Bs1GC3a, were selected for their overall properties and compared to the single antibodies or combinations of antibodies from which they derived (FIG. 6).

TABLE 10

Extremely potent neutralization of GM-CSF by multispecific antibodies. Less stringent conditions: 50 pg/ml GM-CSF and 1,000 TF-1/well. Stringent conditions: 50 pg/ml GM-CSF and 10,000 TF-1/well. More stringent conditions: 500 pg/ml GM-CSF and 1,000 TF-1/well. Very stringent conditions: 500 pg/ml GM-CSF and 10,000 TF-1/well

| Name | IC90 (ng/ml) less stringent conditions | IC90 (ng/ml) stringent conditions | IC90 (ng/ml) more stringent conditions | IC90 (ng/ml) very stringent conditions |
|---|---|---|---|---|
| Ts1GC1 | 0.3516 | 0.2828 | 2.965 | 2.813 |
| Ts1GC2a | 0.2649 | 0.2806 | 3.173 | 2.534 |
| Ts2GC2b | 0.5257 | 0.5615 | 4.705 | 5.951 |
| Ts2GC2c | 0.5465 | 0.6898 | 4.284 | 5.862 |

TABLE 10-continued

Extremely potent neutralization of GM-CSF by multispecific antibodies. Less stringent conditions: 50 pg/ml GM-CSF and 1,000 TF-1/well. Stringent conditions: 50 pg/ml GM-CSF and 10,000 TF-1/well. More stringent conditions: 500 pg/ml GM-CSF and 1,000 TF-1/well. Very stringent conditions: 500 pg/ml GM-CSF and 10,000 TF-1/well

| Name | IC90 (ng/ml) less stringent conditions | IC90 (ng/ml) stringent conditions | IC90 (ng/ml) more stringent conditions | IC90 (ng/ml) very stringent conditions |
|---|---|---|---|---|
| Ts3GC2d | 0.5363 | 0.4132 | 0.7954 | 0.7681 |
| Ts3GC2e | 0.2963 | 0.2718 | 3.289 | 3.684 |
| Bs3GC1a | 0.6812 | 0.9625 | 4.721 | 6.235 |
| Bs3GC1b | 0.5546 | 0.7118 | 4.369 | 5.928 |
| Bs2GC1c | 0.8525 | 1.239 | 4.496 | 6.227 |
| Bs2GC1d | 3.075 | 6.299 | 9.596 | 15.89 |
| Bs1GC2a | 2.77 | 31.37 | 9.917 | 217.1 |
| Bs3GC2b | 0.5595 | 1.068 | 6.207 | 11.18 |
| Bs1GC3a | 0.7436 | 0.7371 | 4.636 | 13.3 |
| Bs3GC3b | 1.279 | 2.957 | 17.81 | 123.8 |
| Bs3GC4 | 9.257 | 90.78 | 97.5 | 738.9 |
| Bs3GC5 | 1.305 | 4.177 | 6.465 | 10.25 |
| *MOR103* | *24.86* | *159.4* | *172.5* | *1490* |
| *Namilumab* | *1772* | *798.3* | *1972* | *19820* |

Example 9

Figure 7:
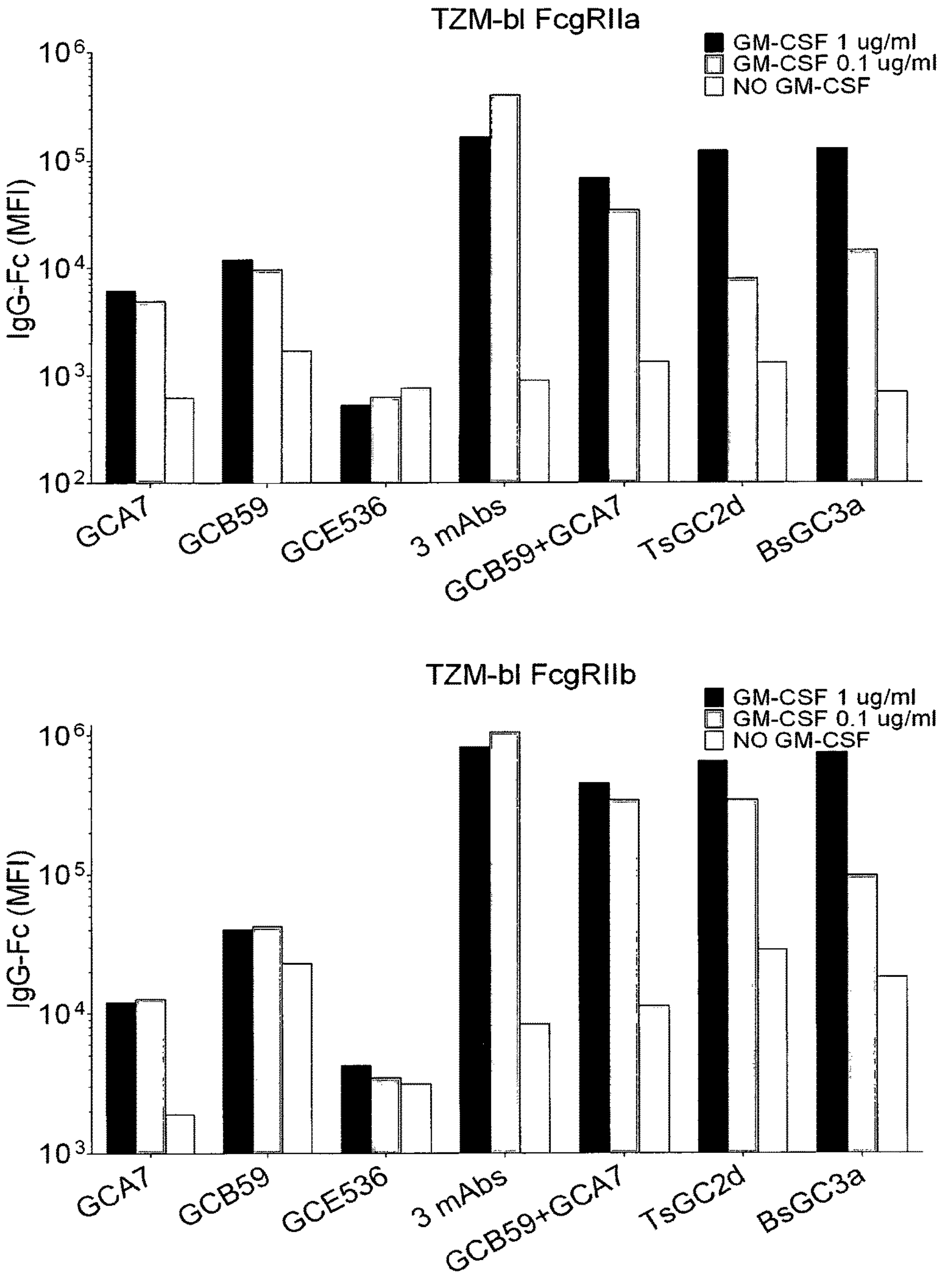
FIG. 7 shows the binding of immune complexes formed by GM-CSF and TsGC2d or BsGC3a to TZM-bl cells expressing FcγRIIa or FcγRIIb, as measured by flow cytometry using an anti-IgG Fc specific antibody. The binding is compared to that of single antibodies and combinations of the 2 or 3 antibodies forming BsGC3a and TsGC2d, respectively.

Immune Complexes of GM-CSF with Multispecific Antibodies Bind to Fcγ Receptors IIa and IIb To address the engagement of Fcγ receptors, immune complexes formed between GM-CSF and multispecific antibodies were tested for their capacity to bind to TZM-bl cells expressing FcγRIIa and FcγRIIb receptors. Multispecific antibodies were mixed with 0.05 μg/ml of GM-CSF, or staining buffer. Samples were incubated at 37° C. for 30 min to allow the formation of immune complexes and then cooled down to 4° C. before adding them to TZM-bl cells for 30 minutes. Cells were washed twice and stained with anti-human IgG Fcγ fragment specific F(ab')2 fragment. Samples were analyzed on BD FACSCanto (BD Biosciences) and median intensity fluorescence was analyzed and compared between samples. Strong binding was observed with immune complexes formed by GM-CSF and different multispecific antibodies on FcγRIIa- and FcγRIIb-expressing cells (Table 11). In particular Ts3GC2d and Bs1GC3a showed the strongest binding to FcγRIIa and FcγRIIb in presence of GM-CSF, while they poorly bound the same FcRs in absence of GM-CSF (FIG. 7). Taken together, the above results suggest that GM-CSF in immune complexes with a multispecific monoclonal antibody can be cleared from the human body through an Fc-dependent mechanism.

TABLE 11

Binding of immune complexes formed by GM-CSF and different multispecific mAbs to TZM-bl cells expressing FcγRIIa or FcγRIIb, as measured by flow cytometry using an anti-IgG Fc specific antibody. Shown is the median fluorescence intensity (MFI) of multispecific antibodies alone or complexed with low (1:10 mAb:GM-CSF ratio) or high GM-CSF concentrations (1:1 mAb:GM-CSF ratio), and the average ratio of binding in presence and in absence of GM-CSF. Dark grey cells indicate the GM-CSF complexes formed with multispecific antibodies that poorly bind to FcRs in absence of GM-CSF.

| Name | FcgRIIa (MFI) w/o GM-CSF | FcgRIIa (MFI) w/low GM-CSF | FcgRIIa (MFI) w/high GM-CSF | Average RATIO FcgRIIa | FcgRIIb (MFI) w/o GM-CSF | FcgRIIb (MFI) w/low GM-CSF | FcgRIIb (MFI) w/high GM-CSF | Average RATIO FcgRIIb |
|---|---|---|---|---|---|---|---|---|
| Ts1GC1 | 52422 | 117643 | 215686 | 3.18 | 350077 | 527988 | 1230711 | 2.51 |
| Ts1GC2a | 2850 | 4131 | 9872 | 2.46 | 67215 | 135509 | 397219 | 3.96 |
| Ts2GC2b | 11341 | 135974 | 725556 | 37.98 | 168007 | 852217 | 1262147 | 6.29 |
| Ts2GC2c | 9989 | 91425 | 189657 | 14.07 | 379395 | 896907 | 712072 | 2.12 |
| Ts3GC2d | 1313 | 7898 | 122101 | 49.50 | 28963 | 343854 | 651881 | 17.19 |
| Ts3GC2e | 1869 | 2181 | 189634 | 51.31 | 52524 | 109361 | 1236720 | 12.81 |
| Bs3GC1a | 687 | 1270 | 65292 | 48.44 | 20590 | 175426 | 510410 | 16.65 |
| Bs3GC1b | 3548 | 2937 | 37183 | 5.65 | 53830 | 60053 | 378584 | 4.07 |
| Bs2GC1c | 1590 | 5003 | 427407 | 135.98 | 107869 | 416283 | 942605 | 6.30 |
| Bs2GC1d | 2906 | 10922 | 319374 | 56.83 | 125493 | 435244 | 1219560 | 6.59 |
| Bs1GC2a | 662 | 9141 | 566165 | 434.52 | 11787 | 398084 | 1437205 | 77.85 |
| Bs3GC2b | 6906 | 7127 | 268634 | 19.97 | 96743 | 181252 | 1303031 | 7.67 |
| Bs1GC3a | 694 | 14400 | 128441 | 102.91 | 18221 | 98121 | 752715 | 23.35 |
| Bs3GC3b | 650 | 8290 | 54962 | 48.66 | 2627 | 57837 | 432575 | 93.34 |
| Bs3GC4 | 6733 | 24478 | 19481 | 3.26 | 122923 | 137194 | 62612 | 0.81 |
| Bs3GC5 | 1105 | 30163 | 468183 | 225.50 | 176650 | 393019 | 1578476 | 5.58 |

Table of Sequences and SEQ ID Numbers

| SEQ ID NO | Description | Sequence |
|---|---|---|
| | | GCA7 ANTIBODY |
| 1 | CDRH1 aa | **gftvstny** |
| 2 | CDRH2 aa | **lyaggyt** |
| 3 | CDRH3 aa | **akhydsgystidhfds** |
| 4 | CDRL1 aa | **qsvfytsknkny** |
| 5 | CDRL2 aa | **was** |
| 6 | CDRL2 long aa | LIY**was**TRE |
| 7 | CDRL3 aa | **qqyystpft** |
| 8 | CDRH1 nuc varS1 | **GGATTCACCGTCAGTACCAACTAC** |
| 9 | CDRH1 nuc varS2 | **GGGTTTACTGTGTCTACAAACTAC** |
| 10 | CDRH1 nuc varN1 | **GGCTTTACTGTCTCTACAAACTAC** |
| 11 | CDRH1 nuc varC1 | **GGCTTCACCGTGTCAACAAACTAC** |
| 12 | CDRH1 nuc varC2 | **GGGTTTACCGTCTCTACAAACTAC** |
| 13 | CDRH2 nuc varS1 | **CTTTATGCCGGAGGTGTCACA** |
| 14 | CDRH2 nuc varS2/N1/C2 | **CTGTACGCTGGCGGGGTGACC** |
| 15 | CDRH2 nuc varC1 | **CTGTACGCCGGAGGCGTGACT** |
| 16 | CDRH3 nuc varS1 | **GCGAAACACTATGATTCGGGATATTCTACCATAGATCACTTTGACTCC** |
| 17 | CDRH3 nuc varS2 | **GCCAAACACTATGATAGTGGGTACTCCACTATTGACCATTTTGACTCT** |
| 18 | CDRH3 nuc varN1 | **GCCAAACACTATGATAGTGGGTATAGCACAATCGACCATTTTGACAGC** |
| 19 | CDRH3 nuc varC1 | **GCAAAACACTACGATTCTGGGTATAGTACAATTGACCATTTTGATTCT** |
| 20 | CDRH3 nuc varC2 | **GCCAAACACTATGATAGTGGGTACAGTACCATTGACCATTTCGATAGC** |
| 21 | CDRL1 nuc varS1 | **CAGAGTGTTTTCTACACCTCCAAAAATAAAAACTAC** |
| 22 | CDRL1 nuc varS2 | **CAGTCCGTCTTCTACACCAGTAAGAACAAAAACTAT** |
| 23 | CDRL1 nuc varN1 | **CAGAGCGTGTTCTACACCAGTAAGAACAAAAACTAT** |
| 24 | CDRL1 nuc varC1 | **CAGTCCGTGTTCTACACTTCTAAGAACAAAAACTAT** |
| 25 | CDRL1 nuc varC2 | **CAGAGTGTCTTCTACACCAGTAAGAACAAAAACTAT** |
| 26 | CDRL2 nuc varS1 | **TGGGCATCT** |
| 27 | CDRL2 nuc varS2/N1/C2 | **TGGGCTAGC** |
| 28 | CDRL2 nuc varC1 | **TGGGCCTCA** |
| 29 | CDRL2 long nuc varS1 | CTCATTTACTGGGCATCTACCCGGGAG |
| 30 | CDRL2 long nuc varS2/N1/C2 | CTGATCTACTGGGCTAGCACTAGAGAG |
| 31 | CDRL2 long nuc varC1 | CTGATCTACTGGGCCTCAACCCGAGAG |
| 32 | CDRL3 nuc varS1 | **CAGCAATATTATAGTACCCCTTTCACT** |
| 33 | CDRL3 nuc varS2 | **CAGCAGTATTATTCTACCCCCTTCACA** |
| 34 | CDRL3 nuc varN1 | **CAGCAGTATTACAGCACCCCATTCACA** |
| 35 | CDRL3 nuc varC1 | **CAGCAGTACTATAGCACTCCATTCACC** |
| 36 | CDRL3 nuc varC2 | **CAGCAGTATTATTCAACACCCTTCACA** |
| 37 | heavy chain variable domain (VH) aa | GVQLVQSGGGLVQPGGSLRLSCAASg**ftvstny**MSWVRQAPGKGLEWVSI**lyaggvt**RYADSVKTRFTISRDNSKNTLFLQMNALSAEDTAIYYC**akhydsgystidhfds**WGQGTLVTVSS |
| 38 | light chain variable domain (VL) aa | DIQMTQSPDSVAVSLGERATINCKSS**qsvfytsknkny**LAWFQQKPGQPPKLLIY**was**TRESGVPDRFSGSGSGTDFTLTISSLRPEDVAVYYC**qqyystpft**FGPGTKVDIK |
| 39 | heavy chain variable domain (VH) nuc varS1 | ggggtgcaactggtgcagtctgggggaggcttggtccagccggggggtccctgagactctcctgtgcagcctct**GGATTCACCGTCAGTACCAACTAC**atgagctgggtccgccaggctccagggaaggggctggagtgggtctcaatt**CTTTATGCCGGAGGTGTCACA**aggtacgcagactccgtgaagaccagattcaccatctccagagacaattccaagaacactctctttcttcaaatgaacgccctgagcgccgaggacacggctatatattactgt**GCGAAACACTATGATTCGGGATATTCTACCATAGATCACTTTGACTCC**tggggccagggaaccctggtcaccgtctcctca |
| 40 | heavy chain variable domain (VH) nuc varS2 | GGCGTGCAGCTGGTGCAGAGCGGCGGCGGCCTGGTGCAGCCTGGAGGGTCACTGAGACTGTCATGCGCAGCAAGC**GGGTTTACTGTGTCTACAAACTAC**ATGTCTTGGGTGAGGCAGGCACCTGGAAAGGGACTGGAGTGGGTCTCAATC**CTGTACGCTGGCGGGGTGACC**CGGTATGCAGACAGCGTCAAGACCCGGTTCACAATTAGCAGAGATAACTCCAAAAATACTCTGTTTCTGCAGATGAATGCCCTGTCCGCTGAAGACACCGCAATCTACTATTGC**GCCAAACACTATGATAGTGGGTACTCCACTATTGACCATTTTGACTCT**TGGGGGCAGGGGACTCTGGTGACTGTCTCTTCA |
| 41 | heavy chain variable domain (VH) nuc varN1 | GGCGTCCAGCTGGTGCAGAGCGGAGGGGGCCTGGTGCAGCCTGGCGGGTCCCTGAGACTGAGTTGTGCCGCAAGT**GGCTTTACTGTCTCTACAAACTAC**ATGTCTTGGGTGAGGCAGGCACCTGGAAAGGGACTGGAGTGGGTCTCAATC**CTGT** |

-continued

| SEQ ID NO | Description | Sequence |
|---|---|---|
| | | **ACGCTGGCGGGGTGACC**CGGTATGCAGACAGCGTCAAG<br>ACCCGGTTCACAATTAGCAGAGATAACTCCAAAAATACTC<br>AATCTACTATTGC**GCCAAACACTATGATAGTGGGTATAGC**<br>**ACAATCGACCATTTTGACAGC**TGGGGACAGGGAACTCTG<br>GTGACAGTCTCATCA |
| 42 | heavy chain variable domain (VH) nuc varC1 | GGAGTGCAGCTGGTCCAGAGCGGAGGAGGACTGGTGC<br>AGCCAGGAGGGTCACTGAGGCTGAGCTGCGCAGCTTCC<br>**GGCTTCACCGTGTCAACAAACTACA**TGAGCTGGGTCCGC<br>CAGGCACCTGGGAAGGGACTGGAGTGGGTGTCCATCCT<br>**GTACGCCGGAGGCGTGACT**CGATATGCTGACTCTGTCAA<br>GACTCGGTTCACCATCTCTAGAGATAACAGTAAGAACACC<br>CTGTTTCTGCAGATGAATGCACTGAGTGCCGAAGACACA<br>GCTATCTACTATTGT**GCAAAACACTACGATTCTGGGTATA**<br>**GTACAATTGACCTTTTGATTCT**TGGGGCCAGGGGACACT<br>GGTGACTGTCAGCTCC |
| 43 | heavy chain variable domain (VH) nuc varC2 | GGCGTGCAGCTGGTCCAGAGCGGAGGCGGACTGGTCCA<br>GCCCGGCGGATCACTGAGACTGTCATGTGCCGCAAGC**G**<br>**GGTTTACCGTCTCTACAAACTAC**ATGTCTTGGGTGAGGCA<br>GGCACCTGGAAAGGGACTGGAGTGGGTCTCAATC**CTGTA**<br>**CGCTGGCGGGGTGAC**CCGGTATGCAGACAGCGTCAAGA<br>CCCGGTTCACAATTAGCAGAGATAACTCCAAAAATACTCT<br>GTTTCTGCAGATGAATGCCCTGTCCGCTGAAGACACCGC<br>AATCTACTATTGCGCC**AAACACTATGATAGTGGGTACAGT**<br>**ACCATTGACCATTTCGATAGC**TGGGGGCAGGGGACTCTG<br>GTGACCGTCTCATCA |
| 44 | light chain variable domain (VL) nuc varS1 | gacatccagatgacccagtctccagactccgtggctgtgtctctgggcgagagggcca<br>ccatcaactgcaagtccagc**CAGAGTGTTTTCTACACCTCCAAAAA**<br>**TAAAAACTAC**ttagcttggttccagcagaaaccaggacagcctcctaaactgct<br>catttac**TGGGCATCT**acccgggagtccggggtccctgaccgattcagtggcag<br>cgggtctgggacagatttcactctcaccatcagcagcctgcggcctgaagatgtggca<br>gtttattactgt**CAGCAATATTATAGTACCCCTTTCACT**ttcggccctgg<br>gaccaaagtggatatcaaa |
| 45 | light chain variable domain (VL) nuc varS2 | GACATTCAGATGACCCAGAGTCCTGACAGCGTGGCCGTC<br>TCACTGGGGGAAAGGGCTACTATCAATTGTAAAAGTTCA**C**<br>**AGTCCGTCTTCTACACCAGTAAGAACAAAAACTAT**CTGGC<br>CTGGTTTCAGCAGAAGCCAGGCCAGCCCCCTAAACTGCT<br>GATCTACTGGGCTAGCACTAGAGAGTCTGGAGTGCCAGA<br>CAGATTCTCTGGCAGTGGGTCAGGAACCGACTTCACCCT<br>GACAATTAGCTCCCTGAGGCCCGAAGACGTGGCCGTCTA<br>TTATTGT**CAGCAGTATTATTCTACCCCCTTCACA**TTCGGAC<br>CTGGGACTAAAGTGGATATCAAA |
| 46 | light chain variable domain (VL) nuc varN1 | GACATTCAGATGACCCAGAGTCCTGATTCCGTGGCTGTCT<br>CACTGGGGGAGCGAGCAACTATTAACTGCAAGTCTTCAC<br>**AGAGCGTGTTCTACACCAGTAAGAACAAAAACTAT**CTGGC<br>CTGGTTTCAGCAGAAGCCAGGCCAGCCCCCTAAACTGCT<br>GATCTACTGGGCTAGCACTAGAGAGTCTGGAGTGCCAGA<br>CAGATTCTCTGGCAGTGGGTCAGGAACCGACTTCACCCT<br>GACAATTAGCTCCCTGAGGCCCGAAGACGTGGCCGTCTA<br>CTATTGT**CAGCAGTATTACAGCACCCCATTCACA**TTCGGC<br>CCTGGAACCAAAGTGGATATTAAG |
| 47 | light chain variable domain (VL) nuc varC1 | GACATCCAGATGACTCAGTCTCCCGATAGTGTGGCCGTCT<br>CCCTGGGGGAGAGGGCTACAATTAACTGCAAGAGCTCCC<br>**AGTCCGTGTTCTACACTTCTAAGAACAAAAACTAT**CTGGC<br>ATGGTTTCAGCAGAAGCCTGGACAGCCCCCTAAACTGCT<br>GATCTACTGGGCCTCAACCCGAGAGAGCGGAGTCCCAG<br>ACAGATTCTCAGGCAGCGGGTCCGGAACAGATTTTACCC<br>TGACAATTTCTAGTCTGCGGCCTGAAGACGTGGCTGTCTA<br>CTATTGT**CAGCAGTACTATAGCACTCCATTCACC**TTTGGCC<br>CCGGGACAAAGGTGGATATCAAA |
| 48 | light chain variable domain (VL) nuc varC2 | GATATTCAGATGACCCAGAGTCCTGATTCCGTCGCTGTCT<br>CACTGGGAGAAAGGGCAACCATTAACTGTAAAAGCTCAC<br>**AGAGTGTCTTCTACACCAGTAAGAACAAAAACTAT**CTGGC<br>CTGGTTTCAGCAGAAGCCAGGCCAGCCCCCTAAACTGCT<br>GATCTACTGGGCTAGCACTAGAGAGTCTGGAGTGCCAGA<br>CAGATTCTCTGGCAGTGGGTCAGGAACCGACTTCACCCT<br>GACAATTAGCTCCCTGAGGCCCGAAGACGTGGCCGTCTA<br>CTATTGT**CAGCAGTATTATTCAACACCCTTCACA**TTCGGAG<br>CAGGAACAAAAGTGGATATTAAG |
| | GCA21 ANTIBODY | |
| 49 | CDRH1 aa | **gftfsnyp** |
| 50 | CDRH2 aa | **ilpdgnrk** |
| 51 | CDRH3 aa | **trdgtyysnggvyqtyrrffdf** |
| 52 | CDRL1 aa | **qnilnw** |
| 53 | CDRL2 aa | **kas** |

-continued

| SEQ ID NO | Description | Sequence |
|---|---|---|
| 54 | CDRL2 long aa | LIYkasDLQ |
| 55 | CDRL3 aa | qhynsyplt |
| 56 | CDRH1 nuc | GGATTCACCTTTTCGAACTATCCT |
| 57 | CDRH2 nuc | ATTTTACCTGATGGGAACAGAAAA |
| 58 | CDRH3 nuc | ACGAGAGATGGCACGTATTACTCTAATGGTGGTGTTTATC<br>AGACATATCGAAGGTTCTTCGATTTC |
| 59 | CDRL1 nuc | CAGAATATCCTTAATTGG |
| 60 | CDRL2 nuc | AAGGCGTCT |
| 61 | CDRL2 long nuc | ctgatatatAAGGCGTCTgatttacaa |
| 62 | CDRL3 nuc | CAGCATTATAATAGTTATCCTCTCACT |
| 63 | heavy chain variable domain (VH) aa | QVQLMESGGGVVQPGRSLRLSCSAFgftfsnypMHWVRQAPG<br>KGLEWVAIilpdnrkNYGRSVTGRFTISRDNSNNSLYLQMNNL<br>TTEDTAMYYCtrdgtyysnggvyqtyrrffdfWGRGTLVTVSS |
| 64 | light chain variable domain (VL) aa | DIQMTQSPSTLSTSVGDRVTITCRASqnilnwLAWYQQKPGNA<br>PNLLIYkasDLQSGVPSRFSGSGSGTEFTLTISSLQPDDFATYYC<br>qhynsypltFGGGTKVEIK |
| 65 | heavy chain variable domain (VH) nuc | caggtgcaattgatggagtctgggggaggcgtggtccagcctgggaggtccctgcgac<br>tctcatgcagtgcctttGGATTCACCTTTTCGAACTATCCTatgcactgg<br>gtccgccaggctccaggcaagggacttgagtgggtggctatcATTTTACCTGAT<br>GGGAACAGAAAAaactatggaaggtccgtgacgggccgattcaccatctcca<br>gagacaattccaacaacagcattatttgcaaatgaacaacctgacgactgaggacac<br>ggctatgtactattgtACGAGAGATGGCACGTATTACTCTAATGGT<br>GGTGTTTATCAGACATATCGAAGGTTCTTCGATTTCtggggcc<br>gtggcaccctggtcaccgtctcctca |
| 66 | light chain variable domain (VL) nuc | gacatccagatgacccagtctccttccaccctgtctacatctgtgggagacagagtcac<br>catcacttgccgggccagtCAGAATATCCTTAATTGGttggcctggtatcaa<br>cagaaaccagggaacgcccctaacctcctgatatatAAGGCGTCTgatttacaa<br>agtggggtcccctcaagattcagcggcagtgggtctgggacagaattcactctcaccat<br>cagcagcctgcagcctgatgattttgcaacttattactgcCAGCATTATAATAG<br>TTATCCTCTCACTttcggcggagggaccaaggtggaaatcaaa |

GCB59 ANTIBODY

| SEQ ID NO | Description | Sequence |
|---|---|---|
| 67 | CDRH1 aa | GLSFSSSG |
| 68 | CDRH2 aa | ISGSQNYK |
| 69 | CDRH3 aa | VGGFPYWLPPSDFSGFHV |
| 70 | CDRL1 aa | NIGSKS |
| 71 | CDRL2 aa | ADN |
| 72 | CDRL2 long aa | VVYADNDRP |
| 73 | CDRL3 aa | QVWDGNTDHVV |
| 74 | CDRH1 nuc varS1 | GGATTGTCCTTCAGTAGTTCAGGC |
| 75 | CDRH1 nuc varN1/N2 | GGCCTGTCCTTCAGCTCCTCTGGC |
| 76 | CDRH1 nuc varC1 | GGGCTGAGCTMAGCTCCTCTGGA |
| 77 | CDRH2 nuc varS1 | ATTAGTGGTAGTCAGAACTACAAA |
| 78 | CDRH2 nuc varN1/N2 | ATTAGCGGGTCCCAGAAT1ACAAG |
| 79 | CDRH2 nuc varC1 | ATTTCTGGCAGTCAGAATTACAAG |
| 80 | CDRH3 nuc varS1 | GTGGGAGGTTTCCCCTATTGGTTACCCCCGAGCGACTTCT<br>CCGGTTTCCATGTC |
| 81 | CDRH3 nuc varN1/N2 | GTCGGCGGGTTTCCCTATTGGCTGCCTCCAAGCGAC<br>CAGGGTTTCATGTC |
| 82 | CDRH3 nuc varC1 | GTCGGGGGATTTCCCTATTGGCTGCCCCCTTCCGATTTCT<br>CTGGCTTTCACGTG |
| 83 | CDRL1 nuc varS1 | AACATTGGAAGTAAAAGT |
| 84 | CDRL1 nuc varN1/N2 | AACATCGGCAGCAAGAGC |
| 85 | CDRL1 nuc varC1 | AACATCGGGTCTAAGAGT |
| 86 | CDRL2 nuc varS1 | GCTGATAAC |
| 87 | CDRL2 nuc var N1/N2 | GCTGACAAC |
| 88 | CDRL2 nuc varC1 | GCCGACAAT |
| 89 | CDRL2 long nuc varS1 | GTCGTCTATGCTGATAACGACAGGCCC |
| 90 | CDRL2 long nuc varN1/N2 | GTGGTCTATGCTGACAACGATCGGCCC |
| 91 | CDRL2 long nuc varC1 | GTGGTCTATGCCGACAATGATCGGCCA |
| 92 | CDRL3 nuc varS1 | CAGGTGTGGGATGGTAATACTGATCATGTGGTC |
| 93 | CDRL3 nuc varN1/N2 | CAGGTCTGGGATGGGAATACTGACCACGTCGTC |
| 94 | CDRL3 nuc varC1 | CAGGTCTGGGACGGGAACACAGATCATGTGGTC |
| 95 | heavy chain variable domain (VH) aa | EVQLVESGGDLVKAGGSLRLSCAVSGLSFSSSGMNWVRQAP<br>GKGLEWISSISGSQNYKYYADSVKGRFVVSRDNARNFLYLQM<br>DSLRAEDTAVYFCVGGFPYWLPPSDFSGFHVWGQGTTVTVS<br>S |

-continued

| SEQ ID NO | Description | Sequence |
|---|---|---|
| 96 | light chain variable domain (VL) aa | SYVLTQPPSVSVAPGQTASLTCGGT**NIGSKS**VHWYQQKAGQ<br>APVLVVY**ADN**DRPSGVPERFSGSNSGNTATLTISRVEAEDESD<br>YFC**QVWDGNTDHVV**FGGGTKLTVL |
| 97 | heavy chain variable domain (VH) nuc varS1 | gaggtacaattggtggagtctgggggagacctggtcaaggcggggggtccctgaga<br>ctctcctgtgccgtctct**ggattgtccttcagtagttcagg**catgaattgggtccgccagg<br>ctccagggaaggggctggagtggatctcatcg**attagtggtagtcagaactacaaa**tac<br>tatgcagactcagtgaagggccgattcgtcgtctccagagacaacgcccgcaactttct<br>atatctgcaaatggacagcctgagggccgaggatacggctgtgtatttttgt**gtgggagg**<br>**tttcccctattggttacccccgagcgacttctccggtttccatgtct**ggggccaagggac<br>cacggtcaccgtctcctca |
| 98 | heavy chain variable domain (VH) nuc varN1 | GAGGTGCAGCTGGTGGAAAGCGGAGGGGATCTGGTGA<br>AAGCAGGAGGGAGCCTGAGACTGTCATGCGCCGTGAGC<br>**GGGCTGTCATTCAGCTCCTCTGGC**ATGAACTGGGTGCGA<br>CAGGCTCCTGGAAAGGGACTGGAGTGGATCAGTTCA**ATT**<br>**AGCGGGTCCCAGAATTACAAGT**ACTATGCAGACTCTGTCA<br>AAGGAAGGTTCGTGGTCAGCCGGGATAACGCCAGAAATT<br>TTCTGTATCTGCAGATGGACAGCCTGCGCGCCGAAGATA<br>CCGCCGTGTACTTCTGCGTCGGC**GGGTTTCCCTATTGGCT**<br>**GCCTCCAAGCGATTTCAGCGGATTTCATGTC**TGGGGGCA<br>GGGAACTACAGTGACCGTCTCATCA |
| 99 | heavy chain variable domain (VH) nuc varN2 | GAGGTGCAGCTGGTGGAAAGTGGGGGCGATCTGGTCAA<br>AGCCGGAGGGTCTCTGCGACTGTCTTGTGCTGTGAGCGG<br>CCTGTCCTTCAGCTCCTCTGGCATGAACTGGGTGCGACA<br>GGCTCCTGGAAAGGGACTGGAGTGGATCAGTTCA**ATTAG**<br>**CGGGTCCCAGAATTACAAG**TACTATGCAGACTCTGTCAAA<br>GGAAGGTTCGTGGTCAGCCGGGATAACGCCAGAAATTTT<br>CTGTATCTGCAGATGGACAGCCTGCGCGCCGAAGATACC<br>GCCGTGTACTTCTGC**GTCGGCGGGTTTCCCTATTGGCTGC**<br>**CTCCAAGCGACTTTTCAGGGTTTCATGT**CTGGGGGCAGG<br>GAACTACCGTGACCGTCTCATCT |
| 100 | heavy chain variable domain (VH) nuc varC1 | GAGGTGCAGCTGGTCGAATCTGGCGGGGACCTGGTGAA<br>GGCAGGAGGCAGTCTGAGGCTGTCATGCGCCGTCTCA**G**<br>**GGCTGAGCTTCAGCTCCTCTGGA**ATGAACTGGGTGCGCC<br>AGGCACCAGGCAAAGGACTGGAGTGGATCAGTTCA**ATTT**<br>**CTGGCAGTCAGAATTACAAG**TACTATGCTGACAGTGTGAA<br>AGGGCGATTCGTGGTCTCCCGGGATAACGCAAGAAATTT<br>TCTGTATCTGCAGATGGACAGCCTGAGAGCCGAAGATAC<br>TGCTGTGTACTTCTGTGTCGGGGG**ATTTCCCTATTGGCTG**<br>**CCCCCTTCCGATTTCTCTGGCTTTTCACGTG**TGGGGACAGG<br>GCACCACAGTGACCGTCAGCTCC |
| 101 | light chain variable domain (VL) nuc varS1 | TCATATGTGCTGACTCAACCACCCTCGGTGTCAGTGGCCC<br>CAGGACAGACGGCCAGTCTAACCTGTGGGGGAACT**AAC**<br>**ATTGGAAGTAAAAGT**GTTCATTGGTACCAGCAAAAGGCA<br>GGCCAGGCCCCTGTGTTGGTCGTCTAT**GCTGATAA**CGAC<br>AGGCCCTCAGGGGTCCCTGAGCGATTCTCTGGCTCCAAC<br>TCTGGGAACACGGCCACCCTGACCATCAGCAGGGTCGA<br>GGCCGAGGATGAGTCCGACTATTTCTGT**CAGGTGTGGGA**<br>**TGGTAATACTGATCATGTGGTC**TTCGGCGGAGGGACCAA<br>GCTGACCGTCCTG |
| 102 | light chain variable domain (VL) nuc varN1 | TCTTACGTCCTGACCCAGCCACCTAGCGTGAGCGTCGCA<br>CCAGGGCAGACAGCTTCACTGACTTGCGGAGGCACA**AAC**<br>**ATTGGCAGCAAGAGC**GTGCACTGGTACCAGCAGAAAGC<br>CGGACAGGCTCCCGTCCTGGTGGTCTAT**GCTGACAA**CGA<br>TCGGCCCTCTGGCGTGCCTGAAAGATTCAGCGGCTCCAA<br>CTCTGGGAATACCGCAACACTGACCATCAGTAGGGTCGA<br>GGCCGAAGACGAGTCAGATTACTTTTGC**CAGGTGTGGGA**<br>**CGGCAATACTGACCATGTCGTGT**TCGGCGGCGGGACCAA<br>ACTGACTGTGCTG |
| 103 | light chain variable domain (VL) nuc varN2 | TCCTACGTCCTGACTCAGCCACCTAGCGTGTCCGTCGCAC<br>CTGGGCAGACAGCATCACTGACTTGCGGGGGAACCAAC<br>ATCGGCAGCAAGAGCGTGCACTGGTACCAGCAGAAAGC<br>CGGACAGGCTCCCGTCCTGGTGGTCTATGCTGACAACGA<br>TCGGCCCTCTGGCGTGCCTGAAAGATTCAGCGGCTCCAA<br>CTCTGGGAATACCGCAACACTGACCATCAGTAGGGTCGA<br>GGCCGAAGACGAGTCAGATTACTTTTGCCAGGTCTGGGA<br>TGGGAATACTGACCACGTCGTCTTCGGAGGCGGAACCAA<br>ACTGACTGTCCTG |
| 104 | light chain variable domain (VL) nuc varC1 | TCCTACGTGCTGACTCAGCCACCTAGCGTGTCCGTCGCAC<br>CTGGACAGACTGCCAGCCTGACCTGCGGAGGAACAAAC<br>ATCGGGTCTAAGAGTGTGCACTGGTACCAGCAGAAAGCC<br>GGACAGGCTCCCGTCCTGGTGGTCTATGCCGACAATGAT<br>CGGCCATCTGGCGTGCCCGAAAGATTCTCAGGAAGCAAC<br>TCCGGCAATACCGCTACACTGACTATTTCTAGGGTGGAG |

-continued

| SEQ ID NO | Description | Sequence |
|---|---|---|
| | | GCAGAAGACGAGAGTGATTATTTCTGTCAGGTCTGGGAC<br>GGGAACACAGATCATGTGGTCTTTGGAGGCGGGACCAA<br>GCTGACAGTGCTG |
| | | GCE536 ANTIBODY |
| 105 | CDRH1 aa | **GYVFTSYY** |
| 106 | CDRH2 aa | **ISPGDVNT** |
| 107 | CDRH3 aa | **ARGPRSKPPYLYFALDV** |
| 108 | CDRL1 aa | **QSVSSSL** |
| 109 | CDRL2 aa | **GAS** |
| 110 | CDRL2 long aa | **LIYGASNRA** |
| 111 | CDRL3 aa | **QHYGSRVT** |
| 112 | CDRH1 nuc varS1 | **GGATACGTGTTCACCTCTTACTAT** |
| 113 | CDRH1 nuc varS2 | **GGATACGTCTTTACCTCTTACTAT** |
| 114 | CDRH1 nuc varN1/C1 | **GGATACGTC1TCACCTC1TACTAT** |
| 115 | CDRH2 nuc varS1/S2/N1/C1 | **ATCTCTCCCGGAGACGTGAACACT** |
| 116 | CDRH3 nuc varS1 | **GCTAGGGGGCCCCGCAGCAAGCCTCC1TATCTGTATTTTG<br>CTCTGGATGTG** |
| 117 | CDRH3 nuc varS2 | **GCTAGGGGGCCCCGCAGCAAGCCTCCTTATCTGTACTTC<br>GCTCTGGATGTC** |
| 118 | CDRH3 nuc varN1/C1 | **GCTAGGGGGCCCCGCAGCAAGCCTCCTTATCTGTATTTC<br>GCTCTGGATGTC** |
| 119 | CDRL1 nuc varS1 | **CAGAGTGTCAGCAGCAGCCTC** |
| 120 | CDRL1 nuc varS2 | **CAGTCTGTGAGCTCCTCTCTG** |
| 121 | CDRL1 nuc varN1/C1 | **CAGTCCGTGAGCTCCTCTCTG** |
| 122 | CDRL2 nuc varS1 | **GGTGCATCC** |
| 123 | CDRL2 nuc varS2/N1/C1 | **GGCGCCTCC** |
| 124 | CDRL2 long nuc varS1 | CTCATCTACGGTGCATCCAATAGGGCC |
| 125 | CDRL2 long nuc varS2/N1/C1 | CTGATCTATGGCGCCTCCAACCGCGCT |
| 126 | CDRL3 nuc varS1 | **CAGCACTATGGCTCACGGGTCACT** |
| 127 | CDRL3 nuc varS2 | **CAGCACTATGGCAGCAGGGTCACT** |
| 128 | CDRL3 nuc varN1 | **CAGCATTATGGGTCACGGGTCACT** |
| 129 | CDRL3 nuc varC1 | **CAGCATTATGGAAGCAGGGTCACC** |
| 130 | heavy chain variable domain (VH) aa | QLQLVQSGTEVKKPGASVKVSCKSSGYVFTSYYLVWVRQAP<br>GQGLEWMATISPGDVNTSYEQRFQGRVTVTTDASTNTVDM<br>ELRSLRSEDTAVYYCARGPRSKPPYLYFALDVWGQGTAVTVSS |
| 131 | light chain variable domain (VL) aa | EIVLTQSPGTLSLSPGETAILSCRASQSVSSSLLAWYQQKPGQA<br>PRLLIYGASNRATGIRGRFSGSGSGTDFTLTISRLEPEDFVLYYC<br>QHYGSRVTFGQGTKLEIK |
| 132 | heavy chain variable domain (VH) nuc varS1 | CAGCTGCAGCTGGTCCAGTCAGGCACAGAGGTCAAAAA<br>GCCAGGAGCATCAGTGAAGGTGTCTTGTAAGTCATCAGG<br>ATACGTGTTCACCTCTTACTATCTGGTGTGGGTCCGGCAG<br>GCACCAGGACAGGGACTGGAGTGGATGGCCACAATCTC<br>TCCCGGAGACGTGAACACTAGTTACGAACAGCGATTCCA<br>GGGCAGAGTGACCGTCACCACAGACGCTTCAACTAATAC<br>CGTGGATATGGAGCTGCGGAGCCTGAGATCCGAAGATA<br>CAGCCGTCTACTATTGCGCTAGGGGGCCCCGCAGCAAGC<br>CTCCTTATCTGTATTTTGCTCTGGATGTGTGGGGGCAGGG<br>GACCGCTGTCACCGTGTCAAGC |
| 133 | heavy chain variable domain (VH) nuc varS2 | CAGCTGCAGCTGGTCCAGTCAGGCACAGAAGTCAAAAAA<br>CCCGGCGCAAGCGTGAAGGTCTCATGTAAATCATCAGGA<br>TACGTCTTTACCTCTTACTATCTGGTGTGGGTCCGGCAGG<br>CACCAGGACAGGGACTGGAGTGGATGGCCACAATCTCTC<br>CCGGAGACGTGAACACTAGTTACGAACAGCGATTCCAGG<br>GCAGAGTGACCGTCACCACAGACGCTTCAACTAATACCG<br>TGGATATGGAGCTGCGGAGCCTGAGATCCGAAGATACA<br>GCCGTCTACTATTGCGCTAGGGGGCCCCGCAGCAAGCCT<br>CCTTATCTGTACTTCGCTCTGGATGTCTGGGGGCAGGGG<br>ACCGCCGTCACCGTCTCAAGC |
| 134 | heavy chain variable domain (VH) nuc varN1 | CAGCTGCAGCTGGTCCAGAGCGGCACAGAGGTGAAAAA<br>GCCAGGAGCATCAGTCAAAGTGTCTTGTAAGTCATCAGG<br>ATACGTCTTCACCTCTTACTATCTGGTGTGGGTCCGGCAG<br>GCACCAGGACAGGGACTGGAGTGGATGGCCACAATCTC<br>TCCCGGAGACGTGAACACTAGTTACGAACAGCGATTCCA<br>GGGCAGAGTGACCGTCACCACAGACGCTTCAACTAATAC<br>CGTGGATATGGAGCTGCGGAGCCTGAGATCCGAAGATA<br>CAGCCGTCTACTATTGCGCTAGGGGGCCCCGCAGCAAGC<br>CTCCT1ATCTGTA1TTCGCTCTGGATGTCTGGGGGCAGGG<br>AACAGCAGTCACCGTCTCTTCT |

-continued

| SEQ ID NO | Description | Sequence |
|---|---|---|
| 135 | heavy chain variable domain (VH) nuc varC1 | CAGCTGCAGCTGGTCCAGAGCGGAACCGAAGTGAAGAA<br>ACCCGGCGCAAGCGTCAAAGTCTCATGCAAATCAAGCGG<br>ATACGTCTTCACCTCTTACTATCTGGTGTGGGTCCGGCAG<br>GCACCAGGACAGGGACTGGAGTGGATGGCCACAATCTC<br>TCCCGGAGACGTGAACACTAGTTACGAACAGCGATTCCA<br>GGGCAGAGTGACCGTCACCACAGACGCTTCAACTAATAC<br>CGTGGATATGGAGCTGCGGAGCCTGAGATCCGAAGATA<br>CAGCCGTCTACTATTGCGCTAGGGGGCCCCGCAGCAAGC<br>CTCCTTATCTGTATTTCGCTCTGGATGTCTGGGGGCAGGG<br>AACAGCAGTCACCGTCTCAAGC |
| 136 | light chain variable domain (VL) nuc varS1 | gaaattgtgttgacgcagtctcctggcaccctgtctttgtctccaggggaaacagccatc<br>ctctcctgcagggccag**tcagagtgtcagcagcagcctctt**agcctggtaccagcaaa<br>aacctggccaggctcccaggctcctcatctac**ggtgcat**ccaatagggccactggcat<br>cagaggcaggtttagtggcagtgggtctgggacagacttcactctcaccatcagtagatt<br>ggagcctgaagattttgtactttattactgt**cagcactatggctcacgggtcact**ttggcc<br>aggggaccaagctggagatcaaac |
| 137 | light chain variable domain (VL) nuc varS2 | GAAATCGTGCTGACCCAGTCTCCTGGAACTCTGTCTCTGT<br>CACCTGGCGAAACCGCAATCCTGTCCTGTAGGGCAAGTC<br>AGTCTGTGAGCTCCTCTCTGCTGGCATGGTACCAGCAGA<br>AGCCCGGACAGGCCCCTAGGCTGCTGATCTATGGCGCCT<br>CCAACCGCGCTACTGGCATTCGGGGGAGATTCAGTGGCT<br>CAGGGAGCGGAACCGACTTTACCCTGACAATCAGCCGGC<br>TGGAGCCCGAAGATTTCGTGCTGTATTACTGTCAGCACTA<br>TGGCAGCAGGGTCACTTTTGGGCAGGGGACTAAACTGG<br>AGATTAAA |
| 138 | light chain variable domain (VL) nuc varN1 | GAAATCGTCCTGACCCAGTCACCTGGCACCCTGAGTCTG<br>AGTCCTGGCGAAACAGCAATCCTGTCTTGTCGGGCTTCAC<br>AGTCCGTGAGCTCCTCTCTGCTGGCATGGTACCAGCAGA<br>AGCCCGGACAGGCCCCTAGGCTGCTGATCTATGGCGCCT<br>CCAACCGCGCTACTGGCATTCGGGGGAGATTCAGTGGCT<br>CAGGGAGCGGAACCGACTTTACCCTGACAATCAGCCGGC<br>TGGAGCCCGAAGATTTCGTGCTGTACTACTGTCAGCATTA<br>TGGGTCACGGGTCACTTTTGGGCAGGGGACTAAACTGGA<br>AATCAAG |
| 139 | light chain variable domain (VL) nuc varC1 | GAGATTGTCCTGACCCAGTCACCTGGCACCCTGAGCCTG<br>AGTCCTGGAGAGACCGCTATTCTGTCTTGTCGGGCATCAC<br>AGTCCGTGAGCTCCTCTCTGCTGGCATGGTACCAGCAGA<br>AGCCCGGACAGGCCCCTAGGCTGCTGATCTATGGCGCCT<br>CCAACCGCGCTACTGGCATTCGGGGGAGATTCAGTGGCT<br>CAGGGAGCGGAACCGACTTTACCCTGACAATCAGCCGGC<br>TGGAGCCCGAAGATTTCGTGCTGTACTATTGTCAGCATTA<br>TGGAAGCAGGGTCACCTTCGGACAGGGAACTAAACTGG<br>AAATCAAG |
| | Constant regions | |
| 140 | IgG1 CH1-CH2-CH3 aa | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGGPSVFLFPPKP<br>KDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKGFYPS<br>DIAVEWESNGQPENNYKTTPPVLDSDGSFFLYSKLTVDKSRW<br>QQGNVFSCSVMHEALHNHYTQKSLSLSPGK |
| 141 | IgG CK aa | RTVAAPSVFIFPPSDEQLKSGTASVVCLLNNFYPREAKVQWKV<br>DNALQSGNSQESVTEQDSKDSTYSLSSTLTLSKADYEKHKVYA<br>CEVTHQGLSSPVTKSFNRGEC |
| 142 | IgG CL aa | GQPKAAPSVTLFPPSSEELQANKATLVCLISDFYPGAVTVAWK<br>ADSSPVKAGVETTTPSKQSNNKYAASSYLSLTPEQWKSHRSYS<br>CQVTHEGSTVEKTVAPTECS |
| 143 | Short linker aa | GGGGS |
| 144 | Long linker aa | GGGGSGGGGSGGGGS |
| 145 | IgG1 CH1-CH2-CH3 nucl varS1 | gcgtcgaccaagggcccatcggtcttccccctggcaccctcctccaagagcacctct<br>gggggcacagcggccctgggctgcctggtcaaggactacttccccgaacctgtgacg<br>gtctcgtggaactcaggcgccctgaccagcggcgtgcacaccttcccggctgtcctac<br>agtcctcaggactctactccctcagcagcgtggtgaccgtgccctccagcagcttggg<br>cacccagacctacatctgcaacgtgaatcacaagcccagcaacaccaaggtggaca<br>agagagttgagcccaaatcttgtgacaaaactcacacatgcccaccgtgcccagcac<br>ctgaactcctggggggaccgtcagtcttcctcttccccccaaaacccaaggacaccct<br>catgatctcccggacccctgaggtcacatgcgtggtggtggacgtgagccacgaGga<br>Tcctgaggtcaagttcaactggtacgtggacggcgtggaggtgcataatgccaagaca<br>aagccgcgggaggagcagtacaacagcacgtaccgtgtggtcagcgtcctcaccgt<br>cctgcaccaggactggctgaatggcaaggagtacaagtgcaaggtctccaacaaag<br>ccctcccagcccccatcgagaaaaccatctccaaagccaaagggcagccccgaga<br>accacaggtgtacaccctgcccccatcccgggaggagatgaccaagaaccaggtca<br>gcctgacctgcctggtcaaaggcttctatcccagcgacatcgccgtggagtgggagag |

-continued

| SEQ ID NO | Description | Sequence |
|---|---|---|
| | | caatgggcagccggagaacaactacaagaccacgcctcccgtgctggactccgacg<br>gctccttcttcctctatagcaagctcaccgtggacaagagcaggtggcagcaggggaa<br>cgtcttctcatgctccgtgatgcatgaggctctgcacaaccactacacgcagaagagc<br>ctctccctgtccccgggtaaa |
| 146 | IgG1 CH1-CH2-CH3 nucl varS2 | GCGTCGACCAAGGGCCCATCGGTCTTCCCCCTGGCACCC<br>TCCTCCAAGAGCACCTCTGGGGGCACAGCGGCCCTGGG<br>CTGCCTGGTCAAGGACTACTTCCCCGAACCTGTGACGGT<br>CTCGTGGAACTCAGGCGCCCTGACCAGCGGCGTGCACA<br>CCTTCCCGGCTGTCCTACAGTCCTCAGGACTCTACTCCCT<br>CAGCAGCGTGGTGACCGTGCCCTCCAGCAGCTTGGGCA<br>CCCAGACCTACATCTGCAACGTGAATCACAAGCCCAGCA<br>ACACCAAGGTGGACAAGAGAGTTGAGCCCAAATCTTGTG<br>ACAAAACTCACACATGCCCACCGTGCCCAGCACCTGAACT<br>CCTGGGGGGACCGTCAGTCTTCCTCTTCCCCCCAAAACCC<br>AAGGACACCCTCATGATCTCCCGGACCCCTGAGGTCACA<br>TGCGTGGTGGTGGACGTGAGCCACGAGGATCCTGAAGT<br>CAAGTTCAACTGGTACGTGGATGGCGTCGAGGTGCATAA<br>TGCCAAGACAAAACCCCGGGAGGAACAGTACAACTCAAC<br>TTATAGAGTCGTGAGCGTCCTGACCGTGCTGCATCAGGA<br>CTGGCTGAACGGCAAAGAATACAAGTGCAAAGTGTCTAA<br>TAAGGCCCTGCCTGCTCCAATCGAGAAAACAATTAGCAA<br>GGCAAAAGGGCAGCCCAGGGAACCTCAGGTGTACACTC<br>TGCCTCCAAGCCGCGAGGAAATGACCAAGAACCAGGTCT<br>CCCTGACATGTCTGGTGAAAGGATTCTATCCTAGTGACAT<br>TGCCGTGGAGTGGGAATCAAATGGCCAGCCAGAGAACA<br>ATTACAAGACCACACCCCCTGTGCTGGACTCTGATGGGA<br>GTTTCTTTCTGTATTCCAAGCTGACCGTGGATAAATCTAGA<br>TGGCAGCAGGGAAATGTCTTTAGCTGTTCCGTGATGCAT<br>GAGGCACTGCACAACCATTACACCCAGAAATCACTGTCAC<br>TGTCCCCAGGAAAA |
| 147 | IgG CK nucl | cgTacGgtggctgcaccatctgtcttcatcttcccgccatctgatgagcagttgaaatct<br>ggaactgcctctgttgtgtgcctgctgaataacttctatcccagagaggccaaagtacag<br>tggaaggtggataacgccctccaatcgggtaactcccaggagagtgtcacagagcag<br>gacagcaaggacagcacctacagcctcagcagcaccctgacgctgagcaaagcag<br>actacgagaaacacaaagtctacgcctgcgaagtcacccatcagggcctgagctcg<br>cccgtcacaaagagcttcaacaggggagagtgt |
| 148 | IgG CL nucl | ggtcagcccaaggctgccccctcggtcactctgttcccgccctcctctgaggagcttca<br>agccaacaaggccacactggtgtgtctcataagtgacttctacccgggagccgtgaca<br>gtggcttggaaagcagatagcagccccgtcaaggcgggagtggagaccaccacacc<br>agcagtggaagtcccacagaagctacagctgccaggtcacgcatgaagggagcacc<br>gtggagaagacagtggcccctacagaatgttca |
| 149 | Short linker nucl | GGCGGGGGAGGCTCT |
| 150 | Long linker nucl | GGCGGGGGAGGCTCTGGGGGAGGCGGGAGTGGAGGC<br>GGGGGATCA |

Engineered chains of multispecific antibodies

| SEQ ID NO | Description | Sequence |
|---|---|---|
| 151 | Ts1GC1 heavy chain aa | QVQLMESGGGVVQPGRSLRLSCSAFGFTFSNYPMHWVRQA<br>PGKGLEWVAIILPDGNRKNYGRSVTGRFTISRDNSNNSLYLQ<br>MNNLTTEDTAMYYCTRDGTYYSNGGVYQTYRRFFDFWGRG<br>TLVTVSSASTKGPSVFPLAPSSKSTSGGTAALGCLVKDYFPEPVT<br>VSWNSGALTSGVHTFPAVLQSSGLYSLSSVVTVPSSSLGTQTYI<br>CNVNHKPSNTKVDKRVEPKSCDKTHTCPPCPAPELLGGPSVF<br>LFPPKPKDTLMISRTPEVTCVVVDVSHEDPEVKFNWYVDGVE<br>VHNAKTKPREEQYNSTYRVVSVLTVLHQDWLNGKEYKCKVS<br>NKALPAPIEKTISKAKGQPREPQVYTLPPSREEMTKNQVSLTCL<br>VKGFYPSDIAVEWESNGQPENNYKTTPPVLDSDGSFFLYSKLT<br>VDKSRWQQGNVFSCSVMHEALHNHYTQKSLSLSPGKGGG<br>GSGVQLVQSGGGLVQPGGSLRLSCAASGFTVSTNYMSWVR<br>QAPGKGLEWVSILYAGGVTRYADSVKTRFTISRDNSKNTLFLQ<br>MNALSAEDTAIYYCAKHYDSGYSTDHFDSWGQGTLVTVSS<br>GGGGSGGGGSGGGGSDIQMTQSPDSVAVSLGERATINCKS<br>SQSVFYTSKNKNYLAWFQQKPGQPPKLLIYWASTRESGVPDR<br>FSGSGSGTDFTLTISSLRPEDVAVYYCQQYYSTPFTFGPGTKVD<br>IKGGGGSEVQLVESGGDLVKAGGSLRLSCAVSGLSFSSSGMN<br>WVRQAPGKGLEWISSISGSQNYKYYADSVKGRFVVSRDNAR<br>NFLYLQMDSLRAEDTAVYFCVGGFPYWLPPSDFSGFHVWG<br>QGTTVTVSSGGGGSGGGGSGGGGSSYVLTQPPSVSVAPGQ<br>TASLTCGGTNIGSKSVHWYQQKAGQAPVLVVYADNDRPSG<br>VPERFSGSNSGNTATLTISRVEAEDESDYFCQVWDGNTDHVV<br>FGGGTKLTVL |
| 152 | Ts1GC1 heavy chain nucl | CAGGTGCAATTGATGGAGTCTGGGGGAGGCGTGGTCCA<br>GCCTGGGAGGTCCCTGCGACTCTCATGCAGTGCCTTTGG<br>ATTCACCTTTTCGAACTATCCTATGCACTGGGTCCGCCAG<br>GCTCCAGGCAAGGGACTTGAGTGGGTGGCTATCATTTTA<br>CCTGATGGGAACAGAAAAAACTATGGAAGGTCCGTGACG |

| SEQ ID NO | Description | Sequence |
|---|---|---|
| | | GGCCGATTCACCATCTCCAGAGACAATTCCAACAACAGCC<br>TTTATTTGCAAATGAACAACCTGACGACTGAGGACACGGC<br>TATGTACTATTGTACGAGAGATGGCACGTATTACTCTAAT<br>GGTGGTGTTTATCAGACATATCGAAGGTTCTTCGATTTCT<br>GGGGCCGTGGCACCCTGGTCACCGTCTCCTCAGCGTCGA<br>CCAAGGGCCCATCGGTCTTCCCCCTGGCACCCTCCTCCAA<br>GAGCACCTCTGGGGGCACAGCGGCCCTGGGCTGCCTGG<br>TCAAGGACTACTTCCCCGAACCTGTGACGGTCTCGTGGA<br>ACTCAGGCGCCCTGACCAGCGGCGTGCACACCTTCCCGG<br>CTGTCCTACAGTCCTCAGGACTCTACTCCCTCAGCAGCGT<br>GGTGACCGTGCCCTCCAGCAGCTTGGGCACCCAGACCTA<br>CATCTGCAACGTGAATCACAAGCCCAGCAACACCAAGGT<br>GGACAAGAGAGTTGAGCCCAAATCTTGTGACAAAACTCA<br>CACATGCCCACCGTGCCCAGCACCTGAACTCCTGGGGGG<br>ACCGTCAGTCTTCCTCTTCCCCCCAAAACCCAAGGACACC<br>CTCATGATCTCCCGGACCCCTGAGGTCACATGCGTGGTG<br>GTGGACGTGAGCCACGAGGATCCTGAAGTCAAGTTCAAC<br>TGGTACGTGGATGGCGTCGAGGTGCATAATGCCAAGACA<br>AAACCCCGGGAGGAACAGTACAACTCAACTTATAGAGTC<br>GTGAGCGTCCTGACCGTGCTGCATCAGGACTGGCTGAAC<br>GGCAAAGAATACAAGTGCAAAGTGTCTAATAAGGCCCTG<br>CCTGCTCCAATCGAGAAAACAATTAGCAAGGCAAAAGGG<br>CAGCCCAGGGAACCTCAGGTGTACACTCTGCCTCCAAGC<br>CGCGAGGAAATGACCAAGAACCAGGTCTCCCTGACATGT<br>CTGGTGAAAGGATTCTATCCTAGTGACATTGCCGTGGAGT<br>GGGAATCAAATGGCCAGCCAGAGAACAATTACAAGACCA<br>CACCCCCTGTGCTGGACTCTGATGGGAGTTTCTTTCTGTA<br>TTCCAAGCTGACCGTGGATAAATCTAGATGGCAGCAGGG<br>AAATGTCTTTAGCTGTTCCGTGATGCATGAGGCACTGCAC<br>AACCATTACACCCAGAAATCACTGTCACTGTCCCCAGGAA<br>AAGGCGGGGAGGCTCTGGAGTGCAGCTGGTCCAGAG<br>CGGAGGAGGACTGGTGCAGCCAGGAGGGTCACTGAGG<br>CTGAGCTGCGCAGCTTCCGGCTTCACCGTGTCAACAAACT<br>ACATGAGCTGGGTCCGCCAGGCACCTGGGAAGGGACTG<br>GAGTGGGTGTCCATCCTGTACGCCGGAGGCGTGACTCG<br>ATATGCTGACTCTGTCAAGACTCGGTTCACCATCTCTAGA<br>GATAACAGTAAGAACACCCTGTTTCTGCAGATGAATGCAC<br>TGAGTGCCGAAGACACAGCTATCTACTATTGTGCAAAACA<br>CTACGATTCTGGGTATAGTACAATTGACCATTTTGATTCTT<br>GGGGCCAGGGGACACTGGTGACTGTCAGCTCCGGCGG<br>GGGAGGCTCTGGGGGAGGCGGGAGTGGAGGCGGGGG<br>ATCAGACATCCAGATGACTCAGTCTCCCGATAGTGTGGCC<br>GTCTCCCTGGGGGAGAGGGCTACAATTAACTGCAAGAGC<br>TCCCAGTCCGTGTTCTACACTTCTAAGAACAAAAACTATCT<br>GGCATGGTTTCAGCAGAAGCCTGGACAGCCCCCTAAACT<br>GCTGATCTACTGGGCCTCAACCCGAGAGAGCGGAGTCCC<br>AGACAGATTCTCAGGCAGCGGGTCCGGAACAGATTTTAC<br>CCTGACAATTTCTAGTCTGCGGCCTGAAGACGTGGCTGTC<br>TACTATTGTCAGCAGTACTATAGCACTCCATTCACCTTTGG<br>CCCCGGGACAAAGGTGGATATCAAAGGCGGGGGAGGCT<br>CTGAGGTGCAGCTGGTCGAATCTGGCGGGGACCTGGTG<br>AAGGCAGGAGGCAGTCTGAGGCTGTCATGCGCCGTCTC<br>AGGGCTGAGCTTCAGCTCCTCTGGAATGAACTGGGTGCG<br>CCAGGCACCAGGCAAAGGACTGGAGTGGATCAGTTCAAT<br>TTCTGGCAGTCAGAATTACAAGTACTATGCTGACAGTGTG<br>AAAGGGCGATTCGTGGTCTCCCGGGATAACGCAAGAAAT<br>TTTCTGTATCTGCAGATGGACAGCCTGAGAGCCGAAGAT<br>ACTGCTGTGTACTTCTGTGTCGGGGGATTTCCCTATTGGC<br>TGCCCCCTTCCGATTTCTCTGGCTTTCACGTGTGGGGACA<br>GGGCACCACAGTGACCGTCAGCTCCGGCGGGGGAGGCT<br>CTGGGGGAGGCGGGAGTGGAGGCGGGGGATCATCCTA<br>CGTGCTGACTCAGCCACCTAGCGTGTCCGTCGCACCTGG<br>ACAGACTGCCAGCCTGACCTGCGGAGGAACAAACATCG<br>GGTCTAAGAGTGTGCACTGGTACCAGCAGAAAGCCGGA<br>CAGGCTCCCGTCCTGGTGGTCTATGCCGACAATGATCGG<br>CCATCTGGCGTGCCCGAAAGATTCTCAGGAAGCAACTCC<br>GGCAATACCGCTACACTGACTATTTCTAGGGTGGAGGCA<br>GAAGACGAGAGTGATTATTTCTGTCAGGTCTGGGACGGG<br>AACACAGATCATGTGGTCTTTGGAGGCGGGACCAAGCTG<br>ACAGTGCTG |
| 153 | Ts1GC2a heavy chain aa | QLQLVQSGTEVKKPGASVKVSCKSSGYVFTSYYLVWVRQAP<br>GQGLEWMATISPGDVNTSYEQRFQGRVTVTTDASTNTVDM<br>ELRSLRSEDTAVYYCARGPRSKPPYLYFALDVWGQGTAVTVSS<br>ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGGPSVFLFPPKP |

-continued

| SEQ ID NO | Description | Sequence |
|---|---|---|
| | | KDTLMISRTPEVTCVVVDVSHEDPEVKFNWYVDGVEVHNAK |
| | | TKPREEQYNSTYRVVSVLTVLHQDWLNGKEYKCKVSNKALPA |
| | | PIEKTISKAKGQPREPQVYTLPPSREEMTKNQVSLTCLVKGFYPS |
| | | DIAVEWESNGQPENNYKTTPPVLDSDGSFFLYSKLTVDKSRW |
| | | QQGNVFSCSVMHEALHNHYTQKSLSLSPGKGGGGSGVQLV |
| | | QSGGGLVQPGGSLRLSCAASGFTVSTNYMSWVRQAPGKGL |
| | | EWVSILYAGGVTRYADSVKTRFTISRDNSKNTLFLQMNALSAE |
| | | DTAIYYCAKHYDSGYSTIDHFDSWGQGTLVTVSSGGGGSGG |
| | | GGSGGGGSDIQMTQSPDSVAVSLGERATINCKSSQSVFYTSK |
| | | NKNYLAWFQQKPGQPPKLLIYWASTRESGVPDRFSGSGSGT |
| | | DFTLTISSLRPEDVAVYYCQQYYSTPFTFGPGTKVDIKGGGGS |
| | | EVQLVESGGDLVKAGGSLRLSCAVSGLSFSSSGMNWVRQAP |
| | | GKGLEWISSISGSQNYKYYADSVKGRFVVSRDNARNFLYLQM |
| | | DSLRAEDTAVYFCVGGFPYWLPPSDFSGFHVWGQGTTVTVS |
| | | SGGGGSGGGGSGGGGSSYVLTQPPSVSVAPGQTASLTCGG |
| | | TNIGSKSVHWYQQKAGQAPVLVVYADNDRPSGVPERFSGS |
| | | NSGNTATLTISRVEAEDESDYFCQVWDGNTDHVVFGGGTKL |
| | | TVL |
| 154 | Ts1GC2a heavy chain nucl | CAGCTGCAGCTGGTCCAGTCAGGCACAGAGGTCAAAAA |
| | | GCCAGGAGCATCAGTGAAGGTGTCTTGTAAGTCATCAGG |
| | | ATACGTGTTCACCTCTTACTATCTGGTGTGGGTCCGGCAG |
| | | GCACCAGGACAGGGACTGGAGTGGATGGCCACAATCTC |
| | | TCCCGGAGACGTGAACACTAGTTACGAACAGCGATTCCA |
| | | GGGCAGAGTGACCGTCACCACAGACGCTTCAACTAATAC |
| | | CGTGGATATGGAGCTGCGGAGCCTGAGATCCGAAGATA |
| | | CAGCCGTCTACTATTGCGCTAGGGGGCCCCGCAGCAAGC |
| | | CTCCTTATCTGTATTTTGCTCTGGATGTGTGGGGGCAGGG |
| | | GACCGCTGTCACCGTGTCAAGCGCGTCGACCAAGGGCC |
| | | CATCGGTCTTCCCCCTGGCACCCTCCTCCAAGAGCACCTC |
| | | TGGGGGCACAGCGGCCCTGGGCTGCCTGGTCAAGGACT |
| | | ACTTCCCCGAACCTGTGACGGTCTCGTGGAACTCAGGCG |
| | | CCCTGACCAGCGGCGTGCACACCTTCCCGGCTGTCCTAC |
| | | AGTCCTCAGGACTCTACTCCCTCAGCAGCGTGGTGACCG |
| | | TGCCCTCCAGCAGCTTGGGCACCCAGACCTACATCTGCA |
| | | ACGTGAATCACAAGCCCAGCAACACCAAGGTGGACAAGA |
| | | GAGTTGAGCCCAAATCTTGTGACAAAACTCACACATGCCC |
| | | ACCGTGCCCAGCACCTGAACTCCTGGGGGGACCGTCAGT |
| | | CTTCCTCTTCCCCCCAAAACCCAAGGACACCCTCATGATCT |
| | | CCCGGACCCCTGAGGTCACATGCGTGGTGGTGGACGTG |
| | | AGCCACGAGGATCCTGAAGTCAAGTTCAACTGGTACGTG |
| | | GATGGCGTCGAGGTGCATAATGCCAAGACAAAACCCCG |
| | | GGAGGAACAGTACAACTCAACTTATAGAGTCGTGAGCGT |
| | | CCTGACCGTGCTGCATCAGGACTGGCTGAACGGCAAAGA |
| | | ATACAAGTGCAAAGTGTCTAATAAGGCCCTGCCTGCTCCA |
| | | ATCGAGAAAACAATTAGCAAGGCAAAAGGGCAGCCCAG |
| | | GGAACCTCAGGTGTACACTCTGCCTCCAAGCCGCGAGGA |
| | | AATGACCAAGAACCAGGTCTCCCTGACATGTCTGGTGAA |
| | | AGGATTCTATCCTAGTGACATTGCCGTGGAGTGGGAATC |
| | | AAATGGCCAGCCAGAGAACAATTACAAGACCACACCCCC |
| | | TGTGCTGGACTCTGATGGGAGTTTCTTTCTGTATTCCAAG |
| | | CTGACCGTGGATAAATCTAGATGGCAGCAGGGAAATGTC |
| | | TTTAGCTGTTCCGTGATGCATGAGGCACTGCACAACCATT |
| | | ACACCCAGAAATCACTGTCACTGTCCCCAGGAAAAGGCG |
| | | GGGGAGGCTCTGGAGTGCAGCTGGTCCAGAGCGGAGG |
| | | AGGACTGGTGCAGCCAGGAGGGTCACTGAGGCTGAGCT |
| | | GCGCAGCTTCCGGCTTCACCGTGTCAACAAACTACATGA |
| | | GCTGGGTCCGCCAGGCACCTGGGAAGGGACTGGAGTG |
| | | GGTGTCCATCCTGTACGCCGGAGGCGTGACTCGATATGC |
| | | TGACTCTGTCAAGACTCGGTTCACCATCTCTAGAGATAAC |
| | | AGTAAGAACACCCTGTTTCTGCAGATGAATGCACTGAGTG |
| | | CCGAAGACACAGCTATCTACTATTGTGCAAAACACTACGA |
| | | TTCTGGGTATAGTACAATTGACCATTTTGATTCTTGGGGCC |
| | | AGGGGACACTGGTGACTGTCAGCTCCGGCGGGGGAGG |
| | | CTCTGGGGGAGGCGGGAGTGGAGGCGGGGGATCAGAC |
| | | ATCCAGATGACTCAGTCTCCCGATAGTGTGGCCGTCTCCC |
| | | TGGGGGAGAGGGCTACAATTAACTGCAAGAGCTCCCAGT |
| | | CCGTGTTCTACACTTCTAAGAACAAAAACTATCTGGCATG |
| | | GTTTCAGCAGAAGCCTGGACAGCCCCCTAAACTGCTGAT |
| | | CTACTGGGCCTCAACCCGAGAGAGCGGAGTCCCAGACA |
| | | GATTCTCAGGCAGCGGGTCCGGAACAGATTTTACCCTGA |
| | | CAATTTCTAGTCTGCGGCCTGAAGACGTGGCTGTCTACTA |
| | | TTGTCAGCAGTACTATAGCACTCCATTCACCTTTGGCCCC |
| | | GGGACAAAGGTGGATATCAAAGGCGGGGGAGGCTCTGA |
| | | GGTGCAGCTGGTCGAATCTGGCGGGGACCTGGTGAAGG |
| | | CAGGAGGCAGTCTGAGGCTGTCATGCGCCGTCTCAGGG |
| | | CTGAGCTTCAGCTCCTCTGGAATGAACTGGGTGCGCCAG |

-continued

| SEQ ID NO | Description | Sequence |
|---|---|---|
| | | GCACCAGGCAAAGGACTGGAGTGGATCAGTTCAATTTCT<br>GGCAGTCAGAATTACAAGTACTATGCTGACAGTGTGAAA<br>GGGCGATTCGTGGTCTCCCGGGATAACGCAAGAAATTTT<br>CTGTATCTGCAGATGGACAGCCTGAGAGCCGAAGATACT<br>GCTGTGTACTTCTGTGTCGGGGGATTTCCCTATTGGCTGC<br>CCCCTTCCGATTTCTCTGGCTTTCACGTGTGGGGACAGGG<br>CACCACAGTGACCGTCAGCTCCGGCGGGGGAGGCTCTG<br>GGGGAGGCGGGAGTGGAGGCGGGGGATCATCCTACGT<br>GCTGACTCAGCCACCTAGCGTGTCCGTCGCACCTGGACA<br>GACTGCCAGCCTGACCTGCGGAGGAACAAACATCGGGT<br>CTAAGAGTGTGCACTGGTACCAGCAGAAAGCCGGACAG<br>GCTCCCGTCCTGGTGGTCTATGCCGACAATGATCGGCCA<br>TCTGGCGTGCCCGAAAGATTCTCAGGAAGCAACTCCGGC<br>AATACCGCTACACTGACTATTTCTAGGGTGGAGGCAGAA<br>GACGAGAGTGATTATTTCTGTCAGGTCTGGGACGGGAAC<br>ACAGATCATGTGGTCTTTGGAGGCGGGACCAAGCTGACA<br>GTGCTG |
| 155 | Ts2GC2b/Bs1GC2 a heavy chain aa | EVQLVESGGDLVKAGGSLRLSCAVSGLSFSSSGMNWVRQAP<br>GKGLEWISSISGSQNYKYYADSVKGRFVVSRDNARNFLYLQM<br>DSLRAEDTAVYFCVGGFPYWLPPSDFSGFHVWGQGTTVTVS<br>SGGGGSGGGGSGGGGSSYVLTQPPSVSVAPGQTASLTCGG<br>TNIGSKSVHWYQQKAGQAPVLVVYADNDRPSGVPERFSGS<br>NSGNTATLTISRVEAEDESDYFCQVWDGNTDHVVFGGGTKL<br>TVLGGGGSQLQLVQSGTEVKKPGASVKVSCKSSGYVFTSYYL<br>VWVRQAPGQGLEWMATISPGDVNTSYEQRFQGRVTVTTDA<br>STNTVDMELRSLRSEDTAVYYCARGPRSKPPYLYFALDVWGQ<br>GTAVTVSSASTKGPSVFPLAPSSKSTSGGTAALGCLVKDYFPEP<br>VTVSWNSGALTSGVHTFPAVLQSSGLYSLSSVVTVPSSSLGTQ<br>TYICNVNHKPSNTKVDKRVEPKSCDKTHTCPPCPAPELLGGPS<br>VFLFPPKPKDTLMISRTPEVTCVVVDVSHEDPEVKFNWYVDG<br>VEVHNAKTKPREEQYNSTYRVVSVLTVLHQDWLNGKEYKCK<br>VSNKALPAPIEKTISKAKGQPREPQVYTLPPSREEMTKNQVSLT<br>CLVKGFYPSDIAVEWESNGQPENNYKTTPPVLDSDGSFFLYSK<br>LTVDKSRWQQGNVFSCSVMHEALHNHYTQKSLSLSPGK |
| 156 | Ts2GC2b/Bs1GC2 a heavy chain nucl | GAGGTGCAGCTGGTGGAAAGCGGAGGGGATCTGGTGA<br>AAGCAGGAGGGAGCCTGAGACTGTCATGCGCCGTGAGC<br>GGGCTGTCATTCAGCTCCTCTGGCATGAACTGGGTGCGA<br>CAGGCTCCTGGAAAGGGACTGGAGTGGATCAGTTCAATT<br>AGCGGGTCCCAGAATTACAAGTACTATGCAGACTCTGTCA<br>AAGGAAGGTTCGTGGTCAGCCGGGATAACGCCAGAAATT<br>TTCTGTATCTGCAGATGGACAGCCTGCGCGCCGAAGATA<br>CCGCCGTGTACTTCTGCGTCGGCGGGTTTCCCTATMGCT<br>GCCTCCAAGCGATTTCAGCGGATTTCATGTCTGGGGGCA<br>GGGAACTACAGTGACCGTCTCATCAGGCGGGGGAGGCT<br>CTGGGGGAGGCGGGAGTGGAGGCGGGGGATCATCTTA<br>CGTCCTGACCCAGCCACCTAGCGTGAGCGTCGCACCAGG<br>GCAGACAGCTTCACTGACTTGCGGAGGCACAAACATTGG<br>CAGCAAGAGCGTGCACTGGTACCAGCAGAAAGCCGGAC<br>AGGCTCCCGTCCTGGTGGTCTATGCTGACAACGATCGGC<br>CCTCTGGCGTGCCTGAAAGATTCAGCGGCTCCAACTCTG<br>GGAATACCGCAACACTGACCATCAGTAGGGTCGAGGCC<br>GAAGACGAGTCAGATTACTTTTGCCAGGTGTGGGACGGC<br>AATACTGACCATGTCGTGTTCGGCGGCGGGACCAAACTG<br>ACTGTGCTGGGCGGGGGAGGCTCTCAGCTGCAGCTGGT<br>CCAGTCAGGCACAGAAGTCAAAAAACCCGGCGCAAGCG<br>TGAAGGTCTCATGTAAATCATCAGGATACGTCTTTACCTCT<br>TACTATCTGGTGTGGGTCCGGCAGGCACCAGGACAGGG<br>ACTGGAGTGGATGGCCACAATCTCTCCCGGAGACGTGAA<br>CACTAGTTACGAACAGCGATTCCAGGGCAGAGTGACCGT<br>CACCACAGACGCTTCAACTAATACCGTGGATATGGAGCT<br>GCGGAGCCTGAGATCCGAAGATACAGCCGTCTACTATTG<br>CGCTAGGGGGCCCCGCAGCAAGCCTCCTTATCTGTACTr<br>CGCTCTGGATGTCTGGGGGCAGGGGACCGCCGTCACCG<br>TCTCAAGCGCGTCGACCAAGGGCCCATCGGTCTTCCCCC<br>TGGCACCCTCCTCCAAGAGCACCTCTGGGGGCACAGCG<br>GCCCTGGGCTGCCTGGTCAAGGACTACTTCCCCGAACCT<br>GTGACGGTCTCGTGGAACTCAGGCGCCCTGACCAGCGG<br>CGTGCACACCTTCCCGGCTGTCCTACAGTCCTCAGGACTC<br>TACTCCCTCAGCAGCGTGGTGACCGTGCCCTCCAGCAGC<br>TTGGGCACCCAGACCTACATCTGCAACGTGAATCACAAG<br>CCCAGCAACACCAAGGTGGACAAGAGAGTTGAGCCCAA<br>ATCTTGTGACAAAACTCACACATGCCCACCGTGCCCAGCA<br>CCTGAACTCCTGGGGGGACCGTCAGTCTTCCTCTTCCCCC<br>CAAAACCCAAGGACACCCTCATGATCTCCCGGACCCCTG<br>AGGTCACATGCGTGGTGGTGGACGTGAGCCACGAGGAT<br>CCTGAGGTCAAGTTCAACTGGTACGTGGACGGCGTGGA |

-continued

| SEQ ID NO | Description | Sequence |
|---|---|---|
| | | GGTGCATAATGCCAAGACAAAGCCGCGGGAGGAGCAGT<br>ACAACAGCACGTACCGTGTGGTCAGCGTCCTCACCGTCC<br>TGCACCAGGACTGGCTGAATGGCAAGGAGTACAAGTGC<br>AAGGTCTCCAACAAAGCCCTCCCAGCCCCCATCGAGAAA<br>ACCATCTCCAAAGCCAAAGGGCAGCCCCGAGAACCACAG<br>GTGTACACCCTGCCCCCATCCCGGGAGGAGATGACCAAG<br>AACCAGGTCAGCCTGACCTGCCTGGTCAAAGGCTTCTATC<br>CCAGCGACATCGCCGTGGAGTGGGAGAGCAATGGGCAG<br>CCGGAGAACAACTACAAGACCACGCCTCCCGTGCTGGAC<br>TCCGACGGCTCCTTCTTCCTCTATAGCAAGCTCACCGTGG<br>ACAAGAGCAGGTGGCAGCAGGGGAACGTCTTCTCATGCT<br>CCGTGATGCATGAGGCTCTGCACAACCACTACACGCAGA<br>AGAGCCTCTCCCTGTCCCCGGGTAAA |
| 157 | Ts2GC2b/Bs2GC1 c light chain aa | GVQLVQSGGGLVQPGGSLRLSCAASGFTVSTNYMSWVRQA<br>PGKGLEWVSILYAGGVTRYADSVKTRFTISRDNSKNTLFLQM<br>NALSAEDTAIYYCAKHYDSGYSTIDHFDSWGQGTLVTVSSGG<br>GGSGGGGSGGGGSDIQMTQSPDSVAVSLGERATINCKSSQS<br>VFYTSKNKNYLAWFQQKPGQPPKLLIYWASTRESGVPDRFSG<br>SGSGTDFTLTISSLRPEDVAVYYCQQYYSTPFTFGPGTKVDIKG<br>GGGSEIVLTQSPGTLSLSPGETAILSCRASQSVSSSLLAWYQQK<br>PGQAPRLLIYGASNRATGIRGRFSGSGSGTDFTLTISRLEPEDFV<br>LYYCQHYGSRVTFGQGTKLEIKRTVAAPSVFIFPPSDEQLKSGT<br>ASVVCLLNNFYPREAKVQWKVDNALQSGNSQESVTEQDSK<br>DSTYSLSSTLTLSKADYEKHKVYACEVTHQGLSSPVTKSFNRGE<br>C |
| 158 | Ts2GC2b/Bs2GC1 c light chain nucl | GGCGTCCAGCTGGTGCAGAGCGGAGGGGGCCTGGTGC<br>AGCCTGGCGGGTCCCTGAGACTGAGTTGTGCCGCAAGT<br>GGCTTTACTGTCTCTACAAACTACATGTCTTGGGTGAGGC<br>AGGCACCTGGAAAGGGACTGGAGTGGGTCTCAATCCTGT<br>ACGCTGGCGGGGTGACCCGGTATGCAGACAGCGTCAAG<br>ACCCGGTTCACAATTAGCAGAGATAACTCCAAAAATACTC<br>TGTTTCTGCAGATGAATGCCCTGTCCGCTGAAGACACCGC<br>AATCTACTATTGCGCCAAACACTATGATAGTGGGTATAGC<br>ACAATCGACCATTTTGACAGCTGGGGACAGGGAACTCTG<br>GTGACAGTCTCATCAGGCGGGGGAGGCTCTGGGGGAG<br>GCGGGAGTGGAGGCGGGGGATCAGACATTCAGATGACC<br>CAGAGTCCTGATTCCGTGGCTGTCTCACTGGGGGAGCGA<br>GCAACTATTAACTGCAAGTCTTCACAGAGCGTGTTCTACA<br>CCAGTAAGAACAAAAACTATCTGGCCTGGTTTCAGCAGAA<br>GCCAGGCCAGCCCCCTAAACTGCTGATCTACTGGGCTAG<br>CACTAGAGAGTCTGGAGTGCCAGACAGATTCTCTGGCAG<br>TGGGTCAGGAACCGACTTCACCCTGACAATTAGCTCCCTG<br>AGGCCCGAAGACGTGGCCGTCTACTATTGTCAGCAGTAT<br>TACAGCACCCCATTCACATTCGGCCCTGGAACCAAAGTG<br>GATATTAAGGGCGGGGGAGGCTCTGAAATCGTGCTGAC<br>CCAGTCTCCTGGAACTCTGTCTCTGTCACCTGGCGAAACC<br>GCAATCCTGTCCTGTAGGGCAAGTCAGTCTGTGAGCTCCT<br>CTCTGCTGGCATGGTACCAGCAGAAGCCCGGACAGGCC<br>CCTAGGCTGCTGATCTATGGCGCCTCCAACCGCGCTACT<br>GGCATTCGGGGGAGATTCAGTGGCTCAGGGAGCGGAAC<br>CGACTTTACCCTGACAATCAGCCGGCTGGAGCCCGAAGA<br>TTTCGTGCTGTATTACTGTCAGCACTATGGCAGCAGGGTC<br>ACTTTTGGGCAGGGGACTAAACTGGAGATTAAAcgTacGgt<br>ggctgcaccatctgtcttcatcttcccgccatctgatgagcagttgaaatctggaactgc<br>ctctgttgtgtgcctgctgaataacttctatcccagagaggccaaagtacagtggaaggt<br>ggataacgccctccaatcgggtaactcccaggagagtgtcacagagcaggacagca<br>aggacagcacctacagcctcagcagcaccctgacgctgagcaaagcagactacga<br>gaaacacaaagtctacgcctgcgaagtcacccatcagggcctgagctcgcccgtca<br>caaagagcttcaacaggggagagtgt |
| 159 | Ts2GC2dBs1GC3 a heavy chain aa | EVQLVESGGDLVKAGGSLRLSCAVSGLSFSSSGMNWVRQAP<br>GKGLEWISSISGSQNYKYYADSVKGRFVVSRDNARNFLYLQM<br>DSLRAEDTAVYFCVGGFPYWLPPSDFSGFHVWGQGTTVTVS<br>SGGGGSGGGGSGGGGSSYVLTQPPSVSVAPGQTASLTCGG<br>TNIGSKSVHWYQQKAGQAPVLVVYADNDRPSGVPERFSGS<br>NSGNTATLTISRVEAEDESDYFCQVWDGNTDHVVFGGGTKL<br>TVLGGGGSGVQLVQSGGGLVQPGGSLRLSCAASGFTVSTNY<br>MSWVRQAPGKGLEWVSILYAGGVTRYADSVKTRFTISRDNSK<br>NTLFLQMNALSAEDTAIYYCAKHYDSGYSTIDHFDSWGQGT<br>LVTVSSASTKGPSVFPLAPSSKSTSGGTAALGCLVKDYFPEPVT<br>VSWNSGALTSGVHTFPAVLQSSGLYSLSSVVTVPSSSLGTQTYI<br>CNVNHKPSNTKVDKRVEPKSCDKTHTCPPCPAPELLGGPSVF<br>LFPPKPKDTLMISRTPEVTCVVVDVSHEDPEVKFNWYVDGVE<br>VHNAKTKPREEQYNSTYRVVSVLTVLHQDWLNGKEYKCKVS<br>NKALPAPIEKTISKAKGQPREPQVYTLPPSREEMTKNQVSLTCL<br>VKGFYPSDIAVEWESNGQPENNYKTTPPVLDSDGSFFLYSKLT<br>VDKSRWQQGNVFSCSVMHEALHNHYTQKSLSLSPGK |

-continued

| SEQ ID NO | Description | Sequence |
|---|---|---|
| 160 | Ts2GC2c/Bs1GC3 a heavy chain nucl | GAGGTGCAGCTGGTGGAAAGTGGGGGCGATCTGGTCAA AGCCGGAGGGTCTCTGCGACTGTCTTGTGCTGTGAGCGG CCTGTCCTTCAGCTCCTCTGGCATGAACTGGGTGCGACA GGCTCCTGGAAAGGGACTGGAGTGGATCAGTTCAATTAG CGGGTCCCAGAATTACAAGTACTATGCAGACTCTGTCAAA GGAAGGTTCGTGGTCAGCCGGGATAACGCCAGAAATTTT CTGTATCTGCAGATGGACAGCCTGCGCGCCGAAGATACC GCCGTGTACTTCTGCGTCGGCGGGTTTCCCTATMGCTGC CTCCAAGCGACTTTTCAGGGTTTCATGTCTGGGGGCAGG GAACTACCGTGACCGTCTCATCTGGCGGGGGAGGCTCTG GGGGAGGCGGGAGTGGAGGCGGGGGATCATCCTACGT CCTGACTCAGCCACCTAGCGTGTCCGTCGCACCTGGGCA GACAGCATCACTGACTTGCGGGGGAACCAACATCGGCA GCAAGAGCGTGCACTGGTACCAGCAGAAAGCCGGACAG GCTCCCGTCCTGGTGGTCTATGCTGACAACGATCGGCCC TCTGGCGTGCCTGAAAGATTCAGCGGCTCCAACTCTGGG AATACCGCAACACTGACCATCAGTAGGGTCGAGGCCGAA GACGAGTCAGATTACTTTTGCCAGGTCTGGGATGGGAAT ACTGACCACGTCGTCTTCGGAGGCGGAACCAAACTGACT GTCCTGGGCGGGGGAGGCTCTGGCGTGCAGCTGGTGCA GAGCGGCGGCGGCCTGGTGCAGCCTGGAGGGTCACTG AGACTGTCATGCGCAGCAAGCGGGTfTACTGTGTCTACA AACTACATGTCTTGGGTGAGGCAGGCACCTGGAAAGGG ACTGGAGTGGGTCTCAATCCTGTACGCTGGCGGGGTGAC CCGGTATGCAGACAGCGTCAAGACCCGGTTCACAATTAG CAGAGATAACTCCAAAAATACTCTGTTTCTGCAGATGAAT GCCCTGTCCGCTGAAGACACCGCAATCTACTATTGCGCCA AACACTATGATAGTGGGTACTCCACTATTGACCATTTTGAC TCTTGGGGGCAGGGGACTCTGGTGACTGTCTCTTCAGCG TCGACCAAGGGCCCATCGGTCTTCCCCCTGGCACCCTCCT CCAAGAGCACCTCTGGGGGCACAGCGGCCCTGGGCTGC CTGGTCAAGGACTACTTCCCCGAACCTGTGACGGTCTCGT GGAACTCAGGCGCCCTGACCAGCGGCGTGCACACCTTCC CGGCTGTCCTACAGTCCTCAGGACTCTACTCCCTCAGCAG CGTGGTGACCGTGCCCTCCAGCAGCTTGGGCACCCAGAC CTACATCTGCAACGTGAATCACAAGCCCAGCAACACCAA GGTGGACAAGAGAGTTGAGCCCAAATCTTGTGACAAAAC TCACACATGCCCACCGTGCCCAGCACCTGAACTCCTGGG GGGACCGTCAGTCTTCCTCTTCCCCCCAAAACCCAAGGAC ACCCTCATGATCTCCCGGACCCCTGAGGTCACATGCGTG GTGGTGGACGTGAGCCACGAGGATCCTGAGGTCAAGTT CAACTGGTACGTGGACGGCGTGGAGGTGCATAATGCCA AGACAAAGCCGCGGGAGGAGCAGTACAACAGCACGTAC CGTGTGGTCAGCGTCCTCACCGTCCTGCACCAGGACTGG CTGAATGGCAAGGAGTACAAGTGCAAGGTCTCCAACAAA GCCCTCCCAGCCCCCATCGAGAAAACCATCTCCAAAGCC AAAGGGCAGCCCCGAGAACCACAGGTGTACACCCTGCC CCCATCCCGGGAGGAGATGACCAAGAACCAGGTCAGCC TGACCTGCCTGGTCAAAGGCTTCTATCCCAGCGACATCGC CGTGGAGTGGGAGAGCAATGGGCAGCCGGAGAACAACT ACAAGACCACGCCTCCCGTGCTGGACTCCGACGGCTCCT TCTTCCTCTATAGCAAGCTCACCGTGGACAAGAGCAGGT GGCAGCAGGGGAACGTCTTCTCATGCTCCGTGATGCATG AGGCTCTGCACAACCACTACACGCAGAAGAGCCTCTCCC TGTCCCCGGGTAAA |
| 161 | Ts2GC2c/Bs2GC1d light chain aa | QLQLVQSGTEVKKPGASVKVSCKSSGYVFTSYYLVWVRQAP GQGLEWMATISPGDVNTSYEQRFQGRVTVTTDASTNTVDM ELRSLRSEDTAVYYCARGPRSKPPYLYFALDVWGQGTAVTVSS GGGGSGGGGSGGGGSEIVLTQSPGTLSLSPGETAILSCRASQS VSSSLLAWYQQKPGQAPRLLIYGASNRATGIRGRFSGSGSGT DFTLTISRLEPEDFVLYYCQHYGSRVTFGQGTKLEIKGGGGSDI QMTQSPDSVAVSLGERATINCKSSQSVFYTSKNKNYLAWFQ QKPGQPPKLLIYWASTRESGVPDRFSGSGSGTDFTLTISSLRPE DVAVYYCQQYYSTPFTFGPGTKVDIKRTVAAPSVFIFPPSDEQ LKSGTASVVCLLNNFYPREAKVQWKVDNALQSGNSQESVTE QDSKDSTYSLSSTLTLSKADYEKHKVYACEVTHQGLSSPVTKSF NRGEC |
| 162 | Ts2GC2c/Bs2GC1d light chain nucl | CAGCTGCAGCTGGTCCAGAGCGGCACAGAGGTGAAAAA GCCAGGAGCATCAGTCAAAGTGTCTTGTAAGTCATCAGG ATACGTCTTCACCTCTTACTATCTGGTGTGGGTCCGGCAG GCACCAGGACAGGGACTGGAGTGGATGGCCACAATCTC TCCCGGAGACGTGAACACTAGTTACGAACAGCGATTCCA GGGCAGAGTGACCGTCACCACAGACGCTTCAACTAATAC CGTGGATATGGAGCTGCGGAGCCTGAGATCCGAAGATA CAGCCGTCTACTATTGCGCTAGGGGGCCCCGCAGCAAGC CTCCTTATCTGTATTTCGCTCTGGATGTCTGGGGGCAGGG |

-continued

| SEQ ID NO | Description | Sequence |
|---|---|---|
| | | AACAGCAGTCACCGTCTCTTCTGGCGGGGGAGGCTCTGG GGGAGGCGGGAGTGGAGGCGGGGGATCAGAAATCGTC CTGACCCAGTCACCTGGCACCCTGAGTCTGAGTCCTGGC GAAACAGCAATCCTGTCTTGTCGGGCTTCACAGTCCGTGA GCTCCTCTCTGCTGGCATGGTACCAGCAGAAGCCCGGAC AGGCCCCTAGGCTGCTGATCTATGGCGCCTCCAACCGCG CTACTGGCATTCGGGGGAGATTCAGTGGCTCAGGGAGC GGAACCGACTTTACCCTGACAATCAGCCGGCTGGAGCCC GAAGATTTCGTGCTGTACTACTGTCAGCATTATGGGTCAC GGGTCACTTTTGGGCAGGGGACTAAACTGGAAATCAAGG GCGGGGGAGGCTCTGACATTCAGATGACCCAGAGTCCT GACAGCGTGGCCGTCTCACTGGGGGAAAGGGCTACTAT CAATTGTAAAAGTTCACAGTCCGTCTTCTACACCAGTAAG AACAAAAACTATCTGGCCTGGTTTCAGCAGAAGCCAGGC CAGCCCCCTAAACTGCTGATCTACTGGGCTAGCACTAGA GAGTCTGGAGTGCCAGACAGATTCTCTGGCAGTGGGTCA GGAACCGACTTCACCCTGACAATTAGCTCCCTGAGGCCC GAAGACGTGGCCGTCTATTATTGTCAGCAGTATTATTCTA CCCCCTTCACATTCGGACCTGGGACTAAAGTGGATATCAA ACGTACGGTGGCTGCACCATCTGTCTTCATCTTCCCGCCA TCTGATGAGCAGTTGAAATCTGGAACTGCCTCTGTTGTGT GCCTGCTGAATAACTTCTATCCCAGAGAGGCCAAAGTACA GTGGAAGGTGGATAACGCCCTCCAATCGGGTAACTCCCA GGAGAGTGTCACAGAGCAGGACAGCAAGGACAGCACCT ACAGCCTCAGCAGCACCCTGACGCTGAGCAAAGCAGACT ACGAGAAACACAAAGTCTACGCCTGCGAAGTCACCCATC AGGGCCTGAGCTCGCCCGTCACAAAGAGCTTCAACAGG GGAGAGTGT |
| 163 | Ts3GC2d heavy chain aa | EVQLVESGGDLVKAGGSLRLSCAVSGLSFSSSGMNWVRQAP GKGLEWISSISGSQNYKYYADSVKGRFVVSRDNARNFLYLQM DSLRAEDTAVYFCVGGFPYWLPPSDFSGFHVWGQGTTVTVS SGGGGSGGGGSGGGGSSYVLTQPPSVSVAPGQTASLTCGG TNIGSKSVHWYQQKAGQAPVLVVYADNDRPSGVPERFSGS NSGNTATLTISRVEAEDESDYFCQVWDGNTDHVVFGGGTKL TVLGGGGSQLQLVQSGTEVKKPGASVKVSCKSSGYVFTSYYL VWVRQAPGQGLEWMATISPGDVNTSYEQRFQGRVTVTTDA STNTVDMELRSLRSEDTAVYYCARGPRSKPPYLYFALDVWGQ GTAVTVSSASTKGPSVFPLAPSSKSTSGGTAALGCLVKDYFPEP VTVSWNSGALTSGVHTFPAVLQSSGLYSLSSVVTVPSSSLGTQ TYICNVNHKPSNTKVDKRVEPKSCDKTHTCPPCPAPELLGGPS VFLFPPKPKDTLMISRTPEVTCVVVDVSHEDPEVKFNWYVDG VEVHNAKTKPREEQYNSTYRVVSVLTVLHQDWLNGKEYKCK VSNKALPAPIEKTISKAKGQPREPQVYTLPPSREEMTKNQVSLT CLVKGFYPSDIAVEWESNGQPENNYKTTPPVLDSDGSFFLYSK LTVDKSRWQQGNVFSCSVMHEALHNHYTQKSLSLSPGKGG GGSGVQLVQSGGGLVQPGGSLRLSCAASGFTVSTNYMSWV RQAPGKGLEWVSILYAGGVTRYADSVKTRFTISRDNSKNTLFL QMNALSAEDTAIYYCAKHYDSGYSTIDHFDSWGQGTLVTVS SGGGGSGGGGSGGGGSDIQMTQSPDSVAVSLGERATINCK SSQSVFYTSKNKNYLAWFQQKPGQPPKLLIYWASTRESGVPD RFSGSGSGTDFTLTISSLRPEDVAVYYCQQYYSTPFTFGPGTKV DIK |
| 164 | Ts3GC2d heavy chain nucl | GAGGTGCAGCTGGTGGAAAGCGGAGGGGATCTGGTGA AAGCAGGAGGGAGCCTGAGACTGTCATGCGCCGTGAGC GGGCTGTCATECAGCTCCTCTGGCATGAACTGGGTGCGA CAGGCTCCTGGAAAGGGACTGGAGTGGATCAGTTCAATT AGCGGGTCCCAGAATTACAAGTACTATGCAGACTCTGTCA AAGGAAGGTTCGTGGTCAGCCGGGATAACGCCAGAAATT TTCTGTATCTGCAGATGGACAGCCTGCGCGCCGAAGATA CCGCCGTGTACTTCTGCGTCGGCGGGTTTCCCTATTGGCT GCCTCCAAGCGATTTCAGCGGATTTCATGTCTGGGGGCA GGGAACTACAGTGACCGTCTCATCAGGCGGGGGAGGCT CTGGGGGAGGCGGGAGTGGAGGCGGGGGATCATCTTA CGTCCTGACCCAGCCACCTAGCGTGAGCGTCGCACCAGG GCAGACAGCTTCACTGACTTGCGGAGGCACAAACATTGG CAGCAAGAGCGTGCACTGGTACCAGCAGAAAGCCGGAC AGGCTCCCGTCCTGGTGGTCTATGCTGACAACGATCGGC CCTCTGGCGTGCCTGAAAGATTCAGCGGCTCCAACTCTG GGAATACCGCAACACTGACCATCAGTAGGGTCGAGGCC GAAGACGAGTCAGATTACTTTTGCCAGGTGTGGGACGGC AATACTGACCATGTCGTGTTCGGCGGCGGGACCAAACTG ACTGTGCTGGGCGGGGGAGGCTCTCAGCTGCAGCTGGT CCAGTCAGGCACAGAAGTCAAAAAACCCGGCGCAAGCG TGAAGGTCTCATGTAAATCATCAGGATACGTCTTTACCTCT TACTATCTGGTGTGGGTCCGGCAGGCACCAGGACAGGG ACTGGAGTGGATGGCCACAATCTCTCCCGGAGACGTGAA |

-continued

| SEQ ID NO | Description | Sequence |
|---|---|---|
| | | CACTAGTTACGAACAGCGATTCCAGGGCAGAGTGACCGT<br>CACCACAGACGCTTCAACTAATACCGTGGATATGGAGCT<br>GCGGAGCCTGAGATCCGAAGATACAGCCGTCTACTATTG<br>CGCTAGGGGGCCCCGCAGCAAGCCTCCTTATCTGTACTT<br>CGCTCTGGATGTCTGGGGGCAGGGGACCGCCGTCACCG<br>TCTCAAGCGCGTCGACCAAGGGCCCATCGGTCTTCCCCC<br>TGGCACCCTCCTCCAAGAGCACCTCTGGGGGCACAGCG<br>GCCCTGGGCTGCCTGGTCAAGGACTACTTCCCCGAACCT<br>GTGACGGTCTCGTGGAACTCAGGCGCCCTGACCAGCGG<br>CGTGCACACCTTCCCGGCTGTCCTACAGTCCTCAGGACTC<br>TACTCCCTCAGCAGCGTGGTGACCGTGCCCTCCAGCAGC<br>TTGGGCACCCAGACCTACATCTGCAACGTGAATCACAAG<br>CCCAGCAACACCAAGGTGGACAAGAGAGTTGAGCCCAA<br>ATCTTGTGACAAAACTCACACATGCCCACCGTGCCCAGCA<br>CCTGAACTCCTGGGGGGACCGTCAGTCTTCCTCTTCCCCC<br>CAAAACCCAAGGACACCCTCATGATCTCCCGGACCCCTG<br>AGGTCACATGCGTGGTGGTGGACGTGAGCCACGAGGAT<br>CCTGAAGTCAAGTTCAACTGGTACGTGGATGGCGTCGAG<br>GTGCATAATGCCAAGACAAAACCCCGGGAGGAACAGTAC<br>AACTCAACTTATAGAGTCGTGAGCGTCCTGACCGTGCTGC<br>ATCAGGACTGGCTGAACGGCAAAGAATACAAGTGCAAAG<br>TGTCTAATAAGGCCCTGCCTGCTCCAATCGAGAAAACAAT<br>TAGCAAGGCAAAAGGGCAGCCCAGGGAACCTCAGGTGT<br>ACACTCTGCCTCCAAGCCGCGAGGAAATGACCAAGAACC<br>AGGTCTCCCTGACATGTCTGGTGAAAGGATTCTATCCTAG<br>TGACATTGCCGTGGAGTGGGAATCAAATGGCCAGCCAGA<br>GAACAATTACAAGACCACACCCCCTGTGCTGGACTCTGAT<br>GGGAGTTTCTTTCTGTATTCCAAGCTGACCGTGGATAAAT<br>CTAGATGGCAGCAGGGAAATGTCTTTAGCTGTTCCGTGAT<br>GCATGAGGCACTGCACAACCATTACACCCAGAAATCACT<br>GTCACTGTCCCCAGGAAAAGGCGGGGGAGGCTCTGGCG<br>TGCAGCTGGTCCAGAGCGGAGGCGGACTGGTCCAGCCC<br>GGCGGATCACTGAGACTGTCATGTGCCGCAAGCGGGTTT<br>ACCGTCTCTACAAACTACATGTCTTGGGTGAGGCAGGCA<br>CCTGGAAAGGGACTGGAGTGGGTCTCAATCCTGTACGCT<br>GGCGGGGTGACCCGGTATGCAGACAGCGTCAAGACCCG<br>GTTCACAATTAGCAGAGATAACTCCAAAAATACTCTGTTTC<br>TGCAGATGAATGCCCTGTCCGCTGAAGACACCGCAATCT<br>ACTATTGCGCCAAACACTATGATAGTGGGTACAGTACCAT<br>TGACCATTTCGATAGCTGGGGGCAGGGGACTCTGGTGAC<br>CGTCTCATCAGGCGGGGGAGGCTCTGGGGGAGGCGGG<br>AGTGGAGGCGGGGGATCAGATATTCAGATGACCCAGAG<br>TCCTGATTCCGTCGCTGTCTCACTGGGAGAAAGGGCAAC<br>CATTAACTGTAAAAGCTCACAGAGTGTCTTCTACACCAGT<br>AAGAACAAAAACTATCTGGCCTGGTTTCAGCAGAAGCCA<br>GGCCAGCCCCCTAAACTGCTGATCTACTGGGCTAGCACT<br>AGAGAGTCTGGAGTGCCAGACAGATTCTCTGGCAGTGG<br>GTCAGGAACCGACTTCACCCTGACAATTAGCTCCCTGAG<br>GCCCGAAGACGTGGCCGTCTACTATTGTCAGCAGTATTAT<br>TCAACACCCT1CACATTCGGACCAGGAACAAAAGTGGATA<br>TTAAG |
| 165 | Ts3GC2e heavy chain aa | EVQLVESGGDLVKAGGSLRLSCAVSGLSFSSSGMNWVRQAP<br>GKGLEWISSISGSQNYKYYADSVKGRFVVSRDNARNFLYLQM<br>DSLRAEDTAVYFCVGGFPYWLPPSDFSGFHVWGQGTTVTVS<br>SGGGGSGGGGSGGGGSSYVLTQPPSVSVAPGQTASLTCGG<br>TNIGSKSVHWYQQKAGQAPVLVVYADNDRPSGVPERFSGS<br>NSGNTATLTISRVEAEDESDYFCQVWDGNTDHVVFGGGTKL<br>TVLGGGGSGVQLVQSGGGLVQPGGSLRLSCAASGFTVSTNY<br>MSWVRQAPGKGLEWVSILYAGGVTRYADSVKTRFTISRDNSK<br>NTLFLQMNALSAEDTAIYYCAKHYDSGYSTIDHFDSWGQGT<br>LVTVSSASTKGPSVFPLAPSSKSTSGGTAALGCLVKDYFPEPVT<br>VSWNSGALTSGVHTFPAVLQSSGLYSLSSVVTVPSSSLGTQTYI<br>CNVNHKPSNTKVDKRVEPKSCDKTHTCPPCPAPELLGGPSVF<br>LFPPKPKDTLMISRTPEVTCVVVDVSHEDPEVKFNWYVDGVE<br>VHNAKTKPREEQYNSTYRVVSVLTVLHQDWLNGKEYKCKVS<br>NKALPAPIEKTISKAKGQPREPQVYTLPPSREEMTKNQVSLTCL<br>VKGFYPSDIAVEWESNGQPENNYKTTPPVLDSDGSFFLYSKLT<br>VDKSRWQQGNVFSCSVMHEALHNHYTQKSLSLSPGKGGG<br>GSQLQLVQSGTEVKKPGASVKVSCKSSGYVFTSYYLVWVRQA<br>PGQGLEWMATISPGDVNTSYEQRFQGRVTVTTDASTNTVD<br>MELRSLRSEDTAVYYCARGPRSKPPYLYFALDVWGQGTAVTV<br>SSGGGGSGGGGSGGGGSEIVLTQSPGTLSLSPGETAILSCRAS<br>QSVSSSLLAWYQQKPGQAPRLLIYGASNRATGIRGRFSGSGS<br>GTDFTLTISRLEPEDEVLYYCQHYGSRVTFGQGTKLEIK |

-continued

| SEQ ID NO | Description | Sequence |
|---|---|---|
| 166 | Ts3GC2e heavy chain nucl | GAGGTGCAGCTGGTGGAAAGTGGGGGCGATCTGGTCAA<br>AGCCGGAGGGTCTCTGCGACTGTCTTGTGCTGTGAGCGG<br>CCTGTCCTTCAGCTCCTCTGGCATGAACTGGGTGCGACA<br>GGCTCCTGGAAAGGGACTGGAGTGGATCAGTTCAATTAG<br>CGGGTCCCAGAATTACAAGTACTATGCAGACTCTGTCAAA<br>GGAAGGTTCGTGGTCAGCCGGGATAACGCCAGAAATTTT<br>CTGTATCTGCAGATGGACAGCCTGCGCGCCGAAGATACC<br>GCCGTGTACTTCTGCGTCGGCGGGTTTCCCTATTGGCTGC<br>CTCCAAGCGACTTTTCAGGGTTTCATGTCTGGGGGCAGG<br>GAACTACCGTGACCGTCTCATCTGGCGGGGGAGGCTCTG<br>GGGGAGGCGGGAGTGGAGGCGGGGGATCATCCTACGT<br>CCTGACTCAGCCACCTAGCGTGTCCGTCGCACCTGGGCA<br>GACAGCATCACTGACTTGCGGGGGAACCAACATCGGCA<br>GCAAGAGCGTGCACTGGTACCAGCAGAAAGCCGGACAG<br>GCTCCCGTCCTGGTGGTCTATGCTGACAACGATCGGCCC<br>TCTGGCGTGCCTGAAAGATTCAGCGGCTCCAACTCTGGG<br>AATACCGCAACACTGACCATCAGTAGGGTCGAGGCCGAA<br>GACGAGTCAGATTACTTTTGCCAGGTCTGGGATGGGAAT<br>ACTGACCACGTCGTCTTCGGAGGCGGAACCAAACTGACT<br>GTCCTGGGCGGGGGAGGCTCTGGCGTGCAGCTGGTGCA<br>GAGCGGCGGCGGCCTGGTGCAGCCTGGAGGGTCACTG<br>AGACTGTCATGCGCAGCAAGCGGGTTTACTGTGTCTACA<br>AACTACATGTCTTGGGTGAGGCAGGCACCTGGAAAGGG<br>ACTGGAGTGGGTCTCAATCCTGTACGCTGGCGGGGTGAC<br>CCGGTATGCAGACAGCGTCAAGACCCGGTTCACAATTAG<br>CAGAGATAACTCCAAAAATACTCTGTTTCTGCAGATGAAT<br>GCCCTGTCCGCTGAAGACACCGCAATCTACTATTGCGCCA<br>AACACTATGATAGTGGGTACTCCACTATTGACCATTTTGAC<br>TCTTGGGGGCAGGGGACTCTGGTGACTGTCTCTTCAGCG<br>TCGACCAAGGGCCCATCGGTCTTCCCCCTGGCACCCTCCT<br>CCAAGAGCACCTCTGGGGGCACAGCGGCCCTGGGCTGC<br>CTGGTCAAGGACTACTTCCCCGAACCTGTGACGGTCTCGT<br>GGAACTCAGGCGCCCTGACCAGCGGCGTGCACACCTTCC<br>CGGCTGTCCTACAGTCCTCAGGACTCTACTCCCTCAGCAG<br>CGTGGTGACCGTGCCCTCCAGCAGCTTGGGCACCCAGAC<br>CTACATCTGCAACGTGAATCACAAGCCCAGCAACACCAA<br>GGTGGACAAGAGAGTTGAGCCCAAATCTTGTGACAAAAC<br>TCACACATGCCCACCGTGCCCAGCACCTGAACTCCTGGG<br>GGGACCGTCAGTCTTCCTCTTCCCCCCAAAACCCAAGGAC<br>ACCCTCATGATCTCCCGGACCCCTGAGGTCACATGCGTG<br>GTGGTGGACGTGAGCCACGAGGATCCTGAAGTCAAGTTC<br>AACTGGTACGTGGATGGCGTCGAGGTGCATAATGCCAAG<br>ACAAAACCCCGGGAGGAACAGTACAACTCAACTTATAGA<br>GTCGTGAGCGTCCTGACCGTGCTGCATCAGGACTGGCTG<br>AACGGCAAAGAATACAAGTGCAAAGTGTCTAATAAGGCC<br>CTGCCTGCTCCAATCGAGAAAACAATTAGCAAGGCAAAA<br>GGGCAGCCCAGGGAACCTCAGGTGTACACTCTGCCTCCA<br>AGCCGCGAGGAAATGACCAAGAACCAGGTCTCCCTGACA<br>TGTCTGGTGAAAGGATTCTATCCTAGTGACATTGCCGTGG<br>AGTGGGAATCAAATGGCCAGCCAGAGAACAATTACAAGA<br>CCACACCCCCTGTGCTGGACTCTGATGGGAGTTTCTTTCT<br>GTATTCCAAGCTGACCGTGGATAAATCTAGATGGCAGCA<br>GGGAAATGTCTTTAGCTGTTCCGTGATGCATGAGGCACT<br>GCACAACCATTACACCCAGAAATCACTGTCACTGTCCCCA<br>GGAAAAGGCGGGGGAGGCTCTCAGCTGCAGCTGGTCCA<br>GAGCGGAACCGAAGTGAAGAAACCCGGCGCAAGCGTCA<br>AAGTCTCATGCAAATCAAGCGGATACGTCTTCACCTCTTA<br>CTATCTGGTGTGGGTCCGGCAGGCACCAGGACAGGGAC<br>TGGAGTGGATGGCCACAATCTCTCCCGGAGACGTGAACA<br>CTAGTTACGAACAGCGATTCCAGGGCAGAGTGACCGTCA<br>CCACAGACGCTTCAACTAATACCGTGGATATGGAGCTGC<br>GGAGCCTGAGATCCGAAGATACAGCCGTCTACTATTGCG<br>CTAGGGGGCCCCGCAGCAAGCCTCCTTATCTGTATTTCGC<br>TCTGGATGTCTGGGGGCAGGGAACAGCAGTCACCGTCTC<br>AAGCGGCGGGGGAGGCTCTGGGGGAGGCGGGAGTGG<br>AGGCGGGGGATCAGAGATTGTCCTGACCCAGTCACCTG<br>GCACCCTGAGCCTGAGTCCTGGAGAGACCGCTATTCTGT<br>CTTGTCGGGCATCACAGTCCGTGAGCTCCTCTCTGCTGGC<br>ATGGTACCAGCAGAAGCCCGGACAGGCCCCTAGGCTGC<br>TGATCTATGGCGCCTCCAACCGCGCTACTGGCATTCGGG<br>GGAGATTCAGTGGCTCAGGGAGCGGAACCGACTTTACCC<br>TGACAATCAGCCGGCTGGAGCCCGAAGATTTCGTGCTGT<br>ACTATTGTCAGCATTATGGAAGCAGGGTCACCTTCGGACA<br>GGGAACTAAACTGGAAATCAAG |

-continued

| SEQ ID NO | Description | Sequence |
|---|---|---|
| 167 | Bs3GC1a heavy chain aa | QLQLVQSGTEVKKPGASVKVSCKSSGYVFTSYYLVWVRQAP<br>GQGLEWMATISPGDVNTSYEQRFQGRVTVTTDASTNTVDM<br>ELRSLRSEDTAVYYCARGPRSKPPYLYFALDVWGQGTAVTVSS<br>ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGGPSVFLFPPKP<br>KDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKG FYPS<br>DIAVEWESNGQPENNYKTTPPVLDSDGSFFLYSKLTVDKSRW<br>QQGNVFSCSVMHEALHNHYTQKSLSLSPGKGGGGSGVQLV<br>QSGGGLVQPGGSLRLSCAASGFTVSTNYMSWVRQAPGKGL<br>EWVSILYAGGVTRYADSVKTRFTISRDNSKNTLFLQMNALSAE<br>DTAIYYCAKHYDSGYSTIDHFDSWGQGTLVTVSSGGGGSGG<br>GGSGGGGSDIQMTQSPDSVAVSLGERATINCKSSQSVFYTSK<br>NKNYLAWFQQKPGQPPKLLIYWASTRESGVPDRFSGSGSGT<br>DFTLTISSLRPEDVAVYYCQQYYSTPFTFGPGTKVDIK |
| 168 | Bs3GC1a heavy chain nucl | CAGCTGCAGCTGGTCCAGTCAGGCACAGAGGTCAAAAA<br>GCCAGGAGCATCAGTGAAGGTGTCTTGTAAGTCATCAGG<br>ATACGTGTTCACCTCTTACTATCTGGTGTGGGTCCGGCAG<br>GCACCAGGACAGGGACTGGAGTGGATGGCCACAATCTC<br>TCCCGGAGACGTGAACACTAGTTACGAACAGCGATTCCA<br>GGGCAGAGTGACCGTCACCACAGACGCTTCAACTAATAC<br>CGTGGATATGGAGCTGCGGAGCCTGAGATCCGAAGATA<br>CAGCCGTCTACTATTGCGCTAGGGGGCCCCGCAGCAAGC<br>CTCCTTATCTGTATTTTGCTCTGGATGTGTGGGGGCAGGG<br>GACCGCTGTCACCGTGTCAAGCGCGTCGACCAAGGGCC<br>CATCGGTCTTCCCCCTGGCACCCTCCTCCAAGAGCACCTC<br>TGGGGGCACAGCGGCCCTGGGCTGCCTGGTCAAGGACT<br>ACTTCCCCGAACCTGTGACGGTCTCGTGGAACTCAGGCG<br>CCCTGACCAGCGGCGTGCACACCTTCCCGGCTGTCCTAC<br>AGTCCTCAGGACTCTACTCCCTCAGCAGCGTGGTGACCG<br>TGCCCTCCAGCAGCTTGGGCACCCAGACCTACATCTGCA<br>ACGTGAATCACAAGCCCAGCAACACCAAGGTGGACAAGA<br>GAGTTGAGCCCAAATCTTGTGACAAAACTCACACATGCCC<br>ACCGTGCCCAGCACCTGAACTCCTGGGGGGACCGTCAGT<br>CTTCCTCTTCCCCCCAAAACCCAAGGACACCCTCATGATCT<br>CCCGGACCCCTGAGGTCACATGCGTGGTGGTGGACGTG<br>AGCCACGAGGATCCTGAAGTCAAGTTCAACTGGTACGTG<br>GATGGCGTCGAGGTGCATAATGCCAAGACAAAACCCCG<br>GGAGGAACAGTACAACTCAACTTATAGAGTCGTGAGCGT<br>CCTGACCGTGCTGCATCAGGACTGGCTGAACGGCAAAGA<br>ATACAAGTGCAAAGTGTCTAATAAGGCCCTGCCTGCTCCA<br>ATCGAGAAAACAATTAGCAAGGCAAAAGGGCAGCCCAG<br>GGAACCTCAGGTGTACACTCTGCCTCCAAGCCGCGAGGA<br>AATGACCAAGAACCAGGTCTCCCTGACATGTCTGGTGAA<br>AGGATTCTATCCTAGTGACATTGCCGTGGAGTGGGAATC<br>AAATGGCCAGCCAGAGAACAATTACAAGACCACACCCCC<br>TGTGCTGGACTCTGATGGGAGTTTCTTTCTGTATTCCAAG<br>CTGACCGTGGATAAATCTAGATGGCAGCAGGGAAATGTC<br>TTTAGCTGTTCCGTGATGCATGAGGCACTGCACAACCATT<br>ACACCCAGAAATCACTGTCACTGTCCCCAGGAAAAGGCG<br>GGGGAGGCTCTGGCGTGCAGCTGGTCCAGAGCGGAGG<br>CGGACTGGTCCAGCCCGGCGGATCACTGAGACTGTCATG<br>TGCCGCAAGCGGGTTTACCGTCTCTACAAACTACATGTCT<br>TGGGTGAGGCAGGCACCTGGAAAGGGACTGGAGTGGG<br>TCTCAATCCTGTACGCTGGCGGGGTGACCCGGTATGCAG<br>ACAGCGTCAAGACCCGGTTCACAATTAGCAGAGATAACT<br>CCAAAAATACTCTGTTTCTGCAGATGAATGCCCTGTCCGC<br>TGAAGACACCGCAATCTACTATTGCGCCAAACACTATGAT<br>AGTGGGTACAGTACCATTGACCATTTCGATAGCTGGGGG<br>CAGGGGACTCTGGTGACCGTCTCATCAGGCGGGGGAGG<br>CTCTGGGGGAGGCGGGAGTGGAGGCGGGGGATCAGAT<br>ATTCAGATGACCCAGAGTCCTGATTCCGTCGCTGTCTCAC<br>TGGGAGAAAGGGCAACCATTAACTGTAAAAGCTCACAGA<br>GTGTCTTCTACACCAGTAAGAACAAAAACTATCTGGCCTG<br>GTTTCAGCAGAAGCCAGGCCAGCCCCCTAAACTGCTGAT<br>CTACTGGGCTAGCACTAGAGAGTCTGGAGTGCCAGACAG<br>ATTCTCTGGCAGTGGGTCAGGAACCGACTTCACCCTGAC<br>AATTAGCTCCCTGAGGCCCGAAGACGTGGCCGTCTACTA<br>TTGTCAGCAGTATTATTCAACACCCTTCACATTCGGACCAG<br>GAACAAAAGTGGATATTAAG |
| 169 | Bs3GC1b heavy chain aa | GVQLVQSGGGLVQPGGSLRLSCAASGFTVSTNYMSWVRQA<br>PGKGLEWVSILYAGGVTRYADSVKTRFTISRDNSKNTLFLQM<br>NALSAEDTAIYYCAKHYDSGYSTIDHFDSWGQGTLVTVSSAS<br>TKGPSVFPLAPSSKSTSGGTAALGCLVKDYFPEPVIVSWNSGA |

-continued

| SEQ ID NO | Description | Sequence |
|---|---|---|
| | | LTSGVHTFPAVLQSSGLYSLSSVVTVPSSSLGTQTYICNVNHKP<br>SNTKVDKRVEPKSCDKTHTCPPCPAPELLGGPSVFLFPPKPKDT<br>LMISRTPEVTCVVVDVSHEDPEVKFNWYVDGVEVHNAKTKP<br>REEQYNSTYRVVSVLTVLHQDWLNGKEYKCKVSNKALPAPIE<br>KTISKAKGQPREPQVYTLPPSREEMTKNQVSLTCLVKGFYPSDI<br>AVEWESNGQPENNYKTTPPVLDSDGSFFLYSKLTVDKSRWQ<br>QGNVFSCSVMHEALHNHYTQKSLSLSPGKGGGGSQLQLVQ<br>SGTEVKKPGASVKVSCKSSGYVFTSYYLVWVRQAPGQGLEW<br>MATISPGDVNTSYEQRFQGRVTVTTDASTNTVDMELRSLRSE<br>DTAVYYCARGPRSKPPYLYFALDVWGQGTAVTVSSGGGGS<br>GGGGSGGGGSEIVLTQSPGTLSLSPGETAILSCRASQSVSSSLL<br>AWYQQKPGQAPRLLIYGASNRATGIRGRFSGSGSGTDFTLTIS<br>RLEPEDFVLYYCQHYGSRVTFGQGTKLEIK |
| 170 | Bs3GC1b heavy chain nucl | ggggtgcaactggtgcagtctgggggaggcttggtccagccgggggggtccctgaga<br>ctctcctgtgcagcctct**GGATTCACCGTCAGTACCAACTAC**atgagct<br>gggtccgccaggctccagggaaggggctggagtgggtctcaatt**CTTTATGCCG**<br>**GAGGTGTCACA**aggtacgcagactccgtgaagaccagattcaccatctccag<br>agacaattccaagaacactctctttcttcaaatgaacgccctgagcgccgaggacacg<br>gctatatattactgt**GCGAAACACTATGATTCGGGATATTCTACCA**<br>**TAGATCACTTTGACTCC**tggggccagggaaccctggtcaccgtctcctca<br>GCGTCGACCAAGGGCCCATCGGTCTTCCCCCTGGCACCC<br>TCCTCCAAGAGCACCTCTGGGGGCACAGCGGCCCTGGG<br>CTGCCTGGTCAAGGACTACTTCCCCGAACCTGTGACGGT<br>CTCGTGGAACTCAGGCGCCCTGACCAGCGGCGTGCACA<br>CCTTCCCGGCTGTCCTACAGTCCTCAGGACTCTACTCCCT<br>CAGCAGCGTGGTGACCGTGCCCTCCAGCAGCTTGGGCA<br>CCCAGACCTACATCTGCAACGTGAATCACAAGCCCAGCA<br>ACACCAAGGTGGACAAGAGAGTTGAGCCCAAATCTTGTG<br>ACAAAACTCACACATGCCCACCGTGCCCAGCACCTGAACT<br>CCTGGGGGGACCGTCAGTCTTCCTCTTCCCCCCAAAACCC<br>AAGGACACCCTCATGATCTCCCGGACCCCTGAGGTCACA<br>TGCGTGGTGGTGGACGTGAGCCACGAGGATCCTGAAGT<br>CAAGTTCAACTGGTACGTGGATGGCGTCGAGGTGCATAA<br>TGCCAAGACAAAACCCCGGGAGGAACAGTACAACTCAAC<br>TTATAGAGTCGTGAGCGTCCTGACCGTGCTGCATCAGGA<br>CTGGCTGAACGGCAAAGAATACAAGTGCAAAGTGTCTAA<br>TAAGGCCCTGCCTGCTCCAATCGAGAAAACAATTAGCAA<br>GGCAAAAGGGCAGCCCAGGGAACCTCAGGTGTACACTC<br>TGCCTCCAAGCCGCGAGGAAATGACCAAGAACCAGGTCT<br>CCCTGACATGTCTGGTGAAAGGATTCTATCCTAGTGACAT<br>TGCCGTGGAGTGGGAATCAAATGGCCAGCCAGAGAACA<br>ATTACAAGACCACACCCCCTGTGCTGGACTCTGATGGGA<br>GTTTCTTTCTGTATTCCAAGCTGACCGTGGATAAATCTAGA<br>TGGCAGCAGGGAAATGTCTTTAGCTGTTCCGTGATGCAT<br>GAGGCACTGCACAACCATTACACCCAGAAATCACTGTCAC<br>TGTCCCCAGGAAAAGGCGGGGGAGGCTCTCAGCTGCAG<br>CTGGTCCAGAGCGGAACCGAAGTGAAGAAACCCGGCGC<br>AAGCGTCAAAGTCTCATGCAAATCAAGCGGATACGTCTTC<br>ACCTCTTACTATCTGGTGTGGGTCCGGCAGGCACCAGGA<br>CAGGGACTGGAGTGGATGGCCACAATCTCTCCCGGAGA<br>CGTGAACACTAGTTACGAACAGCGATTCCAGGGCAGAGT<br>GACCGTCACCACAGACGCTTCAACTAATACCGTGGATATG<br>GAGCTGCGGAGCCTGAGATCCGAAGATACAGCCGTCTAC<br>TATTGCGCTAGGGGGCCCCGCAGCAAGCCTCCTTATCTG<br>TATTTCGCTCTGGATGTCTGGGGGCAGGGAACAGCAGTC<br>ACCGTCTCAAGCGGCGGGGGAGGCTCTGGGGGAGGCG<br>GGAGTGGAGGCGGGGGATCAGAGATTGTCCTGACCCAG<br>TCACCTGGCACCCTGAGCCTGAGTCCTGGAGAGACCGCT<br>ATTCTGTCTTGTCGGGCATCACAGTCCGTGAGCTCCTCTC<br>TGCTGGCATGGTACCAGCAGAAGCCCGGACAGGCCCCT<br>AGGCTGCTGATCTATGGCGCCTCCAACCGCGCTACTGGC<br>ATTCGGGGGAGATTCAGTGGCTCAGGGAGCGGAACCGA<br>CTTTACCCTGACAATCAGCCGGCTGGAGCCCGAAGATTTC<br>GTGCTGTACTATTGTCAGCATTATGGAAGCAGGGTCACCT<br>TCGGACAGGGAACTAAACTGGAAATCAAG |
| 171 | Bs3GC2b heavy chain aa | EVQLVESGGDLVKAGGSLRLSCAVSGLSFSSSGMNWVRQAP<br>GKGLEWISSISGSQNYKYYADSVKGRFVVSRDNARNFLYLQM<br>DSLRAEDTAVYFCVGGFPYWLPPSDFSGFHVWGQGTTVTVS<br>SASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGGPSVFLFPPKP<br>KDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKGFYPS<br>DIAVEWESNGQPENNYKTTPPVLDSDGSFFLYSKLTVDKSRW<br>QQGNVFSCSVMHEALHNHYTQKSLSLSPGKGGGGSQLQLV |

-continued

| SEQ ID NO | Description | Sequence |
|---|---|---|
| | | QSGTEVKKPGASVKVSCKSSGYVFTSYYLVVVVRQAPGQGLE<br>WMATISPGDVNTSYEQRFQGRVTVTTDASTNTVDMELRSLRS<br>EDTAVYYCARGPRSKPPYLYFALDVWGQGTAVTVSSGGGGS<br>GGGGSGGGGSEIVLTQSPGTLSLSPGETAILSCRASQSVSSSLL<br>AWYQQKPGQAPRLLIYGASNRATGIRGRFSGSGSGTDFTLTIS<br>RLEPEDFVLYYCQHYGSRVTFGQGTKLEIK |
| 172 | Bs3GC2b heavy chain nucl | GAGGTACAATTGGTGGAGTCTGGGGGAGACCTGGTCAA<br>GGCGGGGGGGTCCCTGAGACTCTCCTGTGCCGTCTCTG<br>GATTGTCCTTCAGTAGTTCAGGCATGAATTGGGTCCGCCA<br>GGCTCCAGGGAAGGGGCTGGAGTGGATCTCATCGATTA<br>GTGGTAGTCAGAACTACAAATACTATGCAGACTCAGTGAA<br>GGGCCGATTCGTCGTCTCCAGAGACAACGCCCGCAACTT<br>TCTATATCTGCAAATGGACAGCCTGAGGGCCGAGGATAC<br>GGCTGTGTATTTTTGTGTGGGAGGTTTCCCCTATTGGTTA<br>CCCCCGAGCGACTTCTCCGGTTTCCATGTCTGGGGCCAA<br>GGGACCACGGTCACCGTCTCCTCAGCGTCGACCAAGGG<br>CCCATCGGTCTTCCCCCTGGCACCCTCCTCCAAGAGCACC<br>TCTGGGGGCACAGCGGCCCTGGGCTGCCTGGTCAAGGA<br>CTACTTCCCCGAACCTGTGACGGTCTCGTGGAACTCAGG<br>CGCCCTGACCAGCGGCGTGCACACCTTCCCGGCTGTCCT<br>ACAGTCCTCAGGACTCTACTCCCTCAGCAGCGTGGTGAC<br>CGTGCCCTCCAGCAGCTTGGGCACCCAGACCTACATCTG<br>CAACGTGAATCACAAGCCCAGCAACACCAAGGTGGACAA<br>GAGAGTTGAGCCCAAATCTTGTGACAAAACTCACACATGC<br>CCACCGTGCCCAGCACCTGAACTCCTGGGGGGACCGTCA<br>GTCTTCCTCTTCCCCCCAAAACCCAAGGACACCCTCATGA<br>TCTCCCGGACCCCTGAGGTCACATGCGTGGTGGTGGACG<br>TGAGCCACGAGGATCCTGAAGTCAAGTTCAACTGGTACG<br>TGGATGGCGTCGAGGTGCATAATGCCAAGACAAAACCCC<br>GGGAGGAACAGTACAACTCAACTTATAGAGTCGTGAGCG<br>TCCTGACCGTGCTGCATCAGGACTGGCTGAACGGCAAAG<br>AATACAAGTGCAAAGTGTCTAATAAGGCCCTGCCTGCTCC<br>AATCGAGAAAACAATTAGCAAGGCAAAAGGGCAGCCCA<br>GGGAACCTCAGGTGTACACTCTGCCTCCAAGCCGCGAGG<br>AAATGACCAAGAACCAGGTCTCCCTGACATGTCTGGTGA<br>AAGGATTCTATCCTAGTGACATTGCCGTGGAGTGGGAAT<br>CAAATGGCCAGCCAGAGAACAATTACAAGACCACACCCC<br>CTGTGCTGGACTCTGATGGGAGTTTCTTTCTGTATTCCAA<br>GCTGACCGTGGATAAATCTAGATGGCAGCAGGGAAATGT<br>CTTTAGCTGTTCCGTGATGCATGAGGCACTGCACAACCAT<br>TACACCCAGAAATCACTGTCACTGTCCCCAGGAAAAGGC<br>GGGGGAGGCTCTCAGCTGCAGCTGGTCCAGAGCGGAAC<br>CGAAGTGAAGAAACCCGGCGCAAGCGTCAAAGTCTCATG<br>CAAATCAAGCGGATACGTCTTCACCTCTTACTATCTGGTGT<br>GGGTCCGGCAGGCACCAGGACAGGGACTGGAGTGGAT<br>GGCCACAATCTCTCCCGGAGACGTGAACACTAGTTACGA<br>ACAGCGATTCCAGGGCAGAGTGACCGTCACCACAGACG<br>CTTCAACTAATACCGTGGATATGGAGCTGCGGAG CCTGA<br>GATCCGAAGATACAGCCGTCTACTATTGCGCTAGGGGGC<br>CCCGCAGCAAGCCTCCTTATCTGTATTTCGCTCTGGATGT<br>CTGGGGGCAGGGAACAGCAGTCACCGTCTCAAGCGGCG<br>GGGGAGGCTCTGGGGGAGGCGGGAGTGGAGGCGGGG<br>GATCAGAGATTGTCCTGACCCAGTCACCTGGCACCCTGA<br>GCCTGAGTCCTGGAGAGACCGCTATTCTGTCTTGTCGGG<br>CATCACAGTCCGTGAGCTCCTCTCTGCTGGCATGGTACCA<br>GCAGAAGCCCGGACAGGCCCCTAGGCTGCTGATCTATG<br>GCGCCTCCAACCGCGCTACTGGCATTCGGGGGAGATTCA<br>GTGGCTCAGGGAGCGGAACCGACTTTACCCTGACAATCA<br>GCCGGCTGGAGCCCGAAGATTTCGTGCTGTACTATTGTC<br>AGCATTATGGAAGCAGGGTCACCTTCGGACAGGGAACTA<br>AACTGGAAATCAAG |
| 173 | Bs3GC3b heavy chain aa | EVQLVESGGDLVKAGGSLRLSCAVSGLSFSSSGMNWVRQAP<br>GKGLEWISSISGSQNYKYYADSVKGRFVVSRDNARNFLYLQM<br>DSLRAEDTAVYFCVGGFPYWLPPSDFSGFHVWGQGTTVTVS<br>SASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGGPSVFLFPPKP<br>KDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKGFYPS<br>DIAVEWESNGQPENNYKTTPPVLDSDGSFFLYSKLTVDKSRW<br>QQGNVFSCSVMHEALHNHYTQKSLSLSPGKGGGGSGVQLV<br>QSGGGLVQPGGSLRLSCAASGFTVSTNYMSWVRQAPGKGL<br>EWVSILYAGGVTRYADSVKTRFTISRDNSKNTLFLQMNALSAE<br>DTAIYYCAKHYDSGYSTIDHFDSWGQGTLVTVSSGGGGSGG<br>GGSGGGGSDIQMTQSPDSVAVSLGERATINCKSSQSVFYTSK |

-continued

| SEQ ID NO | Description | Sequence |
|---|---|---|
| | | NKNYLAWFQQKPGQPPKLLIYWASTRESGVPDRFSGSGSGT DFTLTISSLRPEDVAVYYCQQYYSTPFTFGPGTKVDIK |
| 174 | Bs3GC3b heavy chain nucl | GAGGTACAATTGGTGGAGTCTGGGGGAGACCTGGTCAA GGCGGGGGGGTCCCTGAGACTCTCCTGTGCCGTCTCTG GATTGTCCTTCAGTAGTTCAGGCATGAATTGGGTCCGCCA GGCTCCAGGGAAGGGGCTGGAGTGGATCTCATCGATTA GTGGTAGTCAGAACTACAAATACTATGCAGACTCAGTGAA GGGCCGATTCGTCGTCTCCAGAGACAACGCCCGCAACTT TCTATATCTGCAAATGGACAGCCTGAGGGCCGAGGATAC GGCTGTGTATTTTTGTGTGGGAGGTTTCCCCTATTGGTTA CCCCCGAGCGACTTCTCCGGTTTCCATGTCTGGGGCCAA GGGACCACGGTCACCGTCTCCTCAGCGTCGACCAAGGG CCCATCGGTCTTCCCCCTGGCACCCTCCTCCAAGAGCACC TCTGGGGGCACAGCGGCCCTGGGCTGCCTGGTCAAGGA CTACTTCCCCGAACCTGTGACGGTCTCGTGGAACTCAGG CGCCCTGACCAGCGGCGTGCACACCTTCCCGGCTGTCCT ACAGTCCTCAGGACTCTACTCCCTCAGCAGCGTGGTGAC CGTGCCCTCCAGCAGCTTGGGCACCCAGACCTACATCTG CAACGTGAATCACAAGCCCAGCAACACCAAGGTGGACAA GAGAGTTGAGCCCAAATCTTGTGACAAAACTCACACATGC CCACCGTGCCCAGCACCTGAACTCCTGGGG GTCTTCCTCTTCCCCCCAAAACCCAAGGACACCCTCATGA TCTCCCGGACCCCTGAGGTCACATGCGTGGTGGTGGACG TGAGCCACGAGGATCCTGAAGTCAAGTTCAACTGGTACG TGGATGGCGTCGAGGTGCATAATGCCAAGACAAAACCCC GGGAGGAACAGTACAACTCAACTTATAGAGTCGTGAGCG TCCTGACCGTGCTGCATCAGGACTGGCTGAACGGCAAAG AATACAAGTGCAAAGTGTCTAATAAGGCCCTGCCTGCTCC AATCGAGAAAACAATTAGCAAGGCAAAAGGGCAGCCCA GGGAACCTCAGGTGTACACTCTGCCTCCAAGCCGCGAGG AAATGACCAAGAACCAGGTCTCCCTGACATGTCTGGTGA AAGGATTCTATCCTAGTGACATTGCCGTGGAGTGGGAAT CAAATGGCCAGCCAGAGAACAATTACAAGACCACACCCC CTGTGCTGGACTCTGATGGGAGTTTCTTTCTGTATTCCAA GCTGACCGTGGATAAATCTAGATGGCAGCAGGGAAATGT CTTTAGCTGTTCCGTGATGCATGAGGCACTGCACAACCAT TACACCCAGAAATCACTGTCACTGTCCCCAGGAAAAGGC GGGGGAGGCTCTGGCGTGCAGCTGGTCCAGAGCGGAG GCGGACTGGTCCAGCCCGGCGGATCACTGAGACTGTCAT GTGCCGCAAGCGGGTTTACCGTCTCTACAAACTACATGTC TTGGGTGAGGCAGGCACCTGGAAAGGGACTGGAGTGG GTCTCAATCCTGTACGCTGGCGGGGTGACCCGGTATGCA GACAGCGTCAAGACCCGGTTCACAATTAGCAGAGATAAC TCCAAAAATACTCTGTTTCTGCAGATGAATGCCCTGTCCG CTGAAGACACCGCAATCTACTATTGCGCCAAACACTATGA TAGTGGGTACAGTACCATTGACCATTTCGATAGCTGGGG GCAGGGGACTCTGGTGACCGTCTCATCAGGCGGGGGAG GCTCTGGGGGAGGCGGGAGTGGAGGCGGGGGATCAGA TATTCAGATGACCCAGAGTCCTGATTCCGTCGCTGTCTCA CTGGGAGAAAGGGCAACCATTAACTGTAAAAGCTCACAG AGTGTCTTCTACACCAGTAAGAACAAAAACTATCTGGCCT GGTTTCAGCAGAAGCCAGGCCAGCCCCCTAAACTGCTGA TCTACTGGGCTAGCACTAGAGAGTCTGGAGTGCCAGACA GATTCTCTGGCAGTGGGTCAGGAACCGACTTCACCCTGA CAATTAGCTCCCTGAGGCCCGAAGACGTGGCCGTCTACT ATTGTCAGCAGTATTAT1CAACACCCTTCACATTCGGACCA GGAACAAAAGTGGATATTAAG |
| 175 | Bs3GC4 heavy chain aa | QVQLMESGGGVVQPGRSLRLSCSAFGFTFSNYPMHWVRQA PGKGLEWVAIILPDGNRKNYGRSVTGRFTISRDNSNNSLYLQ MNNLTTEDTAMYYCTRDGTYYSNGGVYQTYRRFFDFWGRG TLVTVSSASTKGPSVFPLAPSSKSTSGGTAALGCLVKDYFPEPVT VSWNSGALTSGVHTFPAVLQSSGLYSLSSVVTVPSSSLGTQTYI CNVNHKPSNTKVDKRVEPKSCDKTHTCPPCPAPELLGGPSVF LFPPKPKDTLMISRTPEVTCVVVDVSHEDPEVKFNWYVDGVE VHNAKTKPREEQYNSTYRVVSVLTVLHQDWLNGKEYKCKVS NKALPAPIEKTISKAKGQPREPQVYTLPPSREEMTKNQVSLTCL VKGFYPSDIAVEWESNGQPENNYKTTPPVLDSDGSFFLYSKLT VDKSRWQQGNVFSCSVMHEALHNHYTQKSLSLSPGKGGG GSQLQLVQSGTEVKKPGASVKVSCKSSGYVFTSYYLVWVRQA PGQGLEWMATISPGDVNTSYEQRFQGRVTVTTDASTNTVD MELRSLRSEDTAVYYCARGPRSKPPYLYFALDVWGQGTAVTV SSGGGGSGGGGSGGGGSEIVLTQSPGTLSLSPGETAILSCRAS QSVSSSLLAWYQQKPGQAPRLLIYGASNRATGIRGRFSGSGS GTDFTLTISRLEPEDEVLYYCQHYGSRVTFGQGTKLEIK |

-continued

| SEQ ID NO | Description | Sequence |
|---|---|---|
| 176 | Bs3GC4 heavy chain nucl | CAGGTGCAATTGATGGAGTCTGGGGGAGGCGTGGTCCA GCCTGGGAGGTCCCTGCGACTCTCATGCAGTGCCTTTGG ATTCACCTTTTCGAACTATCCTATGCACTGGGTCCGCCAG GCTCCAGGCAAGGGACTTGAGTGGGTGGCTATCATTTTA CCTGATGGGAACAGAAAAAACTATGGAAGGTCCGTGACG GGCCGATTCACCATCTCCAGAGACAATTCCAACAACAGCC TTTATTTGCAAATGAACAACCTGACGACTGAGGACACGGC TATGTACTATTGTACGAGAGATGGCACGTATTACTCTAAT GGTGGTGTTTATCAGACATATCGAAGGTTCTTCGATTTCT GGGGCCGTGGCACCCTGGTCACCGTCTCCTCAGCGTCGA CCAAGGGCCCATCGGTCTTCCCCCTGGCACCCTCCTCCAA GAGCACCTCTGGGGGCACAGCGGCCCTGGGCTGCCTGG TCAAGGACTACTTCCCCGAACCTGTGACGGTCTCGTGGA ACTCAGGCGCCCTGACCAGCGGCGTGCACACCTTCCCGG CTGTCCTACAGTCCTCAGGACTCTACTCCCTCAGCAGCGT GGTGACCGTGCCCTCCAGCAGCTTGGGCACCCAGACCTA CATCTGCAACGTGAATCACAAGCCCAGCAACACCAAGGT GGACAAGAGAGTTGAGCCCAAATCTTGTGACAAAACTCA CACATGCCCACCGTGCCCAGCACCTGAACTCCTGGGGGG ACCGTCAGTCTTCCTCTTCCCCCCAAAACCCAAGGACACC CTCATGATCTCCCGGACCCCTGAGGTCACATGCGTGGTG GTGGACGTGAGCCACGAGGATCCTGAAGTCAAGTTCAAC TGGTACGTGGATGGCGTCGAGGTGCATAATGCCAAGACA AAACCCCGGGAGGAACAGTACAACTCAACTTATAGAGTC GTGAGCGTCCTGACCGTGCTGCATCAGGACTGGCTGAAC GGCAAAGAATACAAGTGCAAAGTGTCTAATAAGGCCCTG CCTGCTCCAATCGAGAAAACAATTAGCAAGGCAAAAGGG CAGCCCAGGGAACCTCAGGTGTACACTCTGCCTCCAAGC CGCGAGGAAATGACCAAGAACCAGGTCTCCCTGACATGT CTGGTGAAAGGATTCTATCCTAGTGACATTGCCGTGGAGT GGGAATCAAATGGCCAGCCAGAGAACAATTACAAGACCA CACCCCCTGTGCTGGACTCTGATGGGAGTTTCTTTCTGTA TTCCAAGCTGACCGTGGATAAATCTAGATGGCAGCAGGG AAATGTCTTTAGCTGTTCCGTGATGCATGAGGCACTGCAC AACCATTACACCCAGAAATCACTGTCACTGTCCCCAGGAA AAGGCGGGGGAGGCTCTCAGCTGCAGCTGGTCCAG AGCGGAACCGAAGTGAAGAAACCCGGCGCAAGCGT CAAAGTCTCATGCAAATCAAGCGGATACGTCTTCACC TCTTACTATCTGGTGTGGGTCCGGCAGGCACCAGGA CAGGGACTGGAGTGGATGGCCACAATCTCTCCCGG AGACGTGAACACTAGTTACGAACAGCGATTCCAGGG CAGAGTGACCGTCACCACAGACGCTTCAACTAATAC CGTGGATATGGAGCTGCGGAGCCTGAGATCCGAAG ATACAGCCGTCTACTATTGCGCTAGGGGGCCCCGCA GCAAGCCTCCTTATCTGTATTTCGCTCTGGATGTCTG GGGGCAGGGAACAGCAGTCACCGTCTCAAGCGGC GGGGGAGGCTCTGGGGGAGGCGGGAGTGGAGGC GGGGGATCAGAGATTGTCCTGACCCAGTCACCTGG CACCCTGAGCCTGAGTCCTGGAGAGACCGCTATTCT GTCTTGTCGGGCATCACAGTCCGTGAGCTCCTCTCT GCTGGCATGGTACCAGCAGAAGCCCGGACAGGCCC CTAGGCTGCTGATCTATGGCGCCTCCAACCGCGCTA CTGGCATTCGGGGGAGATTCAGTGGCTCAGGGAGC GGAACCGACTTTACCCTGACAATCAGCCGGCTGGAG CCCGAAGATTTCGTGCTGTACTATTGTCAGCATTATG GAAGCAGGGTCACCTTCGGACAGGGAACTAAACTG GAAATCAAG |
| 177 | Bs3GC5 heavy chain aa | QVQLMESGGGVVQPGRSLRLSCSAFGFTFSNYPMHWVRQA PGKGLEWVAIILPDGNRKNYGRSVTGRFTISRDNSNNSLYLQ MNNLTTEDTAMYYCTRDGTYYSNGGVYQTYRRFFDFWGRG TLVTVSSASTKGPSVFPLAPSSKSTSGGTAALGCLVKDYFPEPVT VSWNSGALTSGVHTFPAVLQSSGLYSLSSVVTVPSSSLGTQTYI CNVNHKPSNTKVDKRVEPKSCDKTHTCPPCPAPELLGGPSVF LFPPKPKDTLMISRTPEVTCVVVDVSHEDPEVKFNWYVDGVE VHNAKTKPREEQYNSTYRVVSVLTVLHQDWLNGKEYKCKVS NKALPAPIEKTISKAKGQPREPQVYTLPPSREEMTKNQVSLTCL VKGFYPSDIAVEWESNGQPENNYKTTPPVLDSDGSFFLYSKLT VDKSRWQQGNVFSCSVMHEALHNHYTQKSLSLSPGKGGG GSGVQLVQSGGGLVQPGGSLRLSCAASGFTVSTNYMSWVR QAPGKGLEWVSILYAGGVTRYADSVKTRFTISRDNSKNTLFLQ MNALSAEDTAIYYCAKHYDSGYSTIDHFDSWGQGTLVTVSS GGGGSGGGGSGGGGSDIQMTQSPDSVAVSLGERATINCKS SQSVFYTSKNKNYLAWFQQKPGQPPKLLIYWASTRESGVPDR FSGSGSGTDFTLTISSLRPEDVAVYYCQQYYSTPFTFGPGTKVD IK |

-continued

| SEQ ID NO | Description | Sequence |
|---|---|---|
| 178 | Bs3GC5 heavy chain nucl | CAGGTGCAATTGATGGAGTCTGGGGGAGGCGTGGT<br>CCAGCCTGGGAGGTCCCTGCGACTCTCATGCAGTGC<br>CTTTGGATTCACCTTTTCGAACTATCCTATGCACTGG<br>GTCCGCCAGGCTCCAGGCAAGGGACTTGAGTGGGT<br>GGCTATCATTTTACCTGATGGGAACAGAAAAAACTAT<br>GGAAGGTCCGTGACGGGCCGATTCACCATCTCCAG<br>AGACAATTCCAACAACAGCCTTTATTTGCAAATGAAC<br>AACCTGACGACTGAGGACACGGCTATGTACTATTGT<br>ACGAGAGATGGCACGTATTACTCTAATGGTGGTGTT<br>TATCAGACATATCGAAGGTTCTTCGATTTCTGGGGCC<br>GTGGCACCCTGGTCACCGTCTCCTCAGCGTCGACCA<br>AGGGCCCATCGGTCTTCCCCCTGGCACCCTCCTCCA<br>AGAGCACCTCTGGGGGCACAGCGGCCCTGGGCTGC<br>CTGGTCAAGGACTACTTCCCCGAACCTGTGACGGTC<br>TCGTGGAACTCAGGCGCCCTGACCAGCGGCGTGCA<br>CACCTTCCCGGCTGTCCTACAGTCCTCAGGACTCTAC<br>TCCCTCAGCAGCGTGGTGACCGTGCCCTCCAGCAGC<br>TTGGGCACCCAGACCTACATCTGCAACGTGAATCAC<br>AAGCCCAGCAACACCAAGGTGGACAAGAGAGTTGA<br>GCCCAAATCTTGTGACAAAACTCACACATGCCCACC<br>GTGCCCAGCACCTGAACTCCTGGGGGGACCGTCAG<br>TCTTCCTCTTCCCCCCAAAACCCAAGGACACCCTCAT<br>GATCTCCCGGACCCCTGAGGTCACATGCGTGGTGGT<br>GGACGTGAGCCACGAGGATCCTGAAGTCAAGTTCA<br>ACTGGTACGTGGATGGCGTCGAGGTGCATAATGCC<br>AAGACAAAACCCCGGGAGGAACAGTACAACTCAACT<br>TATAGAGTCGTGAGCGTCCTGACCGTGCTGCATCAG<br>GACTGGCTGAACGGCAAAGAATACAAGTGCAAAGT<br>GTCTAATAAGGCCCTGCCTGCTCCAATCGAGAAAAC<br>AATTAGCAAGGCAAAAGGGCAGCCCAGGGAACCTC<br>AGGTGTACACTCTGCCTCCAAGCCGCGAGGAAATGA<br>CCAAGAACCAGGTCTCCCTGACATGTCTGGTGAAAG<br>GATTCTATCCTAGTGACATTGCCGTGGAGTGGGAAT<br>CAAATGGCCAGCCAGAGAACAATTACAAGACCACAC<br>CCCCTGTGCTGGACTCTGATGGGAGTTTCTTTCTGTA<br>TTCCAAGCTGACCGTGGATAAATCTAGATGGCAGCA<br>GGGAAATGTCTTTAGCTGTTCCGTGATGCATGAGGC<br>ACTGCACAACCATTACACCCAGAAATCACTGTCACTG<br>TCCCCAGGAAAAGGCGGGGGAGGCTCTGGCGTGCAG<br>CTGGTCCAGAGCGGAGGCGGACTGGTCCAGCCCGGCG<br>GATCACTGAGACTGTCATGTGCCGCAAGCGGGTTTACCG<br>TCTCTACAAACTACATGTCTTGGGTGAGGCAGGCACCTG<br>GAAAGGGACTGGAGTGGGTCTCAATCCTGTACGCTGGC<br>GGGGTGACCCGGTATGCAGACAGCGTCAAGACCCGGTT<br>CACAATTAGCAGAGATAACTCCAAAAATACTCTGTTTCTGC<br>AGATGAATGCCCTGTCCGCTGAAGACACCGCAATCTACTA<br>TTGCGCCAAACACTATGATAGTGGGTACAGTACCATTGAC<br>CATTTCGATAGCTGGGGCAGGGGACTCTGGTGACCGTC<br>TCATCAGGCGGGGGAGGCTCTGGGGGAGGCGGGAGTG<br>GAGGCGGGGGATCAGATATTCAGATGACCCAGAGTCCT<br>GATTCCGTCGCTGTCTCACTGGGAGAAAGGGCAACCATT<br>AACTGTAAAAGCTCACAGAGTGTCTTCTACACCAGTAAGA<br>ACAAAAACTATCTGGCCTGGTTTCAGCAGAAGCCAGGCC<br>AGCCCCCTAAACTGCTGATCTACTGGGCTAGCACTAGAG<br>AGTCTGGAGTGCCAGACAGATTCTCTGGCAGTGGGTCAG<br>GAACCGACTTCACCCTGACAATTAGCTCCCTGAGGCCCG<br>AAGACGTGGCCGTCTACTATTGTCAGCAGTATTATTCAAC<br>ACCCTTCACATTCGGACCAGGAACAAAAGTGGATATTAAG |
| | | Non-engineered chains of multispecific antibodies |
| 179 | GCA7 heavy chain aa | GVQLVQSGGGLVQPGGSLRLSCAAS**gftystny**MSWVRQAPG<br>KGLEWVS**IlyaggvtR**YADSVKTRFTISRDNSKNTLFLQMNALSA<br>EDTAIYYC**akhydsgystidhfds**WGQGTLVTVSSASTKGPSVFPLA<br>PSSKSTSGGTAALGCLVKDYFPEPVTVSWNSGALTSGVHTFPA<br>VLQSSGLYSLSSVVTVPSSSLGTQTYICNVNHKPSNTKVDKRV<br>EPKSCDKTHTCPPCPAPELLGGPSVFLFPPKPKDTLMISRTPEVT<br>CVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSREEMTKNQVSLTCLVKGFYPSDIAVEWESNGQP<br>ENNYKTTPPVLDSDGSFFLYSKLTVDKSRWQQGNVFSCSVM<br>HEALHNHYTQKSLSLSPGK |
| 180 | GCA7 heavy chain nucl | ggggtgcaactggtgcagtctgggggaggcttggtccagccggggggtccctgaga<br>ctctcctgtgcagcctct**GGATTCACCGTCAGTACCAACTAC**atgagct<br>gggtccgccaggctccagggaaggggctggagtgggtctcaatt**CTTTATGCCG**<br>**GAGGTGTCACA**aggtacgcagactccgtgaagaccagattcaccatctccag |

-continued

| SEQ ID NO | Description | Sequence |
|---|---|---|
| | | agacaattccaagaacactctctttcttcaaatgaacgccctgagcgccgaggacacg<br>gctatatattactgt**GCGAAACACTATGATTCGGGATATTCTACCA**<br>**TAGATCACTTTGACTCC**tggggccagggaaccctggtcaccgtctcctcag<br>cgtcgaccaagggcccatcggtcttccccctggcaccctcctccaagagcacctctg<br>ggggcacagcggccctgggctgcctggtcaaggactacttccccgaacctgtgacgg<br>tctcgtggaactcaggcgccctgaccagcggcgtgcacaccttcccggctgtcctaca<br>gtcctcaggactctactccctcagcagcgtggtgaccgtgccctccagcagatgggc<br>acccagacctacatctgcaacgtgaatcacaagcccagcaacaccaaggtggacaa<br>gagagttgagcccaaatcttgtgacaaaactcacacatgcccaccgtgcccagcacc<br>tgaactcctggggggaccgtcagtcttcctcttccccccaaaacccaaggacaccctc<br>atgatctcccggacccctgaggtcacatgcgtggtggtggacgtgagccacgaGgaT<br>cctgaggtcaagttcaactggtacgtggacggcgtggaggtgcataatgccaagacaa<br>agccgcgggaggagcagtacaacagcacgtaccgtgtggtcagcgtcctcaccgtc<br>ctgcaccaggactggctgaatggcaaggagtacaagtgcaaggtctccaacaaagc<br>cctcccagcccccatcgagaaaaccatctccaaagccaaagggcagccccgagaa<br>ccacaggtgtacaccctgcccccatcccgggaggagatgaccaagaaccaggtcag<br>cctgacctgcctggtcaaaggcttctatcccagcgacatcgccgtggagtgggagagc<br>aatgggcagccggagaacaactacaagaccacgcctcccgtgctggactccgacgg<br>ctccttcttcctctatagcaagctcaccgtggacaagagcaggtggcagcaggggaac<br>gtcttctcatgctccgtgatgcatgaggctctgcacaaccactacacgcagaagagcct<br>ctccctgtccccgggtaaa |
| 181 | GCA7 light chain aa | DIQMTQSPDSVAVSLGERATINCKSS**qsvfytsknkny**LAWFQQK<br>PGQPPKLLIY**was**TRESGVPDRFSGSGSGTDFTLTISSLRPEDVA<br>VYYC**qqyystpft**FGPGTKVDIKRTVAAPSVFIFPPSDEQLKSGTAS<br>VVCLLNNFYPREAKVQWKVDNALQSGNSQESVTEQDSKDST<br>YSLSSTLTLSKADYEKHKVYACEVTHQGLSSPVTKSFNRGEC |
| 182 | GCA7 light chain nucl | gacatccagatgacccagtctccagactccgtggctgtgtctctgggcgagagggcca<br>ccatcaactgcaagtccagc**CAGAGTGTTTTCTACACCTCCAAAAA**<br>**TAAAAACTAC**ttagcttggttccagcagaaaccaggacagcctcctaaactgct<br>catttacTGGGCATCTacccgggagtccggggtccctgaccgattcagtggcag<br>cgggtctgggacagatttcactctcaccatcagcagcctgcggcctgaagatgtggca<br>gtttattactgt**CAGCAATATTATAGTACCCCTTTCACT**ttcggccctgg<br>gaccaaagtggatatcaaacgTacGgtggctgcaccatctgtcttcatcttcccgcca<br>tctgatgagcagttgaaatctggaactgcctctgttgtgtgcctgctgaataacttctatcc<br>cagagaggccaaagtacagtggaaggtggataacgccctccaatcgggtaactccc<br>aggagagtgtcacagagcaggacagcaaggacagcacctacagcctcagcagcac<br>cctgacgctgagcaaagcagactacgagaaacacaaagtctacgcctgcgaagtca<br>cccatcagggcctgagctcgcccgtcacaaagagcttcaacaggggagagtgt |
| 183 | GCA21 light chain aa | DIQMTQSPSTLSTSVGDRVTITCRAS**qnilnw**LAWYQQKPGNA<br>PNLLIY**kas**DLQSGVPSRFSGSGSGTEFTLTISSLQPDDFATYYC<br>qhynsypltFGGGTKVEIKRTVAAPSVFIFPPSDEQLKSGTASVVC<br>LLNNFYPREAKVQWKVDNALQSGNSQESVTEQDSKDSTYSL<br>SSTLTLSKADYEKHKVYACEVTHQGLSSPVTKSFNRGEC |
| 184 | GCA21 light chain nucl | gacatccagatgacccagtctccttccaccctgtctacatctgtgggagacagagtcac<br>catcacttgccgggccagt**CAGAATATCCTTAATTGG**ttggcctggtatcaa<br>cagaaaccagggaacgcccctaacctcctgatatat**AAGGCGTCT**gatttacaa<br>agtggggtcccctcaagattcagcggcagtgggtctgggacagaattcactctcaccat<br>cagcagcctgcagcctgatgattttgcaacttattactgc**CAGCATTATAATAG**<br>**TTATCCTCTCACT**ttcggcggagggaccaaggtggaaatcaaacgTacGgt<br>ggctgcaccatctgtcttcatcttcccgccatctgatgagcagttgaaatctggaactgc<br>ctctgttgtgtgcctgctgaataacttctatcccagagaggccaaagtacagtggaaggt<br>ggataacgccctccaatcgggtaactcccaggagagtgtcacagagcaggacagca<br>aggacagcacctacagcctcagcagcaccctgacgctgagcaaagcagactacga<br>gaaacacaaagtctacgcctgcgaagtcacccatcagggcctgagctcgcccgtca<br>caaagagcttcaacaggggagagtgt |
| 185 | GCB59 light chain aa | SYVLTQPPSVSVAPGQTASLTCGGT**NIGSKS**VHWYQQKAGQ<br>APVLVVY**ADN**DRPSGVPERFSGSNSGNTATLTISRVEAEDESD<br>YFC**QVWDGNTDHVVF**GGGTKLTVLGQPKAAPSVTLFPPSSE<br>ELQANKATLVCLISDFYPGAVTVAWKADSSPVKAGVETTTPSK<br>QSNNKYAASSYLSLTPEQWKSHRSYSCQVTHEGSTVEKTVAP<br>TECS |
| 186 | GCB59 light chain nucl | TCATATGTGCTGACTCAACCACCCTCGGTGTCAGTGGCCC<br>CAGGACAGACGGCCAGTCTAACCTGTGGGGGAACT**AAC**<br>**ATTGGAAGTAAAAGT**GTTCATTGGTACCAGCAAAAGGCA<br>GGCCAGGCCCCTGTGTTGGTCGTCTAT**GCTGATAA**CGAC<br>AGGCCCTCAGGGGTCCCTGAGCGATTCTCTGGCTCCAAC<br>TCTGGGAACACGGCCACCCTGACCATCAGCAGGGTCGA<br>GGCCGAGGATGAGTCCGACTATTTCTGT**CAGGTGTGGGA**<br>**TGGTAATACTGATCATGTGGTC**TTCGGCGGAGGGACCAA<br>GCTGACCGTCCTGggtcagcccaaggctgccccctcggtcactctgttcccg<br>ccctcctctgaggagcttcaagccaacaaggccacactggtgtgtctcataagtgactt<br>ctacccgggagccgtgacagtggcttggaaagcagatagcagccccgtcaaggcgg<br>gagtggagaccaccacaccctccaaacaaagcaacaacaagtacgcggccagca<br>gctatctgagcctgacgcctgagcagtggaagtcccacagaagctacagctgccagg<br>tcacgcatgaagggagcaccgtggagaagacagtggcccctacagaatgttca |

-continued

| SEQ ID NO | Description | Sequence |
|---|---|---|
| 187 | GCE536 heavy chain aa | QLQLVQSGTEVKKPGASVKVSCKSSG**YVFTSYY**LVWVRQAP<br>GQGLEWMAT**ISPGDVNTS**YEQRFQGRVTVTTDASTNTVDM<br>ELRSLRSEDTAVYYC**ARGPRSKPPYLYFALDV**VVGQGTAVTVSS<br>ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGGPSVFLFPPKP<br>KDTLMISRTPEVTCVVVDVSTTTEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKGFYPS<br>DIAVEWESNGQPENNYKTTPPVLDSDGSFFLYSKLTVDKSRW<br>QQGNVFSCSVMHEALHNHYTQKSLSLSPGK |
| 188 | GCE536 heavy chain nucl | CAGCTGCAGCTGGTCCAGTCAGGCACAGAGGTCAAAAA<br>GCCAGGAGCATCAGTGAAGGTGTCTTGTAAGTCATCAGG<br>ATACGTGTTCACCTCTTACTATCTGGTGTGGGTCCGGCAG<br>GCACCAGGACAGGGACTGGAGTGGATGGCCACAATCTC<br>TCCCGGAGACGTGAACACTAGTTACGAACAGCGATTCCA<br>GGGCAGAGTGACCGTCACCACAGACGCTTCAACTAATAC<br>CGTGGATATGGAGCTGCGGAGCCTGAGATCCGAAGATA<br>CAGCCGTCTACTATTGCGCTAGGGGGCCCCGCAGCAAGC<br>CTCCTTATCTGTATTTTGCTCTGGATGTGTGGGGGCAGGG<br>GACCGCTGTCACCGTGTCAAGCgcgtcgaccaagggcccatcggtct<br>tcccctggcaccctcctccaagagcacctctgggggcacagcggccctgggctgc<br>ctggtcaaggactacttccccgaacctgtgacggtctcgtggaactcaggcgccctga<br>ccagcggcgtgcacaccttcccggctgtcctacagtcctcaggactctactccctcag<br>cagcgtggtgaccgtgccctccagcagcttgggcacccagacctacatctgcaacgt<br>gaatcacaagcccagcaacaccaaggtggacaagagagttgagcccaaatcttgtg<br>acaaaactcacacatgcccaccgtgcccagcacctgaactcctggggggaccgtca<br>gtcttcctcttccccccaaaacccaaggacaccctcatgatctcccggacccctgagg<br>tcacatgcgtggtggtggacgtgagccacgaGgaTcctgaggtcaagttcaactggta<br>cgtggacggcgtggaggtgcataatgccaagacaaagccgcgggaggagcagtaca<br>acagcacgtaccgtgtggtcagcgtcctcaccgtcctgcaccaggactggctgaatgg<br>caaggagtacaagtgcaaggtctccaacaaagccctcccagcccccatcgagaaaa<br>ccatctccaaagccaaagggcagccccgagaaccacaggtgtacaccctgcccccc<br>atcccgggaggagatgaccaagaaccaggtcagcctgacctgcctggtcaaaggctt<br>ctatcccagcgacatcgccgtggagtgggagagcaatgggcagccggagaacaact<br>acaagaccacgcctcccgtgctggactccgacggctccttcttcctctatagcaagctc<br>accgtggacaagagcaggtggcagcaggggaacgtcttctcatgctccgtgatgcatg<br>aggctctgcacaaccactacacgcagaagagcctctccctgtccccgggtaaa |
| 189 | GCE536 light chain aa | EIVLTQSPGTLSLSPGETAILSCRAS**QSVSSSL**LAWYQQKPGQA<br>PRLLIY**GAS**NRATGIRGRFSGSGSGTDFTLTISRLEPEDFVLYYC<br>**QHYGSRVT**FGQGTKLEIKRTVAAPSVFIFPPSDEQLKSGTASVV<br>CLLNNFYPREAKVQWKVDNALQSGNSQESVTEQDSKDSTYS<br>LSSTLTLSKADYEKHKVYACEVTHQGLSSPVTKSFNRGEC |
| 190 | GCE536 light chain nucl | gaaattgtgttgacgcagtctcctggcaccctgtctttgtctccaggggaaacagccatc<br>ctctcctgcagggccagt**cagagtgtcagcagcag**cctcttagcctggtaccagcaaa<br>aacctggccaggctcccaggctcctcatctac**ggtgca**tccaatagggccactggcat<br>cagaggcaggtttagtggcagtgggtctgggacagacttcactctcaccatcagtagatt<br>ggagcctgaagattagtactttattactgt**cagcactatggctcacgggtcact**tttggcc<br>aggggaccaagctggagatcaaacgTacGgtggctgcaccatctgtcttcatcttccc<br>gccatctgatgagcagttgaaatctggaactgcctctgttgtgtgcctgctgaataacttct<br>atcccagagaggccaaagtacagtggaaggtggataacgccctccaatcgggtaact<br>cccaggagagtgtcacagagcaggacagcaaggacagcacctacagcctcagcag<br>caccctgacgctgagcaaagcagactacgagaaacacaaagtctacgcctgcgaag<br>tcacccatcagggcctgagctcgcccgtcacaaagagcttcaacaggggagagtgt |

* the sequences highlighted in bold are CDR regions (nucleotide or aa) and the underlined residues are mutated residues as compared to the "germ line" sequence.

The invention claimed is:

1. An isolated multispecific anti GM-CSF antibody, or an antigen binding fragment thereof, comprising:

(a) at least two epitope binding sites, wherein each of the at least two epitope binding sites is specific for a different epitope of a GM-CSF, whereby the different epitopes of the GM-CSF are non-overlapping epitopes; and (b) an Fc moiety, wherein the antibody or antigen binding fragment comprises a heavy chain comprising at least one CDRH1, at least one CDRH2 and at least one CDRH3, and a light chain comprising at least one CDRL1, at least one CDRL2 and at least one CDRL3, wherein two of the at least two epitope binding sites each independently comprise:

(i) CDRH1, CDRH2, and CDRH3 amino acid sequences and CDRL1, CDRL2, and CDRL3 amino acid sequences according to SEQ ID NOs: 1-5 and 7, or functional sequence variants thereof, respectively, or according to SEQ ID NOs: 1-4 and 6-7, or functional sequence variants thereof, respectively;

(ii) CDRH1, CDRH2, and CDRH3 amino acid sequences and CDRL1, CDRL2, and CDRL3 amino acid sequences according to SEQ ID NOs: 49-53 and 55, or functional sequence variants thereof, respectively, or according to SEQ ID NOs: 49-52 and 54-55, or functional sequence variants thereof, respectively;

(iii) CDRH1, CDRH2, and CDRH3 amino acid sequences and light chain CDRL1, CDRL2, and CDRL3 amino acid sequences according to SEQ ID NOs: 67-71 and 73, or functional sequence variants thereof, respectively, or according to SEQ ID NOs: 67-70 and 72-73, or functional sequence variants thereof, respectively; and/or (iv) heavy chain CDRH1, CDRH2, and CDRH3 amino acid sequences and light chain CDRL1, CDRL2, and CDRL3 amino acid sequences according to SEQ ID NOs: 105-109 and 111, or functional sequence variants thereof, respectively, or according to SEQ ID NOs: 105-108 and 110-111, or functional sequence variants thereof, respectively.

2. The antibody, or the antigen binding fragment thereof, according to claim 1, wherein the antibody, or the antigen binding fragment thereof, is bispecific, trispecific, tetraspecific or pentaspecific.

3. The antibody, or the antigen binding fragment thereof, according to claim 1, wherein the antibody, or the antigen binding fragment thereof, consists of two different epitope binding sites specific for two different, non-overlapping epitopes of the GM-CSF.

4. The antibody, or the antigen binding fragment thereof, according to claim 2, wherein the antibody, or the antigen binding fragment thereof, is a bispecific tetravalent antibody or a trispecific hexavalent antibody.

5. The antibody, or the antigen binding fragment thereof, according to claim 1, wherein the antibody, or the antigen binding fragment thereof, further comprises:

(c) at least one linker.

6. The antibody, or the antigen binding fragment thereof, according to claim 5, wherein the linker comprises or consists of an amino acid sequence according to SEQ ID NO: 143 or SEQ ID NO: 144 or a functional sequence variant thereof.

7. The antibody, or the antigen binding fragment thereof, according to claim 1, wherein the antibody, or the antigen binding fragment thereof, comprises:

(a) an IgG type, (b) an IgG1 type, (c) a heavy chain constant region of the IgG1 CH1-CH2-CH3 type and a light chain constant region of the IgG CK type, or (d) a heavy chain constant region of the IgG1 CH1-CH2-CH3 type comprising or consisting of an amino acid sequence according to SEQ ID NO: 140 or functional sequence variants thereof, and a light chain constant region of the IgG CK type comprising or consisting of an amino acid sequence according to SEQ ID NO: 141 or functional sequence variants thereof.

8. The antibody, or the antigen binding fragment thereof, according to claim 1, wherein the antibody, or the antigen binding fragment thereof, is of a construct type selected from the group comprising Bs1, Bs2, Bs3, Ts1, Ts2 and Ts3.

9. The antibody, or the antigen binding fragment thereof, according to claim 8, wherein the antibody, or the antigen binding fragment thereof, comprises a construct type Ts3 or comprises a trispecific antibody according to the construct type Ts3.

10. The antibody, or the antigen binding fragment thereof, according to claim 1, wherein the antibody, or the antigen binding fragment thereof, is a human antibody, a monoclonal antibody, a human monoclonal antibody, a purified antibody, or a single chain antibody, or an antigen binding fragment thereof.

11. The antibody, or the antigen binding fragment thereof, according to claim 1, wherein the antibody, or the antigen binding fragment thereof, neutralizes the GM-CF:

under stringent conditions with an $IC_{90}$ of 150 ng/ml or less;

(ii) under less stringent conditions with an $IC_{90}$ of 20 ng/ml or less;

(iii) under more stringent conditions with an $IC_{90}$ of 160 ng/ml or less; and/or (iv) under very stringent conditions with an $IC_{90}$ of 1000 ng/ml or less.

12. The antibody, or the antigen binding fragment thereof, according to claim 1, wherein the antibody or antigen binding fragment comprises:

(i) a VH amino acid sequence according to SEQ ID NO: 37 or a functional sequence variant thereof and a VL amino acid sequence according to SEQ ID NO: 38 or a functional sequence variant thereof;

(ii) a VH amino acid sequence according to SEQ ID NO: 63 or a functional sequence variant thereof and a VL amino acid sequence according to SEQ ID NO: 64 or a functional sequence variant thereof;

(iii) a VH amino acid sequence according to SEQ ID NO: 95 or a functional sequence variant thereof and a VL amino acid sequence according to SEQ ID NO: 96 or a functional sequence variant thereof; and/or (iv) a VH amino acid sequence according to SEQ ID NO: 130 or a functional sequence variant thereof and a VL amino acid sequence according to SEQ ID NO: 131 or a functional sequence variant thereof.

13. The antibody, or the antigen binding fragment thereof, according to claim 1, wherein the heavy chain of the antibody or antigen binding fragment comprises a VL amino acid sequence selected from the amino acid sequences according to SEQ ID NOs: 38, 64, 96, 131, or functional sequence variants thereof; or the heavy chain of the antibody or antigen binding fragment comprises a VL amino acid sequence according to SEQ ID NOs: 38 or 96, or functional sequence variants thereof; or the heavy chain of the antibody or antigen binding fragment comprises a VL amino acid sequence according to SEQ ID NO: 96 or functional sequence variants thereof.

14. The antibody, or the antigen binding fragment thereof, according to claim 1, wherein the antibody or the antigen binding fragment:

(i) is of a construct type selected from the group consisting of the construct types Bs1, Bs2, Bs3, Ts1, Ts2 and Ts3; and (ii) comprises at any of the positions A and/or C a CDRH1 amino acid sequence, a CDRH2 amino acid sequence, a CDRH3 amino acid sequence, a CDRL1 amino acid sequence, a CDRL2 amino acid sequence and a CDRL3 amino acid sequence selected from the group consisting of amino acid sequences according to SEQ ID NOs: 1-7 and 67-73, or functional sequence variants thereof.

15. The antibody, or the antigen binding fragment thereof, according to claim 1, wherein the antibody, or the antigen binding fragment thereof, is according to gTs1GC1, gTs1GC2a, gTs2GC2b, gTs2GC2c, gTs3GC2d, gTs3GC2e, gBs3GC1a, gBs3GC1b, gBs2GC1c, gBs2GC1d, gBs1GC2a, gBs3GC2b, gBs1GC3a, gBs3GC3b, gBs3GC4, or gBs3GC5.

16. The antibody, or the antigen binding fragment thereof, according to claim 15, wherein the antibody, or the antigen binding fragment thereof, is Ts1GC1, Ts1GC2a, Ts2GC2b, Ts2GC2c, Ts3GC2d, Ts3GC2e, Bs3GC1a, Bs3GC1b, Bs2GC1c, Bs2GC1d, Bs1GC2a, Bs3GC2b, Bs1GC3a, Bs3GC3b, Bs3GC4, or Bs3GC5.

17. A nucleic acid molecule, comprising a polynucleotide encoding the antibody, or the antigen binding fragment thereof, according to claim 1.

18. The nucleic acid molecule according to claim 17, wherein the polynucleotide encoding the antibody or antigen binding fragment thereof comprises a nucleic acid sequence according to any one of SEQ ID NOs: 8-36, 39-48, 56-62, 65-66, 74-94, 97-104, 112-129, 132-139, 152, 154, 156, 158, 160, 162, 164, 166, 168, 170, 172, 174, 176, 178, 180, 182, 184, 186, 188, or 190, or a functional sequence variant thereof.

19. The nucleic acid molecule according to claim 18, wherein the polynucleotide comprises a nucleic acid sequence according to any one of SEQ ID NOs: 39-48, 65-66, 97-104, 132-139, 152, 154, 156, 158, 160, 162, 164, 166, 168, 170, 172, 174, 176, 178, 180, 182, 184, 186, 188, or 190, or a functional sequence variant thereof.

20. A vector, comprising the nucleic acid molecule according to claim 17.

21. A cell expressing the antibody, or the antigen binding fragment thereof, comprising the nucleic acid molecule according to claim 17.

22. A pharmaceutical composition comprising the antibody, or the antigen binding fragment thereof, according to claim 1, and a pharmaceutically acceptable excipient, diluent or carrier.

23. The antibody, or the antigen binding fragment thereof, according to claim 14, wherein the antibody or antigen binding fragment comprises at position A a CDRH1 amino acid sequence, a CDRH2 amino acid sequence, a CDRH3 amino acid sequence, a CDRL1 amino acid sequence, a CDRL2 amino acid sequence and a CDRL3 amino acid sequence according to SEQ ID NOs: 67-71 and 73, or functional sequence variants thereof, or according to SEQ ID NOs: 67-70 and 72-73, or functional sequence variants thereof.

24. The antibody, or the antigen binding fragment thereof, according to claim 1, wherein the antibody or antigen binding fragment comprises:

(i) a VH amino acid sequence that is at least 80% identical to SEQ ID NO: 37 and a VL amino acid sequence that is at least 80% identical to SEQ ID NO: 38;

(ii) a VH amino acid sequence that is at least 80% identical to SEQ ID NO: 63 and a VL amino acid sequence that is at least 80% identical to SEQ ID NO: 64;

(iii) a VH amino acid sequence that is at least 80% identical to SEQ ID NO: 95 and a VL amino acid sequence that is at least 80% identical to SEQ ID NO: 96; and/or (iv) a VH amino acid sequence that is at least 80% identical to SEQ ID NO: 130 and a VL amino acid sequence that is at least 80% identical to SEQ ID NO: 131.

25. The antibody, or the antigen binding fragment thereof, according to claim 16, wherein the antibody, or the antigen binding fragment thereof, is Bs1GC3a.

26. The antibody, or the antigen binding fragment thereof, according to claim 16, wherein the antibody, or the antigen binding fragment thereof, is Ts3GC2d.

* * * * *

UNITED STATES PATENT AND TRADEMARK OFFICE

CERTIFICATE OF CORRECTION

PATENT NO. : 10,526,404 B2
APPLICATION NO. : 15/568325
DATED : January 7, 2020
INVENTOR(S) : Davide Corti et al.

It is certified that error appears in the above-identified patent and that said Letters Patent is hereby corrected as shown below:

In the Claims

Claim 11, Column 298, Line 64:
"under stringent conditions with an IC90 of 150 ng/ml or" should read --(i) under stringent conditions with an IC90 of 150 ng/ml or--

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 191

<210> SEQ ID NO 1
<211> LENGTH: 8
<212> TYPE: PRT
<213> ORGANISM: Artificial Sequence
<220> FEATURE:
<223> OTHER INFORMATION: GCA7 CDRH1 aa

<400> SEQUENCE: 1

Gly Phe Thr Val Ser Thr Asn Tyr
1               5

-continued

<210> SEQ ID NO 2
<211> LENGTH: 7
<212> TYPE: PRT
<213> ORGANISM: Artificial Sequence
<220> FEATURE:
<223> OTHER INFORMATION: GCA7 CDRH2 aa

<400> SEQUENCE: 2

Leu Tyr Ala Gly Gly Val Thr
1 5

<210> SEQ ID NO 3
<211> LENGTH: 16
<212> TYPE: PRT
<213> ORGANISM: Artificial Sequence
<220> FEATURE:
<223> OTHER INFORMATION: GCA7 CDRH3 aa

<400> SEQUENCE: 3

Ala Lys His Tyr Asp Ser Gly Tyr Ser Thr Ile Asp His Phe Asp Ser
1 5 10 15

<210> SEQ ID NO 4
<211> LENGTH: 12
<212> TYPE: PRT
<213> ORGANISM: Artificial Sequence
<220> FEATURE:
<223> OTHER INFORMATION: GCA7 CDRL1 aa

<400> SEQUENCE: 4

Gln Ser Val Phe Tyr Thr Ser Lys Asn Lys Asn Tyr
1 5 10

<210> SEQ ID NO 5

<400> SEQUENCE: 5

000

<210> SEQ ID NO 6
<211> LENGTH: 9
<212> TYPE: PRT
<213> ORGANISM: Artificial Sequence
<220> FEATURE:
<223> OTHER INFORMATION: GCA7 CDRL2 long aa

<400> SEQUENCE: 6

Leu Ile Tyr Trp Ala Ser Thr Arg Glu
1 5

<210> SEQ ID NO 7
<211> LENGTH: 9
<212> TYPE: PRT
<213> ORGANISM: Artificial Sequence
<220> FEATURE:
<223> OTHER INFORMATION: GCA7 CDRL3 aa

<400> SEQUENCE: 7

Gln Gln Tyr Tyr Ser Thr Pro Phe Thr
1 5

<210> SEQ ID NO 8
<211> LENGTH: 24
<212> TYPE: DNA
<213> ORGANISM: Artificial Sequence
<220> FEATURE:
<223> OTHER INFORMATION: GCA7 CDRH1 nuc varS1

<400> SEQUENCE: 8
ggattcaccg tcagtaccaa ctac 24

<210> SEQ ID NO 9
<211> LENGTH: 24
<212> TYPE: DNA
<213> ORGANISM: Artificial Sequence
<220> FEATURE:
<223> OTHER INFORMATION: GCA7 CDRH1 nuc varS2

<400> SEQUENCE: 9
gggtttactg tgtctacaaa ctac 24

<210> SEQ ID NO 10
<211> LENGTH: 24
<212> TYPE: DNA
<213> ORGANISM: Artificial Sequence
<220> FEATURE:
<223> OTHER INFORMATION: GCA7 CDRH1 nuc varN1

<400> SEQUENCE: 10
ggctttactg tctctacaaa ctac 24

<210> SEQ ID NO 11
<211> LENGTH: 24
<212> TYPE: DNA
<213> ORGANISM: Artificial Sequence
<220> FEATURE:
<223> OTHER INFORMATION: GCA7 CDRH1 nuc varC1

<400> SEQUENCE: 11
ggcttcaccg tgtcaacaaa ctac 24

<210> SEQ ID NO 12
<211> LENGTH: 24
<212> TYPE: DNA
<213> ORGANISM: Artificial Sequence
<220> FEATURE:
<223> OTHER INFORMATION: GCA7 CDRH1 nuc varC2

<400> SEQUENCE: 12
gggtttaccg tctctacaaa ctac 24

<210> SEQ ID NO 13
<211> LENGTH: 21
<212> TYPE: DNA
<213> ORGANISM: Artificial Sequence
<220> FEATURE:
<223> OTHER INFORMATION: GCA7 CDRH2 nuc varS1

<400> SEQUENCE: 13
ctttatgccg gaggtgtcac a 21

<210> SEQ ID NO 14
<211> LENGTH: 21
<212> TYPE: DNA
<213> ORGANISM: Artificial Sequence
<220> FEATURE:
<223> OTHER INFORMATION: GCA7 CDRH2 nuc varS2/N1/C2

<400> SEQUENCE: 14
ctgtacgctg gcggggtgac c 21

<210> SEQ ID NO 15

<211> LENGTH: 21
<212> TYPE: DNA
<213> ORGANISM: Artificial Sequence
<220> FEATURE:
<223> OTHER INFORMATION: GCA7 CDRH2 nuc varC1

<400> SEQUENCE: 15
ctgtacgccg gaggcgtgac t 21

<210> SEQ ID NO 16
<211> LENGTH: 48
<212> TYPE: DNA
<213> ORGANISM: Artificial Sequence
<220> FEATURE:
<223> OTHER INFORMATION: GCA7 CDRH3 nuc varS1

<400> SEQUENCE: 16
gcgaaacact atgattcggg atattctacc atagatcact ttgactcc 48

<210> SEQ ID NO 17
<211> LENGTH: 48
<212> TYPE: DNA
<213> ORGANISM: Artificial Sequence
<220> FEATURE:
<223> OTHER INFORMATION: GCA7 CDRH3 nuc varS2

<400> SEQUENCE: 17
gccaaacact atgatagtgg gtactccact attgaccatt ttgactct 48

<210> SEQ ID NO 18
<211> LENGTH: 48
<212> TYPE: DNA
<213> ORGANISM: Artificial Sequence
<220> FEATURE:
<223> OTHER INFORMATION: GCA7 CDRH3 nuc varN1

<400> SEQUENCE: 18
gccaaacact atgatagtgg gtatagcaca atcgaccatt ttgacagc 48

<210> SEQ ID NO 19
<211> LENGTH: 48
<212> TYPE: DNA
<213> ORGANISM: Artificial Sequence
<220> FEATURE:
<223> OTHER INFORMATION: GCA7 CDRH3 nuc varC1

<400> SEQUENCE: 19
gcaaaacact acgattctgg gtatagtaca attgaccatt ttgattct 48

<210> SEQ ID NO 20
<211> LENGTH: 48
<212> TYPE: DNA
<213> ORGANISM: Artificial Sequence
<220> FEATURE:
<223> OTHER INFORMATION: GCA7 CDRH3 nuc varC2

<400> SEQUENCE: 20
gccaaacact atgatagtgg gtacagtacc attgaccatt tcgatagc 48

<210> SEQ ID NO 21
<211> LENGTH: 36
<212> TYPE: DNA
<213> ORGANISM: Artificial Sequence
<220> FEATURE:
<223> OTHER INFORMATION: GCA7 CDRL1 nuc varS1

<400> SEQUENCE: 21

-continued cagagtgttt tctacacctc caaaaataaa aactac 36

<210> SEQ ID NO 22
<211> LENGTH: 36
<212> TYPE: DNA
<213> ORGANISM: Artificial Sequence
<220> FEATURE:
<223> OTHER INFORMATION: GCA7 CDRL1 nuc varS2

<400> SEQUENCE: 22
cagtccgtct tctacaccag taagaacaaa aactat 36

<210> SEQ ID NO 23
<211> LENGTH: 36
<212> TYPE: DNA
<213> ORGANISM: Artificial Sequence
<220> FEATURE:
<223> OTHER INFORMATION: GCA7 CDRL1 nuc varN1

<400> SEQUENCE: 23
cagagcgtgt tctacaccag taagaacaaa aactat 36

<210> SEQ ID NO 24
<211> LENGTH: 36
<212> TYPE: DNA
<213> ORGANISM: Artificial Sequence
<220> FEATURE:
<223> OTHER INFORMATION: GCA7 CDRL1 nuc varC1

<400> SEQUENCE: 24
cagtccgtgt tctacacttc taagaacaaa aactat 36

<210> SEQ ID NO 25
<211> LENGTH: 36
<212> TYPE: DNA
<213> ORGANISM: Artificial Sequence
<220> FEATURE:
<223> OTHER INFORMATION: GCA7 CDRL1 nuc varC2

<400> SEQUENCE: 25
cagagtgtct tctacaccag taagaacaaa aactat 36

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29
<211> LENGTH: 27
<212> TYPE: DNA
<213> ORGANISM: Artificial Sequence
<220> FEATURE:
<223> OTHER INFORMATION: GCA7 CDRL2 long nuc varS1

<400> SEQUENCE: 29
ctcatttact gggcatctac ccgggag 27

<210> SEQ ID NO 30
<211> LENGTH: 27
<212> TYPE: DNA
<213> ORGANISM: Artificial Sequence
<220> FEATURE:
<223> OTHER INFORMATION: GCA7 CDRL2 long nuc varS2/N1/C2

<400> SEQUENCE: 30
ctgatctact gggctagcac tagagag 27

<210> SEQ ID NO 31
<211> LENGTH: 27
<212> TYPE: DNA
<213> ORGANISM: Artificial Sequence
<220> FEATURE:
<223> OTHER INFORMATION: GCA7 CDRL2 long nuc varC1

<400> SEQUENCE: 31
ctgatctact gggcctcaac ccgagag 27

<210> SEQ ID NO 32
<211> LENGTH: 27
<212> TYPE: DNA
<213> ORGANISM: Artificial Sequence
<220> FEATURE:
<223> OTHER INFORMATION: GCA7 CDRL3 nuc varS1

<400> SEQUENCE: 32
cagcaatatt atagtacccc tttcact 27

<210> SEQ ID NO 33
<211> LENGTH: 27
<212> TYPE: DNA
<213> ORGANISM: Artificial Sequence
<220> FEATURE:
<223> OTHER INFORMATION: GCA7 CDRL3 nuc varS2

<400> SEQUENCE: 33
cagcagtatt attctacccc cttcaca 27

<210> SEQ ID NO 34
<211> LENGTH: 27
<212> TYPE: DNA
<213> ORGANISM: Artificial Sequence
<220> FEATURE:
<223> OTHER INFORMATION: GCA7 CDRL3 nuc varN1

<400> SEQUENCE: 34
cagcagtatt acagcacccc attcaca 27

<210> SEQ ID NO 35
<211> LENGTH: 27
<212> TYPE: DNA
<213> ORGANISM: Artificial Sequence
<220> FEATURE:
<223> OTHER INFORMATION: GCA7 CDRL3 nuc varC1

<400> SEQUENCE: 35
cagcagtact atagcactcc attcacc 27

<210> SEQ ID NO 36

<211> LENGTH: 27
<212> TYPE: DNA
<213> ORGANISM: Artificial Sequence
<220> FEATURE:
<223> OTHER INFORMATION: GCA7 CDRL3 nuc varC2

<400> SEQUENCE: 36
cagcagtatt attcaacacc cttcaca 27

<210> SEQ ID NO 37
<211> LENGTH: 122
<212> TYPE: PRT
<213> ORGANISM: Artificial Sequence
<220> FEATURE:
<223> OTHER INFORMATION: GCA7 heavy chain variable domain (VH) aa

<400> SEQUENCE: 37

```
Gly Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Ser Thr Asn
            20                  25                  30

Tyr Met Ser Trp Val Arg Gln Ala Pro Gly Lys Gly Leu Glu Trp Val
        35                  40                  45

Ser Ile Leu Tyr Ala Gly Gly Val Thr Arg Tyr Ala Asp Ser Val Lys
    50                  55                  60

Thr Arg Phe Thr Ile Ser Arg Asp Asn Ser Lys Asn Thr Leu Phe Leu
65                  70                  75                  80

Gln Met Asn Ala Leu Ser Ala Glu Asp Thr Ala Ile Tyr Tyr Cys Ala
                85                  90                  95

Lys His Tyr Asp Ser Gly Tyr Ser Thr Ile Asp His Phe Asp Ser Trp
            100                 105                 110

Gly Gln Gly Thr Leu Val Thr Val Ser Ser
        115                 120
```

<210> SEQ ID NO 38
<211> LENGTH: 113
<212> TYPE: PRT
<213> ORGANISM: Artificial Sequence
<220> FEATURE:
<223> OTHER INFORMATION: GCA7 light chain variable domain (VL) aa

<400> SEQUENCE: 38

```
Asp Ile Gln Met Thr Gln Ser Pro Asp Ser Val Ala Val Ser Leu Gly
1               5                   10                  15

Glu Arg Ala Thr Ile Asn Cys Lys Ser Ser Gln Ser Val Phe Tyr Thr
            20                  25                  30

Ser Lys Asn Lys Asn Tyr Leu Ala Trp Phe Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Arg Pro Glu Asp Val Ala Val Tyr Tyr Cys Gln Gln
                85                  90                  95

Tyr Tyr Ser Thr Pro Phe Thr Phe Gly Pro Gly Thr Lys Val Asp Ile
            100                 105                 110

Lys
```

<210> SEQ ID NO 39

-continued

<211> LENGTH: 366
<212> TYPE: DNA
<213> ORGANISM: Artificial Sequence
<220> FEATURE:
<223> OTHER INFORMATION: GCA7 heavy chain variable domain (VH) nuc varS1

<400> SEQUENCE: 39
ggggtgcaac tggtgcagtc tgggggaggc ttggtccagc cggggggggtc cctgagactc 60 tcctgtgcag cctctggatt caccgtcagt accaactaca tgagctgggt ccgccaggct 120
ccagggaagg ggctggagtg ggtctcaatt ctttatgccg gaggtgtcac aaggtacgca 180
gactccgtga agaccagatt caccatctcc agagacaatt ccaagaacac tctctttctt 240
caaatgaacg ccctgagcgc cgaggacacg gctatatatt actgtgcgaa acactatgat 300
tcgggatatt ctaccataga tcactttgac tcctggggcc agggaaccct ggtcaccgtc 360
tcctca 366

<210> SEQ ID NO 40
<211> LENGTH: 366
<212> TYPE: DNA
<213> ORGANISM: Artificial Sequence
<220> FEATURE:
<223> OTHER INFORMATION: GCA7 heavy chain variable domain (VH) nuc varS2

<400> SEQUENCE: 40
ggcgtgcagc tggtgcagag cggcggcggc ctggtgcagc ctggagggtc actgagactg 60
tcatgcgcag caagcgggtt tactgtgtct acaaactaca tgtcttgggt gaggcaggca 120
cctggaaagg gactggagtg ggtctcaatc ctgtacgctg gcggggtgac ccggtatgca 180
gacagcgtca agacccggtt cacaattagc agagataact ccaaaaatac tctgtttctg 240
cagatgaatg ccctgtccgc tgaagacacc gcaatctact attgcgccaa acactatgat 300
agtgggtact ccactattga ccattttgac tcttgggggc aggggactct ggtgactgtc 360
tcttca 366

<210> SEQ ID NO 41
<211> LENGTH: 366
<212> TYPE: DNA
<213> ORGANISM: Artificial Sequence
<220> FEATURE:
<223> OTHER INFORMATION: GCA7 heavy chain variable domain (VH) nuc varN1

<400> SEQUENCE: 41
ggcgtccagc tggtgcagag cggagggggc ctggtgcagc ctggcgggtc cctgagactg 60
agttgtgccg caagtggctt tactgtctct acaaactaca tgtcttgggt gaggcaggca 120
cctggaaagg gactggagtg ggtctcaatc ctgtacgctg gcggggtgac ccggtatgca 180
gacagcgtca agacccggtt cacaattagc agagataact ccaaaaatac tctgtttctg 240
cagatgaatg ccctgtccgc tgaagacacc gcaatctact attgcgccaa acactatgat 300
agtgggtata gcacaatcga ccattttgac agctggggac agggaactct ggtgacagtc 360
tcatca 366

<210> SEQ ID NO 42
<211> LENGTH: 366
<212> TYPE: DNA
<213> ORGANISM: Artificial Sequence
<220> FEATURE:
<223> OTHER INFORMATION: GCA7 heavy chain variable domain (VH) nuc varC1

<400> SEQUENCE: 42

```
ggagtgcagc tggtccagag cggaggagga ctggtgcagc caggagggtc actgaggctg     60

agctgcgcag cttccggctt caccgtgtca acaaactaca tgagctgggt ccgccaggca    120

cctgggaagg gactggagtg ggtgtccatc ctgtacgccg gaggcgtgac tcgatatgct    180

gactctgtca agactcggtt caccatctct agagataaca gtaagaacac cctgtttctg    240

cagatgaatg cactgagtgc cgaagacaca gctatctact attgtgcaaa acactacgat    300

tctgggtata gtacaattga ccattttgat tcttggggcc aggggacact ggtgactgtc    360

agctcc                                                               366


<210> SEQ ID NO 43
<211> LENGTH: 366
<212> TYPE: DNA
<213> ORGANISM: Artificial Sequence
<220> FEATURE:
<223> OTHER INFORMATION: GCA7 heavy chain variable domain (VH) nuc varC2

<400> SEQUENCE: 43

ggcgtgcagc tggtccagag cggaggcgga ctggtccagc ccggcggatc actgagactg     60

tcatgtgccg caagcgggtt taccgtctct acaaactaca tgtcttgggt gaggcaggca    120

cctggaaagg gactggagtg ggtctcaatc ctgtacgctg gcggggtgac ccggtatgca    180

gacagcgtca agacccggtt cacaattagc agagataact ccaaaaatac tctgtttctg    240

cagatgaatg ccctgtccgc tgaagacacc gcaatctact attgcgccaa acactatgat    300

agtgggtaca gtaccattga ccatttcgat agctgggggc aggggactct ggtgaccgtc    360

tcatca                                                               366


<210> SEQ ID NO 44
<211> LENGTH: 339
<212> TYPE: DNA
<213> ORGANISM: Artificial Sequence
<220> FEATURE:
<223> OTHER INFORMATION: GCA7 light chain variable domain (VL) nuc varS1

<400> SEQUENCE: 44

gacatccaga tgacccagtc tccagactcc gtggctgtgt ctctgggcga gagggccacc     60

atcaactgca agtccagcca gagtgttttc tacacctcca aaaataaaaa ctacttagct    120

tggttccagc agaaaccagg acagcctcct aaactgctca tttactgggc atctacccgg    180

gagtccgggg tccctgaccg attcagtggc agcgggtctg ggacagattt cactctcacc    240

atcagcagcc tgcggcctga agatgtggca gtttattact gtcagcaata ttatagtacc    300

cctttcactt tcggccctgg gaccaaagtg gatatcaaa                           339


<210> SEQ ID NO 45
<211> LENGTH: 339
<212> TYPE: DNA
<213> ORGANISM: Artificial Sequence
<220> FEATURE:
<223> OTHER INFORMATION: GCA7 light chain variable domain (VL) nuc varS2

<400> SEQUENCE: 45

gacattcaga tgacccagag tcctgacagc gtggccgtct cactggggga aagggctact     60

atcaattgta aaagttcaca gtccgtcttc tacaccagta agaacaaaaa ctatctggcc    120

tggtttcagc agaagccagg ccagcccccct aaactgctga tctactgggc tagcactaga    180

gagtctggag tgccagacag attctctggc agtgggtcag gaaccgactt caccctgaca    240
```

attagctccc tgaggcccga agacgtggcc gtctattatt gtcagcagta ttattctacc 300
cccttcacat tcggacctgg gactaaagtg gatatcaaa 339

<210> SEQ ID NO 46
<211> LENGTH: 339
<212> TYPE: DNA
<213> ORGANISM: Artificial Sequence
<220> FEATURE:
<223> OTHER INFORMATION: GCA7 light chain variable domain (VL) nuc varN1

<400> SEQUENCE: 46
gacattcaga tgacccagag tcctgattcc gtggctgtct cactggggga gcgagcaact 60
attaactgca agtcttcaca gagcgtgttc tacaccagta agaacaaaaa ctatctggcc 120
tggtttcagc agaagccagg ccagccccct aaactgctga tctactgggc tagcactaga 180
gagtctggag tgccagacag attctctggc agtgggtcag gaaccgactt caccctgaca 240
attagctccc tgaggcccga agacgtggcc gtctactatt gtcagcagta ttacagcacc 300
ccattcacat tcggccctgg aaccaaagtg gatattaag 339

<210> SEQ ID NO 47
<211> LENGTH: 339
<212> TYPE: DNA
<213> ORGANISM: Artificial Sequence
<220> FEATURE:
<223> OTHER INFORMATION: GCA7 light chain variable domain (VL) nuc varC1

<400> SEQUENCE: 47
gacatccaga tgactcagtc tcccgatagt gtggccgtct ccctggggga gagggctaca 60
attaactgca agagctccca gtccgtgttc tacacttcta agaacaaaaa ctatctggca 120
tggtttcagc agaagcctgg acagccccct aaactgctga tctactgggc ctcaacccga 180
gagagcggag tcccagacag attctcaggc agcgggtccg gaacagattt taccctgaca 240
atttctagtc tgcggcctga agacgtggct gtctactatt gtcagcagta ctatagcact 300
ccattcacct ttggccccgg gacaaaggtg gatatcaaa 339

<210> SEQ ID NO 48
<211> LENGTH: 339
<212> TYPE: DNA
<213> ORGANISM: Artificial Sequence
<220> FEATURE:
<223> OTHER INFORMATION: GCA7 light chain variable domain (VL) nuc varC2

<400> SEQUENCE: 48
gatattcaga tgacccagag tcctgattcc gtcgctgtct cactgggaga aagggcaacc 60
attaactgta aaagctcaca gagtgtcttc tacaccagta agaacaaaaa ctatctggcc 120
tggtttcagc agaagccagg ccagccccct aaactgctga tctactgggc tagcactaga 180
gagtctggag tgccagacag attctctggc agtgggtcag gaaccgactt caccctgaca 240
attagctccc tgaggcccga agacgtggcc gtctactatt gtcagcagta ttattcaaca 300
cccttcacat tcggaccagg aacaaaagtg gatattaag 339

<210> SEQ ID NO 49
<211> LENGTH: 8
<212> TYPE: PRT
<213> ORGANISM: Artificial Sequence
<220> FEATURE:
<223> OTHER INFORMATION: GCA21 CDRH1 aa

<400> SEQUENCE: 49

```
Gly Phe Thr Phe Ser Asn Tyr Pro
1               5


<210> SEQ ID NO 50
<211> LENGTH: 8
<212> TYPE: PRT
<213> ORGANISM: Artificial Sequence
<220> FEATURE:
<223> OTHER INFORMATION: GCA21 CDRH2 aa

<400> SEQUENCE: 50

Ile Leu Pro Asp Gly Asn Arg Lys
1               5


<210> SEQ ID NO 51
<211> LENGTH: 22
<212> TYPE: PRT
<213> ORGANISM: Artificial Sequence
<220> FEATURE:
<223> OTHER INFORMATION: GCA21 CDRH3 aa

<400> SEQUENCE: 51

Thr Arg Asp Gly Thr Tyr Tyr Ser Asn Gly Gly Val Tyr Gln Thr Tyr
1               5                   10                  15

Arg Arg Phe Phe Asp Phe
            20


<210> SEQ ID NO 52
<211> LENGTH: 6
<212> TYPE: PRT
<213> ORGANISM: Artificial Sequence
<220> FEATURE:
<223> OTHER INFORMATION: GCA21 CDRL1 aa

<400> SEQUENCE: 52

Gln Asn Ile Leu Asn Trp
1               5


<210> SEQ ID NO 53

<400> SEQUENCE: 53

000


<210> SEQ ID NO 54
<211> LENGTH: 9
<212> TYPE: PRT
<213> ORGANISM: Artificial Sequence
<220> FEATURE:
<223> OTHER INFORMATION: GCA21 CDRL2 long aa

<400> SEQUENCE: 54

Leu Ile Tyr Lys Ala Ser Asp Leu Gln
1               5


<210> SEQ ID NO 55
<211> LENGTH: 9
<212> TYPE: PRT
<213> ORGANISM: Artificial Sequence
<220> FEATURE:
<223> OTHER INFORMATION: GCA21 CDRL3 aa

<400> SEQUENCE: 55

Gln His Tyr Asn Ser Tyr Pro Leu Thr
1               5
```

<210> SEQ ID NO 56
<211> LENGTH: 24
<212> TYPE: DNA
<213> ORGANISM: Artificial Sequence
<220> FEATURE:
<223> OTHER INFORMATION: GCA21 CDRH1 nuc

<400> SEQUENCE: 56
ggattcacct tttcgaacta tcct 24

<210> SEQ ID NO 57
<211> LENGTH: 24
<212> TYPE: DNA
<213> ORGANISM: Artificial Sequence
<220> FEATURE:
<223> OTHER INFORMATION: GCA21 CDRH2 nuc

<400> SEQUENCE: 57
attttacctg atgggaacag aaaa 24

<210> SEQ ID NO 58
<211> LENGTH: 66
<212> TYPE: DNA
<213> ORGANISM: Artificial Sequence
<220> FEATURE:
<223> OTHER INFORMATION: GCA21 CDRH3 nuc

<400> SEQUENCE: 58
acgagagatg gcacgtatta ctctaatggt ggtgtttatc agacatatcg aaggttcttc 60
gatttc 66

<210> SEQ ID NO 59
<211> LENGTH: 18
<212> TYPE: DNA
<213> ORGANISM: Artificial Sequence
<220> FEATURE:
<223> OTHER INFORMATION: GCA21 CDRL1 nuc

<400> SEQUENCE: 59
cagaatatcc ttaattgg 18

<210> SEQ ID NO 60

<400> SEQUENCE: 60

000

<210> SEQ ID NO 61
<211> LENGTH: 27
<212> TYPE: DNA
<213> ORGANISM: Artificial Sequence
<220> FEATURE:
<223> OTHER INFORMATION: GCA21 CDRL2 long nuc

<400> SEQUENCE: 61
ctgatatata aggcgtctga tttacaa 27

<210> SEQ ID NO 62
<211> LENGTH: 27
<212> TYPE: DNA
<213> ORGANISM: Artificial Sequence
<220> FEATURE:
<223> OTHER INFORMATION: GCA21 CDRL3 nuc

<400> SEQUENCE: 62
cagcattata atagttatcc tctcact 27

<210> SEQ ID NO 63
<211> LENGTH: 129
<212> TYPE: PRT
<213> ORGANISM: Artificial Sequence
<220> FEATURE:
<223> OTHER INFORMATION: GCA21 heavy chain variable domain (VH) aa

<400> SEQUENCE: 63

```
Gln Val Gln Leu Met Glu Ser Gly Gly Gly Val Val Gln Pro Gly Arg
1               5                   10                  15

Ser Leu Arg Leu Ser Cys Ser Ala Phe Gly Phe Thr Phe Ser Asn Tyr
            20                  25                  30

Pro Met His Trp Val Arg Gln Ala Pro Gly Lys Gly Leu Glu Trp Val
        35                  40                  45

Ala Ile Ile Leu Pro Asp Gly Asn Arg Lys Asn Tyr Gly Arg Ser Val
    50                  55                  60

Thr Gly Arg Phe Thr Ile Ser Arg Asp Asn Ser Asn Asn Ser Leu Tyr
65                  70                  75                  80

Leu Gln Met Asn Asn Leu Thr Thr Glu Asp Thr Ala Met Tyr Tyr Cys
                85                  90                  95

Thr Arg Asp Gly Thr Tyr Tyr Ser Asn Gly Gly Val Tyr Gln Thr Tyr
            100                 105                 110

Arg Arg Phe Phe Asp Phe Trp Gly Arg Gly Thr Leu Val Thr Val Ser
        115                 120                 125

Ser
```

<210> SEQ ID NO 64
<211> LENGTH: 107
<212> TYPE: PRT
<213> ORGANISM: Artificial Sequence
<220> FEATURE:
<223> OTHER INFORMATION: GCA21 light chain variable domain (VL) aa

<400> SEQUENCE: 64

```
Asp Ile Gln Met Thr Gln Ser Pro Ser Thr Leu Ser Thr Ser Val Gly
1               5                   10                  15

Asp Arg Val Thr Ile Thr Cys Arg Ala Ser Gln Asn Ile Leu Asn Trp
            20                  25                  30

Leu Ala Trp Tyr Gln Gln Lys Pro Gly Asn Ala Pro Asn Leu Leu Ile
        35                  40                  45

Tyr Lys Ala Ser Asp Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Asn Ser Tyr Pro Leu
                85                  90                  95

Thr Phe Gly Gly Gly Thr Lys Val Glu Ile Lys
            100                 105
```

<210> SEQ ID NO 65
<211> LENGTH: 387
<212> TYPE: DNA
<213> ORGANISM: Artificial Sequence
<220> FEATURE:
<223> OTHER INFORMATION: GCA21 heavy chain variable domain (VH) nuc

<400> SEQUENCE: 65

```
caggtgcaat tgatggagtc tgggggaggc gtggtccagc ctgggaggtc cctgcgactc     60

tcatgcagtg cctttggatt caccttttcg aactatccta tgcactgggt ccgccaggct    120

ccaggcaagg gacttgagtg ggtggctatc attttacctg atgggaacag aaaaaactat    180

ggaaggtccg tgacgggccg attcaccatc tccagagaca attccaacaa cagcctttat    240

ttgcaaatga acaacctgac gactgaggac acggctatgt actattgtac gagagatggc    300

acgtattact ctaatggtgg tgtttatcag acatatcgaa ggttcttcga tttctggggc    360

cgtggcaccc tggtcaccgt ctcctca                                        387
```

<210> SEQ ID NO 66
<211> LENGTH: 321
<212> TYPE: DNA
<213> ORGANISM: Artificial Sequence
<220> FEATURE:
<223> OTHER INFORMATION: GCA21 light chain variable domain (VL) nuc

<400> SEQUENCE: 66

```
gacatccaga tgacccagtc tccttccacc ctgtctacat ctgtgggaga cagagtcacc     60

atcacttgcc gggccagtca gaatatcctt aattggttgg cctggtatca acagaaacca    120

gggaacgccc ctaacctcct gatatataag gcgtctgatt tacaaagtgg ggtcccctca    180

agattcagcg gcagtgggtc tgggacagaa ttcactctca ccatcagcag cctgcagcct    240

gatgattttg caacttatta ctgccagcat tataatagtt atcctctcac tttcggcgga    300

gggaccaagg tggaaatcaa a                                              321
```

<210> SEQ ID NO 67
<211> LENGTH: 8
<212> TYPE: PRT
<213> ORGANISM: Artificial Sequence
<220> FEATURE:
<223> OTHER INFORMATION: GCB59 CDRH1 aa

<400> SEQUENCE: 67

```
Gly Leu Ser Phe Ser Ser Ser Gly
1               5
```

<210> SEQ ID NO 68
<211> LENGTH: 8
<212> TYPE: PRT
<213> ORGANISM: Artificial Sequence
<220> FEATURE:
<223> OTHER INFORMATION: GCB59 CDRH2 aa

<400> SEQUENCE: 68

```
Ile Ser Gly Ser Gln Asn Tyr Lys
1               5
```

<210> SEQ ID NO 69
<211> LENGTH: 18
<212> TYPE: PRT
<213> ORGANISM: Artificial Sequence
<220> FEATURE:
<223> OTHER INFORMATION: GCB59 CDRH3 aa

<400> SEQUENCE: 69

```
Val Gly Gly Phe Pro Tyr Trp Leu Pro Pro Ser Asp Phe Ser Gly Phe
1               5                   10                  15

His Val
```

<210> SEQ ID NO 70

<211> LENGTH: 6
<212> TYPE: PRT
<213> ORGANISM: Artificial Sequence
<220> FEATURE:
<223> OTHER INFORMATION: GCB59 CDRL1 aa

<400> SEQUENCE: 70

Asn Ile Gly Ser Lys Ser
1 5

<210> SEQ ID NO 71

<400> SEQUENCE: 71

000

<210> SEQ ID NO 72
<211> LENGTH: 9
<212> TYPE: PRT
<213> ORGANISM: Artificial Sequence
<220> FEATURE:
<223> OTHER INFORMATION: GCB59 CDRL2 long aa

<400> SEQUENCE: 72

Val Val Tyr Ala Asp Asn Asp Arg Pro
1 5

<210> SEQ ID NO 73
<211> LENGTH: 11
<212> TYPE: PRT
<213> ORGANISM: Artificial Sequence
<220> FEATURE:
<223> OTHER INFORMATION: GCB59 CDRL3 aa

<400> SEQUENCE: 73

Gln Val Trp Asp Gly Asn Thr Asp His Val Val
1 5 10

<210> SEQ ID NO 74
<211> LENGTH: 24
<212> TYPE: DNA
<213> ORGANISM: Artificial Sequence
<220> FEATURE:
<223> OTHER INFORMATION: GCB59 CDRH1 nuc varS1

<400> SEQUENCE: 74
ggattgtcct tcagtagttc aggc 24

<210> SEQ ID NO 75
<211> LENGTH: 24
<212> TYPE: DNA
<213> ORGANISM: Artificial Sequence
<220> FEATURE:
<223> OTHER INFORMATION: GCB59 CDRH1 nuc varN1/N2

<400> SEQUENCE: 75
ggcctgtcct tcagctcctc tggc 24

<210> SEQ ID NO 76
<211> LENGTH: 24
<212> TYPE: DNA
<213> ORGANISM: Artificial Sequence
<220> FEATURE:
<223> OTHER INFORMATION: GCB59 CDRH1 nuc varC1

<400> SEQUENCE: 76
gggctgagct tcagctcctc tgga 24

<210> SEQ ID NO 77
<211> LENGTH: 24
<212> TYPE: DNA
<213> ORGANISM: Artificial Sequence
<220> FEATURE:
<223> OTHER INFORMATION: GCB59 CDRH2 nuc var S1

<400> SEQUENCE: 77
attagtggta gtcagaacta caaa 24

<210> SEQ ID NO 78
<211> LENGTH: 24
<212> TYPE: DNA
<213> ORGANISM: Artificial Sequence
<220> FEATURE:
<223> OTHER INFORMATION: GCB59 CDRH2 nuc varN1/N2

<400> SEQUENCE: 78
attagcgggt cccagaatta caag 24

<210> SEQ ID NO 79
<211> LENGTH: 24
<212> TYPE: DNA
<213> ORGANISM: Artificial Sequence
<220> FEATURE:
<223> OTHER INFORMATION: GCB59 CDRH2 nuc varC1

<400> SEQUENCE: 79
atttctggca gtcagaatta caag 24

<210> SEQ ID NO 80
<211> LENGTH: 54
<212> TYPE: DNA
<213> ORGANISM: Artificial Sequence
<220> FEATURE:
<223> OTHER INFORMATION: GCB59 CDRH3 nuc varS1

<400> SEQUENCE: 80
gtgggaggtt tcccctattg gttacccccg agcgacttct ccggtttcca tgtc 54

<210> SEQ ID NO 81
<211> LENGTH: 54
<212> TYPE: DNA
<213> ORGANISM: Artificial Sequence
<220> FEATURE:
<223> OTHER INFORMATION: GCB59 CDRH3 nuc varN1/N2

<400> SEQUENCE: 81
gtcggcgggt ttccctattg gctgcctcca agcgactttt cagggtttca tgtc 54

<210> SEQ ID NO 82
<211> LENGTH: 54
<212> TYPE: DNA
<213> ORGANISM: Artificial Sequence
<220> FEATURE:
<223> OTHER INFORMATION: GCB59 CDRH3 nuc varC1

<400> SEQUENCE: 82
gtcgggggat ttccctattg gctgccccct tccgatttct ctggctttca cgtg 54

<210> SEQ ID NO 83
<211> LENGTH: 18
<212> TYPE: DNA
<213> ORGANISM: Artificial Sequence
<220> FEATURE:

<223> OTHER INFORMATION: GCB59 CDRL1 nuc varS1

<400> SEQUENCE: 83
aacattggaa gtaaaagt 18

<210> SEQ ID NO 84
<211> LENGTH: 18
<212> TYPE: DNA
<213> ORGANISM: Artificial Sequence
<220> FEATURE:
<223> OTHER INFORMATION: GCB59 CDRL1 nuc varN1/N2

<400> SEQUENCE: 84
aacatcggca gcaagagc 18

<210> SEQ ID NO 85
<211> LENGTH: 18
<212> TYPE: DNA
<213> ORGANISM: Artificial Sequence
<220> FEATURE:
<223> OTHER INFORMATION: GCB59 CDRL1 nuc varC1

<400> SEQUENCE: 85
aacatcgggt ctaagagt 18

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89
<211> LENGTH: 27
<212> TYPE: DNA
<213> ORGANISM: Artificial Sequence
<220> FEATURE:
<223> OTHER INFORMATION: GCB59 CDRL2 long nuc varS1

<400> SEQUENCE: 89
gtcgtctatg ctgataacga caggccc 27

<210> SEQ ID NO 90
<211> LENGTH: 27
<212> TYPE: DNA
<213> ORGANISM: Artificial Sequence
<220> FEATURE:
<223> OTHER INFORMATION: GCB59 CDRL2 long nuc varN1/N2

<400> SEQUENCE: 90
gtggtctatg ctgacaacga tcggccc 27

<210> SEQ ID NO 91
<211> LENGTH: 27
<212> TYPE: DNA

<213> ORGANISM: Artificial Sequence
<220> FEATURE:
<223> OTHER INFORMATION: GCB59 CDRL2 long nuc varC1

<400> SEQUENCE: 91
gtggtctatg ccgacaatga tcggcca 27

<210> SEQ ID NO 92
<211> LENGTH: 33
<212> TYPE: DNA
<213> ORGANISM: Artificial Sequence
<220> FEATURE:
<223> OTHER INFORMATION: GCB59 CDRL3 nuc var S1

<400> SEQUENCE: 92
caggtgtggg atggtaatac tgatcatgtg gtc 33

<210> SEQ ID NO 93
<211> LENGTH: 33
<212> TYPE: DNA
<213> ORGANISM: Artificial Sequence
<220> FEATURE:
<223> OTHER INFORMATION: GCB59 CDRL3 nuc var N1/N2

<400> SEQUENCE: 93
caggtctggg atgggaatac tgaccacgtc gtc 33

<210> SEQ ID NO 94
<211> LENGTH: 33
<212> TYPE: DNA
<213> ORGANISM: Artificial Sequence
<220> FEATURE:
<223> OTHER INFORMATION: GCB59 CDRL3 nuc varC1

<400> SEQUENCE: 94
caggtctggg acgggaacac agatcatgtg gtc 33

<210> SEQ ID NO 95
<211> LENGTH: 125
<212> TYPE: PRT
<213> ORGANISM: Artificial Sequence
<220> FEATURE:
<223> OTHER INFORMATION: GCB59 heavy chain variable domain (VH) aa

<400> SEQUENCE: 95

```
Glu Val Gln Leu Val Glu Ser Gly Gly Asp Leu Val Lys Ala Gly Gly
1               5                   10                  15

Ser Leu Arg Leu Ser Cys Ala Val Ser Gly Leu Ser Phe Ser Ser Ser
            20                  25                  30

Gly Met Asn Trp Val Arg Gln Ala Pro Gly Lys Gly Leu Glu Trp Ile
        35                  40                  45

Ser Ser Ile Ser Gly Ser Gln Asn Tyr Lys Tyr Tyr Ala Asp Ser Val
    50                  55                  60

Lys Gly Arg Phe Val Val Ser Arg Asp Asn Ala Arg Asn Phe Leu Tyr
65                  70                  75                  80

Leu Gln Met Asp Ser Leu Arg Ala Glu Asp Thr Ala Val Tyr Phe Cys
                85                  90                  95

Val Gly Gly Phe Pro Tyr Trp Leu Pro Pro Ser Asp Phe Ser Gly Phe
            100                 105                 110

His Val Trp Gly Gln Gly Thr Thr Val Thr Val Ser Ser
        115                 120                 125
```

<210> SEQ ID NO 96
<211> LENGTH: 108
<212> TYPE: PRT
<213> ORGANISM: Artificial Sequence
<220> FEATURE:
<223> OTHER INFORMATION: GCB59 light chain variable domain (VL) aa

<400> SEQUENCE: 96

```
Ser Tyr Val Leu Thr Gln Pro Pro Ser Val Ser Val Ala Pro Gly Gln
1               5                   10                  15

Thr Ala Ser Leu Thr Cys Gly Gly Thr Asn Ile Gly Ser Lys Ser Val
            20                  25                  30

His Trp Tyr Gln Gln Lys Ala Gly Gln Ala Pro Val Leu Val Val Tyr
        35                  40                  45

Ala Asp Asn Asp Arg Pro Ser Gly Val Pro Glu Arg Phe Ser Gly Ser
    50                  55                  60

Asn Ser Gly Asn Thr Ala Thr Leu Thr Ile Ser Arg Val Glu Ala Glu
65                  70                  75                  80

Asp Glu Ser Asp Tyr Phe Cys Gln Val Trp Asp Gly Asn Thr Asp His
                85                  90                  95

Val Val Phe Gly Gly Gly Thr Lys Leu Thr Val Leu
            100                 105
```

<210> SEQ ID NO 97
<211> LENGTH: 375
<212> TYPE: DNA
<213> ORGANISM: Artificial Sequence
<220> FEATURE:
<223> OTHER INFORMATION: GCB59 heavy chain variable domain (VH) nuc varS1

<400> SEQUENCE: 97

```
gaggtacaat tggtggagtc tgggggagac ctggtcaagg cgggggggtc cctgagactc     60

tcctgtgccg tctctggatt gtccttcagt agttcaggca tgaattgggt ccgccaggct    120

ccagggaagg ggctggagtg gatctcatcg attagtggta gtcagaacta caaatactat    180

gcagactcag tgaagggccg attcgtcgtc tccagagaca acgcccgcaa ctttctatat    240

ctgcaaatgg acagcctgag ggccgaggat acggctgtgt atttttgtgt gggaggtttc    300

ccctattggt tacccccgag cgacttctcc ggtttccatg tctggggcca agggaccacg    360

gtcaccgtct cctca                                                     375
```

<210> SEQ ID NO 98
<211> LENGTH: 375
<212> TYPE: DNA
<213> ORGANISM: Artificial Sequence
<220> FEATURE:
<223> OTHER INFORMATION: GCB59 heavy chain variable domain (VH) nuc var N1

<400> SEQUENCE: 98

```
gaggtgcagc tggtggaaag cggaggggat ctggtgaaag caggagggag cctgagactg     60

tcatgcgccg tgagcgggct gtcattcagc tcctctggca tgaactgggt gcgacaggct    120

cctggaaagg gactggagtg gatcagttca attagcgggt cccagaatta caagtactat    180

gcagactctg tcaaaggaag gttcgtggtc agccgggata acgccagaaa ttttctgtat    240

ctgcagatgg acagcctgcg cgccgaagat accgccgtgt acttctgcgt cggcgggttt    300

ccctattggc tgcctccaag cgatttcagc ggatttcatg tctgggggca gggaactaca    360

gtgaccgtct catca                                                     375
```

<210> SEQ ID NO 99
<211> LENGTH: 375
<212> TYPE: DNA
<213> ORGANISM: Artificial Sequence
<220> FEATURE:
<223> OTHER INFORMATION: GCB59 heavy chain variable domain (VH) nuc var
N2

<400> SEQUENCE: 99
gaggtgcagc tggtggaaag tgggggcgat ctggtcaaag ccggagggtc tctgcgactg 60
tcttgtgctg tgagcggcct gtccttcagc tcctctggca tgaactgggt gcgacaggct 120
cctggaaagg gactggagtg gatcagttca attagcgggt cccagaatta caagtactat 180
gcagactctg tcaaaggaag gttcgtggtc agccgggata acgccagaaa ttttctgtat 240
ctgcagatgg acagcctgcg cgccgaagat accgccgtgt acttctgcgt cggcgggttt 300
ccctattggc tgcctccaag cgacttttca gggtttcatg tctgggggca gggaactacc 360
gtgaccgtct catct 375

<210> SEQ ID NO 100
<211> LENGTH: 375
<212> TYPE: DNA
<213> ORGANISM: Artificial Sequence
<220> FEATURE:
<223> OTHER INFORMATION: GCB59 heavy chain variable domain (VH) nuc
varC1

<400> SEQUENCE: 100
gaggtgcagc tggtcgaatc tggcggggac ctggtgaagg caggaggcag tctgaggctg 60
tcatgcgccg tctcagggct gagcttcagc tcctctggaa tgaactgggt gcgccaggca 120
ccaggcaaag gactggagtg gatcagttca atttctggca gtcagaatta caagtactat 180
gctgacagtg tgaaagggcg attcgtggtc tcccgggata acgcaagaaa ttttctgtat 240
ctgcagatgg acagcctgag agccgaagat actgctgtgt acttctgtgt cgggggattt 300
ccctattggc tgccccccttc cgatttctct ggctttcacg tgtggggaca gggcaccaca 360
gtgaccgtca gctcc 375

<210> SEQ ID NO 101
<211> LENGTH: 324
<212> TYPE: DNA
<213> ORGANISM: Artificial Sequence
<220> FEATURE:
<223> OTHER INFORMATION: GCB59 light chain variable domain (VL) nuc
varS1

<400> SEQUENCE: 101
tcatatgtgc tgactcaacc accctcggtg tcagtggccc caggacagac ggccagtcta 60
acctgtgggg gaactaacat tggaagtaaa agtgttcatt ggtaccagca aaaggcaggc 120
caggcccctg tgttggtcgt ctatgctgat aacgacaggc cctcaggggt ccctgagcga 180
ttctctggct ccaactctgg gaacacggcc accctgacca tcagcagggt cgaggccgag 240
gatgagtccg actatttctg tcaggtgtgg gatggtaata ctgatcatgt ggtcttcggc 300
ggagggacca agctgaccgt cctg 324

<210> SEQ ID NO 102
<211> LENGTH: 324
<212> TYPE: DNA
<213> ORGANISM: Artificial Sequence
<220> FEATURE:
<223> OTHER INFORMATION: GCB59 light chain variable domain (VL) nuc var N1

<400> SEQUENCE: 102

```
tcttacgtcc tgacccagcc acctagcgtg agcgtcgcac cagggcagac agcttcactg     60

acttgcggag gcacaaacat tggcagcaag agcgtgcact ggtaccagca gaaagccgga    120

caggctcccg tcctggtggt ctatgctgac aacgatcggc cctctggcgt gcctgaaaga    180

ttcagcggct ccaactctgg gaataccgca acactgacca tcagtagggt cgaggccgaa    240

gacgagtcag attacttttg ccaggtgtgg gacggcaata ctgaccatgt cgtgttcggc    300

ggcgggacca aactgactgt gctg                                           324
```

<210> SEQ ID NO 103
<211> LENGTH: 324
<212> TYPE: DNA
<213> ORGANISM: Artificial Sequence
<220> FEATURE:
<223> OTHER INFORMATION: GCB59 light chain variable domain (VL) nuc var N2

<400> SEQUENCE: 103

```
tcctacgtcc tgactcagcc acctagcgtg tccgtcgcac ctgggcagac agcatcactg     60

acttgcgggg gaaccaacat cggcagcaag agcgtgcact ggtaccagca gaaagccgga    120

caggctcccg tcctggtggt ctatgctgac aacgatcggc cctctggcgt gcctgaaaga    180

ttcagcggct ccaactctgg gaataccgca acactgacca tcagtagggt cgaggccgaa    240

gacgagtcag attacttttg ccaggtctgg gatgggaata ctgaccacgt cgtcttcgga    300

ggcggaacca aactgactgt cctg                                           324
```

<210> SEQ ID NO 104
<211> LENGTH: 324
<212> TYPE: DNA
<213> ORGANISM: Artificial Sequence
<220> FEATURE:
<223> OTHER INFORMATION: GCB59 light chain variable domain (VL) nuc varC1

<400> SEQUENCE: 104

```
tcctacgtgc tgactcagcc acctagcgtg tccgtcgcac ctggacagac tgccagcctg     60

acctgcggag gaacaaacat cgggtctaag agtgtgcact ggtaccagca gaaagccgga    120

caggctcccg tcctggtggt ctatgccgac aatgatcggc catctggcgt gcccgaaaga    180

ttctcaggaa gcaactccgg caataccgct acactgacta tttctagggt ggaggcagaa    240

gacgagagtg attatttctg tcaggtctgg gacgggaaca cagatcatgt ggtctttgga    300

ggcgggacca agctgacagt gctg                                           324
```

<210> SEQ ID NO 105
<211> LENGTH: 8
<212> TYPE: PRT
<213> ORGANISM: Artificial Sequence
<220> FEATURE:
<223> OTHER INFORMATION: GCE536 CDRH1 aa

<400> SEQUENCE: 105

```
Gly Tyr Val Phe Thr Ser Tyr Tyr
1               5
```

<210> SEQ ID NO 106

<211> LENGTH: 8
<212> TYPE: PRT
<213> ORGANISM: Artificial Sequence
<220> FEATURE:
<223> OTHER INFORMATION: GCE536 CDRH2 aa

<400> SEQUENCE: 106

Ile Ser Pro Gly Asp Val Asn Thr
1 5

<210> SEQ ID NO 107
<211> LENGTH: 17
<212> TYPE: PRT
<213> ORGANISM: Artificial Sequence
<220> FEATURE:
<223> OTHER INFORMATION: GCE536 CDRH3 aa

<400> SEQUENCE: 107

Ala Arg Gly Pro Arg Ser Lys Pro Pro Tyr Leu Tyr Phe Ala Leu Asp
1 5 10 15

Val

<210> SEQ ID NO 108
<211> LENGTH: 7
<212> TYPE: PRT
<213> ORGANISM: Artificial Sequence
<220> FEATURE:
<223> OTHER INFORMATION: GCE536 CDRL1 aa

<400> SEQUENCE: 108

Gln Ser Val Ser Ser Ser Leu
1 5

<210> SEQ ID NO 109

<400> SEQUENCE: 109

000

<210> SEQ ID NO 110
<211> LENGTH: 9
<212> TYPE: PRT
<213> ORGANISM: Artificial Sequence
<220> FEATURE:
<223> OTHER INFORMATION: GCE536 CDRL2 long aa

<400> SEQUENCE: 110

Leu Ile Tyr Gly Ala Ser Asn Arg Ala
1 5

<210> SEQ ID NO 111
<211> LENGTH: 8
<212> TYPE: PRT
<213> ORGANISM: Artificial Sequence
<220> FEATURE:
<223> OTHER INFORMATION: GCE536 CDRL3 aa

<400> SEQUENCE: 111

Gln His Tyr Gly Ser Arg Val Thr
1 5

<210> SEQ ID NO 112
<211> LENGTH: 24
<212> TYPE: DNA
<213> ORGANISM: Artificial Sequence
<220> FEATURE:
<223> OTHER INFORMATION: GCE536 CDRH1 nuc varS1

<400> SEQUENCE: 112
ggatacgtgt tcacctctta ctat 24

<210> SEQ ID NO 113
<211> LENGTH: 24
<212> TYPE: DNA
<213> ORGANISM: Artificial Sequence
<220> FEATURE:
<223> OTHER INFORMATION: GCE536 CDRH1 nuc varS2

<400> SEQUENCE: 113
ggatacgtct ttacctctta ctat 24

<210> SEQ ID NO 114
<211> LENGTH: 24
<212> TYPE: DNA
<213> ORGANISM: Artificial Sequence
<220> FEATURE:
<223> OTHER INFORMATION: GCE536 CDRH1 nuc varN1/C1

<400> SEQUENCE: 114
ggatacgtct tcacctctta ctat 24

<210> SEQ ID NO 115
<211> LENGTH: 24
<212> TYPE: DNA
<213> ORGANISM: Artificial Sequence
<220> FEATURE:
<223> OTHER INFORMATION: GCE536 CDRH2 nuc varS1/S2/N1/C1

<400> SEQUENCE: 115
atctctcccg gagacgtgaa cact 24

<210> SEQ ID NO 116
<211> LENGTH: 51
<212> TYPE: DNA
<213> ORGANISM: Artificial Sequence
<220> FEATURE:
<223> OTHER INFORMATION: GCE536 CDRH3 nuc varS1

<400> SEQUENCE: 116
gctagggggc cccgcagcaa gcctccttat ctgtattttg ctctggatgt g 51

<210> SEQ ID NO 117
<211> LENGTH: 51
<212> TYPE: DNA
<213> ORGANISM: Artificial Sequence
<220> FEATURE:
<223> OTHER INFORMATION: GCE536 CDRH3 nuc varS2

<400> SEQUENCE: 117
gctagggggc cccgcagcaa gcctccttat ctgtacttcg ctctggatgt c 51

<210> SEQ ID NO 118
<211> LENGTH: 51
<212> TYPE: DNA
<213> ORGANISM: Artificial Sequence
<220> FEATURE:
<223> OTHER INFORMATION: GCE536 CDRH3 nuc varN1/C1

<400> SEQUENCE: 118
gctagggggc cccgcagcaa gcctccttat ctgtatttcg ctctggatgt c 51

<210> SEQ ID NO 119

<211> LENGTH: 21
<212> TYPE: DNA
<213> ORGANISM: Artificial Sequence
<220> FEATURE:
<223> OTHER INFORMATION: GCE536 CDRL1 nuc varS1

<400> SEQUENCE: 119
cagagtgtca gcagcagcct c 21

<210> SEQ ID NO 120
<211> LENGTH: 21
<212> TYPE: DNA
<213> ORGANISM: Artificial Sequence
<220> FEATURE:
<223> OTHER INFORMATION: GCE536 CDRL1 nuc varS2

<400> SEQUENCE: 120
cagtctgtga gctcctctct g 21

<210> SEQ ID NO 121
<211> LENGTH: 21
<212> TYPE: DNA
<213> ORGANISM: Artificial Sequence
<220> FEATURE:
<223> OTHER INFORMATION: GCE536 CDRL1 nuc varN1/C1

<400> SEQUENCE: 121
cagtccgtga gctcctctct g 21

<210> SEQ ID NO 122

<400> SEQUENCE: 122

000

<210> SEQ ID NO 123

<400> SEQUENCE: 123

000

<210> SEQ ID NO 124
<211> LENGTH: 27
<212> TYPE: DNA
<213> ORGANISM: Artificial Sequence
<220> FEATURE:
<223> OTHER INFORMATION: GCE536 CDRL2 long nuc varS1

<400> SEQUENCE: 124
ctcatctacg gtgcatccaa tagggcc 27

<210> SEQ ID NO 125
<211> LENGTH: 27
<212> TYPE: DNA
<213> ORGANISM: Artificial Sequence
<220> FEATURE:
<223> OTHER INFORMATION: GCE536 CDRL2 long nuc varS2/N1/C1

<400> SEQUENCE: 125
ctgatctatg gcgcctccaa ccgcgct 27

<210> SEQ ID NO 126
<211> LENGTH: 24
<212> TYPE: DNA
<213> ORGANISM: Artificial Sequence
<220> FEATURE:
<223> OTHER INFORMATION: GCE536 CDRL3 nuc varS1

<400> SEQUENCE: 126
cagcactatg gctcacgggt cact 24

<210> SEQ ID NO 127
<211> LENGTH: 24
<212> TYPE: DNA
<213> ORGANISM: Artificial Sequence
<220> FEATURE:
<223> OTHER INFORMATION: GCE536 CDRL3 nuc varS2

<400> SEQUENCE: 127
cagcactatg gcagcagggt cact 24

<210> SEQ ID NO 128
<211> LENGTH: 24
<212> TYPE: DNA
<213> ORGANISM: Artificial Sequence
<220> FEATURE:
<223> OTHER INFORMATION: GCE536 CDRL3 nuc varN1

<400> SEQUENCE: 128
cagcattatg ggtcacgggt cact 24

<210> SEQ ID NO 129
<211> LENGTH: 24
<212> TYPE: DNA
<213> ORGANISM: Artificial Sequence
<220> FEATURE:
<223> OTHER INFORMATION: GCE536 CDRL3 nuc varC1

<400> SEQUENCE: 129
cagcattatg gaagcagggt cacc 24

<210> SEQ ID NO 130
<211> LENGTH: 124
<212> TYPE: PRT
<213> ORGANISM: Artificial Sequence
<220> FEATURE:
<223> OTHER INFORMATION: GCE536 heavy chain variable domain (VH) aa

<400> SEQUENCE: 130

Gln Leu Gln Leu Val Gln Ser Gly Thr Glu Val Lys Lys Pro Gly Ala
1 5 10 15

Ser Val Lys Val Ser Cys Lys Ser Ser Gly Tyr Val Phe Thr Ser Tyr
20 25 30

Tyr Leu Val Trp Val Arg Gln Ala Pro Gly Gln Gly Leu Glu Trp Met
35 40 45

Ala Thr Ile Ser Pro Gly Asp Val Asn Thr Ser Tyr Glu Gln Arg Phe
50 55 60

Gln Gly Arg Val Thr Val Thr Thr Asp Ala Ser Thr Asn Thr Val Asp
65 70 75 80

Met Glu Leu Arg Ser Leu Arg Ser Glu Asp Thr Ala Val Tyr Tyr Cys
85 90 95

Ala Arg Gly Pro Arg Ser Lys Pro Pro Tyr Leu Tyr Phe Ala Leu Asp
100 105 110

Val Trp Gly Gln Gly Thr Ala Val Thr Val Ser Ser
115 120

<210> SEQ ID NO 131
<211> LENGTH: 107
<212> TYPE: PRT

<213> ORGANISM: Artificial Sequence
<220> FEATURE:
<223> OTHER INFORMATION: GCE536 light chain variable domain (VL) aa

<400> SEQUENCE: 131

Glu Ile Val Leu Thr Gln Ser Pro Gly Thr Leu Ser Leu Ser Pro Gly
1 5 10 15

Glu Thr Ala Ile Leu Ser Cys Arg Ala Ser Gln Ser Val Ser Ser Ser
20 25 30

Leu Leu Ala Trp Tyr Gln Gln Lys Pro Gly Gln Ala Pro Arg Leu Leu
35 40 45

Ile Tyr Gly Ala Ser Asn Arg Ala Thr Gly Ile Arg Gly Arg Phe Ser
50 55 60

Gly Ser Gly Ser Gly Thr Asp Phe Thr Leu Thr Ile Ser Arg Leu Glu
65 70 75 80

Pro Glu Asp Phe Val Leu Tyr Tyr Cys Gln His Tyr Gly Ser Arg Val
85 90 95

Thr Phe Gly Gln Gly Thr Lys Leu Glu Ile Lys
100 105

<210> SEQ ID NO 132
<211> LENGTH: 372
<212> TYPE: DNA
<213> ORGANISM: Artificial Sequence
<220> FEATURE:
<223> OTHER INFORMATION: GCE536 heavy chain variable domain (VH) nuc varS1

<400> SEQUENCE: 132
cagctgcagc tggtccagtc aggcacagag gtcaaaaagc caggagcatc agtgaaggtg 60
tcttgtaagt catcaggata cgtgttcacc tcttactatc tggtgtgggt ccggcaggca 120
ccaggacagg gactggagtg gatggccaca atctctcccg gagacgtgaa cactagttac 180
gaacagcgat tccagggcag agtgaccgtc accacagacg cttcaactaa taccgtggat 240
atggagctgc ggagcctgag atccgaagat acagccgtct actattgcgc tagggggccc 300
cgcagcaagc ctccttatct gtattttgct ctggatgtgt gggggcaggg gaccgctgtc 360
accgtgtcaa gc 372

<210> SEQ ID NO 133
<211> LENGTH: 372
<212> TYPE: DNA
<213> ORGANISM: Artificial Sequence
<220> FEATURE:
<223> OTHER INFORMATION: GCE536 heavy chain variable domain (VH) nuc varS2

<400> SEQUENCE: 133
cagctgcagc tggtccagtc aggcacagaa gtcaaaaaac ccggcgcaag cgtgaaggtc 60
tcatgtaaat catcaggata cgtctttacc tcttactatc tggtgtgggt ccggcaggca 120
ccaggacagg gactggagtg gatggccaca atctctcccg gagacgtgaa cactagttac 180
gaacagcgat tccagggcag agtgaccgtc accacagacg cttcaactaa taccgtggat 240
atggagctgc ggagcctgag atccgaagat acagccgtct actattgcgc tagggggccc 300
cgcagcaagc ctccttatct gtacttcgct ctggatgtct gggggcaggg gaccgccgtc 360
accgtctcaa gc 372

<210> SEQ ID NO 134

<211> LENGTH: 372
<212> TYPE: DNA
<213> ORGANISM: Artificial Sequence
<220> FEATURE:
<223> OTHER INFORMATION: GCE536 heavy chain variable domain (VH) nuc varN1

<400> SEQUENCE: 134
cagctgcagc tggtccagag cggcacagag gtgaaaaagc caggagcatc agtcaaagtg 60
tcttgtaagt catcaggata cgtcttcacc tcttactatc tggtgtgggt ccggcaggca 120
ccaggacagg gactggagtg gatggccaca atctctcccg gagacgtgaa cactagttac 180
gaacagcgat tccagggcag agtgaccgtc accacagacg cttcaactaa taccgtggat 240
atggagctgc ggagcctgag atccgaagat acagccgtct actattgcgc tagggggccc 300
cgcagcaagc ctccttatct gtatttcgct ctggatgtct gggggcaggg aacagcagtc 360
accgtctctt ct 372

<210> SEQ ID NO 135
<211> LENGTH: 372
<212> TYPE: DNA
<213> ORGANISM: Artificial Sequence
<220> FEATURE:
<223> OTHER INFORMATION: GCE536 heavy chain variable domain (VH) nuc varC1

<400> SEQUENCE: 135
cagctgcagc tggtccagag cggaaccgaa gtgaagaaac ccggcgcaag cgtcaaagtc 60
tcatgcaaat caagcggata cgtcttcacc tcttactatc tggtgtgggt ccggcaggca 120
ccaggacagg gactggagtg gatggccaca atctctcccg gagacgtgaa cactagttac 180
gaacagcgat tccagggcag agtgaccgtc accacagacg cttcaactaa taccgtggat 240
atggagctgc ggagcctgag atccgaagat acagccgtct actattgcgc tagggggccc 300
cgcagcaagc ctccttatct gtatttcgct ctggatgtct gggggcaggg aacagcagtc 360
accgtctcaa gc 372

<210> SEQ ID NO 136
<211> LENGTH: 322
<212> TYPE: DNA
<213> ORGANISM: Artificial Sequence
<220> FEATURE:
<223> OTHER INFORMATION: GCE536 light chain variable domain (VL) nuc varS1

<400> SEQUENCE: 136
gaaattgtgt tgacgcagtc tcctggcacc ctgtctttgt ctccagggga aacagccatc 60
ctctcctgca gggccagtca gagtgtcagc agcagcctct tagcctggta ccagcaaaaa 120
cctggccagg ctcccaggct cctcatctac ggtgcatcca atagggccac tggcatcaga 180
ggcaggttta gtggcagtgg gtctgggaca gacttcactc tcaccatcag tagattggag 240
cctgaagatt ttgtacttta ttactgtcag cactatggct cacgggtcac ttttggccag 300
gggaccaagc tggagatcaa ac 322

<210> SEQ ID NO 137
<211> LENGTH: 321
<212> TYPE: DNA
<213> ORGANISM: Artificial Sequence
<220> FEATURE:
<223> OTHER INFORMATION: GCE536 light chain variable domain (VL) nuc varS2

<400> SEQUENCE: 137
gaaatcgtgc tgacccagtc tcctggaact ctgtctctgt cacctggcga aaccgcaatc 60
ctgtcctgta gggcaagtca gtctgtgagc tcctctctgc tggcatggta ccagcagaag 120
cccggacagg cccctaggct gctgatctat ggcgcctcca accgcgctac tggcattcgg 180
gggagattca gtggctcagg gagcggaacc gactttaccc tgacaatcag ccggctggag 240
cccgaagatt tcgtgctgta ttactgtcag cactatggca gcagggtcac ttttgggcag 300
gggactaaac tggagattaa a 321

<210> SEQ ID NO 138
<211> LENGTH: 321
<212> TYPE: DNA
<213> ORGANISM: Artificial Sequence
<220> FEATURE:
<223> OTHER INFORMATION: GCE536 light chain variable domain (VL) nuc varN1

<400> SEQUENCE: 138
gaaatcgtcc tgacccagtc acctggcacc ctgagtctga gtcctggcga aacagcaatc 60
ctgtcttgtc gggcttcaca gtccgtgagc tcctctctgc tggcatggta ccagcagaag 120
cccggacagg cccctaggct gctgatctat ggcgcctcca accgcgctac tggcattcgg 180
gggagattca gtggctcagg gagcggaacc gactttaccc tgacaatcag ccggctggag 240
cccgaagatt tcgtgctgta ctactgtcag cattatgggt cacgggtcac ttttgggcag 300
gggactaaac tggaaatcaa g 321

<210> SEQ ID NO 139
<211> LENGTH: 321
<212> TYPE: DNA
<213> ORGANISM: Artificial Sequence
<220> FEATURE:
<223> OTHER INFORMATION: GCE536 light chain variable domain (VL) nuc varC1

<400> SEQUENCE: 139
gagattgtcc tgacccagtc acctggcacc ctgagcctga gtcctggaga gaccgctatt 60
ctgtcttgtc gggcatcaca gtccgtgagc tcctctctgc tggcatggta ccagcagaag 120
cccggacagg cccctaggct gctgatctat ggcgcctcca accgcgctac tggcattcgg 180
gggagattca gtggctcagg gagcggaacc gactttaccc tgacaatcag ccggctggag 240
cccgaagatt tcgtgctgta ctattgtcag cattatggaa gcagggtcac cttcggacag 300
ggaactaaac tggaaatcaa g 321

<210> SEQ ID NO 140
<211> LENGTH: 330
<212> TYPE: PRT
<213> ORGANISM: Artificial Sequence
<220> FEATURE:
<223> OTHER INFORMATION: IgG1 CH1-CH2-CH3 aa

<400> SEQUENCE: 140

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 141
<211> LENGTH: 107
<212> TYPE: PRT
<213> ORGANISM: Artificial Sequence
<220> FEATURE:
<223> OTHER INFORMATION: IgG CK aa

<400> SEQUENCE: 141

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

```
Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 142
<211> LENGTH: 106
<212> TYPE: PRT
<213> ORGANISM: Artificial Sequence
<220> FEATURE:
<223> OTHER INFORMATION: IgG CL aa

<400> SEQUENCE: 142

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 143
<211> LENGTH: 5
<212> TYPE: PRT
<213> ORGANISM: Artificial Sequence
<220> FEATURE:
<223> OTHER INFORMATION: Short linker aa

<400> SEQUENCE: 143

Gly Gly Gly Gly Ser
1               5


<210> SEQ ID NO 144
<211> LENGTH: 15
<212> TYPE: PRT
<213> ORGANISM: Artificial Sequence
<220> FEATURE:
<223> OTHER INFORMATION: Long linker aa

<400> SEQUENCE: 144

Gly Gly Gly Gly Ser Gly Gly Gly Gly Ser Gly Gly Gly Gly Ser
1               5                   10                  15


<210> SEQ ID NO 145
<211> LENGTH: 990
<212> TYPE: DNA
<213> ORGANISM: Artificial Sequence
<220> FEATURE:
<223> OTHER INFORMATION: IgG1 CH1-CH2-CH3 nucl varS1

<400> SEQUENCE: 145

gcgtcgacca agggcccatc ggtcttcccc ctggcaccct cctccaagag cacctctggg      60

ggcacagcgg ccctgggctg cctggtcaag gactacttcc ccgaacctgt gacggtctcg     120

tggaactcag gcgccctgac cagcggcgtg cacaccttcc cggctgtcct acagtcctca     180
```

ggactctact ccctcagcag cgtggtgacc gtgccctcca gcagcttggg cacccagacc 240
tacatctgca acgtgaatca caagcccagc aacaccaagg tggacaagag agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaggatc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctat agcaagctca ccgtggacaa gagcaggtgg 900
cagcagggga acgtcttctc atgctccgtg atgcatgagg ctctgcacaa ccactacacg 960
cagaagagcc tctccctgtc cccgggtaaa 990

<210> SEQ ID NO 146
<211> LENGTH: 990
<212> TYPE: DNA
<213> ORGANISM: Artificial Sequence
<220> FEATURE:
<223> OTHER INFORMATION: IgG1 CH1-CH2-CH3 nucl varS2

<400> SEQUENCE: 146
gcgtcgacca agggcccatc ggtcttcccc ctggcaccct cctccaagag cacctctggg 60
ggcacagcgg ccctgggctg cctggtcaag gactacttcc ccgaacctgt gacggtctcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagag agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaggatc ctgaagtcaa gttcaactgg 480
tacgtggatg gcgtcgaggt gcataatgcc aagacaaaac cccgggagga acagtacaac 540
tcaacttata gagtcgtgag cgtcctgacc gtgctgcatc aggactggct gaacggcaaa 600
gaatacaagt gcaaagtgtc taataaggcc ctgcctgctc caatcgagaa aacaattagc 660
aaggcaaaag ggcagcccag ggaacctcag gtgtacactc tgcctccaag ccgcgaggaa 720
atgaccaaga accaggtctc cctgacatgt ctggtgaaag gattctatcc tagtgacatt 780
gccgtggagt gggaatcaaa tggccagcca gagaacaatt acaagaccac accccctgtg 840
ctggactctg atgggagttt ctttctgtat tccaagctga ccgtggataa atctagatgg 900
cagcagggaa atgtctttag ctgttccgtg atgcatgagg cactgcacaa ccattacacc 960
cagaaatcac tgtcactgtc cccaggaaaa 990

<210> SEQ ID NO 147
<211> LENGTH: 321
<212> TYPE: DNA
<213> ORGANISM: Artificial Sequence
<220> FEATURE:

<223> OTHER INFORMATION: IgG CK nucl

<400> SEQUENCE: 147
cgtacggtgg ctgcaccatc tgtcttcatc ttcccgccat ctgatgagca gttgaaatct 60
ggaactgcct ctgttgtgtg cctgctgaat aacttctatc ccagagaggc caaagtacag 120
tggaaggtgg ataacgccct ccaatcgggt aactcccagg agagtgtcac agagcaggac 180
agcaaggaca gcacctacag cctcagcagc accctgacgc tgagcaaagc agactacgag 240
aaacacaaag tctacgcctg cgaagtcacc catcagggcc tgagctcgcc cgtcacaaag 300
agcttcaaca ggggagagtg t 321

<210> SEQ ID NO 148
<211> LENGTH: 318
<212> TYPE: DNA
<213> ORGANISM: Artificial Sequence
<220> FEATURE:
<223> OTHER INFORMATION: IgG CL nucl

<400> SEQUENCE: 148
ggtcagccca aggctgcccc ctcggtcact ctgttcccgc cctcctctga ggagcttcaa 60
gccaacaagg ccacactggt gtgtctcata agtgacttct acccgggagc cgtgacagtg 120
gcttggaaag cagatagcag ccccgtcaag gcgggagtgg agaccaccac accctccaaa 180
caaagcaaca acaagtacgc ggccagcagc tatctgagcc tgacgcctga gcagtggaag 240
tcccacagaa gctacagctg ccaggtcacg catgaaggga gcaccgtgga gaagacagtg 300
gcccctacag aatgttca 318

<210> SEQ ID NO 149
<211> LENGTH: 15
<212> TYPE: DNA
<213> ORGANISM: Artificial Sequence
<220> FEATURE:
<223> OTHER INFORMATION: Short linker nucl

<400> SEQUENCE: 149
ggcgggggag gctct 15

<210> SEQ ID NO 150
<211> LENGTH: 45
<212> TYPE: DNA
<213> ORGANISM: Artificial Sequence
<220> FEATURE:
<223> OTHER INFORMATION: Long linker nucl

<400> SEQUENCE: 150
ggcgggggag gctctggggg aggcgggagt ggaggcgggg gatca 45

<210> SEQ ID NO 151
<211> LENGTH: 967
<212> TYPE: PRT
<213> ORGANISM: Artificial Sequence
<220> FEATURE:
<223> OTHER INFORMATION: Ts1GC1 heavy chain aa

<400> SEQUENCE: 151

Gln Val Gln Leu Met Glu Ser Gly Gly Gly Val Val Gln Pro Gly Arg
1               5                   10                  15

Ser Leu Arg Leu Ser Cys Ser Ala Phe Gly Phe Thr Phe Ser Asn Tyr
            20                  25                  30

Pro Met His Trp Val Arg Gln Ala Pro Gly Lys Gly Leu Glu Trp Val

-continued

```
        35                  40                  45

Ala Ile Ile Leu Pro Asp Gly Asn Arg Lys Asn Tyr Gly Arg Ser Val
    50                  55                  60

Thr Gly Arg Phe Thr Ile Ser Arg Asp Asn Ser Asn Asn Ser Leu Tyr
65                  70                  75                  80

Leu Gln Met Asn Asn Leu Thr Thr Glu Asp Thr Ala Met Tyr Tyr Cys
                85                  90                  95

Thr Arg Asp Gly Thr Tyr Tyr Ser Asn Gly Gly Val Tyr Gln Thr Tyr
            100                 105                 110

Arg Arg Phe Phe Asp Phe Trp Gly Arg Gly Thr Leu Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys Gly Gly Gly Gly Ser
    450                 455                 460
```

-continued

```
Gly Val Gln Leu Val Gln Ser Gly Gly Gly Leu Val Gln Pro Gly Gly
465                 470                 475                 480

Ser Leu Arg Leu Ser Cys Ala Ala Ser Gly Phe Thr Val Ser Thr Asn
                485                 490                 495

Tyr Met Ser Trp Val Arg Gln Ala Pro Gly Lys Gly Leu Glu Trp Val
            500                 505                 510

Ser Ile Leu Tyr Ala Gly Gly Val Thr Arg Tyr Ala Asp Ser Val Lys
        515                 520                 525

Thr Arg Phe Thr Ile Ser Arg Asp Asn Ser Lys Asn Thr Leu Phe Leu
    530                 535                 540

Gln Met Asn Ala Leu Ser Ala Glu Asp Thr Ala Ile Tyr Tyr Cys Ala
545                 550                 555                 560

Lys His Tyr Asp Ser Gly Tyr Ser Thr Ile Asp His Phe Asp Ser Trp
                565                 570                 575

Gly Gln Gly Thr Leu Val Thr Val Ser Ser Gly Gly Gly Gly Ser Gly
            580                 585                 590

Gly Gly Gly Ser Gly Gly Gly Gly Ser Asp Ile Gln Met Thr Gln Ser
        595                 600                 605

Pro Asp Ser Val Ala Val Ser Leu Gly Glu Arg Ala Thr Ile Asn Cys
    610                 615                 620

Lys Ser Ser Gln Ser Val Phe Tyr Thr Ser Lys Asn Lys Asn Tyr Leu
625                 630                 635                 640

Ala Trp Phe Gln Gln Lys Pro Gly Gln Pro Pro Lys Leu Leu Ile Tyr
                645                 650                 655

Trp Ala Ser Thr Arg Glu Ser Gly Val Pro Asp Arg Phe Ser Gly Ser
            660                 665                 670

Gly Ser Gly Thr Asp Phe Thr Leu Thr Ile Ser Ser Leu Arg Pro Glu
        675                 680                 685

Asp Val Ala Val Tyr Tyr Cys Gln Gln Tyr Tyr Ser Thr Pro Phe Thr
    690                 695                 700

Phe Gly Pro Gly Thr Lys Val Asp Ile Lys Gly Gly Gly Gly Ser Glu
705                 710                 715                 720

Val Gln Leu Val Glu Ser Gly Gly Asp Leu Val Lys Ala Gly Gly Ser
                725                 730                 735

Leu Arg Leu Ser Cys Ala Val Ser Gly Leu Ser Phe Ser Ser Ser Gly
            740                 745                 750

Met Asn Trp Val Arg Gln Ala Pro Gly Lys Gly Leu Glu Trp Ile Ser
        755                 760                 765

Ser Ile Ser Gly Ser Gln Asn Tyr Lys Tyr Tyr Ala Asp Ser Val Lys
    770                 775                 780

Gly Arg Phe Val Val Ser Arg Asp Asn Ala Arg Asn Phe Leu Tyr Leu
785                 790                 795                 800

Gln Met Asp Ser Leu Arg Ala Glu Asp Thr Ala Val Tyr Phe Cys Val
                805                 810                 815

Gly Gly Phe Pro Tyr Trp Leu Pro Pro Ser Asp Phe Ser Gly Phe His
            820                 825                 830

Val Trp Gly Gln Gly Thr Thr Val Thr Val Ser Ser Gly Gly Gly Gly
        835                 840                 845

Ser Gly Gly Gly Gly Ser Gly Gly Gly Gly Ser Ser Tyr Val Leu Thr
    850                 855                 860

Gln Pro Pro Ser Val Ser Val Ala Pro Gly Gln Thr Ala Ser Leu Thr
865                 870                 875                 880
```

-continued

```
Cys Gly Gly Thr Asn Ile Gly Ser Lys Ser Val His Trp Tyr Gln Gln
                885                 890                 895

Lys Ala Gly Gln Ala Pro Val Leu Val Val Tyr Ala Asp Asn Asp Arg
            900                 905                 910

Pro Ser Gly Val Pro Glu Arg Phe Ser Gly Ser Asn Ser Gly Asn Thr
        915                 920                 925

Ala Thr Leu Thr Ile Ser Arg Val Glu Ala Glu Asp Glu Ser Asp Tyr
    930                 935                 940

Phe Cys Gln Val Trp Asp Gly Asn Thr Asp His Val Val Phe Gly Gly
945                 950                 955                 960

Gly Thr Lys Leu Thr Val Leu
                965


<210> SEQ ID NO 152
<211> LENGTH: 2901
<212> TYPE: DNA
<213> ORGANISM: Artificial Sequence
<220> FEATURE:
<223> OTHER INFORMATION: Ts1GC1 heavy chain nucl

<400> SEQUENCE: 152

caggtgcaat tgatggagtc tgggggaggc gtggtccagc ctgggaggtc cctgcgactc     60

tcatgcagtg cctttggatt caccttttcg aactatccta tgcactgggt ccgccaggct    120

ccaggcaagg gacttgagtg ggtggctatc attttacctg atgggaacag aaaaaactat    180

ggaaggtccg tgacgggccg attcaccatc tccagagaca attccaacaa cagcctttat    240

ttgcaaatga acaacctgac gactgaggac acggctatgt actattgtac gagagatggc    300

acgtattact ctaatggtgg tgtttatcag acatatcgaa ggttcttcga tttctggggc    360

cgtggcaccc tggtcaccgt ctcctcagcg tcgaccaagg gcccatcggt cttccccctg    420

gcaccctcct ccaagagcac ctctgggggc acagcggccc tgggctgcct ggtcaaggac    480

tacttccccg aacctgtgac ggtctcgtgg aactcaggcg ccctgaccag cggcgtgcac    540

accttcccgg ctgtcctaca gtcctcagga ctctactccc tcagcagcgt ggtgaccgtg    600

ccctccagca gcttgggcac ccagacctac atctgcaacg tgaatcacaa gcccagcaac    660

accaaggtgg acaagagagt tgagcccaaa tcttgtgaca aaactcacac atgcccaccg    720

tgcccagcac ctgaactcct ggggggaccg tcagtcttcc tcttcccccc aaaacccaag    780

gacaccctca tgatctcccg gacccctgag gtcacatgcg tggtggtgga cgtgagccac    840

gaggatcctg aagtcaagtt caactggtac gtggatggcg tcgaggtgca taatgccaag    900

acaaaacccc gggaggaaca gtacaactca acttatagag tcgtgagcgt cctgaccgtg    960

ctgcatcagg actggctgaa cggcaaagaa tacaagtgca aagtgtctaa taaggccctg   1020

cctgctccaa tcgagaaaac aattagcaag gcaaaagggc agcccaggga acctcaggtg   1080

tacactctgc ctccaagccg cgaggaaatg accaagaacc aggtctccct gacatgtctg   1140

gtgaaaggat tctatcctag tgacattgcc gtggagtggg aatcaaatgg ccagccagag   1200

aacaattaca agaccacacc ccctgtgctg gactctgatg ggagtttctt tctgtattcc   1260

aagctgaccg tggataaatc tagatggcag cagggaaatg tctttagctg ttccgtgatg   1320

catgaggcac tgcacaacca ttacacccag aaatcactgt cactgtcccc aggaaaaggc   1380

gggggaggct ctggagtgca gctggtccag agcggaggag gactggtgca gccaggaggg   1440

tcactgaggc tgagctgcgc agcttccggc ttcaccgtgt caacaaacta catgagctgg   1500

gtccgccagg cacctgggaa gggactggag tgggtgtcca tcctgtacgc cggaggcgtg   1560
```

```
actcgatatg ctgactctgt caagactcgg ttcaccatct ctagagataa cagtaagaac   1620

accctgtttc tgcagatgaa tgcactgagt gccgaagaca cagctatcta ctattgtgca   1680

aaacactacg attctgggta tagtacaatt gaccattttg attcttgggg ccaggggaca   1740

ctggtgactg tcagctccgg cgggggaggc tctgggggag gcgggagtgg aggcggggga   1800

tcagacatcc agatgactca gtctcccgat agtgtggccg tctccctggg ggagagggct   1860

acaattaact gcaagagctc ccagtccgtg ttctacactt ctaagaacaa aaactatctg   1920

gcatggtttc agcagaagcc tggacagccc cctaaactgc tgatctactg ggcctcaacc   1980

cgagagagcg gagtcccaga cagattctca ggcagcgggt ccggaacaga ttttaccctg   2040

acaatttcta gtctgcggcc tgaagacgtg gctgtctact attgtcagca gtactatagc   2100

actccattca cctttggccc cgggacaaag gtggatatca aaggcggggg aggctctgag   2160

gtgcagctgg tcgaatctgg cggggacctg gtgaaggcag gaggcagtct gaggctgtca   2220

tgcgccgtct cagggctgag cttcagctcc tctggaatga actgggtgcg ccaggcacca   2280

ggcaaaggac tggagtggat cagttcaatt tctggcagtc agaattacaa gtactatgct   2340

gacagtgtga aagggcgatt cgtggtctcc cgggataacg caagaaattt tctgtatctg   2400

cagatggaca gcctgagagc cgaagatact gctgtgtact tctgtgtcgg gggatttccc   2460

tattggctgc ccccttccga tttctctggc tttcacgtgt ggggacaggg caccacagtg   2520

accgtcagct ccggcggggg aggctctggg ggaggcggga gtggaggcgg gggatcatcc   2580

tacgtgctga ctcagccacc tagcgtgtcc gtcgcacctg gacagactgc cagcctgacc   2640

tgcggaggaa caaacatcgg gtctaagagt gtgcactggt accagcagaa agccggacag   2700

gctcccgtcc tggtggtcta tgccgacaat gatcggccat ctggcgtgcc cgaaagattc   2760

tcaggaagca actccggcaa taccgctaca ctgactattt ctagggtgga ggcagaagac   2820

gagagtgatt atttctgtca ggtctgggac gggaacacag atcatgtggt ctttggaggc   2880

gggaccaagc tgacagtgct g                                               2901
```

<210> SEQ ID NO 153
<211> LENGTH: 962
<212> TYPE: PRT
<213> ORGANISM: Artificial Sequence
<220> FEATURE:
<223> OTHER INFORMATION: Ts1GC2a heavy chain aa

<400> SEQUENCE: 153

```
Gln Leu Gln Leu Val Gln Ser Gly Thr Glu Val Lys Lys Pro Gly Ala
1               5                   10                  15

Ser Val Lys Val Ser Cys Lys Ser Ser Gly Tyr Val Phe Thr Ser Tyr
            20                  25                  30

Tyr Leu Val Trp Val Arg Gln Ala Pro Gly Gln Gly Leu Glu Trp Met
        35                  40                  45

Ala Thr Ile Ser Pro Gly Asp Val Asn Thr Ser Tyr Glu Gln Arg Phe
    50                  55                  60

Gln Gly Arg Val Thr Val Thr Thr Asp Ala Ser Thr Asn Thr Val Asp
65                  70                  75                  80

Met Glu Leu Arg Ser Leu Arg Ser Glu Asp Thr Ala Val Tyr Tyr Cys
                85                  90                  95

Ala Arg Gly Pro Arg Ser Lys Pro Pro Tyr Leu Tyr Phe Ala Leu Asp
            100                 105                 110

Val Trp Gly Gln Gly Thr Ala Val Thr Val Ser Ser Ala Ser Thr Lys
```

-continued

```
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Gly Gly Ser Gly Val Gln Leu Val
    450                 455                 460

Gln Ser Gly Gly Gly Leu Val Gln Pro Gly Gly Ser Leu Arg Leu Ser
465                 470                 475                 480

Cys Ala Ala Ser Gly Phe Thr Val Ser Thr Asn Tyr Met Ser Trp Val
                485                 490                 495

Arg Gln Ala Pro Gly Lys Gly Leu Glu Trp Val Ser Ile Leu Tyr Ala
            500                 505                 510

Gly Gly Val Thr Arg Tyr Ala Asp Ser Val Lys Thr Arg Phe Thr Ile
        515                 520                 525

Ser Arg Asp Asn Ser Lys Asn Thr Leu Phe Leu Gln Met Asn Ala Leu
    530                 535                 540
```

-continued

```
Ser Ala Glu Asp Thr Ala Ile Tyr Tyr Cys Ala Lys His Tyr Asp Ser
545                 550                 555                 560

Gly Tyr Ser Thr Ile Asp His Phe Asp Ser Trp Gly Gln Gly Thr Leu
                565                 570                 575

Val Thr Val Ser Ser Gly Gly Gly Gly Ser Gly Gly Gly Gly Ser Gly
            580                 585                 590

Gly Gly Gly Ser Asp Ile Gln Met Thr Gln Ser Pro Asp Ser Val Ala
        595                 600                 605

Val Ser Leu Gly Glu Arg Ala Thr Ile Asn Cys Lys Ser Ser Gln Ser
    610                 615                 620

Val Phe Tyr Thr Ser Lys Asn Lys Asn Tyr Leu Ala Trp Phe Gln Gln
625                 630                 635                 640

Lys Pro Gly Gln Pro Pro Lys Leu Leu Ile Tyr Trp Ala Ser Thr Arg
                645                 650                 655

Glu Ser Gly Val Pro Asp Arg Phe Ser Gly Ser Gly Ser Gly Thr Asp
            660                 665                 670

Phe Thr Leu Thr Ile Ser Ser Leu Arg Pro Glu Asp Val Ala Val Tyr
        675                 680                 685

Tyr Cys Gln Gln Tyr Tyr Ser Thr Pro Phe Thr Phe Gly Pro Gly Thr
    690                 695                 700

Lys Val Asp Ile Lys Gly Gly Gly Gly Ser Glu Val Gln Leu Val Glu
705                 710                 715                 720

Ser Gly Gly Asp Leu Val Lys Ala Gly Gly Ser Leu Arg Leu Ser Cys
                725                 730                 735

Ala Val Ser Gly Leu Ser Phe Ser Ser Ser Gly Met Asn Trp Val Arg
            740                 745                 750

Gln Ala Pro Gly Lys Gly Leu Glu Trp Ile Ser Ser Ile Ser Gly Ser
        755                 760                 765

Gln Asn Tyr Lys Tyr Tyr Ala Asp Ser Val Lys Gly Arg Phe Val Val
    770                 775                 780

Ser Arg Asp Asn Ala Arg Asn Phe Leu Tyr Leu Gln Met Asp Ser Leu
785                 790                 795                 800

Arg Ala Glu Asp Thr Ala Val Tyr Phe Cys Val Gly Gly Phe Pro Tyr
                805                 810                 815

Trp Leu Pro Pro Ser Asp Phe Ser Gly Phe His Val Trp Gly Gln Gly
            820                 825                 830

Thr Thr Val Thr Val Ser Ser Gly Gly Gly Gly Ser Gly Gly Gly Gly
        835                 840                 845

Ser Gly Gly Gly Gly Ser Ser Tyr Val Leu Thr Gln Pro Pro Ser Val
    850                 855                 860

Ser Val Ala Pro Gly Gln Thr Ala Ser Leu Thr Cys Gly Gly Thr Asn
865                 870                 875                 880

Ile Gly Ser Lys Ser Val His Trp Tyr Gln Gln Lys Ala Gly Gln Ala
                885                 890                 895

Pro Val Leu Val Val Tyr Ala Asp Asn Asp Arg Pro Ser Gly Val Pro
            900                 905                 910

Glu Arg Phe Ser Gly Ser Asn Ser Gly Asn Thr Ala Thr Leu Thr Ile
        915                 920                 925

Ser Arg Val Glu Ala Glu Asp Glu Ser Asp Tyr Phe Cys Gln Val Trp
    930                 935                 940

Asp Gly Asn Thr Asp His Val Val Phe Gly Gly Gly Thr Lys Leu Thr
945                 950                 955                 960
```

Val Leu

<210> SEQ ID NO 154
<211> LENGTH: 2886
<212> TYPE: DNA
<213> ORGANISM: Artificial Sequence
<220> FEATURE:
<223> OTHER INFORMATION: Ts1GC2a heavy chain nucl

<400> SEQUENCE: 154
cagctgcagc tggtccagtc aggcacagag gtcaaaaagc caggagcatc agtgaaggtg 60
tcttgtaagt catcaggata cgtgttcacc tcttactatc tggtgtgggt ccggcaggca 120
ccaggacagg gactggagtg gatggccaca atctctcccg gagacgtgaa cactagttac 180
gaacagcgat tccagggcag agtgaccgtc accacagacg cttcaactaa taccgtggat 240
atggagctgc ggagcctgag atccgaagat acagccgtct actattgcgc taggggggccc 300 cgcagcaagc ctccttatct gtattttgct ctggatgtgt gggggcaggg gaccgctgtc 360
accgtgtcaa gcgcgtcgac caagggccca tcggtcttcc ccctggcacc ctcctccaag 420
agcacctctg gggcacagc ggccctgggc tgcctggtca aggactactt ccccgaacct 480
gtgacggtct cgtggaactc aggcgccctg accagcggcg tgcacacctt cccggctgtc 540
ctacagtcct caggactcta ctccctcagc agcgtggtga ccgtgccctc cagcagcttg 600
ggcacccaga cctacatctg caacgtgaat cacaagccca gcaacaccaa ggtggacaag 660
agagttgagc ccaaatcttg tgacaaaact cacacatgcc caccgtgccc agcacctgaa 720
ctcctggggg gaccgtcagt cttcctcttc cccccaaaac ccaaggacac cctcatgatc 780
tcccggaccc ctgaggtcac atgcgtggtg gtggacgtga gccacgagga tcctgaagtc 840
aagttcaact ggtacgtgga tggcgtcgag gtgcataatg ccaagacaaa accccgggag 900
gaacagtaca actcaactta tagagtcgtg agcgtcctga ccgtgctgca tcaggactgg 960
ctgaacggca aagaatacaa gtgcaaagtg tctaataagg ccctgcctgc tccaatcgag 1020
aaaacaatta gcaaggcaaa agggcagccc agggaacctc aggtgtacac tctgcctcca 1080
agccgcgagg aaatgaccaa gaaccaggtc tccctgacat gtctggtgaa aggattctat 1140
cctagtgaca ttgccgtgga gtgggaatca aatggccagc cagagaacaa ttacaagacc 1200 acacccccctg tgctggactc tgatgggagt ttctttctgt attccaagct gaccgtggat 1260
aaatctagat ggcagcaggg aaatgtcttt agctgttccg tgatgcatga ggcactgcac 1320
aaccattaca cccagaaatc actgtcactg tccccaggaa aaggcggggg aggctctgga 1380
gtgcagctgg tccagagcgg aggaggactg gtgcagccag gagggtcact gaggctgagc 1440
tgcgcagctt ccggcttcac cgtgtcaaca aactacatga gctgggtccg ccaggcacct 1500
gggaagggac tggagtgggt gtccatcctg tacgccggag gcgtgactcg atatgctgac 1560
tctgtcaaga ctcggttcac catctctaga gataacagta agaacaccct gtttctgcag 1620
atgaatgcac tgagtgccga agacacagct atctactatt gtgcaaaaca ctacgattct 1680
gggtatagta caattgacca ttttgattct tggggccagg ggacactggt gactgtcagc 1740
tccggcgggg gaggctctgg gggaggcggg agtggaggcg gggatcaga catccagatg 1800 actcagtctc ccgatagtgt ggccgtctcc ctgggggaga gggctacaat taactgcaag 1860
agctcccagt ccgtgttcta cacttctaag aacaaaaact atctggcatg gtttcagcag 1920
aagcctggac agccccctaa actgctgatc tactgggcct caacccgaga gagcggagtc 1980
ccagacagat tctcaggcag cgggtccgga acagatttta ccctgacaat ttctagtctg 2040

```
cggcctgaag acgtggctgt ctactattgt cagcagtact atagcactcc attcaccttt   2100

ggccccggga caaaggtgga tatcaaaggc gggggaggct ctgaggtgca gctggtcgaa   2160

tctggcgggg acctggtgaa ggcaggaggc agtctgaggc tgtcatgcgc cgtctcaggg   2220

ctgagcttca gctcctctgg aatgaactgg gtgcgccagg caccaggcaa aggactggag   2280

tggatcagtt caatttctgg cagtcagaat tacaagtact atgctgacag tgtgaaaggg   2340

cgattcgtgg tctcccggga taacgcaaga aattttctgt atctgcagat ggacagcctg   2400

agagccgaag atactgctgt gtacttctgt gtcgggggat ttccctattg gctgcccccct   2460

tccgatttct ctggctttca cgtgtgggga cagggcacca cagtgaccgt cagctccggc   2520

gggggaggct ctgggggagg cgggagtgga ggcgggggat catcctacgt gctgactcag   2580

ccacctagcg tgtccgtcgc acctggacag actgccagcc tgacctgcgg aggaacaaac   2640

atcgggtcta agagtgtgca ctggtaccag cagaaagccg gacaggctcc cgtcctggtg   2700

gtctatgccg acaatgatcg gccatctggc gtgcccgaaa gattctcagg aagcaactcc   2760

ggcaataccg ctacactgac tatttctagg gtggaggcag aagacgagag tgattatttc   2820

tgtcaggtct gggacgggaa cacagatcat gtggtctttg gaggcgggac caagctgaca   2880

gtgctg                                                              2886
```

<210> SEQ ID NO 155
<211> LENGTH: 707
<212> TYPE: PRT
<213> ORGANISM: Artificial Sequence
<220> FEATURE:
<223> OTHER INFORMATION: Ts2GC2b/Bs1GC2a heavy chain aa

<400> SEQUENCE: 155

```
Glu Val Gln Leu Val Glu Ser Gly Gly Asp Leu Val Lys Ala Gly Gly
1               5                   10                  15

Ser Leu Arg Leu Ser Cys Ala Val Ser Gly Leu Ser Phe Ser Ser Ser
            20                  25                  30

Gly Met Asn Trp Val Arg Gln Ala Pro Gly Lys Gly Leu Glu Trp Ile
        35                  40                  45

Ser Ser Ile Ser Gly Ser Gln Asn Tyr Lys Tyr Tyr Ala Asp Ser Val
    50                  55                  60

Lys Gly Arg Phe Val Val Ser Arg Asp Asn Ala Arg Asn Phe Leu Tyr
65                  70                  75                  80

Leu Gln Met Asp Ser Leu Arg Ala Glu Asp Thr Ala Val Tyr Phe Cys
                85                  90                  95

Val Gly Gly Phe Pro Tyr Trp Leu Pro Pro Ser Asp Phe Ser Gly Phe
            100                 105                 110

His Val Trp Gly Gln Gly Thr Thr Val Thr Val Ser Ser Gly Gly Gly
        115                 120                 125

Gly Ser Gly Gly Gly Gly Ser Gly Gly Gly Gly Ser Ser Tyr Val Leu
    130                 135                 140

Thr Gln Pro Pro Ser Val Ser Val Ala Pro Gly Gln Thr Ala Ser Leu
145                 150                 155                 160

Thr Cys Gly Gly Thr Asn Ile Gly Ser Lys Ser Val His Trp Tyr Gln
                165                 170                 175

Gln Lys Ala Gly Gln Ala Pro Val Leu Val Val Tyr Ala Asp Asn Asp
            180                 185                 190

Arg Pro Ser Gly Val Pro Glu Arg Phe Ser Gly Ser Asn Ser Gly Asn
        195                 200                 205
```

-continued

```
Thr Ala Thr Leu Thr Ile Ser Arg Val Glu Ala Glu Asp Glu Ser Asp
    210                 215                 220

Tyr Phe Cys Gln Val Trp Asp Gly Asn Thr Asp His Val Val Phe Gly
225                 230                 235                 240

Gly Gly Thr Lys Leu Thr Val Leu Gly Gly Gly Gly Ser Gln Leu Gln
                245                 250                 255

Leu Val Gln Ser Gly Thr Glu Val Lys Lys Pro Gly Ala Ser Val Lys
            260                 265                 270

Val Ser Cys Lys Ser Ser Gly Tyr Val Phe Thr Ser Tyr Tyr Leu Val
        275                 280                 285

Trp Val Arg Gln Ala Pro Gly Gln Gly Leu Glu Trp Met Ala Thr Ile
    290                 295                 300

Ser Pro Gly Asp Val Asn Thr Ser Tyr Glu Gln Arg Phe Gln Gly Arg
305                 310                 315                 320

Val Thr Val Thr Thr Asp Ala Ser Thr Asn Thr Val Asp Met Glu Leu
                325                 330                 335

Arg Ser Leu Arg Ser Glu Asp Thr Ala Val Tyr Tyr Cys Ala Arg Gly
            340                 345                 350

Pro Arg Ser Lys Pro Pro Tyr Leu Tyr Phe Ala Leu Asp Val Trp Gly
        355                 360                 365

Gln Gly Thr Ala Val Thr Val Ser Ser Ala Ser Thr Lys Gly Pro Ser
    370                 375                 380

Val Phe Pro Leu Ala Pro Ser Ser Lys Ser Thr Ser Gly Gly Thr Ala
385                 390                 395                 400

Ala Leu Gly Cys Leu Val Lys Asp Tyr Phe Pro Glu Pro Val Thr Val
                405                 410                 415

Ser Trp Asn Ser Gly Ala Leu Thr Ser Gly Val His Thr Phe Pro Ala
            420                 425                 430

Val Leu Gln Ser Ser Gly Leu Tyr Ser Leu Ser Ser Val Val Thr Val
        435                 440                 445

Pro Ser Ser Ser Leu Gly Thr Gln Thr Tyr Ile Cys Asn Val Asn His
    450                 455                 460

Lys Pro Ser Asn Thr Lys Val Asp Lys Arg Val Glu Pro Lys Ser Cys
465                 470                 475                 480

Asp Lys Thr His Thr Cys Pro Pro Cys Pro Ala Pro Glu Leu Leu Gly
                485                 490                 495

Gly Pro Ser Val Phe Leu Phe Pro Pro Lys Pro Lys Asp Thr Leu Met
            500                 505                 510

Ile Ser Arg Thr Pro Glu Val Thr Cys Val Val Val Asp Val Ser His
        515                 520                 525

Glu Asp Pro Glu Val Lys Phe Asn Trp Tyr Val Asp Gly Val Glu Val
    530                 535                 540

His Asn Ala Lys Thr Lys Pro Arg Glu Glu Gln Tyr Asn Ser Thr Tyr
545                 550                 555                 560

Arg Val Val Ser Val Leu Thr Val Leu His Gln Asp Trp Leu Asn Gly
                565                 570                 575

Lys Glu Tyr Lys Cys Lys Val Ser Asn Lys Ala Leu Pro Ala Pro Ile
            580                 585                 590

Glu Lys Thr Ile Ser Lys Ala Lys Gly Gln Pro Arg Glu Pro Gln Val
        595                 600                 605

Tyr Thr Leu Pro Pro Ser Arg Glu Glu Met Thr Lys Asn Gln Val Ser
    610                 615                 620
```

-continued

```
Leu Thr Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                645                 650                 655

Val Leu Asp Ser Asp Gly Ser Phe Phe Leu Tyr Ser Lys Leu Thr Val
            660                 665                 670

Asp Lys Ser Arg Trp Gln Gln Gly Asn Val Phe Ser Cys Ser Val Met
        675                 680                 685

His Glu Ala Leu His Asn His Tyr Thr Gln Lys Ser Leu Ser Leu Ser
    690                 695                 700

Pro Gly Lys
705
```

<210> SEQ ID NO 156
<211> LENGTH: 2121
<212> TYPE: DNA
<213> ORGANISM: Artificial Sequence
<220> FEATURE:
<223> OTHER INFORMATION: Ts2GC2b/Bs1GC2a heavy chain nucl

<400> SEQUENCE: 156

```
gaggtgcagc tggtggaaag cggaggggat ctggtgaaag caggagggag cctgagactg     60

tcatgcgccg tgagcgggct gtcattcagc tcctctggca tgaactgggt gcgacaggct    120

cctggaaagg gactggagtg gatcagttca attagcgggt cccagaatta caagtactat    180

gcagactctg tcaaaggaag gttcgtggtc agccgggata acgccagaaa ttttctgtat    240

ctgcagatgg acagcctgcg cgccgaagat accgccgtgt acttctgcgt cggcgggttt    300

ccctattggc tgcctccaag cgatttcagc ggatttcatg tctgggggca gggaactaca    360

gtgaccgtct catcaggcgg gggaggctct gggggaggcg ggagtggagg cgggggatca    420

tcttacgtcc tgacccagcc acctagcgtg agcgtcgcac cagggcagac agcttcactg    480

acttgcggag gcacaaacat tggcagcaag agcgtgcact ggtaccagca gaaagccgga    540

caggctcccg tcctggtggt ctatgctgac aacgatcggc cctctggcgt gcctgaaaga    600

ttcagcggct ccaactctgg gaataccgca acactgacca tcagtagggt cgaggccgaa    660

gacgagtcag attacttttg ccaggtgtgg gacggcaata ctgaccatgt cgtgttcggc    720

ggcgggacca aactgactgt gctgggcggg ggaggctctc agctgcagct ggtccagtca    780

ggcacagaag tcaaaaaacc cggcgcaagc gtgaaggtct catgtaaatc atcaggatac    840

gtctttacct cttactatct ggtgtgggtc cggcaggcac caggacaggg actggagtgg    900

atggccacaa tctctcccgg agacgtgaac actagttacg aacagcgatt ccagggcaga    960

gtgaccgtca ccacagacgc ttcaactaat accgtggata tggagctgcg gagcctgaga   1020

tccgaagata cagccgtcta ctattgcgct agggggcccc gcagcaagcc tccttatctg   1080

tacttcgctc tggatgtctg gggcaggggg accgccgtca ccgtctcaag cgcgtcgacc   1140

aagggcccat cggtcttccc cctggcaccc tcctccaaga gcacctctgg gggcacagcg   1200

gccctgggct gcctggtcaa ggactacttc cccgaacctg tgacggtctc gtggaactca   1260

ggcgccctga ccagcggcgt gcacaccttc ccggctgtcc tacagtcctc aggactctac   1320

tccctcagca gcgtggtgac cgtgccctcc agcagcttgg gcacccagac ctacatctgc   1380

aacgtgaatc acaagcccag caacaccaag gtggacaaga gagttgagcc caaatcttgt   1440

gacaaaactc acacatgccc accgtgccca gcacctgaac tcctgggggg accgtcagtc   1500

ttcctcttcc ccccaaaacc caaggacacc ctcatgatct cccggacccc tgaggtcaca   1560
```

tgcgtggtgg tggacgtgag ccacgaggat cctgaggtca agttcaactg gtacgtggac 1620
ggcgtggagg tgcataatgc caagacaaag ccgcgggagg agcagtacaa cagcacgtac 1680
cgtgtggtca gcgtcctcac cgtcctgcac caggactggc tgaatggcaa ggagtacaag 1740
tgcaaggtct ccaacaaagc cctcccagcc cccatcgaga aaaccatctc caaagccaaa 1800
gggcagcccc gagaaccaca ggtgtacacc ctgcccccat cccgggagga gatgaccaag 1860
aaccaggtca gcctgacctg cctggtcaaa ggcttctatc ccagcgacat cgccgtggag 1920
tgggagagca atgggcagcc ggagaacaac tacaagacca cgcctcccgt gctggactcc 1980
gacggctcct tcttcctcta tagcaagctc accgtggaca agagcaggtg gcagcagggg 2040
aacgtcttct catgctccgt gatgcatgag gctctgcaca accactacac gcagaagagc 2100
ctctccctgt ccccgggtaa a 2121

<210> SEQ ID NO 157
<211> LENGTH: 469
<212> TYPE: PRT
<213> ORGANISM: Artificial Sequence
<220> FEATURE:
<223> OTHER INFORMATION: Ts2GC2b/Bs2GC1c light chain aa

<400> SEQUENCE: 157

Gly Val Gln Leu Val Gln Ser Gly Gly Gly Leu Val Gln Pro Gly Gly
1 5 10 15

Ser Leu Arg Leu Ser Cys Ala Ala Ser Gly Phe Thr Val Ser Thr Asn
20 25 30

Tyr Met Ser Trp Val Arg Gln Ala Pro Gly Lys Gly Leu Glu Trp Val
35 40 45

Ser Ile Leu Tyr Ala Gly Gly Val Thr Arg Tyr Ala Asp Ser Val Lys
50 55 60

Thr Arg Phe Thr Ile Ser Arg Asp Asn Ser Lys Asn Thr Leu Phe Leu
65 70 75 80

Gln Met Asn Ala Leu Ser Ala Glu Asp Thr Ala Ile Tyr Tyr Cys Ala
85 90 95

Lys His Tyr Asp Ser Gly Tyr Ser Thr Ile Asp His Phe Asp Ser Trp
100 105 110

Gly Gln Gly Thr Leu Val Thr Val Ser Ser Gly Gly Gly Gly Ser Gly
115 120 125

Gly Gly Gly Ser Gly Gly Gly Gly Ser Asp Ile Gln Met Thr Gln Ser
130 135 140

Pro Asp Ser Val Ala Val Ser Leu Gly Glu Arg Ala Thr Ile Asn Cys
145 150 155 160

Lys Ser Ser Gln Ser Val Phe Tyr Thr Ser Lys Asn Lys Asn Tyr Leu
165 170 175

Ala Trp Phe Gln Gln Lys Pro Gly Gln Pro Pro Lys Leu Leu Ile Tyr
180 185 190

Trp Ala Ser Thr Arg Glu Ser Gly Val Pro Asp Arg Phe Ser Gly Ser
195 200 205

Gly Ser Gly Thr Asp Phe Thr Leu Thr Ile Ser Ser Leu Arg Pro Glu
210 215 220

Asp Val Ala Val Tyr Tyr Cys Gln Gln Tyr Tyr Ser Thr Pro Phe Thr
225 230 235 240

Phe Gly Pro Gly Thr Lys Val Asp Ile Lys Gly Gly Gly Gly Ser Glu
245 250 255

```
Ile Val Leu Thr Gln Ser Pro Gly Thr Leu Ser Leu Ser Pro Gly Glu
            260                 265                 270

Thr Ala Ile Leu Ser Cys Arg Ala Ser Gln Ser Val Ser Ser Ser Leu
        275                 280                 285

Leu Ala Trp Tyr Gln Gln Lys Pro Gly Gln Ala Pro Arg Leu Leu Ile
    290                 295                 300

Tyr Gly Ala Ser Asn Arg Ala Thr Gly Ile Arg Gly Arg Phe Ser Gly
305                 310                 315                 320

Ser Gly Ser Gly Thr Asp Phe Thr Leu Thr Ile Ser Arg Leu Glu Pro
                325                 330                 335

Glu Asp Phe Val Leu Tyr Tyr Cys Gln His Tyr Gly Ser Arg Val Thr
            340                 345                 350

Phe Gly Gln Gly Thr Lys Leu Glu Ile Lys Arg Thr Val Ala Ala Pro
        355                 360                 365

Ser Val Phe Ile Phe Pro Pro Ser Asp Glu Gln Leu Lys Ser Gly Thr
    370                 375                 380

Ala Ser Val Val Cys Leu Leu Asn Asn Phe Tyr Pro Arg Glu Ala Lys
385                 390                 395                 400

Val Gln Trp Lys Val Asp Asn Ala Leu Gln Ser Gly Asn Ser Gln Glu
                405                 410                 415

Ser Val Thr Glu Gln Asp Ser Lys Asp Ser Thr Tyr Ser Leu Ser Ser
            420                 425                 430

Thr Leu Thr Leu Ser Lys Ala Asp Tyr Glu Lys His Lys Val Tyr Ala
        435                 440                 445

Cys Glu Val Thr His Gln Gly Leu Ser Ser Pro Val Thr Lys Ser Phe
    450                 455                 460

Asn Arg Gly Glu Cys
465


<210> SEQ ID NO 158
<211> LENGTH: 1407
<212> TYPE: DNA
<213> ORGANISM: Artificial Sequence
<220> FEATURE:
<223> OTHER INFORMATION: Ts2GC2b/Bs2GC1c light chain nucl

<400> SEQUENCE: 158

ggcgtccagc tggtgcagag cggagggggc ctggtgcagc ctggcgggtc cctgagactg     60

agttgtgccg caagtggctt tactgtctct acaaactaca tgtcttgggt gaggcaggca    120

cctggaaagg gactggagtg ggtctcaatc ctgtacgctg gcggggtgac ccggtatgca    180

gacagcgtca agacccggtt cacaattagc agagataact ccaaaaatac tctgtttctg    240

cagatgaatg ccctgtccgc tgaagacacc gcaatctact attgcgccaa acactatgat    300

agtgggtata gcacaatcga ccattttgac agctggggac agggaactct ggtgacagtc    360

tcatcaggcg gggaggctc tgggggaggc gggagtggag gcgggggatc agacattcag     420

atgacccaga gtcctgattc cgtggctgtc tcactggggg agcgagcaac tattaactgc    480

aagtcttcac agagcgtgtt ctacaccagt aagaacaaaa actatctggc ctggtttcag    540

cagaagccag gccagccccc taaactgctg atctactggg ctagcactag agagtctgga    600

gtgccagaca gattctctgg cagtgggtca ggaaccgact tcaccctgac aattagctcc    660

ctgaggcccg aagacgtggc cgtctactat tgtcagcagt attacagcac cccattcaca    720

ttcggccctg gaaccaaagt ggatattaag ggcgggggag gctctgaaat cgtgctgacc    780

cagtctcctg gaactctgtc tctgtcacct ggcgaaaccg caatcctgtc ctgtagggca    840
```

```
agtcagtctg tgagctcctc tctgctggca tggtaccagc agaagcccgg acaggcccct    900

aggctgctga tctatggcgc ctccaaccgc gctactggca ttcgggggag attcagtggc    960

tcagggagcg gaaccgactt taccctgaca atcagccggc tggagcccga agatttcgtg   1020

ctgtattact gtcagcacta tggcagcagg gtcacttttg ggcaggggac taaactggag   1080

attaaacgta cggtggctgc accatctgtc ttcatcttcc cgccatctga tgagcagttg   1140

aaatctggaa ctgcctctgt tgtgtgcctg ctgaataact tctatcccag agaggccaaa   1200

gtacagtgga aggtggataa cgccctccaa tcgggtaact cccaggagag tgtcacagag   1260

caggacagca aggacagcac ctacagcctc agcagcaccc tgacgctgag caaagcagac   1320

tacgagaaac acaaagtcta cgcctgcgaa gtcacccatc agggcctgag ctcgcccgtc   1380

acaaagagct tcaacagggg agagtgt                                        1407


<210> SEQ ID NO 159
<211> LENGTH: 705
<212> TYPE: PRT
<213> ORGANISM: Artificial Sequence
<220> FEATURE:
<223> OTHER INFORMATION: Ts2GC2c/Bs1GC3a heavy chain aa

<400> SEQUENCE: 159

Glu Val Gln Leu Val Glu Ser Gly Gly Asp Leu Val Lys Ala Gly Gly
1               5                   10                  15

Ser Leu Arg Leu Ser Cys Ala Val Ser Gly Leu Ser Phe Ser Ser Ser
            20                  25                  30

Gly Met Asn Trp Val Arg Gln Ala Pro Gly Lys Gly Leu Glu Trp Ile
        35                  40                  45

Ser Ser Ile Ser Gly Ser Gln Asn Tyr Lys Tyr Tyr Ala Asp Ser Val
    50                  55                  60

Lys Gly Arg Phe Val Val Ser Arg Asp Asn Ala Arg Asn Phe Leu Tyr
65                  70                  75                  80

Leu Gln Met Asp Ser Leu Arg Ala Glu Asp Thr Ala Val Tyr Phe Cys
                85                  90                  95

Val Gly Gly Phe Pro Tyr Trp Leu Pro Pro Ser Asp Phe Ser Gly Phe
            100                 105                 110

His Val Trp Gly Gln Gly Thr Thr Val Thr Val Ser Ser Gly Gly Gly
        115                 120                 125

Gly Ser Gly Gly Gly Gly Ser Gly Gly Gly Gly Ser Ser Tyr Val Leu
    130                 135                 140

Thr Gln Pro Pro Ser Val Ser Val Ala Pro Gly Gln Thr Ala Ser Leu
145                 150                 155                 160

Thr Cys Gly Gly Thr Asn Ile Gly Ser Lys Ser Val His Trp Tyr Gln
                165                 170                 175

Gln Lys Ala Gly Gln Ala Pro Val Leu Val Val Tyr Ala Asp Asn Asp
            180                 185                 190

Arg Pro Ser Gly Val Pro Glu Arg Phe Ser Gly Ser Asn Ser Gly Asn
        195                 200                 205

Thr Ala Thr Leu Thr Ile Ser Arg Val Glu Ala Glu Asp Glu Ser Asp
    210                 215                 220

Tyr Phe Cys Gln Val Trp Asp Gly Asn Thr Asp His Val Val Phe Gly
225                 230                 235                 240

Gly Gly Thr Lys Leu Thr Val Leu Gly Gly Gly Gly Ser Gly Val Gln
                245                 250                 255
```

-continued

```
Leu Val Gln Ser Gly Gly Gly Leu Val Gln Pro Gly Gly Ser Leu Arg
            260                 265                 270

Leu Ser Cys Ala Ala Ser Gly Phe Thr Val Ser Thr Asn Tyr Met Ser
        275                 280                 285

Trp Val Arg Gln Ala Pro Gly Lys Gly Leu Glu Trp Val Ser Ile Leu
    290                 295                 300

Tyr Ala Gly Gly Val Thr Arg Tyr Ala Asp Ser Val Lys Thr Arg Phe
305                 310                 315                 320

Thr Ile Ser Arg Asp Asn Ser Lys Asn Thr Leu Phe Leu Gln Met Asn
                325                 330                 335

Ala Leu Ser Ala Glu Asp Thr Ala Ile Tyr Tyr Cys Ala Lys His Tyr
            340                 345                 350

Asp Ser Gly Tyr Ser Thr Ile Asp His Phe Asp Ser Trp Gly Gln Gly
        355                 360                 365

Thr Leu Val Thr Val Ser Ser Ala Ser Thr Lys Gly Pro Ser Val Phe
    370                 375                 380

Pro Leu Ala Pro Ser Ser Lys Ser Thr Ser Gly Gly Thr Ala Ala Leu
385                 390                 395                 400

Gly Cys Leu Val Lys Asp Tyr Phe Pro Glu Pro Val Thr Val Ser Trp
                405                 410                 415

Asn Ser Gly Ala Leu Thr Ser Gly Val His Thr Phe Pro Ala Val Leu
            420                 425                 430

Gln Ser Ser Gly Leu Tyr Ser Leu Ser Ser Val Val Thr Val Pro Ser
        435                 440                 445

Ser Ser Leu Gly Thr Gln Thr Tyr Ile Cys Asn Val Asn His Lys Pro
    450                 455                 460

Ser Asn Thr Lys Val Asp Lys Arg Val Glu Pro Lys Ser Cys Asp Lys
465                 470                 475                 480

Thr His Thr Cys Pro Pro Cys Pro Ala Pro Glu Leu Leu Gly Gly Pro
                485                 490                 495

Ser Val Phe Leu Phe Pro Pro Lys Pro Lys Asp Thr Leu Met Ile Ser
            500                 505                 510

Arg Thr Pro Glu Val Thr Cys Val Val Val Asp Val Ser His Glu Asp
        515                 520                 525

Pro Glu Val Lys Phe Asn Trp Tyr Val Asp Gly Val Glu Val His Asn
    530                 535                 540

Ala Lys Thr Lys Pro Arg Glu Glu Gln Tyr Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
        595                 600                 605

Leu Pro Pro Ser Arg Glu Glu Met Thr Lys Asn Gln Val Ser Leu Thr
    610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Tyr Ser Lys Leu Thr Val Asp Lys
            660                 665                 670

Ser Arg Trp Gln Gln Gly Asn Val Phe Ser Cys Ser Val Met His Glu
```

```
        675                 680                 685

Ala Leu His Asn His Tyr Thr Gln Lys Ser Leu Ser Leu Ser Pro Gly
    690                 695                 700

Lys
705


<210> SEQ ID NO 160
<211> LENGTH: 2115
<212> TYPE: DNA
<213> ORGANISM: Artificial Sequence
<220> FEATURE:
<223> OTHER INFORMATION: Ts2GC2c/Bs1GC3a heavy chain nucl

<400> SEQUENCE: 160

gaggtgcagc tggtggaaag tgggggcgat ctggtcaaag ccggagggtc tctgcgactg      60

tcttgtgctg tgagcggcct gtccttcagc tcctctggca tgaactgggt gcgacaggct     120

cctggaaagg gactggagtg gatcagttca attagcgggt cccagaatta caagtactat     180

gcagactctg tcaaaggaag gttcgtggtc agccgggata acgccagaaa ttttctgtat     240

ctgcagatgg acagcctgcg cgccgaagat accgccgtgt acttctgcgt cggcgggttt     300

ccctattggc tgcctccaag cgacttttca gggtttcatg tctgggggca gggaactacc     360

gtgaccgtct catctggcgg gggaggctct gggggaggcg ggagtggagg cgggggatca     420

tcctacgtcc tgactcagcc acctagcgtg tccgtcgcac ctgggcagac agcatcactg     480

acttgcgggg gaaccaacat cggcagcaag agcgtgcact ggtaccagca gaaagccgga     540

caggctcccg tcctggtggt ctatgctgac aacgatcggc cctctggcgt gcctgaaaga     600

ttcagcggct ccaactctgg gaataccgca acactgacca tcagtagggt cgaggccgaa     660

gacgagtcag attacttttg ccaggtctgg gatgggaata ctgaccacgt cgtcttcgga     720

ggcggaacca aactgactgt cctgggcggg ggaggctctg gcgtgcagct ggtgcagagc     780

ggcggcggcc tggtgcagcc tggagggtca ctgagactgt catgcgcagc aagcgggttt     840

actgtgtcta caaactacat gtcttgggtg aggcaggcac ctggaaaggg actggagtgg     900

gtctcaatcc tgtacgctgg cggggtgacc cggtatgcag acagcgtcaa gacccggttc     960

acaattagca gagataactc caaaaatact ctgtttctgc agatgaatgc cctgtccgct    1020

gaagacaccg caatctacta ttgcgccaaa cactatgata gtgggtactc cactattgac    1080

cattttgact cttgggggca ggggactctg gtgactgtct cttcagcgtc gaccaagggc    1140

ccatcggtct tccccctggc accctcctcc aagagcacct ctgggggcac agcggccctg    1200

ggctgcctgg tcaaggacta cttccccgaa cctgtgacgg tctcgtggaa ctcaggcgcc    1260

ctgaccagcg gcgtgcacac cttcccggct gtcctacagt cctcaggact ctactccctc    1320

agcagcgtgg tgaccgtgcc ctccagcagc ttgggcaccc agacctacat ctgcaacgtg    1380

aatcacaagc ccagcaacac caaggtggac aagagagttg agcccaaatc ttgtgacaaa    1440

actcacacat gcccaccgtg cccagcacct gaactcctgg ggggaccgtc agtcttcctc    1500

ttccccccaa aacccaagga caccctcatg atctcccgga cccctgaggt cacatgcgtg    1560

gtggtggacg tgagccacga ggatcctgag gtcaagttca actggtacgt ggacggcgtg    1620

gaggtgcata atgccaagac aaagccgcgg gaggagcagt acaacagcac gtaccgtgtg    1680

gtcagcgtcc tcaccgtcct gcaccaggac tggctgaatg gcaaggagta caagtgcaag    1740

gtctccaaca aagccctccc agcccccatc gagaaaacca tctccaaagc caaagggcag    1800

ccccgagaac cacaggtgta caccctgccc ccatcccggg aggagatgac caagaaccag    1860
```

```
gtcagcctga cctgcctggt caaaggcttc tatcccagcg acatcgccgt ggagtgggag   1920

agcaatgggc agccggagaa caactacaag accacgcctc ccgtgctgga ctccgacggc   1980

tccttcttcc tctatagcaa gctcaccgtg gacaagagca ggtggcagca ggggaacgtc   2040

ttctcatgct ccgtgatgca tgaggctctg cacaaccact acacgcagaa gagcctctcc   2100

ctgtccccgg gtaaa                                                    2115


<210> SEQ ID NO 161
<211> LENGTH: 471
<212> TYPE: PRT
<213> ORGANISM: Artificial Sequence
<220> FEATURE:
<223> OTHER INFORMATION: Ts2GC2c/Bs2GC1d light chain aa

<400> SEQUENCE: 161

Gln Leu Gln Leu Val Gln Ser Gly Thr Glu Val Lys Lys Pro Gly Ala
1               5                   10                  15

Ser Val Lys Val Ser Cys Lys Ser Ser Gly Tyr Val Phe Thr Ser Tyr
            20                  25                  30

Tyr Leu Val Trp Val Arg Gln Ala Pro Gly Gln Gly Leu Glu Trp Met
        35                  40                  45

Ala Thr Ile Ser Pro Gly Asp Val Asn Thr Ser Tyr Glu Gln Arg Phe
    50                  55                  60

Gln Gly Arg Val Thr Val Thr Thr Asp Ala Ser Thr Asn Thr Val Asp
65                  70                  75                  80

Met Glu Leu Arg Ser Leu Arg Ser Glu Asp Thr Ala Val Tyr Tyr Cys
                85                  90                  95

Ala Arg Gly Pro Arg Ser Lys Pro Pro Tyr Leu Tyr Phe Ala Leu Asp
            100                 105                 110

Val Trp Gly Gln Gly Thr Ala Val Thr Val Ser Ser Gly Gly Gly Gly
        115                 120                 125

Ser Gly Gly Gly Gly Ser Gly Gly Gly Gly Ser Glu Ile Val Leu Thr
    130                 135                 140

Gln Ser Pro Gly Thr Leu Ser Leu Ser Pro Gly Glu Thr Ala Ile Leu
145                 150                 155                 160

Ser Cys Arg Ala Ser Gln Ser Val Ser Ser Ser Leu Leu Ala Trp Tyr
                165                 170                 175

Gln Gln Lys Pro Gly Gln Ala Pro Arg Leu Leu Ile Tyr Gly Ala Ser
            180                 185                 190

Asn Arg Ala Thr Gly Ile Arg Gly Arg Phe Ser Gly Ser Gly Ser Gly
        195                 200                 205

Thr Asp Phe Thr Leu Thr Ile Ser Arg Leu Glu Pro Glu Asp Phe Val
    210                 215                 220

Leu Tyr Tyr Cys Gln His Tyr Gly Ser Arg Val Thr Phe Gly Gln Gly
225                 230                 235                 240

Thr Lys Leu Glu Ile Lys Gly Gly Gly Gly Ser Asp Ile Gln Met Thr
                245                 250                 255

Gln Ser Pro Asp Ser Val Ala Val Ser Leu Gly Glu Arg Ala Thr Ile
            260                 265                 270

Asn Cys Lys Ser Ser Gln Ser Val Phe Tyr Thr Ser Lys Asn Lys Asn
        275                 280                 285

Tyr Leu Ala Trp Phe Gln Gln Lys Pro Gly Gln Pro Pro Lys Leu Leu
    290                 295                 300

Ile Tyr Trp Ala Ser Thr Arg Glu Ser Gly Val Pro Asp Arg Phe Ser
```

305 310 315 320

Gly Ser Gly Ser Gly Thr Asp Phe Thr Leu Thr Ile Ser Ser Leu Arg
325 330 335

Pro Glu Asp Val Ala Val Tyr Tyr Cys Gln Gln Tyr Tyr Ser Thr Pro
340 345 350

Phe Thr Phe Gly Pro Gly Thr Lys Val Asp Ile Lys Arg Thr Val Ala
355 360 365

Ala Pro Ser Val Phe Ile Phe Pro Pro Ser Asp Glu Gln Leu Lys Ser
370 375 380

Gly Thr Ala Ser Val Val Cys Leu Leu Asn Asn Phe Tyr Pro Arg Glu
385 390 395 400

Ala Lys Val Gln Trp Lys Val Asp Asn Ala Leu Gln Ser Gly Asn Ser
405 410 415

Gln Glu Ser Val Thr Glu Gln Asp Ser Lys Asp Ser Thr Tyr Ser Leu
420 425 430

Ser Ser Thr Leu Thr Leu Ser Lys Ala Asp Tyr Glu Lys His Lys Val
435 440 445

Tyr Ala Cys Glu Val Thr His Gln Gly Leu Ser Ser Pro Val Thr Lys
450 455 460

Ser Phe Asn Arg Gly Glu Cys
465 470

<210> SEQ ID NO 162
<211> LENGTH: 1413
<212> TYPE: DNA
<213> ORGANISM: Artificial Sequence
<220> FEATURE:
<223> OTHER INFORMATION: Ts2GC2c/Bs2GC1d light chain nucl

<400> SEQUENCE: 162
cagctgcagc tggtccagag cggcacagag gtgaaaaagc caggagcatc agtcaaagtg 60
tcttgtaagt catcaggata cgtcttcacc tcttactatc tggtgtgggt ccggcaggca 120
ccaggacagg gactggagtg gatggccaca atctctcccg gagacgtgaa cactagttac 180
gaacagcgat tccagggcag agtgaccgtc accacagacg cttcaactaa taccgtggat 240
atggagctgc ggagcctgag atccgaagat acagccgtct actattgcgc taggggggccc 300 cgcagcaagc ctccttatct gtatttcgct ctggatgtct gggggcaggg aacagcagtc 360
accgtctctt ctggcggggg aggctctggg ggaggcggga gtggaggcgg gggatcagaa 420
atcgtcctga cccagtcacc tggcaccctg agtctgagtc ctggcgaaac agcaatcctg 480
tcttgtcggg cttcacagtc cgtgagctcc tctctgctgg catggtacca gcagaagccc 540
ggacaggccc ctaggctgct gatctatggc gcctccaacc gcgctactgg cattcggggg 600
agattcagtg gctcagggag cggaaccgac tttaccctga caatcagccg gctggagccc 660
gaagatttcg tgctgtacta ctgtcagcat tatgggtcac gggtcacttt tgggcagggg 720
actaaactgg aaatcaaggg cgggggaggc tctgacattc agatgaccca gagtcctgac 780
agcgtggccg tctcactggg ggaaagggct actatcaatt gtaaaagttc acagtccgtc 840
ttctacacca gtaagaacaa aaactatctg gcctggtttc agcagaagcc aggccagccc 900
cctaaactgc tgatctactg ggctagcact agagagtctg gagtgccaga cagattctct 960
ggcagtgggt caggaaccga cttcaccctg acaattagct ccctgaggcc cgaagacgtg 1020
gccgtctatt attgtcagca gtattattct acccccttca cattcggacc tgggactaaa 1080
gtggatatca aacgtacggt ggctgcacca tctgtcttca tcttcccgcc atctgatgag 1140

```
cagttgaaat ctggaactgc ctctgttgtg tgcctgctga ataacttcta tcccagagag   1200

gccaaagtac agtggaaggt ggataacgcc ctccaatcgg gtaactccca ggagagtgtc   1260

acagagcagg acagcaagga cagcacctac agcctcagca gcaccctgac gctgagcaaa   1320

gcagactacg agaaacacaa agtctacgcc tgcgaagtca cccatcaggg cctgagctcg   1380

cccgtcacaa agagcttcaa caggggagag tgt                                1413


<210> SEQ ID NO 163
<211> LENGTH: 962
<212> TYPE: PRT
<213> ORGANISM: Artificial Sequence
<220> FEATURE:
<223> OTHER INFORMATION: Ts3GC2d heavy chain aa

<400> SEQUENCE: 163

Glu Val Gln Leu Val Glu Ser Gly Gly Asp Leu Val Lys Ala Gly Gly
1               5                   10                  15

Ser Leu Arg Leu Ser Cys Ala Val Ser Gly Leu Ser Phe Ser Ser Ser
            20                  25                  30

Gly Met Asn Trp Val Arg Gln Ala Pro Gly Lys Gly Leu Glu Trp Ile
        35                  40                  45

Ser Ser Ile Ser Gly Ser Gln Asn Tyr Lys Tyr Tyr Ala Asp Ser Val
    50                  55                  60

Lys Gly Arg Phe Val Val Ser Arg Asp Asn Ala Arg Asn Phe Leu Tyr
65                  70                  75                  80

Leu Gln Met Asp Ser Leu Arg Ala Glu Asp Thr Ala Val Tyr Phe Cys
                85                  90                  95

Val Gly Gly Phe Pro Tyr Trp Leu Pro Pro Ser Asp Phe Ser Gly Phe
            100                 105                 110

His Val Trp Gly Gln Gly Thr Thr Val Thr Val Ser Ser Gly Gly Gly
        115                 120                 125

Gly Ser Gly Gly Gly Gly Ser Gly Gly Gly Gly Ser Ser Tyr Val Leu
    130                 135                 140

Thr Gln Pro Pro Ser Val Ser Val Ala Pro Gly Gln Thr Ala Ser Leu
145                 150                 155                 160

Thr Cys Gly Gly Thr Asn Ile Gly Ser Lys Ser Val His Trp Tyr Gln
                165                 170                 175

Gln Lys Ala Gly Gln Ala Pro Val Leu Val Val Tyr Ala Asp Asn Asp
            180                 185                 190

Arg Pro Ser Gly Val Pro Glu Arg Phe Ser Gly Ser Asn Ser Gly Asn
        195                 200                 205

Thr Ala Thr Leu Thr Ile Ser Arg Val Glu Ala Glu Asp Glu Ser Asp
    210                 215                 220

Tyr Phe Cys Gln Val Trp Asp Gly Asn Thr Asp His Val Val Phe Gly
225                 230                 235                 240

Gly Gly Thr Lys Leu Thr Val Leu Gly Gly Gly Gly Ser Gln Leu Gln
                245                 250                 255

Leu Val Gln Ser Gly Thr Glu Val Lys Lys Pro Gly Ala Ser Val Lys
            260                 265                 270

Val Ser Cys Lys Ser Ser Gly Tyr Val Phe Thr Ser Tyr Tyr Leu Val
        275                 280                 285

Trp Val Arg Gln Ala Pro Gly Gln Gly Leu Glu Trp Met Ala Thr Ile
    290                 295                 300

Ser Pro Gly Asp Val Asn Thr Ser Tyr Glu Gln Arg Phe Gln Gly Arg
```

305 310 315 320

Val Thr Val Thr Thr Asp Ala Ser Thr Asn Thr Val Asp Met Glu Leu
325 330 335

Arg Ser Leu Arg Ser Glu Asp Thr Ala Val Tyr Tyr Cys Ala Arg Gly
340 345 350

Pro Arg Ser Lys Pro Pro Tyr Leu Tyr Phe Ala Leu Asp Val Trp Gly
355 360 365

Gln Gly Thr Ala Val Thr Val Ser Ser Ala Ser Thr Lys Gly Pro Ser
370 375 380

Val Phe Pro Leu Ala Pro Ser Ser Lys Ser Thr Ser Gly Gly Thr Ala
385 390 395 400

Ala Leu Gly Cys Leu Val Lys Asp Tyr Phe Pro Glu Pro Val Thr Val
405 410 415

Ser Trp Asn Ser Gly Ala Leu Thr Ser Gly Val His Thr Phe Pro Ala
420 425 430

Val Leu Gln Ser Ser Gly Leu Tyr Ser Leu Ser Ser Val Val Thr Val
435 440 445

Pro Ser Ser Ser Leu Gly Thr Gln Thr Tyr Ile Cys Asn Val Asn His
450 455 460

Lys Pro Ser Asn Thr Lys Val Asp Lys Arg Val Glu Pro Lys Ser Cys
465 470 475 480

Asp Lys Thr His Thr Cys Pro Pro Cys Pro Ala Pro Glu Leu Leu Gly
485 490 495

Gly Pro Ser Val Phe Leu Phe Pro Pro Lys Pro Lys Asp Thr Leu Met
500 505 510

Ile Ser Arg Thr Pro Glu Val Thr Cys Val Val Val Asp Val Ser His
515 520 525

Glu Asp Pro Glu Val Lys Phe Asn Trp Tyr Val Asp Gly Val Glu Val
530 535 540

His Asn Ala Lys Thr Lys Pro Arg Glu Glu Gln Tyr Asn Ser Thr Tyr
545 550 555 560

Arg Val Val Ser Val Leu Thr Val Leu His Gln Asp Trp Leu Asn Gly
565 570 575

Lys Glu Tyr Lys Cys Lys Val Ser Asn Lys Ala Leu Pro Ala Pro Ile
580 585 590

Glu Lys Thr Ile Ser Lys Ala Lys Gly Gln Pro Arg Glu Pro Gln Val
595 600 605

Tyr Thr Leu Pro Pro Ser Arg Glu Glu Met Thr Lys Asn Gln Val Ser
610 615 620

Leu Thr Cys Leu Val Lys Gly Phe Tyr Pro Ser Asp Ile Ala Val Glu
625 630 635 640

Trp Glu Ser Asn Gly Gln Pro Glu Asn Asn Tyr Lys Thr Thr Pro Pro
645 650 655

Val Leu Asp Ser Asp Gly Ser Phe Phe Leu Tyr Ser Lys Leu Thr Val
660 665 670

Asp Lys Ser Arg Trp Gln Gln Gly Asn Val Phe Ser Cys Ser Val Met
675 680 685

His Glu Ala Leu His Asn His Tyr Thr Gln Lys Ser Leu Ser Leu Ser
690 695 700

Pro Gly Lys Gly Gly Gly Gly Ser Gly Val Gln Leu Val Gln Ser Gly
705 710 715 720

Gly Gly Leu Val Gln Pro Gly Gly Ser Leu Arg Leu Ser Cys Ala Ala
725 730 735

Ser Gly Phe Thr Val Ser Thr Asn Tyr Met Ser Trp Val Arg Gln Ala
740 745 750

Pro Gly Lys Gly Leu Glu Trp Val Ser Ile Leu Tyr Ala Gly Gly Val
755 760 765

Thr Arg Tyr Ala Asp Ser Val Lys Thr Arg Phe Thr Ile Ser Arg Asp
770 775 780

Asn Ser Lys Asn Thr Leu Phe Leu Gln Met Asn Ala Leu Ser Ala Glu
785 790 795 800

Asp Thr Ala Ile Tyr Tyr Cys Ala Lys His Tyr Asp Ser Gly Tyr Ser
805 810 815

Thr Ile Asp His Phe Asp Ser Trp Gly Gln Gly Thr Leu Val Thr Val
820 825 830

Ser Ser Gly Gly Gly Gly Ser Gly Gly Gly Gly Ser Gly Gly Gly Gly
835 840 845

Ser Asp Ile Gln Met Thr Gln Ser Pro Asp Ser Val Ala Val Ser Leu
850 855 860

Gly Glu Arg Ala Thr Ile Asn Cys Lys Ser Ser Gln Ser Val Phe Tyr
865 870 875 880

Thr Ser Lys Asn Lys Asn Tyr Leu Ala Trp Phe Gln Gln Lys Pro Gly
885 890 895

Gln Pro Pro Lys Leu Leu Ile Tyr Trp Ala Ser Thr Arg Glu Ser Gly
900 905 910

Val Pro Asp Arg Phe Ser Gly Ser Gly Ser Gly Thr Asp Phe Thr Leu
915 920 925

Thr Ile Ser Ser Leu Arg Pro Glu Asp Val Ala Val Tyr Tyr Cys Gln
930 935 940

Gln Tyr Tyr Ser Thr Pro Phe Thr Phe Gly Pro Gly Thr Lys Val Asp
945 950 955 960

Ile Lys

<210> SEQ ID NO 164
<211> LENGTH: 2886
<212> TYPE: DNA
<213> ORGANISM: Artificial Sequence
<220> FEATURE:
<223> OTHER INFORMATION: Ts3GC2d heavy chain nucl

<400> SEQUENCE: 164
gaggtgcagc tggtggaaag cggaggggat ctggtgaaag caggagggag cctgagactg 60
tcatgcgccg tgagcgggct gtcattcagc tcctctggca tgaactgggt gcgacaggct 120
cctggaaagg gactggagtg gatcagttca attagcgggt cccagaatta caagtactat 180
gcagactctg tcaaaggaag gttcgtggtc agccgggata acgccagaaa ttttctgtat 240
ctgcagatgg acagcctgcg cgccgaagat accgccgtgt acttctgcgt cggcgggttt 300
ccctattggc tgcctccaag cgatttcagc ggatttcatg tctgggggca gggaactaca 360
gtgaccgtct catcaggcgg gggaggctct gggggaggcg ggagtggagg cgggggatca 420
tcttacgtcc tgacccagcc acctagcgtg agcgtcgcac cagggcagac agcttcactg 480
acttgcggag gcacaaacat tggcagcaag agcgtgcact ggtaccagca gaaagccgga 540
caggctcccg tcctggtggt ctatgctgac aacgatcggc cctctggcgt gcctgaaaga 600
ttcagcggct ccaactctgg gaataccgca acactgacca tcagtagggt cgaggccgaa 660
gacgagtcag attacttttg ccaggtgtgg gacggcaata ctgaccatgt cgtgttcggc 720

```
ggcgggacca aactgactgt gctgggcggg ggaggctctc agctgcagct ggtccagtca    780

ggcacagaag tcaaaaaacc cggcgcaagc gtgaaggtct catgtaaatc atcaggatac    840

gtctttacct cttactatct ggtgtgggtc cggcaggcac caggacaggg actggagtgg    900

atggccacaa tctctcccgg agacgtgaac actagttacg aacagcgatt ccagggcaga    960

gtgaccgtca ccacagacgc ttcaactaat accgtggata tggagctgcg gagcctgaga   1020

tccgaagata cagccgtcta ctattgcgct agggggcccc gcagcaagcc tccttatctg   1080

tacttcgctc tggatgtctg gggcaggggg accgccgtca ccgtctcaag cgcgtcgacc   1140

aagggcccat cggtcttccc cctggcaccc tcctccaaga gcacctctgg gggcacagcg   1200

gccctgggct gcctggtcaa ggactacttc cccgaacctg tgacggtctc gtggaactca   1260

ggcgccctga ccagcggcgt gcacaccttc ccggctgtcc tacagtcctc aggactctac   1320

tccctcagca gcgtggtgac cgtgccctcc agcagcttgg gcacccagac ctacatctgc   1380

aacgtgaatc acaagcccag caacaccaag gtggacaaga gagttgagcc caaatcttgt   1440

gacaaaactc acacatgccc accgtgccca gcacctgaac tcctgggggg accgtcagtc   1500

ttcctcttcc ccccaaaacc caaggacacc ctcatgatct cccggacccc tgaggtcaca   1560

tgcgtggtgg tggacgtgag ccacgaggat cctgaagtca agttcaactg gtacgtggat   1620

ggcgtcgagg tgcataatgc caagacaaaa ccccgggagg aacagtacaa ctcaacttat   1680

agagtcgtga gcgtcctgac cgtgctgcat caggactggc tgaacggcaa agaatacaag   1740

tgcaaagtgt ctaataaggc cctgcctgct ccaatcgaga aaacaattag caaggcaaaa   1800

gggcagccca gggaacctca ggtgtacact ctgcctccaa gccgcgagga aatgaccaag   1860

aaccaggtct ccctgacatg tctggtgaaa ggattctatc ctagtgacat tgccgtggag   1920

tgggaatcaa atggccagcc agagaacaat tacaagacca cacccccctgt gctggactct   1980

gatgggagtt tctttctgta ttccaagctg accgtggata aatctagatg gcagcaggga   2040

aatgtcttta gctgttccgt gatgcatgag gcactgcaca accattacac ccagaaatca   2100

ctgtcactgt ccccaggaaa aggcggggga ggctctggcg tgcagctggt ccagagcgga   2160

ggcggactgg tccagcccgg cggatcactg agactgtcat gtgccgcaag cgggtttacc   2220

gtctctacaa actacatgtc ttgggtgagg caggcacctg gaaagggact ggagtgggtc   2280

tcaatcctgt acgctggcgg ggtgacccgg tatgcagaca gcgtcaagac ccggttcaca   2340

attagcagag ataactccaa aaatactctg tttctgcaga tgaatgccct gtccgctgaa   2400

gacaccgcaa tctactattg cgccaaacac tatgatagtg ggtacagtac cattgaccat   2460

ttcgatagct gggggcaggg gactctggtg accgtctcat caggcggggg aggctctggg   2520

ggaggcggga gtggaggcgg gggatcagat attcagatga cccagagtcc tgattccgtc   2580

gctgtctcac tgggagaaag ggcaaccatt aactgtaaaa gctcacagag tgtcttctac   2640

accagtaaga acaaaaacta tctggcctgg tttcagcaga agccaggcca gccccctaaa   2700

ctgctgatct actgggctag cactagagag tctggagtgc cagacagatt ctctggcagt   2760

gggtcaggaa ccgacttcac cctgacaatt agctccctga ggcccgaaga cgtggccgtc   2820

tactattgtc agcagtatta ttcaacaccc ttcacattcg gaccaggaac aaaagtggat   2880

attaag                                                              2886
```

<210> SEQ ID NO 165
<211> LENGTH: 956
<212> TYPE: PRT
<213> ORGANISM: Artificial Sequence
<220> FEATURE:
<223> OTHER INFORMATION: Ts3GC2e heavy chain aa

<400> SEQUENCE: 165

```
Glu Val Gln Leu Val Glu Ser Gly Gly Asp Leu Val Lys Ala Gly Gly
1               5                   10                  15

Ser Leu Arg Leu Ser Cys Ala Val Ser Gly Leu Ser Phe Ser Ser Ser
            20                  25                  30

Gly Met Asn Trp Val Arg Gln Ala Pro Gly Lys Gly Leu Glu Trp Ile
        35                  40                  45

Ser Ser Ile Ser Gly Ser Gln Asn Tyr Lys Tyr Tyr Ala Asp Ser Val
    50                  55                  60

Lys Gly Arg Phe Val Val Ser Arg Asp Asn Ala Arg Asn Phe Leu Tyr
65                  70                  75                  80

Leu Gln Met Asp Ser Leu Arg Ala Glu Asp Thr Ala Val Tyr Phe Cys
                85                  90                  95

Val Gly Gly Phe Pro Tyr Trp Leu Pro Pro Ser Asp Phe Ser Gly Phe
            100                 105                 110

His Val Trp Gly Gln Gly Thr Thr Val Thr Val Ser Ser Gly Gly Gly
        115                 120                 125

Gly Ser Gly Gly Gly Gly Ser Gly Gly Gly Gly Ser Ser Tyr Val Leu
    130                 135                 140

Thr Gln Pro Pro Ser Val Ser Val Ala Pro Gly Gln Thr Ala Ser Leu
145                 150                 155                 160

Thr Cys Gly Gly Thr Asn Ile Gly Ser Lys Ser Val His Trp Tyr Gln
                165                 170                 175

Gln Lys Ala Gly Gln Ala Pro Val Leu Val Val Tyr Ala Asp Asn Asp
            180                 185                 190

Arg Pro Ser Gly Val Pro Glu Arg Phe Ser Gly Ser Asn Ser Gly Asn
        195                 200                 205

Thr Ala Thr Leu Thr Ile Ser Arg Val Glu Ala Glu Asp Glu Ser Asp
    210                 215                 220

Tyr Phe Cys Gln Val Trp Asp Gly Asn Thr Asp His Val Val Phe Gly
225                 230                 235                 240

Gly Gly Thr Lys Leu Thr Val Leu Gly Gly Gly Gly Ser Gly Val Gln
                245                 250                 255

Leu Val Gln Ser Gly Gly Gly Leu Val Gln Pro Gly Gly Ser Leu Arg
            260                 265                 270

Leu Ser Cys Ala Ala Ser Gly Phe Thr Val Ser Thr Asn Tyr Met Ser
        275                 280                 285

Trp Val Arg Gln Ala Pro Gly Lys Gly Leu Glu Trp Val Ser Ile Leu
    290                 295                 300

Tyr Ala Gly Gly Val Thr Arg Tyr Ala Asp Ser Val Lys Thr Arg Phe
305                 310                 315                 320

Thr Ile Ser Arg Asp Asn Ser Lys Asn Thr Leu Phe Leu Gln Met Asn
                325                 330                 335

Ala Leu Ser Ala Glu Asp Thr Ala Ile Tyr Tyr Cys Ala Lys His Tyr
            340                 345                 350

Asp Ser Gly Tyr Ser Thr Ile Asp His Phe Asp Ser Trp Gly Gln Gly
        355                 360                 365

Thr Leu Val Thr Val Ser Ser Ala Ser Thr Lys Gly Pro Ser Val Phe
    370                 375                 380

Pro Leu Ala Pro Ser Ser Lys Ser Thr Ser Gly Gly Thr Ala Ala Leu
385                 390                 395                 400
```

```
Gly Cys Leu Val Lys Asp Tyr Phe Pro Glu Pro Val Thr Val Ser Trp
                405                 410                 415

Asn Ser Gly Ala Leu Thr Ser Gly Val His Thr Phe Pro Ala Val Leu
            420                 425                 430

Gln Ser Ser Gly Leu Tyr Ser Leu Ser Ser Val Val Thr Val Pro Ser
        435                 440                 445

Ser Ser Leu Gly Thr Gln Thr Tyr Ile Cys Asn Val Asn His Lys Pro
    450                 455                 460

Ser Asn Thr Lys Val Asp Lys Arg Val Glu Pro Lys Ser Cys Asp Lys
465                 470                 475                 480

Thr His Thr Cys Pro Pro Cys Pro Ala Pro Glu Leu Leu Gly Gly Pro
                485                 490                 495

Ser Val Phe Leu Phe Pro Pro Lys Pro Lys Asp Thr Leu Met Ile Ser
            500                 505                 510

Arg Thr Pro Glu Val Thr Cys Val Val Val Asp Val Ser His Glu Asp
        515                 520                 525

Pro Glu Val Lys Phe Asn Trp Tyr Val Asp Gly Val Glu Val His Asn
    530                 535                 540

Ala Lys Thr Lys Pro Arg Glu Glu Gln Tyr Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
        595                 600                 605

Leu Pro Pro Ser Arg Glu Glu Met Thr Lys Asn Gln Val Ser Leu Thr
    610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Tyr Ser Lys Leu Thr Val Asp Lys
            660                 665                 670

Ser Arg Trp Gln Gln Gly Asn Val Phe Ser Cys Ser Val Met His Glu
        675                 680                 685

Ala Leu His Asn His Tyr Thr Gln Lys Ser Leu Ser Leu Ser Pro Gly
    690                 695                 700

Lys Gly Gly Gly Gly Ser Gln Leu Gln Leu Val Gln Ser Gly Thr Glu
705                 710                 715                 720

Val Lys Lys Pro Gly Ala Ser Val Lys Val Ser Cys Lys Ser Ser Gly
                725                 730                 735

Tyr Val Phe Thr Ser Tyr Tyr Leu Val Trp Val Arg Gln Ala Pro Gly
            740                 745                 750

Gln Gly Leu Glu Trp Met Ala Thr Ile Ser Pro Gly Asp Val Asn Thr
        755                 760                 765

Ser Tyr Glu Gln Arg Phe Gln Gly Arg Val Thr Val Thr Thr Asp Ala
    770                 775                 780

Ser Thr Asn Thr Val Asp Met Glu Leu Arg Ser Leu Arg Ser Glu Asp
785                 790                 795                 800

Thr Ala Val Tyr Tyr Cys Ala Arg Gly Pro Arg Ser Lys Pro Pro Tyr
                805                 810                 815
```

```
Leu Tyr Phe Ala Leu Asp Val Trp Gly Gln Gly Thr Ala Val Thr Val
            820                 825                 830

Ser Ser Gly Gly Gly Gly Ser Gly Gly Gly Gly Ser Gly Gly Gly Gly
        835                 840                 845

Ser Glu Ile Val Leu Thr Gln Ser Pro Gly Thr Leu Ser Leu Ser Pro
    850                 855                 860

Gly Glu Thr Ala Ile Leu Ser Cys Arg Ala Ser Gln Ser Val Ser Ser
865                 870                 875                 880

Ser Leu Leu Ala Trp Tyr Gln Gln Lys Pro Gly Gln Ala Pro Arg Leu
                885                 890                 895

Leu Ile Tyr Gly Ala Ser Asn Arg Ala Thr Gly Ile Arg Gly Arg Phe
            900                 905                 910

Ser Gly Ser Gly Ser Gly Thr Asp Phe Thr Leu Thr Ile Ser Arg Leu
        915                 920                 925

Glu Pro Glu Asp Phe Val Leu Tyr Tyr Cys Gln His Tyr Gly Ser Arg
    930                 935                 940

Val Thr Phe Gly Gln Gly Thr Lys Leu Glu Ile Lys
945                 950                 955


<210> SEQ ID NO 166
<211> LENGTH: 2868
<212> TYPE: DNA
<213> ORGANISM: Artificial Sequence
<220> FEATURE:
<223> OTHER INFORMATION: Ts3GC2e heavy chain nucl

<400> SEQUENCE: 166

gaggtgcagc tggtggaaag tgggggcgat ctggtcaaag ccggagggtc tctgcgactg      60

tcttgtgctg tgagcggcct gtccttcagc tcctctggca tgaactgggt gcgacaggct     120

cctggaaagg gactggagtg gatcagttca attagcgggt cccagaatta caagtactat     180

gcagactctg tcaaaggaag gttcgtggtc agccgggata acgccagaaa ttttctgtat     240

ctgcagatgg acagcctgcg cgccgaagat accgccgtgt acttctgcgt cggcgggttt     300

ccctattggc tgcctccaag cgacttttca gggtttcatg tctgggggca gggaactacc     360

gtgaccgtct catctggcgg gggaggctct gggggaggcg ggagtggagg cgggggatca     420

tcctacgtcc tgactcagcc acctagcgtg tccgtcgcac ctgggcagac agcatcactg     480

acttgcgggg gaaccaacat cggcagcaag agcgtgcact ggtaccagca gaaagccgga     540

caggctcccg tcctggtggt ctatgctgac aacgatcggc cctctggcgt gcctgaaaga     600

ttcagcggct ccaactctgg gaataccgca acactgacca tcagtagggt cgaggccgaa     660

gacgagtcag attacttttg ccaggtctgg gatgggaata ctgaccacgt cgtcttcgga     720

ggcggaacca aactgactgt cctgggcggg ggaggctctg gcgtgcagct ggtgcagagc     780

ggcggcggcc tggtgcagcc tggagggtca ctgagactgt catgcgcagc aagcgggttt     840

actgtgtcta caaactacat gtcttgggtg aggcaggcac ctggaaaggg actggagtgg     900

gtctcaatcc tgtacgctgg cggggtgacc cggtatgcag acagcgtcaa gacccggttc     960

acaattagca gagataactc caaaaatact ctgtttctgc agatgaatgc cctgtccgct    1020

gaagacaccg caatctacta ttgcgccaaa cactatgata gtgggtactc cactattgac    1080

cattttgact cttgggggca ggggactctg gtgactgtct cttcagcgtc gaccaagggc    1140

ccatcggtct tccccctggc accctcctcc aagagcacct ctgggggcac agcggccctg    1200

ggctgcctgg tcaaggacta cttccccgaa cctgtgacgg tctcgtggaa ctcaggcgcc    1260
```

```
ctgaccagcg gcgtgcacac cttcccggct gtcctacagt cctcaggact ctactccctc   1320

agcagcgtgg tgaccgtgcc ctccagcagc ttgggcaccc agacctacat ctgcaacgtg   1380

aatcacaagc ccagcaacac caaggtggac aagagagttg agcccaaatc ttgtgacaaa   1440

actcacacat gcccaccgtg cccagcacct gaactcctgg ggggaccgtc agtcttcctc   1500

ttccccccaa aacccaagga caccctcatg atctcccgga cccctgaggt cacatgcgtg   1560

gtggtggacg tgagccacga ggatcctgaa gtcaagttca actggtacgt ggatggcgtc   1620

gaggtgcata atgccaagac aaaaccccgg gaggaacagt acaactcaac ttatagagtc   1680

gtgagcgtcc tgaccgtgct gcatcaggac tggctgaacg gcaaagaata caagtgcaaa   1740

gtgtctaata aggccctgcc tgctccaatc gagaaaacaa ttagcaaggc aaaagggcag   1800

cccagggaac ctcaggtgta cactctgcct ccaagccgcg aggaaatgac caagaaccag   1860

gtctccctga catgtctggt gaaaggattc tatcctagtg acattgccgt ggagtgggaa   1920

tcaaatggcc agccagagaa caattacaag accacacccc ctgtgctgga ctctgatggg   1980

agtttctttc tgtattccaa gctgaccgtg gataaatcta gatggcagca gggaaatgtc   2040

tttagctgtt ccgtgatgca tgaggcactg cacaaccatt acacccagaa atcactgtca   2100

ctgtccccag gaaaaggcgg gggaggctct cagctgcagc tggtccagag cggaaccgaa   2160

gtgaagaaac ccggcgcaag cgtcaaagtc tcatgcaaat caagcggata cgtcttcacc   2220

tcttactatc tggtgtgggt ccggcaggca ccaggacagg gactggagtg gatggccaca   2280

atctctcccg gagacgtgaa cactagttac gaacagcgat tccagggcag agtgaccgtc   2340

accacagacg cttcaactaa taccgtggat atggagctgc ggagcctgag atccgaagat   2400

acagccgtct actattgcgc tagggggccc cgcagcaagc ctccttatct gtatttcgct   2460

ctggatgtct gggggcaggg aacagcagtc accgtctcaa gcggcggggg aggctctggg   2520

ggaggcggga gtggaggcgg gggatcagag attgtcctga cccagtcacc tggcaccctg   2580

agcctgagtc ctggagagac cgctattctg tcttgtcggg catcacagtc cgtgagctcc   2640

tctctgctgg catggtacca gcagaagccc ggacaggccc ctaggctgct gatctatggc   2700

gcctccaacc gcgctactgg cattcggggg agattcagtg gctcagggag cggaaccgac   2760

tttaccctga caatcagccg gctggagccc gaagatttcg tgctgtacta ttgtcagcat   2820

tatggaagca gggtcacctt cggacaggga actaaactgg aaatcaag                2868
```

<210> SEQ ID NO 167
<211> LENGTH: 709
<212> TYPE: PRT
<213> ORGANISM: Artificial Sequence
<220> FEATURE:
<223> OTHER INFORMATION: Bs3GC1a heavy chain aa

<400> SEQUENCE: 167

```
Gln Leu Gln Leu Val Gln Ser Gly Thr Glu Val Lys Lys Pro Gly Ala
1               5                   10                  15

Ser Val Lys Val Ser Cys Lys Ser Ser Gly Tyr Val Phe Thr Ser Tyr
            20                  25                  30

Tyr Leu Val Trp Val Arg Gln Ala Pro Gly Gln Gly Leu Glu Trp Met
        35                  40                  45

Ala Thr Ile Ser Pro Gly Asp Val Asn Thr Ser Tyr Glu Gln Arg Phe
    50                  55                  60

Gln Gly Arg Val Thr Val Thr Thr Asp Ala Ser Thr Asn Thr Val Asp
65                  70                  75                  80
```

-continued

```
Met Glu Leu Arg Ser Leu Arg Ser Glu Asp Thr Ala Val Tyr Tyr Cys
                85                  90                  95

Ala Arg Gly Pro Arg Ser Lys Pro Pro Tyr Leu Tyr Phe Ala Leu Asp
            100                 105                 110

Val Trp Gly Gln Gly Thr Ala Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Gly Gly Ser Gly Val Gln Leu Val
    450                 455                 460

Gln Ser Gly Gly Gly Leu Val Gln Pro Gly Gly Ser Leu Arg Leu Ser
465                 470                 475                 480

Cys Ala Ala Ser Gly Phe Thr Val Ser Thr Asn Tyr Met Ser Trp Val
                485                 490                 495

Arg Gln Ala Pro Gly Lys Gly Leu Glu Trp Val Ser Ile Leu Tyr Ala
```

```
            500                 505                 510

Gly Gly Val Thr Arg Tyr Ala Asp Ser Val Lys Thr Arg Phe Thr Ile
        515                 520                 525

Ser Arg Asp Asn Ser Lys Asn Thr Leu Phe Leu Gln Met Asn Ala Leu
    530                 535                 540

Ser Ala Glu Asp Thr Ala Ile Tyr Tyr Cys Ala Lys His Tyr Asp Ser
545                 550                 555                 560

Gly Tyr Ser Thr Ile Asp His Phe Asp Ser Trp Gly Gln Gly Thr Leu
                565                 570                 575

Val Thr Val Ser Ser Gly Gly Gly Gly Ser Gly Gly Gly Gly Ser Gly
            580                 585                 590

Gly Gly Gly Ser Asp Ile Gln Met Thr Gln Ser Pro Asp Ser Val Ala
        595                 600                 605

Val Ser Leu Gly Glu Arg Ala Thr Ile Asn Cys Lys Ser Ser Gln Ser
    610                 615                 620

Val Phe Tyr Thr Ser Lys Asn Lys Asn Tyr Leu Ala Trp Phe Gln Gln
625                 630                 635                 640

Lys Pro Gly Gln Pro Pro Lys Leu Leu Ile Tyr Trp Ala Ser Thr Arg
                645                 650                 655

Glu Ser Gly Val Pro Asp Arg Phe Ser Gly Ser Gly Ser Gly Thr Asp
            660                 665                 670

Phe Thr Leu Thr Ile Ser Ser Leu Arg Pro Glu Asp Val Ala Val Tyr
        675                 680                 685

Tyr Cys Gln Gln Tyr Tyr Ser Thr Pro Phe Thr Phe Gly Pro Gly Thr
    690                 695                 700

Lys Val Asp Ile Lys
705
```

<210> SEQ ID NO 168
<211> LENGTH: 2127
<212> TYPE: DNA
<213> ORGANISM: Artificial Sequence
<220> FEATURE:
<223> OTHER INFORMATION: Bs3GC1a heavy chain nucl

<400> SEQUENCE: 168

```
cagctgcagc tggtccagtc aggcacagag gtcaaaaagc caggagcatc agtgaaggtg     60

tcttgtaagt catcaggata cgtgttcacc tcttactatc tggtgtgggt ccggcaggca    120

ccaggacagg gactggagtg gatggccaca atctctcccg gagacgtgaa cactagttac    180

gaacagcgat tccagggcag agtgaccgtc accacagacg cttcaactaa taccgtggat    240

atggagctgc ggagcctgag atccgaagat acagccgtct actattgcgc taggggggccc    300

cgcagcaagc ctccttatct gtattttgct ctggatgtgt gggggcaggg gaccgctgtc    360

accgtgtcaa gcgcgtcgac caagggccca tcggtcttcc ccctggcacc ctcctccaag    420

agcacctctg ggggcacagc ggccctgggc tgcctggtca aggactactt ccccgaacct    480

gtgacggtct cgtggaactc aggcgccctg accagcggcg tgcacacctt cccggctgtc    540

ctacagtcct caggactcta ctccctcagc agcgtggtga ccgtgccctc cagcagcttg    600

ggcacccaga cctacatctg caacgtgaat cacaagccca gcaacaccaa ggtggacaag    660

agagttgagc ccaaatcttg tgacaaaact cacacatgcc caccgtgccc agcacctgaa    720

ctcctggggg gaccgtcagt cttcctcttc cccccaaaac ccaaggacac cctcatgatc    780

tcccggaccc ctgaggtcac atgcgtggtg gtggacgtga gccacgagga tcctgaagtc    840
```

-continued aagttcaact ggtacgtgga tggcgtcgag gtgcataatg ccaagacaaa accccgggag 900
gaacagtaca actcaactta tagagtcgtg agcgtcctga ccgtgctgca tcaggactgg 960
ctgaacggca aagaatacaa gtgcaaagtg tctaataagg ccctgcctgc tccaatcgag 1020
aaaacaatta gcaaggcaaa agggcagccc agggaacctc aggtgtacac tctgcctcca 1080
agccgcgagg aaatgaccaa gaaccaggtc tccctgacat gtctggtgaa aggattctat 1140
cctagtgaca ttgccgtgga gtgggaatca aatggccagc cagagaacaa ttacaagacc 1200 acacccccctg tgctggactc tgatgggagt ttctttctgt attccaagct gaccgtggat 1260
aaatctagat ggcagcaggg aaatgtcttt agctgttccg tgatgcatga ggcactgcac 1320
aaccattaca cccagaaatc actgtcactg tccccaggaa aaggcggggg aggctctggc 1380
gtgcagctgg tccagagcgg aggcggactg gtccagcccg gcggatcact gagactgtca 1440
tgtgccgcaa gcgggtttac cgtctctaca aactacatgt cttgggtgag gcaggcacct 1500
ggaaagggac tggagtgggt ctcaatcctg tacgctggcg gggtgacccg gtatgcagac 1560
agcgtcaaga cccggttcac aattagcaga gataactcca aaaatactct gtttctgcag 1620
atgaatgccc tgtccgctga agacaccgca atctactatt gcgccaaaca ctatgatagt 1680
gggtacagta ccattgacca tttcgatagc tgggggcagg ggactctggt gaccgtctca 1740
tcaggcgggg gaggctctgg gggaggcggg agtggaggcg gggatcaga tattcagatg 1800 acccagagtc ctgattccgt cgctgtctca ctgggagaaa gggcaaccat taactgtaaa 1860
agctcacaga gtgtcttcta caccagtaag aacaaaaact atctggcctg gtttcagcag 1920
aagccaggcc agccccctaa actgctgatc tactgggcta gcactagaga gtctggagtg 1980
ccagacagat tctctggcag tgggtcagga accgacttca ccctgacaat tagctccctg 2040
aggcccgaag acgtggccgt ctactattgt cagcagtatt attcaacacc cttcacattc 2100
ggaccaggaa caaaagtgga tattaag 2127

<210> SEQ ID NO 169
<211> LENGTH: 703
<212> TYPE: PRT
<213> ORGANISM: Artificial Sequence
<220> FEATURE:
<223> OTHER INFORMATION: Bs3GC1b heavy chain aa

<400> SEQUENCE: 169

Gly Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Ser Thr Asn
            20                  25                  30

Tyr Met Ser Trp Val Arg Gln Ala Pro Gly Lys Gly Leu Glu Trp Val
        35                  40                  45

Ser Ile Leu Tyr Ala Gly Gly Val Thr Arg Tyr Ala Asp Ser Val Lys
    50                  55                  60

Thr Arg Phe Thr Ile Ser Arg Asp Asn Ser Lys Asn Thr Leu Phe Leu
65                  70                  75                  80

Gln Met Asn Ala Leu Ser Ala Glu Asp Thr Ala Ile Tyr Tyr Cys Ala
                85                  90                  95

Lys His Tyr Asp Ser Gly Tyr Ser Thr Ile Asp His Phe Asp Ser Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr

-continued

```
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys Gly Gly Gly Gly Ser Gln Leu Gln Leu Val Gln Ser
    450                 455                 460

Gly Thr Glu Val Lys Lys Pro Gly Ala Ser Val Lys Val Ser Cys Lys
465                 470                 475                 480

Ser Ser Gly Tyr Val Phe Thr Ser Tyr Tyr Leu Val Trp Val Arg Gln
                485                 490                 495

Ala Pro Gly Gln Gly Leu Glu Trp Met Ala Thr Ile Ser Pro Gly Asp
            500                 505                 510

Val Asn Thr Ser Tyr Glu Gln Arg Phe Gln Gly Arg Val Thr Val Thr
        515                 520                 525

Thr Asp Ala Ser Thr Asn Thr Val Asp Met Glu Leu Arg Ser Leu Arg
    530                 535                 540

Ser Glu Asp Thr Ala Val Tyr Tyr Cys Ala Arg Gly Pro Arg Ser Lys
545                 550                 555                 560
```

```
Pro Pro Tyr Leu Tyr Phe Ala Leu Asp Val Trp Gly Gln Gly Thr Ala
                565                 570                 575

Val Thr Val Ser Ser Gly Gly Gly Gly Ser Gly Gly Gly Gly Ser Gly
            580                 585                 590

Gly Gly Gly Ser Glu Ile Val Leu Thr Gln Ser Pro Gly Thr Leu Ser
        595                 600                 605

Leu Ser Pro Gly Glu Thr Ala Ile Leu Ser Cys Arg Ala Ser Gln Ser
    610                 615                 620

Val Ser Ser Ser Leu Leu Ala Trp Tyr Gln Gln Lys Pro Gly Gln Ala
625                 630                 635                 640

Pro Arg Leu Leu Ile Tyr Gly Ala Ser Asn Arg Ala Thr Gly Ile Arg
                645                 650                 655

Gly Arg Phe Ser Gly Ser Gly Ser Gly Thr Asp Phe Thr Leu Thr Ile
            660                 665                 670

Ser Arg Leu Glu Pro Glu Asp Phe Val Leu Tyr Tyr Cys Gln His Tyr
        675                 680                 685

Gly Ser Arg Val Thr Phe Gly Gln Gly Thr Lys Leu Glu Ile Lys
    690                 695                 700


<210> SEQ ID NO 170
<211> LENGTH: 2109
<212> TYPE: DNA
<213> ORGANISM: Artificial Sequence
<220> FEATURE:
<223> OTHER INFORMATION: Bs3GC1b heavy chain nucl

<400> SEQUENCE: 170

ggggtgcaac tggtgcagtc tgggggaggc ttggtccagc cggggggggtc cctgagactc      60

tcctgtgcag cctctggatt caccgtcagt accaactaca tgagctgggt ccgccaggct     120

ccagggaagg ggctggagtg ggtctcaatt ctttatgccg gaggtgtcac aaggtacgca     180

gactccgtga agaccagatt caccatctcc agagacaatt ccaagaacac tctctttctt     240

caaatgaacg ccctgagcgc cgaggacacg gctatatatt actgtgcgaa acactatgat     300

tcgggatatt ctaccataga tcactttgac tcctggggcc agggaaccct ggtcaccgtc     360

tcctcagcgt cgaccaaggg cccatcggtc ttccccctgg caccctcctc caagagcacc     420

tctgggggca cagcggccct gggctgcctg gtcaaggact acttccccga acctgtgacg     480

gtctcgtgga actcaggcgc cctgaccagc ggcgtgcaca ccttcccggc tgtcctacag     540

tcctcaggac tctactccct cagcagcgtg gtgaccgtgc cctccagcag cttgggcacc     600

cagacctaca tctgcaacgt gaatcacaag cccagcaaca ccaaggtgga caagagagtt     660

gagcccaaat cttgtgacaa aactcacaca tgcccaccgt gcccagcacc tgaactcctg     720

gggggaccgt cagtcttcct cttcccccca aaacccaagg acaccctcat gatctcccgg     780

acccctgagg tcacatgcgt ggtggtggac gtgagccacg aggatcctga agtcaagttc     840

aactggtacg tggatggcgt cgaggtgcat aatgccaaga caaaaccccg ggaggaacag     900

tacaactcaa cttatagagt cgtgagcgtc ctgaccgtgc tgcatcagga ctggctgaac     960

ggcaaagaat acaagtgcaa agtgtctaat aaggccctgc ctgctccaat cgagaaaaca    1020

attagcaagg caaaagggca gcccagggaa cctcaggtgt acactctgcc tccaagccgc    1080

gaggaaatga ccaagaacca ggtctccctg acatgtctgg tgaaaggatt ctatcctagt    1140

gacattgccg tggagtggga atcaaatggc cagccagaga acaattacaa gaccacaccc    1200

cctgtgctgg actctgatgg gagtttcttt ctgtattcca agctgaccgt ggataaatct    1260
```

```
agatggcagc agggaaatgt ctttagctgt tccgtgatgc atgaggcact gcacaaccat   1320

tacacccaga aatcactgtc actgtcccca ggaaaaggcg gggaggctc tcagctgcag   1380

ctggtccaga gcggaaccga agtgaagaaa cccggcgcaa gcgtcaaagt ctcatgcaaa   1440

tcaagcggat acgtcttcac ctcttactat ctggtgtggg tccggcaggc accaggacag   1500

ggactggagt ggatggccac aatctctccc ggagacgtga acactagtta cgaacagcga   1560

ttccagggca gagtgaccgt caccacagac gcttcaacta ataccgtgga tatggagctg   1620

cggagcctga gatccgaaga tacagccgtc tactattgcg ctagggggcc ccgcagcaag   1680

cctccttatc tgtatttcgc tctggatgtc tgggggcagg gaacagcagt caccgtctca   1740

agcggcgggg gaggctctgg gggaggcggg agtggaggcg gggatcaga gattgtcctg    1800

acccagtcac ctggcaccct gagcctgagt cctggagaga ccgctattct gtcttgtcgg   1860

gcatcacagt ccgtgagctc ctctctgctg gcatggtacc agcagaagcc cggacaggcc   1920

cctaggctgc tgatctatgg cgcctccaac cgcgctactg gcattcgggg gagattcagt   1980

ggctcaggga gcggaaccga ctttaccctg acaatcagcc ggctggagcc cgaagatttc   2040

gtgctgtact attgtcagca ttatggaagc agggtcacct tcggacaggg aactaaactg   2100

gaaatcaag                                                           2109
```

```
<210> SEQ ID NO 171
<211> LENGTH: 706
<212> TYPE: PRT
<213> ORGANISM: Artificial Sequence
<220> FEATURE:
<223> OTHER INFORMATION: Bs3GC2b heavy chain aa

<400> SEQUENCE: 171

Glu Val Gln Leu Val Glu Ser Gly Gly Asp Leu Val Lys Ala Gly Gly
1               5                   10                  15

Ser Leu Arg Leu Ser Cys Ala Val Ser Gly Leu Ser Phe Ser Ser Ser
            20                  25                  30

Gly Met Asn Trp Val Arg Gln Ala Pro Gly Lys Gly Leu Glu Trp Ile
        35                  40                  45

Ser Ser Ile Ser Gly Ser Gln Asn Tyr Lys Tyr Tyr Ala Asp Ser Val
    50                  55                  60

Lys Gly Arg Phe Val Val Ser Arg Asp Asn Ala Arg Asn Phe Leu Tyr
65                  70                  75                  80

Leu Gln Met Asp Ser Leu Arg Ala Glu Asp Thr Ala Val Tyr Phe Cys
                85                  90                  95

Val Gly Gly Phe Pro Tyr Trp Leu Pro Pro Ser Asp Phe Ser Gly Phe
            100                 105                 110

His Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205
```

```
Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Gly Gly Gly Gly Ser Gln Leu Gln Leu
    450                 455                 460

Val Gln Ser Gly Thr Glu Val Lys Lys Pro Gly Ala Ser Val Lys Val
465                 470                 475                 480

Ser Cys Lys Ser Ser Gly Tyr Val Phe Thr Ser Tyr Tyr Leu Val Trp
                485                 490                 495

Val Arg Gln Ala Pro Gly Gln Gly Leu Glu Trp Met Ala Thr Ile Ser
            500                 505                 510

Pro Gly Asp Val Asn Thr Ser Tyr Glu Gln Arg Phe Gln Gly Arg Val
        515                 520                 525

Thr Val Thr Thr Asp Ala Ser Thr Asn Thr Val Asp Met Glu Leu Arg
    530                 535                 540

Ser Leu Arg Ser Glu Asp Thr Ala Val Tyr Tyr Cys Ala Arg Gly Pro
545                 550                 555                 560

Arg Ser Lys Pro Pro Tyr Leu Tyr Phe Ala Leu Asp Val Trp Gly Gln
                565                 570                 575

Gly Thr Ala Val Thr Val Ser Ser Gly Gly Gly Gly Ser Gly Gly Gly
            580                 585                 590

Gly Ser Gly Gly Gly Gly Ser Glu Ile Val Leu Thr Gln Ser Pro Gly
        595                 600                 605

Thr Leu Ser Leu Ser Pro Gly Glu Thr Ala Ile Leu Ser Cys Arg Ala
    610                 615                 620
```

```
Ser Gln Ser Val Ser Ser Ser Leu Leu Ala Trp Tyr Gln Gln Lys Pro
625                 630                 635                 640

Gly Gln Ala Pro Arg Leu Leu Ile Tyr Gly Ala Ser Asn Arg Ala Thr
                645                 650                 655

Gly Ile Arg Gly Arg Phe Ser Gly Ser Gly Ser Gly Thr Asp Phe Thr
            660                 665                 670

Leu Thr Ile Ser Arg Leu Glu Pro Glu Asp Phe Val Leu Tyr Tyr Cys
        675                 680                 685

Gln His Tyr Gly Ser Arg Val Thr Phe Gly Gln Gly Thr Lys Leu Glu
    690                 695                 700

Ile Lys
705


<210> SEQ ID NO 172
<211> LENGTH: 2118
<212> TYPE: DNA
<213> ORGANISM: Artificial Sequence
<220> FEATURE:
<223> OTHER INFORMATION: Bs3GC2b heavy chain nucl

<400> SEQUENCE: 172

gaggtacaat tggtggagtc tggggggagac ctggtcaagg cgggggggtc cctgagactc     60

tcctgtgccg tctctggatt gtccttcagt agttcaggca tgaattgggt ccgccaggct    120

ccagggaagg ggctggagtg gatctcatcg attagtggta gtcagaacta caaatactat    180

gcagactcag tgaagggccg attcgtcgtc tccagagaca acgcccgcaa ctttctatat    240

ctgcaaatgg acagcctgag ggccgaggat acggctgtgt atttttgtgt gggaggtttc    300

ccctattggt tacccccgag cgacttctcc ggtttccatg tctggggcca agggaccacg    360

gtcaccgtct cctcagcgtc gaccaagggc ccatcggtct tcccccctggc accctcctcc    420

aagagcacct ctgggggcac agcggccctg ggctgcctgg tcaaggacta cttccccgaa    480

cctgtgacgg tctcgtggaa ctcaggcgcc ctgaccagcg gcgtgcacac cttcccggct    540

gtcctacagt cctcaggact ctactccctc agcagcgtgg tgaccgtgcc ctccagcagc    600

ttgggcaccc agacctacat ctgcaacgtg aatcacaagc ccagcaacac caaggtggac    660

aagagagttg agcccaaatc ttgtgacaaa actcacacat gcccaccgtg cccagcacct    720

gaactcctgg ggggaccgtc agtcttcctc ttccccccaa aacccaagga caccctcatg    780

atctcccgga cccctgaggt cacatgcgtg gtggtggacg tgagccacga ggatcctgaa    840

gtcaagttca actggtacgt ggatggcgtc gaggtgcata atgccaagac aaaaccccgg    900

gaggaacagt acaactcaac ttatagagtc gtgagcgtcc tgaccgtgct gcatcaggac    960

tggctgaacg gcaaagaata caagtgcaaa gtgtctaata aggccctgcc tgctccaatc   1020

gagaaaacaa ttagcaaggc aaaagggcag cccagggaac ctcaggtgta cactctgcct   1080

ccaagccgcg aggaaatgac caagaaccag gtctccctga catgtctggt gaaaggattc   1140

tatcctagtg acattgccgt ggagtgggaa tcaaatggcc agccagagaa caattacaag   1200

accacacccc ctgtgctgga ctctgatggg agtttctttc tgtattccaa gctgaccgtg   1260

gataaatcta gatggcagca gggaaatgtc tttagctgtt ccgtgatgca tgaggcactg   1320

cacaaccatt acacccagaa atcactgtca ctgtccccag gaaaaggcgg gggaggctct   1380

cagctgcagc tggtccagag cggaaccgaa gtgaagaaac ccggcgcaag cgtcaaagtc   1440

tcatgcaaat caagcggata cgtcttcacc tcttactatc tggtgtgggt ccggcaggca   1500

ccaggacagg gactggagtg gatggccaca atctctcccg gagacgtgaa cactagttac   1560
```

```
gaacagcgat tccagggcag agtgaccgtc accacagacg cttcaactaa taccgtggat   1620

atggagctgc ggagcctgag atccgaagat acagccgtct actattgcgc tagggggccc   1680

cgcagcaagc ctccttatct gtatttcgct ctggatgtct gggggcaggg aacagcagtc   1740

accgtctcaa gcggcggggg aggctctggg ggaggcggga gtggaggcgg gggatcagag   1800

attgtcctga cccagtcacc tggcaccctg agcctgagtc ctggagagac cgctattctg   1860

tcttgtcggg catcacagtc cgtgagctcc tctctgctgg catggtacca gcagaagccc   1920

ggacaggccc ctaggctgct gatctatggc gcctccaacc gcgctactgg cattcggggg   1980

agattcagtg gctcagggag cggaaccgac tttaccctga caatcagccg gctggagccc   2040

gaagatttcg tgctgtacta ttgtcagcat tatggaagca gggtcacctt cggacaggga   2100

actaaactgg aaatcaag                                                  2118

<210> SEQ ID NO 173
<211> LENGTH: 710
<212> TYPE: PRT
<213> ORGANISM: Artificial Sequence
<220> FEATURE:
<223> OTHER INFORMATION: Bs3GC3b heavy chain aa

<400> SEQUENCE: 173

Glu Val Gln Leu Val Glu Ser Gly Gly Asp Leu Val Lys Ala Gly Gly
1               5                  10                  15

Ser Leu Arg Leu Ser Cys Ala Val Ser Gly Leu Ser Phe Ser Ser Ser
            20                  25                  30

Gly Met Asn Trp Val Arg Gln Ala Pro Gly Lys Gly Leu Glu Trp Ile
        35                  40                  45

Ser Ser Ile Ser Gly Ser Gln Asn Tyr Lys Tyr Tyr Ala Asp Ser Val
    50                  55                  60

Lys Gly Arg Phe Val Val Ser Arg Asp Asn Ala Arg Asn Phe Leu Tyr
65                  70                  75                  80

Leu Gln Met Asp Ser Leu Arg Ala Glu Asp Thr Ala Val Tyr Phe Cys
                85                  90                  95

Val Gly Gly Phe Pro Tyr Trp Leu Pro Pro Ser Asp Phe Ser Gly Phe
            100                 105                 110

His Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255
```

-continued

```
Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Gly Gly Gly Gly Ser Gly Val Gln Leu
    450                 455                 460

Val Gln Ser Gly Gly Gly Leu Val Gln Pro Gly Gly Ser Leu Arg Leu
465                 470                 475                 480

Ser Cys Ala Ala Ser Gly Phe Thr Val Ser Thr Asn Tyr Met Ser Trp
                485                 490                 495

Val Arg Gln Ala Pro Gly Lys Gly Leu Glu Trp Val Ser Ile Leu Tyr
            500                 505                 510

Ala Gly Gly Val Thr Arg Tyr Ala Asp Ser Val Lys Thr Arg Phe Thr
        515                 520                 525

Ile Ser Arg Asp Asn Ser Lys Asn Thr Leu Phe Leu Gln Met Asn Ala
    530                 535                 540

Leu Ser Ala Glu Asp Thr Ala Ile Tyr Tyr Cys Ala Lys His Tyr Asp
545                 550                 555                 560

Ser Gly Tyr Ser Thr Ile Asp His Phe Asp Ser Trp Gly Gln Gly Thr
                565                 570                 575

Leu Val Thr Val Ser Ser Gly Gly Gly Gly Ser Gly Gly Gly Gly Ser
            580                 585                 590

Gly Gly Gly Gly Ser Asp Ile Gln Met Thr Gln Ser Pro Asp Ser Val
        595                 600                 605

Ala Val Ser Leu Gly Glu Arg Ala Thr Ile Asn Cys Lys Ser Ser Gln
    610                 615                 620

Ser Val Phe Tyr Thr Ser Lys Asn Lys Asn Tyr Leu Ala Trp Phe Gln
625                 630                 635                 640

Gln Lys Pro Gly Gln Pro Pro Lys Leu Leu Ile Tyr Trp Ala Ser Thr
                645                 650                 655

Arg Glu Ser Gly Val Pro Asp Arg Phe Ser Gly Ser Gly Ser Gly Thr
            660                 665                 670

Asp Phe Thr Leu Thr Ile Ser Ser Leu Arg Pro Glu Asp Val Ala Val
```

675 680 685

Tyr Tyr Cys Gln Gln Tyr Tyr Ser Thr Pro Phe Thr Phe Gly Pro Gly
690 695 700

Thr Lys Val Asp Ile Lys
705 710

<210> SEQ ID NO 174
<211> LENGTH: 2130
<212> TYPE: DNA
<213> ORGANISM: Artificial Sequence
<220> FEATURE:
<223> OTHER INFORMATION: Bs3GC3b heavy chain nucl

<400> SEQUENCE: 174
gaggtacaat tggtggagtc tgggggagac ctggtcaagg cggggggggtc cctgagactc 60
tcctgtgccg tctctggatt gtccttcagt agttcaggca tgaattgggt ccgccaggct 120
ccagggaagg ggctggagtg gatctcatcg attagtggta gtcagaacta caaatactat 180
gcagactcag tgaagggccg attcgtcgtc tccagagaca acgcccgcaa ctttctatat 240
ctgcaaatgg acagcctgag ggccgaggat acggctgtgt atttttgtgt gggaggtttc 300
ccctattggt tacccccgag cgacttctcc ggtttccatg tctggggcca agggaccacg 360
gtcaccgtct cctcagcgtc gaccaagggc ccatcggtct tccccctggc accctcctcc 420
aagagcacct ctgggggcac agcggccctg ggctgcctgg tcaaggacta cttccccgaa 480
cctgtgacgg tctcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcaccc agacctacat ctgcaacgtg aatcacaagc ccagcaacac caaggtggac 660
aagagagttg agcccaaatc ttgtgacaaa actcacacat gcccaccgtg cccagcacct 720
gaactcctgg ggggaccgtc agtcttcctc ttccccccaa aacccaagga caccctcatg 780
atctcccgga cccctgaggt cacatgcgtg gtggtggacg tgagccacga ggatcctgaa 840
gtcaagttca actggtacgt ggatggcgtc gaggtgcata atgccaagac aaaaccccgg 900
gaggaacagt acaactcaac ttatagagtc gtgagcgtcc tgaccgtgct gcatcaggac 960
tggctgaacg gcaaagaata caagtgcaaa gtgtctaata aggccctgcc tgctccaatc 1020
gagaaaacaa ttagcaaggc aaaagggcag cccagggaac ctcaggtgta cactctgcct 1080
ccaagccgcg aggaaatgac caagaaccag gtctccctga catgtctggt gaaaggattc 1140
tatcctagtg acattgccgt ggagtgggaa tcaaatggcc agccagagaa caattacaag 1200
accacacccc ctgtgctgga ctctgatggg agtttctttc tgtattccaa gctgaccgtg 1260
gataaatcta gatggcagca gggaaatgtc tttagctgtt ccgtgatgca tgaggcactg 1320
cacaaccatt acacccagaa atcactgtca ctgtccccag gaaaaggcgg gggaggctct 1380
ggcgtgcagc tggtccagag cggaggcgga ctggtccagc ccggcggatc actgagactg 1440
tcatgtgccg caagcgggtt taccgtctct acaaactaca tgtcttgggt gaggcaggca 1500
cctggaaagg gactggagtg ggtctcaatc ctgtacgctg gcggggtgac ccggtatgca 1560
gacagcgtca agacccggtt cacaattagc agagataact ccaaaaatac tctgtttctg 1620
cagatgaatg ccctgtccgc tgaagacacc gcaatctact attgcgccaa acactatgat 1680
agtgggtaca gtaccattga ccatttcgat agctgggggc aggggactct ggtgaccgtc 1740
tcatcaggcg ggggaggctc tgggggaggc gggagtggag gcgggggatc agatattcag 1800
atgacccaga gtcctgattc cgtcgctgtc tcactgggag aaagggcaac cattaactgt 1860

```
aaaagctcac agagtgtctt ctacaccagt aagaacaaaa actatctggc ctggtttcag   1920

cagaagccag gccagccccc taaactgctg atctactggg ctagcactag agagtctgga   1980

gtgccagaca gattctctgg cagtgggtca ggaaccgact tcaccctgac aattagctcc   2040

ctgaggcccg aagacgtggc cgtctactat tgtcagcagt attattcaac acccttcaca   2100

ttcggaccag gaacaaaagt ggatattaag                                     2130


<210> SEQ ID NO 175
<211> LENGTH: 710
<212> TYPE: PRT
<213> ORGANISM: Artificial Sequence
<220> FEATURE:
<223> OTHER INFORMATION: Bs3GC4 heavy chain aa

<400> SEQUENCE: 175

Gln Val Gln Leu Met Glu Ser Gly Gly Gly Val Val Gln Pro Gly Arg
1               5                   10                  15

Ser Leu Arg Leu Ser Cys Ser Ala Phe Gly Phe Thr Phe Ser Asn Tyr
            20                  25                  30

Pro Met His Trp Val Arg Gln Ala Pro Gly Lys Gly Leu Glu Trp Val
        35                  40                  45

Ala Ile Ile Leu Pro Asp Gly Asn Arg Lys Asn Tyr Gly Arg Ser Val
    50                  55                  60

Thr Gly Arg Phe Thr Ile Ser Arg Asp Asn Ser Asn Asn Ser Leu Tyr
65                  70                  75                  80

Leu Gln Met Asn Asn Leu Thr Thr Glu Asp Thr Ala Met Tyr Tyr Cys
                85                  90                  95

Thr Arg Asp Gly Thr Tyr Tyr Ser Asn Gly Gly Val Tyr Gln Thr Tyr
            100                 105                 110

Arg Arg Phe Phe Asp Phe Trp Gly Arg Gly Thr Leu Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
```

-continued

```
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys Gly Gly Gly Gly Ser
    450                 455                 460

Gln Leu Gln Leu Val Gln Ser Gly Thr Glu Val Lys Lys Pro Gly Ala
465                 470                 475                 480

Ser Val Lys Val Ser Cys Lys Ser Ser Gly Tyr Val Phe Thr Ser Tyr
                485                 490                 495

Tyr Leu Val Trp Val Arg Gln Ala Pro Gly Gln Gly Leu Glu Trp Met
            500                 505                 510

Ala Thr Ile Ser Pro Gly Asp Val Asn Thr Ser Tyr Glu Gln Arg Phe
        515                 520                 525

Gln Gly Arg Val Thr Val Thr Thr Asp Ala Ser Thr Asn Thr Val Asp
    530                 535                 540

Met Glu Leu Arg Ser Leu Arg Ser Glu Asp Thr Ala Val Tyr Tyr Cys
545                 550                 555                 560

Ala Arg Gly Pro Arg Ser Lys Pro Pro Tyr Leu Tyr Phe Ala Leu Asp
                565                 570                 575

Val Trp Gly Gln Gly Thr Ala Val Thr Val Ser Ser Gly Gly Gly Gly
            580                 585                 590

Ser Gly Gly Gly Gly Ser Gly Gly Gly Gly Ser Glu Ile Val Leu Thr
        595                 600                 605

Gln Ser Pro Gly Thr Leu Ser Leu Ser Pro Gly Glu Thr Ala Ile Leu
    610                 615                 620

Ser Cys Arg Ala Ser Gln Ser Val Ser Ser Ser Leu Leu Ala Trp Tyr
625                 630                 635                 640

Gln Gln Lys Pro Gly Gln Ala Pro Arg Leu Leu Ile Tyr Gly Ala Ser
                645                 650                 655

Asn Arg Ala Thr Gly Ile Arg Gly Arg Phe Ser Gly Ser Gly Ser Gly
            660                 665                 670

Thr Asp Phe Thr Leu Thr Ile Ser Arg Leu Glu Pro Glu Asp Phe Val
        675                 680                 685

Leu Tyr Tyr Cys Gln His Tyr Gly Ser Arg Val Thr Phe Gly Gln Gly
    690                 695                 700

Thr Lys Leu Glu Ile Lys
705                 710

<210> SEQ ID NO 176
```

<211> LENGTH: 2130
<212> TYPE: DNA
<213> ORGANISM: Artificial Sequence
<220> FEATURE:
<223> OTHER INFORMATION: Bs3GC4 heavy chain nucl

<400> SEQUENCE: 176
caggtgcaat tgatggagtc tgggggaggc gtggtccagc ctgggaggtc cctgcgactc 60
tcatgcagtg cctttggatt caccttttcg aactatccta tgcactgggt ccgccaggct 120
ccaggcaagg gacttgagtg ggtggctatc attttacctg atgggaacag aaaaaactat 180
ggaaggtccg tgacgggccg attcaccatc tccagagaca attccaacaa cagcctttat 240
ttgcaaatga acaacctgac gactgaggac acggctatgt actattgtac gagagatggc 300
acgtattact ctaatggtgg tgtttatcag acatatcgaa ggttcttcga tttctggggc 360
cgtggcaccc tggtcaccgt ctcctcagcg tcgaccaagg gcccatcggt cttcccccctg 420 gcaccctcct ccaagagcac ctctgggggc acagcggccc tgggctgcct ggtcaaggac 480
tacttccccg aacctgtgac ggtctcgtgg aactcaggcg ccctgaccag cggcgtgcac 540
accttcccgg ctgtcctaca gtcctcagga ctctactccc tcagcagcgt ggtgaccgtg 600
ccctccagca gcttgggcac ccagacctac atctgcaacg tgaatcacaa gcccagcaac 660
accaaggtgg acaagagagt tgagcccaaa tcttgtgaca aaactcacac atgcccaccg 720
tgcccagcac ctgaactcct ggggggaccg tcagtcttcc tcttcccccc aaaacccaag 780
gacaccctca tgatctcccg gacccctgag gtcacatgcg tggtggtgga cgtgagccac 840
gaggatcctg aagtcaagtt caactggtac gtggatggcg tcgaggtgca taatgccaag 900
acaaaacccc gggaggaaca gtacaactca acttatagag tcgtgagcgt cctgaccgtg 960
ctgcatcagg actggctgaa cggcaaagaa tacaagtgca aagtgtctaa taaggccctg 1020
cctgctccaa tcgagaaaac aattagcaag gcaaaagggc agcccaggga acctcaggtg 1080
tacactctgc ctccaagccg cgaggaaatg accaagaacc aggtctccct gacatgtctg 1140
gtgaaaggat tctatcctag tgacattgcc gtggagtggg aatcaaatgg ccagccagag 1200
aacaattaca agaccacacc ccctgtgctg gactctgatg ggagtttctt tctgtattcc 1260
aagctgaccg tggataaatc tagatggcag cagggaaatg tctttagctg ttccgtgatg 1320
catgaggcac tgcacaacca ttacacccag aaatcactgt cactgtcccc aggaaaaggc 1380
gggggaggct ctcagctgca gctggtccag agcggaaccg aagtgaagaa acccggcgca 1440
agcgtcaaag tctcatgcaa atcaagcgga tacgtcttca cctcttacta tctggtgtgg 1500
gtccggcagg caccaggaca gggactggag tggatggcca caatctctcc cggagacgtg 1560
aacactagtt acgaacagcg attccagggc agagtgaccg tcaccacaga cgcttcaact 1620
aataccgtgg atatggagct gcggagcctg agatccgaag atacagccgt ctactattgc 1680
gctagggggc cccgcagcaa gcctccttat ctgtatttcg ctctggatgt ctgggggcag 1740
ggaacagcag tcaccgtctc aagcggcggg ggaggctctg ggggaggcgg gagtggaggc 1800
gggggatcag agattgtcct gacccagtca cctggcaccc tgagcctgag tcctggagag 1860
accgctattc tgtcttgtcg ggcatcacag tccgtgagct cctctctgct ggcatggtac 1920
cagcagaagc ccggacaggc ccctaggctg ctgatctatg gcgcctccaa ccgcgctact 1980
ggcattcggg ggagattcag tggctcaggg agcggaaccg actttaccct gacaatcagc 2040
cggctggagc ccgaagattt cgtgctgtac tattgtcagc attatggaag cagggtcacc 2100
ttcggacagg gaactaaact ggaaatcaag 2130

<210> SEQ ID NO 177
<211> LENGTH: 714
<212> TYPE: PRT
<213> ORGANISM: Artificial Sequence
<220> FEATURE:
<223> OTHER INFORMATION: Bs3GC5 heavy chain aa

<400> SEQUENCE: 177

```
Gln Val Gln Leu Met Glu Ser Gly Gly Gly Val Val Gln Pro Gly Arg
1               5                   10                  15

Ser Leu Arg Leu Ser Cys Ser Ala Phe Gly Phe Thr Phe Ser Asn Tyr
            20                  25                  30

Pro Met His Trp Val Arg Gln Ala Pro Gly Lys Gly Leu Glu Trp Val
        35                  40                  45

Ala Ile Ile Leu Pro Asp Gly Asn Arg Lys Asn Tyr Gly Arg Ser Val
    50                  55                  60

Thr Gly Arg Phe Thr Ile Ser Arg Asp Asn Ser Asn Asn Ser Leu Tyr
65                  70                  75                  80

Leu Gln Met Asn Asn Leu Thr Thr Glu Asp Thr Ala Met Tyr Tyr Cys
                85                  90                  95

Thr Arg Asp Gly Thr Tyr Tyr Ser Asn Gly Gly Val Tyr Gln Thr Tyr
            100                 105                 110

Arg Arg Phe Phe Asp Phe Trp Gly Arg Gly Thr Leu Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Glu
        355                 360                 365
```

```
Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys Gly Gly Gly Gly Ser
    450                 455                 460

Gly Val Gln Leu Val Gln Ser Gly Gly Gly Leu Val Gln Pro Gly Gly
465                 470                 475                 480

Ser Leu Arg Leu Ser Cys Ala Ala Ser Gly Phe Thr Val Ser Thr Asn
                485                 490                 495

Tyr Met Ser Trp Val Arg Gln Ala Pro Gly Lys Gly Leu Glu Trp Val
            500                 505                 510

Ser Ile Leu Tyr Ala Gly Gly Val Thr Arg Tyr Ala Asp Ser Val Lys
        515                 520                 525

Thr Arg Phe Thr Ile Ser Arg Asp Asn Ser Lys Asn Thr Leu Phe Leu
    530                 535                 540

Gln Met Asn Ala Leu Ser Ala Glu Asp Thr Ala Ile Tyr Tyr Cys Ala
545                 550                 555                 560

Lys His Tyr Asp Ser Gly Tyr Ser Thr Ile Asp His Phe Asp Ser Trp
                565                 570                 575

Gly Gln Gly Thr Leu Val Thr Val Ser Ser Gly Gly Gly Gly Ser Gly
            580                 585                 590

Gly Gly Gly Ser Gly Gly Gly Gly Ser Asp Ile Gln Met Thr Gln Ser
        595                 600                 605

Pro Asp Ser Val Ala Val Ser Leu Gly Glu Arg Ala Thr Ile Asn Cys
    610                 615                 620

Lys Ser Ser Gln Ser Val Phe Tyr Thr Ser Lys Asn Lys Asn Tyr Leu
625                 630                 635                 640

Ala Trp Phe Gln Gln Lys Pro Gly Gln Pro Pro Lys Leu Leu Ile Tyr
                645                 650                 655

Trp Ala Ser Thr Arg Glu Ser Gly Val Pro Asp Arg Phe Ser Gly Ser
            660                 665                 670

Gly Ser Gly Thr Asp Phe Thr Leu Thr Ile Ser Ser Leu Arg Pro Glu
        675                 680                 685

Asp Val Ala Val Tyr Tyr Cys Gln Gln Tyr Tyr Ser Thr Pro Phe Thr
    690                 695                 700

Phe Gly Pro Gly Thr Lys Val Asp Ile Lys
705                 710


<210> SEQ ID NO 178
<211> LENGTH: 2142
<212> TYPE: DNA
<213> ORGANISM: Artificial Sequence
<220> FEATURE:
<223> OTHER INFORMATION: Bs3GC5 heavy chain nucl

<400> SEQUENCE: 178

caggtgcaat tgatggagtc tgggggaggc gtggtccagc ctgggaggtc cctgcgactc      60
```

-continued

```
tcatgcagtg cctttggatt caccttttcg aactatccta tgcactgggt ccgccaggct    120
ccaggcaagg gacttgagtg ggtggctatc attttacctg atgggaacag aaaaaactat    180
ggaaggtccg tgacgggccg attcaccatc tccagagaca attccaacaa cagcctttat    240
ttgcaaatga acaacctgac gactgaggac acggctatgt actattgtac gagagatggc    300
acgtattact ctaatggtgg tgtttatcag acatatcgaa ggttcttcga tttctggggc    360
cgtggcaccc tggtcaccgt ctcctcagcg tcgaccaagg gcccatcggt cttccccctg    420
gcaccctcct ccaagagcac ctctgggggc acagcggccc tgggctgcct ggtcaaggac    480
tacttccccg aacctgtgac ggtctcgtgg aactcaggcg ccctgaccag cggcgtgcac    540
accttcccgg ctgtcctaca gtcctcagga ctctactccc tcagcagcgt ggtgaccgtg    600
ccctccagca gcttgggcac ccagacctac atctgcaacg tgaatcacaa gcccagcaac    660
accaaggtgg acaagagagt tgagcccaaa tcttgtgaca aaactcacac atgcccaccg    720
tgcccagcac ctgaactcct ggggggaccg tcagtcttcc tcttcccccc aaaacccaag    780
gacaccctca tgatctcccg gacccctgag gtcacatgcg tggtggtgga cgtgagccac    840
gaggatcctg aagtcaagtt caactggtac gtggatggcg tcgaggtgca taatgccaag    900
acaaaacccc gggaggaaca gtacaactca acttatagag tcgtgagcgt cctgaccgtg    960
ctgcatcagg actggctgaa cggcaaagaa tacaagtgca aagtgtctaa taaggccctg   1020
cctgctccaa tcgagaaaac aattagcaag gcaaaagggc agcccaggga acctcaggtg   1080
tacactctgc ctccaagccg cgaggaaatg accaagaacc aggtctccct gacatgtctg   1140
gtgaaaggat tctatcctag tgacattgcc gtggagtggg aatcaaatgg ccagccagag   1200
aacaattaca agaccacacc ccctgtgctg gactctgatg ggagtttctt tctgtattcc   1260
aagctgaccg tggataaatc tagatggcag cagggaaatg tctttagctg ttccgtgatg   1320
catgaggcac tgcacaacca ttacacccag aaatcactgt cactgtcccc aggaaaaggc   1380
gggggaggct ctggcgtgca gctggtccag agcggaggcg gactggtcca gcccggcgga   1440
tcactgagac tgtcatgtgc cgcaagcggg tttaccgtct ctacaaacta catgtcttgg   1500
gtgaggcagg cacctggaaa gggactggag tgggtctcaa tcctgtacgc tggcggggtg   1560
acccggtatg cagacagcgt caagacccgg ttcacaatta gcagagataa ctccaaaaat   1620
actctgtttc tgcagatgaa tgccctgtcc gctgaagaca ccgcaatcta ctattgcgcc   1680
aaacactatg atagtgggta cagtaccatt gaccatttcg atagctgggg gcaggggact   1740
ctggtgaccg tctcatcagg cgggggaggc tctgggggag gcgggagtgg aggcgggga    1800
tcagatattc agatgaccca gagtcctgat tccgtcgctg tctcactggg agaaagggca   1860
accattaact gtaaaagctc acagagtgtc ttctacacca gtaagaacaa aaactatctg   1920
gcctggtttc agcagaagcc aggccagccc cctaaactgc tgatctactg ggctagcact   1980
agagagtctg gagtgccaga cagattctct ggcagtgggt caggaaccga cttcaccctg   2040
acaattagct ccctgaggcc cgaagacgtg gccgtctact attgtcagca gtattattca   2100
acacccttca cattcggacc aggaacaaaa gtggatatta ag                      2142
```

<210> SEQ ID NO 179
<211> LENGTH: 452
<212> TYPE: PRT
<213> ORGANISM: Artificial Sequence
<220> FEATURE:
<223> OTHER INFORMATION: GCA7 heavy chain aa

<400> SEQUENCE: 179

-continued

```
Gly Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Ser Thr Asn
            20                  25                  30

Tyr Met Ser Trp Val Arg Gln Ala Pro Gly Lys Gly Leu Glu Trp Val
        35                  40                  45

Ser Ile Leu Tyr Ala Gly Gly Val Thr Arg Tyr Ala Asp Ser Val Lys
    50                  55                  60

Thr Arg Phe Thr Ile Ser Arg Asp Asn Ser Lys Asn Thr Leu Phe Leu
65                  70                  75                  80

Gln Met Asn Ala Leu Ser Ala Glu Asp Thr Ala Ile Tyr Tyr Cys Ala
                85                  90                  95

Lys His Tyr Asp Ser Gly Tyr Ser Thr Ile Asp His Phe Asp Ser Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

-continued

```
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 180
<211> LENGTH: 1356
<212> TYPE: DNA
<213> ORGANISM: Artificial Sequence
<220> FEATURE:
<223> OTHER INFORMATION: GCA7 heavy chain nucl

<400> SEQUENCE: 180

ggggtgcaac tggtgcagtc tgggggaggc ttggtccagc cggggggggtc cctgagactc      60

tcctgtgcag cctctggatt caccgtcagt accaactaca tgagctgggt ccgccaggct     120

ccagggaagg ggctggagtg ggtctcaatt ctttatgccg gaggtgtcac aaggtacgca     180

gactccgtga agaccagatt caccatctcc agagacaatt ccaagaacac tctctttctt     240

caaatgaacg ccctgagcgc cgaggacacg gctatatatt actgtgcgaa acactatgat     300

tcgggatatt ctaccataga tcactttgac tcctggggcc agggaaccct ggtcaccgtc     360

tcctcagcgt cgaccaaggg cccatcggtc ttccccctgg caccctcctc caagagcacc     420

tctgggggca cagcggccct gggctgcctg gtcaaggact acttccccga acctgtgacg     480

gtctcgtgga actcaggcgc cctgaccagc ggcgtgcaca ccttcccggc tgtcctacag     540

tcctcaggac tctactccct cagcagcgtg gtgaccgtgc cctccagcag cttgggcacc     600

cagacctaca tctgcaacgt gaatcacaag cccagcaaca ccaaggtgga caagagagtt     660

gagcccaaat cttgtgacaa aactcacaca tgcccaccgt gcccagcacc tgaactcctg     720

gggggaccgt cagtcttcct cttcccccca aaacccaagg acaccctcat gatctcccgg     780

acccctgagg tcacatgcgt ggtggtggac gtgagccacg aggatcctga ggtcaagttc     840

aactggtacg tggacggcgt ggaggtgcat aatgccaaga caaagccgcg ggaggagcag     900

tacaacagca cgtaccgtgt ggtcagcgtc ctcaccgtcc tgcaccagga ctggctgaat     960

ggcaaggagt acaagtgcaa ggtctccaac aaagccctcc cagcccccat cgagaaaacc    1020

atctccaaag ccaaagggca gccccgagaa ccacaggtgt acaccctgcc cccatcccgg    1080

gaggagatga ccaagaacca ggtcagcctg acctgcctgg tcaaaggctt ctatcccagc    1140

gacatcgccg tggagtggga gagcaatggg cagccggaga acaactacaa gaccacgcct    1200

cccgtgctgg actccgacgg ctccttcttc ctctatagca agctcaccgt ggacaagagc    1260

aggtggcagc aggggaacgt cttctcatgc tccgtgatgc atgaggctct gcacaaccac    1320

tacacgcaga agagcctctc cctgtccccg ggtaaa                              1356


<210> SEQ ID NO 181
<211> LENGTH: 220
<212> TYPE: PRT
<213> ORGANISM: Artificial Sequence
<220> FEATURE:
<223> OTHER INFORMATION: GCA7 light chain aa

<400> SEQUENCE: 181

Asp Ile Gln Met Thr Gln Ser Pro Asp Ser Val Ala Val Ser Leu Gly
1               5                   10                  15

Glu Arg Ala Thr Ile Asn Cys Lys Ser Ser Gln Ser Val Phe Tyr Thr
```

```
            20                  25                  30

Ser Lys Asn Lys Asn Tyr Leu Ala Trp Phe Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Arg Pro Glu Asp Val Ala Val Tyr Tyr Cys Gln Gln
                85                  90                  95

Tyr Tyr Ser Thr Pro Phe Thr Phe Gly Pro Gly Thr Lys Val Asp Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 182
<211> LENGTH: 660
<212> TYPE: DNA
<213> ORGANISM: Artificial Sequence
<220> FEATURE:
<223> OTHER INFORMATION: GCA7 light chain nucl

<400> SEQUENCE: 182

```
gacatccaga tgacccagtc tccagactcc gtggctgtgt ctctgggcga gagggccacc     60

atcaactgca agtccagcca gagtgttttc tacacctcca aaaataaaaa ctacttagct    120

tggttccagc agaaaccagg acagcctcct aaactgctca tttactgggc atctacccgg    180

gagtccgggg tccctgaccg attcagtggc agcgggtctg ggacagattt cactctcacc    240

atcagcagcc tgcggcctga agatgtggca gtttattact gtcagcaata ttatagtacc    300

cctttcactt tcggccctgg gaccaaagtg gatatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 183
<211> LENGTH: 214
<212> TYPE: PRT
<213> ORGANISM: Artificial Sequence
<220> FEATURE:
<223> OTHER INFORMATION: GCA21 light chain aa

<400> SEQUENCE: 183

```
Asp Ile Gln Met Thr Gln Ser Pro Ser Thr Leu Ser Thr Ser Val Gly
1               5                   10                  15

Asp Arg Val Thr Ile Thr Cys Arg Ala Ser Gln Asn Ile Leu Asn Trp
            20                  25                  30

Leu Ala Trp Tyr Gln Gln Lys Pro Gly Asn Ala Pro Asn Leu Leu Ile
        35                  40                  45

Tyr Lys Ala Ser Asp Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 184
<211> LENGTH: 642
<212> TYPE: DNA
<213> ORGANISM: Artificial Sequence
<220> FEATURE:
<223> OTHER INFORMATION: GCA21 light chain nucl

<400> SEQUENCE: 184

```
gacatccaga tgacccagtc tccttccacc ctgtctacat ctgtgggaga cagagtcacc     60

atcacttgcc gggccagtca gaatatcctt aattggttgg cctggtatca acagaaacca    120

gggaacgccc ctaacctcct gatatataag gcgtctgatt tacaaagtgg ggtcccctca    180

agattcagcg gcagtgggtc tgggacagaa ttcactctca ccatcagcag cctgcagcct    240

gatgattttg caacttatta ctgccagcat tataatagtt atcctctcac tttcggcgga    300

gggaccaagg tggaaatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                        642
```

<210> SEQ ID NO 185
<211> LENGTH: 214
<212> TYPE: PRT

<213> ORGANISM: Artificial Sequence
<220> FEATURE:
<223> OTHER INFORMATION: GCB59 light chain aa

<400> SEQUENCE: 185

Ser Tyr Val Leu Thr Gln Pro Pro Ser Val Ser Val Ala Pro Gly Gln
1 5 10 15

Thr Ala Ser Leu Thr Cys Gly Gly Thr Asn Ile Gly Ser Lys Ser Val
20 25 30

His Trp Tyr Gln Gln Lys Ala Gly Gln Ala Pro Val Leu Val Val Tyr
35 40 45

Ala Asp Asn Asp Arg Pro Ser Gly Val Pro Glu Arg Phe Ser Gly Ser
50 55 60

Asn Ser Gly Asn Thr Ala Thr Leu Thr Ile Ser Arg Val Glu Ala Glu
65 70 75 80

Asp Glu Ser Asp Tyr Phe Cys Gln Val Trp Asp Gly Asn Thr Asp His
85 90 95

Val Val Phe Gly Gly Gly Thr Lys Leu Thr Val Leu Gly Gln Pro Lys
100 105 110

Ala Ala Pro Ser Val Thr Leu Phe Pro Pro Ser Ser Glu Glu Leu Gln
115 120 125

Ala Asn Lys Ala Thr Leu Val Cys Leu Ile Ser Asp Phe Tyr Pro Gly
130 135 140

Ala Val Thr Val Ala Trp Lys Ala Asp Ser Ser Pro Val Lys Ala Gly
145 150 155 160

Val Glu Thr Thr Thr Pro Ser Lys Gln Ser Asn Asn Lys Tyr Ala Ala
165 170 175

Ser Ser Tyr Leu Ser Leu Thr Pro Glu Gln Trp Lys Ser His Arg Ser
180 185 190

Tyr Ser Cys Gln Val Thr His Glu Gly Ser Thr Val Glu Lys Thr Val
195 200 205

Ala Pro Thr Glu Cys Ser
210

<210> SEQ ID NO 186
<211> LENGTH: 642
<212> TYPE: DNA
<213> ORGANISM: Artificial Sequence
<220> FEATURE:
<223> OTHER INFORMATION: GCB59 light chain nucl

<400> SEQUENCE: 186
tcatatgtgc tgactcaacc accctcggtg tcagtggccc caggacagac ggccagtcta 60
acctgtgggg gaactaacat tggaagtaaa agtgttcatt ggtaccagca aaaggcaggc 120
caggcccctg tgttggtcgt ctatgctgat aacgacaggc cctcaggggt ccctgagcga 180
ttctctggct ccaactctgg gaacacggcc accctgacca tcagcagggt cgaggccgag 240
gatgagtccg actatttctg tcaggtgtgg gatggtaata ctgatcatgt ggtcttcggc 300
ggagggacca agctgaccgt cctgggtcag cccaaggctg ccccctcggt cactctgttc 360
ccgccctcct ctgaggagct tcaagccaac aaggccacac tggtgtgtct cataagtgac 420
ttctacccgg gagccgtgac agtggcttgg aaagcagata gcagccccgt caaggcggga 480
gtggagacca ccacaccctc caaacaaagc aacaacaagt acgcggccag cagctatctg 540
agcctgacgc ctgagcagtg gaagtcccac agaagctaca gctgccaggt cacgcatgaa 600
gggagcaccg tggagaagac agtggcccct acagaatgtt ca 642

<210> SEQ ID NO 187
<211> LENGTH: 454
<212> TYPE: PRT
<213> ORGANISM: Artificial Sequence
<220> FEATURE:
<223> OTHER INFORMATION: GCE536 heavy chain aa

<400> SEQUENCE: 187

```
Gln Leu Gln Leu Val Gln Ser Gly Thr Glu Val Lys Lys Pro Gly Ala
1               5                   10                  15

Ser Val Lys Val Ser Cys Lys Ser Ser Gly Tyr Val Phe Thr Ser Tyr
            20                  25                  30

Tyr Leu Val Trp Val Arg Gln Ala Pro Gly Gln Gly Leu Glu Trp Met
        35                  40                  45

Ala Thr Ile Ser Pro Gly Asp Val Asn Thr Ser Tyr Glu Gln Arg Phe
    50                  55                  60

Gln Gly Arg Val Thr Val Thr Thr Asp Ala Ser Thr Asn Thr Val Asp
65                  70                  75                  80

Met Glu Leu Arg Ser Leu Arg Ser Glu Asp Thr Ala Val Tyr Tyr Cys
                85                  90                  95

Ala Arg Gly Pro Arg Ser Lys Pro Pro Tyr Leu Tyr Phe Ala Leu Asp
            100                 105                 110

Val Trp Gly Gln Gly Thr Ala Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365
```

```
Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 188
<211> LENGTH: 1362
<212> TYPE: DNA
<213> ORGANISM: Artificial Sequence
<220> FEATURE:
<223> OTHER INFORMATION: GCE536 heavy chain nucl

<400> SEQUENCE: 188

```
cagctgcagc tggtccagtc aggcacagag gtcaaaaagc caggagcatc agtgaaggtg     60
tcttgtaagt catcaggata cgtgttcacc tcttactatc tggtgtgggt ccggcaggca    120
ccaggacagg gactggagtg gatggccaca atctctcccg gagacgtgaa cactagttac    180
gaacagcgat tccagggcag agtgaccgtc accacagacg cttcaactaa taccgtggat    240
atggagctgc ggagcctgag atccgaagat acagccgtct actattgcgc taggggggccc   300
cgcagcaagc ctccttatct gtattttgct ctggatgtgt gggggcaggg gaccgctgtc    360
accgtgtcaa gcgcgtcgac caagggccca tcggtcttcc ccctggcacc ctcctccaag    420
agcacctctg ggggcacagc ggccctgggc tgcctggtca aggactactt ccccgaacct    480
gtgacggtct cgtggaactc aggcgccctg accagcggcg tgcacacctt cccggctgtc    540
ctacagtcct caggactcta ctccctcagc agcgtggtga ccgtgccctc cagcagcttg    600
ggcacccaga cctacatctg caacgtgaat cacaagccca gcaacaccaa ggtggacaag    660
agagttgagc ccaaatcttg tgacaaaact cacacatgcc caccgtgccc agcacctgaa    720
ctcctggggg gaccgtcagt cttcctcttc cccccaaaac ccaaggacac cctcatgatc    780
tcccggaccc ctgaggtcac atgcgtggtg gtggacgtga gccacgagga tcctgaggtc    840
aagttcaact ggtacgtgga cggcgtggag gtgcataatg ccaagacaaa gccgcgggag    900
gagcagtaca acagcacgta ccgtgtggtc agcgtcctca ccgtcctgca ccaggactgg    960
ctgaatggca aggagtacaa gtgcaaggtc tccaacaaag ccctcccagc ccccatcgag   1020
aaaaccatct ccaaagccaa agggcagccc cgagaaccac aggtgtacac cctgccccca   1080
tcccgggagg agatgaccaa gaaccaggtc agcctgacct gcctggtcaa aggcttctat   1140
cccagcgaca tcgccgtgga gtgggagagc aatgggcagc cggagaacaa ctacaagacc   1200
acgcctcccg tgctggactc cgacggctcc ttcttcctct atagcaagct caccgtggac   1260
aagagcaggt ggcagcaggg gaacgtcttc tcatgctccg tgatgcatga ggctctgcac   1320
aaccactaca cgcagaagag cctctccctg tccccgggta aa                      1362
```

<210> SEQ ID NO 189
<211> LENGTH: 214
<212> TYPE: PRT

<213> ORGANISM: Artificial Sequence
<220> FEATURE:
<223> OTHER INFORMATION: GCE536 light chain aa

<400> SEQUENCE: 189

Glu Ile Val Leu Thr Gln Ser Pro Gly Thr Leu Ser Leu Ser Pro Gly
1 5 10 15

Glu Thr Ala Ile Leu Ser Cys Arg Ala Ser Gln Ser Val Ser Ser Ser
20 25 30

Leu Leu Ala Trp Tyr Gln Gln Lys Pro Gly Gln Ala Pro Arg Leu Leu
35 40 45

Ile Tyr Gly Ala Ser Asn Arg Ala Thr Gly Ile Arg Gly Arg Phe Ser
50 55 60

Gly Ser Gly Ser Gly Thr Asp Phe Thr Leu Thr Ile Ser Arg Leu Glu
65 70 75 80

Pro Glu Asp Phe Val Leu Tyr Tyr Cys Gln His Tyr Gly Ser Arg Val
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 190
<211> LENGTH: 642
<212> TYPE: DNA
<213> ORGANISM: Artificial Sequence
<220> FEATURE:
<223> OTHER INFORMATION: GCE536 light chain nucl

<400> SEQUENCE: 190
gaaattgtgt tgacgcagtc tcctggcacc ctgtctttgt ctccagggga aacagccatc 60
ctctcctgca gggccagtca gagtgtcagc agcagcctct tagcctggta ccagcaaaaa 120
cctggccagg ctcccaggct cctcatctac ggtgcatcca atagggccac tggcatcaga 180
ggcaggttta gtggcagtgg gtctgggaca gacttcactc tcaccatcag tagattggag 240
cctgaagatt ttgtacttta ttactgtcag cactatggct cacgggtcac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

-continued

```
<210> SEQ ID NO 191
<211> LENGTH: 19
<212> TYPE: PRT
<213> ORGANISM: Artificial Sequence
<220> FEATURE:
<223> OTHER INFORMATION: Chimeric hinge sequence

<400> SEQUENCE: 191

Glu Ser Lys Tyr Gly Pro Pro Cys Pro Pro Cys Pro Ala Pro Pro Val
1               5                   10                  15

Ala Gly Pro
```